United States Patent
Ostrer et al.

(10) Patent No.: US 12,227,809 B2
(45) Date of Patent: Feb. 18, 2025

(54) ROBUST GENOMIC PREDICTOR OF BREAST AND LUNG CANCER METASTASIS

(71) Applicants: Harry Ostrer, New York, NY (US); Johnny C. Loke, Valley Cottage, NY (US); Alexander Pearlman, New York, NY (US)

(72) Inventors: Harry Ostrer, New York, NY (US); Johnny C. Loke, Valley Cottage, NY (US); Alexander Pearlman, New York, NY (US)

( * ) Notice: Subject to any disclaimer, the term of this patent is extended or adjusted under 35 U.S.C. 154(b) by 1076 days.

(21) Appl. No.: 16/983,235

(22) Filed: Aug. 3, 2020

(65) Prior Publication Data

US 2020/0370132 A1 Nov. 26, 2020

Related U.S. Application Data

(63) Continuation of application No. PCT/US2019/016268, filed on Feb. 1, 2019.

(60) Provisional application No. 62/625,553, filed on Feb. 2, 2018.

(51) Int. Cl.
*C12Q 1/6886* (2018.01)
*G06F 17/18* (2006.01)

(52) U.S. Cl.
CPC .......... *C12Q 1/6886* (2013.01); *G06F 17/18* (2013.01); *C12Q 2600/112* (2013.01); *C12Q 2600/118* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 7,482,123 B2 | 1/2009 | Paris et al. | |
| 7,638,278 B2 | 12/2009 | Pollack et al. | |
| 10,519,505 B2 * | 12/2019 | Ostrer | C12Q 1/6886 |
| 2009/0155805 A1 | 6/2009 | Zhang et al. | |
| 2013/0231259 A1 | 9/2013 | Hoon et al. | |
| 2014/0221229 A1 * | 8/2014 | Ostrer | G16H 50/30 |
| | | | 506/9 |
| 2015/0031744 A1 | 1/2015 | Loh et al. | |
| 2015/0152506 A1 | 6/2015 | Gomis et al. | |

FOREIGN PATENT DOCUMENTS

WO WO 2012/145607 A2 10/2012

OTHER PUBLICATIONS

International Search Report dated Apr. 15, 2019 issued in PCT/US2019/016268.
Moelans et al., "Genomic evolution from primary breast carcinoma to distant metastasis: Few copy number changes of breast cancer related genes," Cancer Letters (Oct. 30, 2013), vol. 344, pp. 138-146.

* cited by examiner

*Primary Examiner* — Christian L Fronda
(74) *Attorney, Agent, or Firm* — Scully, Scott, Murphy & Presser, P.C.

(57) ABSTRACT

A method of determining the risk of metastasis of breast or lung cancer in a human subject who has or had breast or lung cancer is disclosed herein. The method is based on detecting in a sample from the subject the number of copies per cell of genes and/or genomic regions of a metastatic gene signature set disclosed herein, and determining alternations in the number of copies per cell of the genes and/or genomic regions in the signature set, as compared to the number of copies per cell in non-cancer cells, thereby determining the risk of breast/lung cancer metastasis.

6 Claims, 11 Drawing Sheets
(10 of 11 Drawing Sheet(s) Filed in Color)

ROBUST GENOMIC PREDICTOR OF BREAST AND LUNG CANCER METASTASIS

CROSS REFERENCE TO RELATED APPLICATION

This application is the continuation of PCT/US2019/016268 which claims the benefit of priority from U.S. Provisional Application No. 62/625,553, filed Feb. 2, 2018, the entire contents of which are incorporated herein by reference.

FIELD OF THE DISCLOSURE

This disclosure relates to metastatic gene signatures. More particularly, this disclosure has identified copy number alterations (CNAs) around genes that are over-represented in breast and lung cancer metastases, which serve as the basis for predicting whether a primary tumor will metastasize.

BACKGROUND OF THE DISCLOSURE

Tumor metastasis to distant sites results in 90% of solid tumor cancer deaths (Nguyen, D. X. et al., *Nat Rev Genet*, 8, 341-52 (2007)). The frequency with which metastasis occurs varies by tumor type and even within a tumor type the time to metastasis can be quite variable from the time at diagnosis to many years in the future. Nonetheless, many of the steps involved in the development of metastasis, invasion beyond the site of origin, escape from apoptosis when detached from the matrix of origin, and colonization of distant sites, are shared across tumor types. These steps are genetically encoded. Metastasis-promoting genes that alter cellular functions in cell lines and in animal models have been identified (Nguyen, D. X. et al., *Nat Rev Genet*, 8, 341-52 (2007); Vogelstein, B. & Kinzler, K. W., *Nat Med*, 10, 789-99 (2004); and Hunter, K. W., *Br J Cancer*, 752-5 (2004)).

Analysis of copy number alterations (CNAs) has proven to be fruitful for identifying recurrent events that are associated with metastasis within specific primary tumor types (Taylor, B. S. et al., *Cancer Cell*, 18, 11-22 (2010); Pearlman, A. et al., *J Probab Stat*, 2012, 873570 (2012) and US Patent Publication No. 2014/0221229). CNAs are the genetic changes most commonly observed in human cancers, reflecting the innate chromosomal instability of many tumors (Vogelstein, B. & Kinzler, K. W., *Nat Med*, 10, 789-99 (2004)). An average one-third of a cancer genome demonstrates CNAs with roughly equal distributions of copy number gains and losses (Beroukhim, R. et al., *Nature*, 463, 899-905 (2010).). CNAs are accentuated when mutations occur in stability genes that affect the repair of DNA, mitotic recombination or chromosomal segregation (Vogelstein, B. & Kinzler, K. W., *Nat Med*, 10, 789-99 (2004)). In a previous study, the inventors observed that despite the high frequency of these CNAs throughout the genome, 366 genes within these regions were commonly altered with similar patterns in prostate cancer metastases and primary tumors (Pearlman, A. et al., *J Probab Stat*, 2012, 873570 (2012)). Sixty-five percent of the genes (241 of 366) were structured on the genome as contiguous gene clumps of two through thirteen genes per clump. The remaining 35% of the genes (125 of 366) were observed as singletons.

Knowledge of these genes and their CNAs could have clinical utility for predicting who might have aggressive disease requiring treatment and whose disease might be indolent. To make such predictions, the inventors developed a metastatic potential score (MPS) that was based on the weighted frequency of specific CNAs overlapping 366 genes observed in prostate cancer metastases (Pearlman, A. et al., *J Probab. Stat.*, 2012, 873570 (2012)). In particular, metastases and metastasis-prone primary tumors all demonstrate enrichment of specific CNAs in one direction. This directionality provided a basis for calculating $Z_{genes}$ scores for the specific genes within the CNAs that included a penalty when the CNA went against the grain of the directionality. The MPS score represented the sum of the $Z_{genes}$ scores, divided by the number of genes being summed. When applied to a small cohort of 60 primary prostate tumors, of which 13 had metastasis outcome, MPS was predictive of the endpoint of metastasis-free survival using a Cox proportional hazards model (Pearlman, A. et al., *J Probab Stat*, 2012, 873570 (2012)).

In this disclosure, the inventors assessed the prevalence of these CNAs among large numbers of primary prostate cancers, triple negative breast cancers, other breast cancers and lung adenocarcinomas with known outcome. The inventors used a subset of the CNA genes to develop a predictive pan-cancer metastatic potential score (panMPS), because the four cohorts were assayed on different array platforms that represented different CNA genes. The panMPS was derived by using 295 of the 366 CNA genes that overlapped across all array platforms. Although 71 CNA genes were not represented in the panMPS, most of these were located in multi-gene clumps, thereby capturing the content of 67 of the 69 clumps, with no loss in the predictive accuracy for the panMPS relative to the MPS using 366 genes (Table 13, except the two pseudogenes (C8orf16 and ERW)). The inventors also observed high frequencies of these alterations in metastatic cell lines for tumors of eight different origins.

BRIEF DESCRIPTION OF THE DRAWINGS

The patent or application file contains at least one drawing executed in color. Copies of this patent or patent application publication with color drawing(s) will be provided by the Office upon request and payment of the necessary fee FIG. 1A-1D. Receiver operating characteristic curves estimate the accuracy of the panMPS for predicting metastatic outcome for prostate cancer (A. MSK cohort, B. Duke cohort), triple negative breast cancer (C. Montefiore cohort) and lung adenocarcinoma (D. MSKCC cohort). For prostate cancer, panMPS was predictive of mPT and iPT status in both the MSK and Duke cohorts. In addition, preoperative PSA, biopsy Gleason score, and percent genomic instability were predictive of mPT and iPT status in the MSK cohort, only. The AUC is indicated for each curve.

DETAILED DESCRIPTION

Figures 1A, 1B, 1C, 1D:
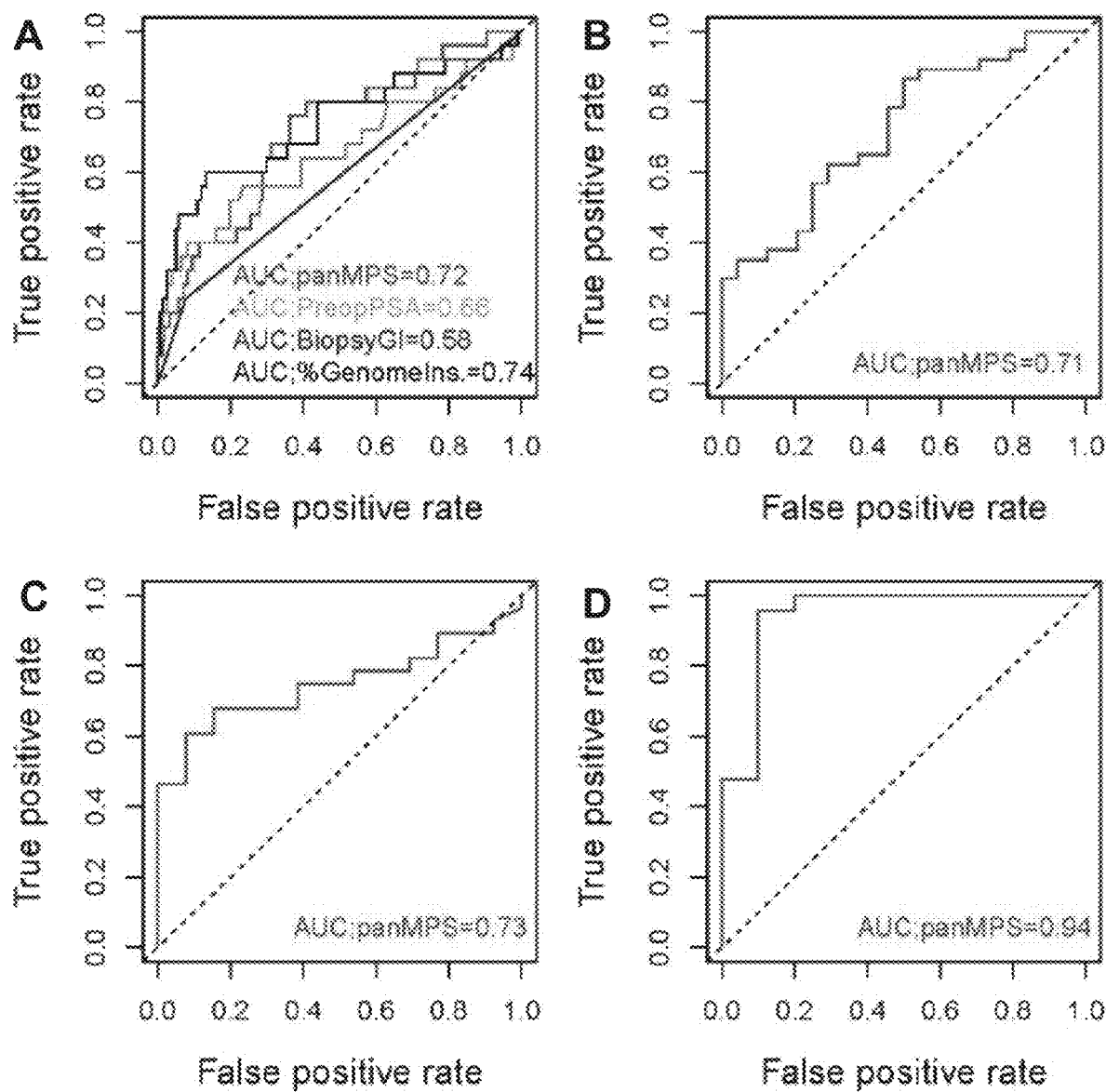
Figure 2A:
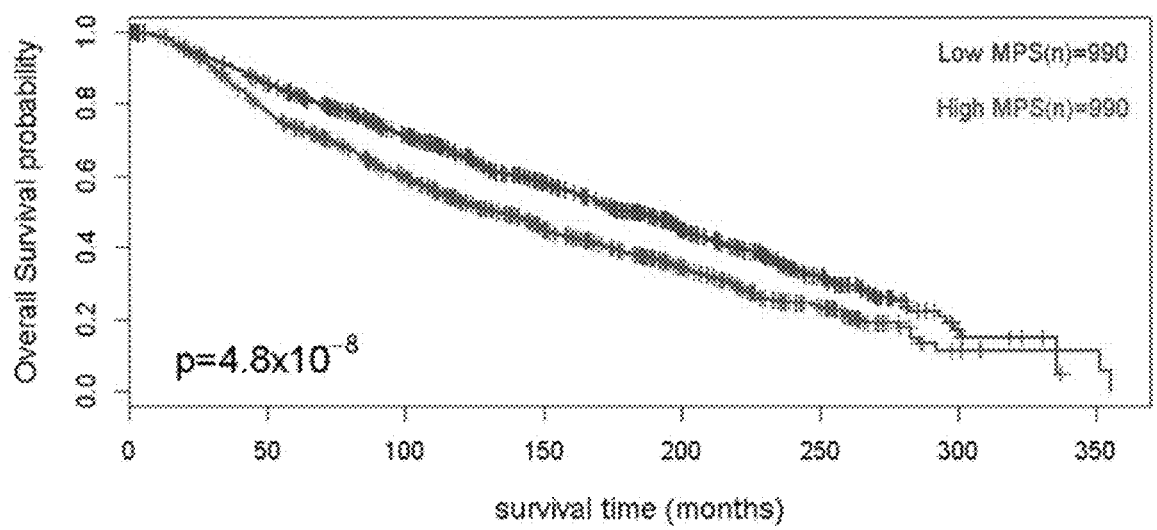
FIG. 2A-2D. Kaplan Meier analysis shows that MPS is associated with overall survival. A. Metabric breast cancer (N=1980); B. TCGA breast cancer (N=1054); C. TCGA prostate cancer (N=482); D. TCGA lung adenocarcinoma (N=483). Y-axis indicates overall survival probability and X axis indicates survival time. p-value calculated by log-rank test.
Figure 2B:
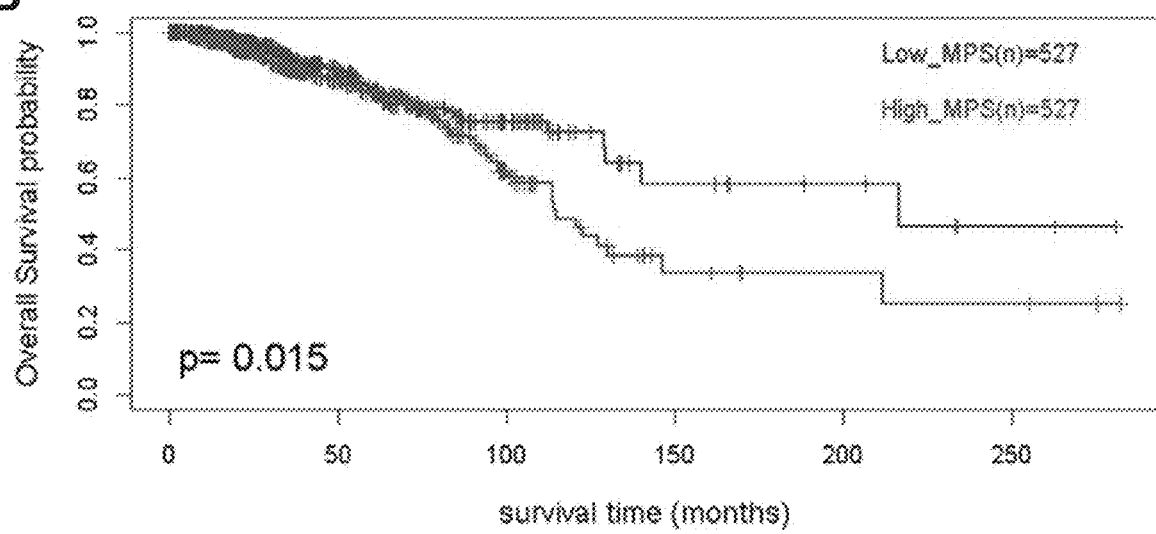
Figure 2C:
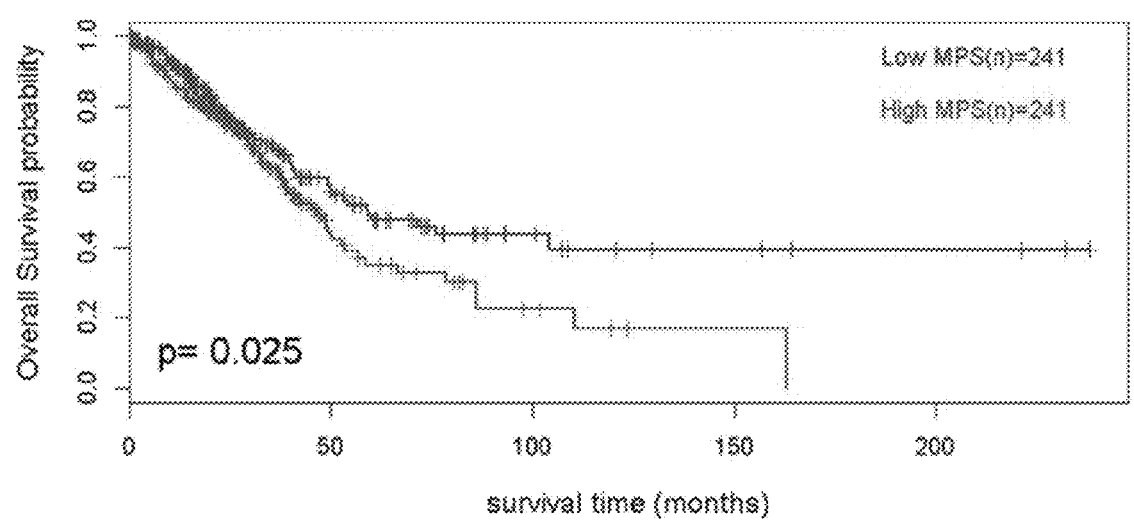
Figure 2D:
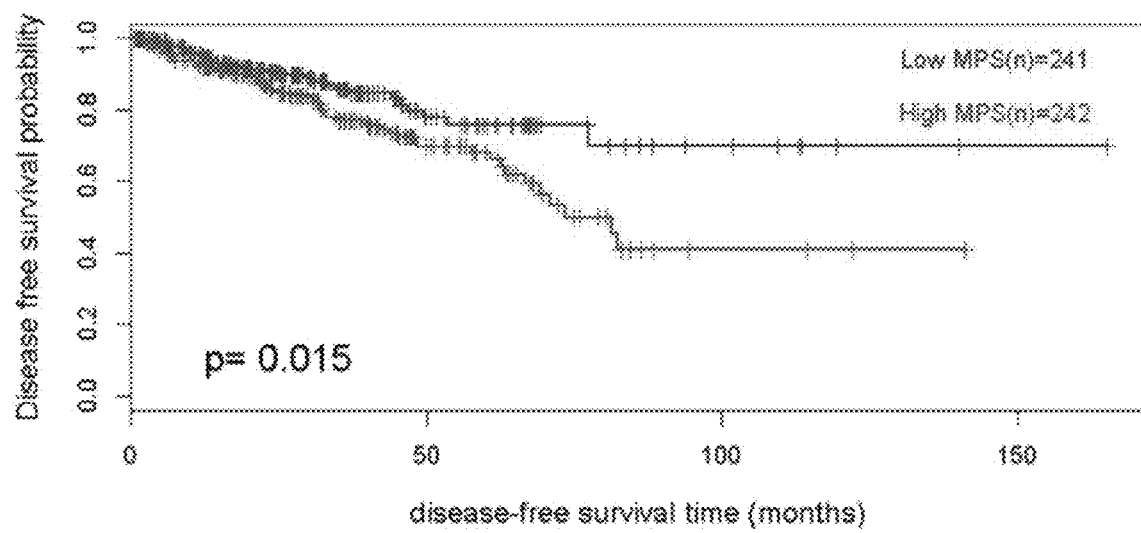

This disclosure provides a risk model that reliably predicts those tumors that are likely to metastasize, while minimizing the false positive rate and increasing the specificity of treatment decisions.

The risk model has been developed through the identification of copy number alterations (CNAs) around genes that were over-represented in metastases and primary tumors that later progressed to metastases. These CNAs are predictive of whether a primary tumor will metastasize. Cross-validation analysis has revealed a predictive accuracy of 80.5% and log rank analysis of the metastatic potential score has been shown to be significantly related to the endpoint of metastasis-free survival (p=0.014). In contrast to other reported risk models, the risk model disclosed herein based on the study of CNAs predicts distant metastasis progression as the clinical endpoint without the use of intermediate endpoints (such as biochemical markers of progression). The hierarchy of the genes and genomic regions that contribute to the prediction of metastatic potential has also been determined.

Accordingly, disclosed herein is a method for determining the risk of metastasis of breast or lung cancer in a human subject who has or had breast or lung cancer. This method is based on determining in a breast or lung sample from the subject, copy number alterations (CNAs) of genes and genomic regions of a metastatic gene signature set, and correlating the CNAs with a risk of breast or lung cancer metastasis.

The present method is useful for diagnosing breast and lung cancer in fluid aspirates or lavage or cell-free DNA in serum, monitoring therapeutic response in tissue, fluid or blood samples, and monitoring disease recurrence or progression in tissue, fluid or blood samples.

Metastatic Gene Signature

Metastatic gene signatures have been developed by the present inventors as described in detail in U.S. patent application Ser. No. 14/114,057 and hereinbelow. Accordingly, in one embodiment, this disclosure provides a metastatic gene signature set which includes the 366 genes identified herein, set forth in Table 13 (Table 13 has 368 genes, but the two pseudogenes C8orf16 and ERW are excluded from the gene signature set).

As displayed in Table 3, the 366 genes include a number of "clumps", each clump identified by a "Clump Index Number". A "clump", as used herein, refers to a group of genes that are adjacent to one another on the chromosome, and copy number alterations are detected for the genomic region which includes this group of genes in connection with prostate cancer metastasis. A multi-member clump may include both drivers (genes that cause or more directly associate with metastasis) and passengers (genes that indirectly associate with metastasis because of its close proximity of a metastasis driver gene).

The term "genomic region" is used herein interchangeably with the term "clump", and is typically used herein in conjunction with the name of a member gene within the genomic region or clump. For example, the PPP3CC gene listed in the first row of Table 14 belongs to Clump Index 26, which also includes the genes KIAA1967, BIN3, SORBS3, PDLIM2, RHOBTB2, SLC39A14, EGR3, and C8orf58. Therefore, Clump Index 26 is also referred to herein as "the PPP3CC genomic region".

While many of the 366 genes belong to clumps, some of the genes do not belong to any clump and copy number alterations have been identified specifically around each of these genes in connection with metastasis of prostate cancer. For example, as shown in Table 14 (with "NA" in the Clump Index column), CDH13, CDH8, CDH2 CTD8, COL19A1, YWHAG, and ENOX1, among many others, are genes which do not belong to any clump.

In other embodiments, this disclosure provides smaller metastatic gene signature sets which include at least 80, at least 40, at least 20, or at least 12, non-overlapping genes and/or genomic regions listed in Table 14.

By "non-overlapping" it is meant that the genes selected to constitute a smaller signature set do not belong to the same genomic region or clump.

Accordingly, in one embodiment, a metastatic gene signature set includes at least the top 80 genes and genomic regions shown in Table 14.

In another embodiment, a metastatic gene signature set includes at least the top 40 genes and genomic regions shown in Table 14.

In still another embodiment, a metastatic gene signature set includes at least the top 20 genes and genomic regions shown in Table 14.

In yet another embodiment, a metastatic gene signature set includes at least the top 12 genes and genomic regions shown in Table 14.

Determination of Copy Number Alterations (CNAs)

A copy number alteration is a variation in the number of copies of a gene or genomic region present in the genome of a cell. A normal diploid cell typically has two copies of each chromosome and the genes contained therein. Copy number alterations may increase the number of copies, or decrease the number of copies.

To determine whether there is any copy number alteration for a given gene or genomic region, a sample is obtained from a subject of interest, wherein the sample can be from lung or breast tissue. A breast sample refers to a cell or tissue sample taken from the breast of a subject of interest which sample contains genomic DNA to be analyzed for CNAs. A lung sample refers to a cell or tissue sample taken from the lung of a subject of interest which sample contains genomic DNA to be analyzed for CNAs. Methods of procuring cell and tissue samples are well known to those skilled in the art, including, for example, tissue sections, needle biopsy, surgical biopsy, and the like. For a cancer patient, cells and tissue can be obtained from a tumor. A cell or tissue sample can be processed to extract, purify or partially purify, or enrich or amplify the nucleic acids in the sample for further analysis.

Nucleic acid probes are designed based on the genes and genomic regions of a metastatic signature gene set which permit detection and quantification of CNAs in the genes and genomic regions.

In one embodiment, the probes are composed of a collection of nucleic acids that specifically hybridize to the full set of 366 genes of the metastatic signature gene set.

In another embodiment, the probes are composed of a collection of nucleic acids that specifically hybridize to the top 80 genes and genomic regions shown in Table 14.

In still another embodiment, the probes are composed of a collection of nucleic acids that specifically hybridize to the top 40 genes and genomic regions shown in Table 14.

In yet another embodiment, the probes are composed of a collection of nucleic acids that specifically hybridize to the top 20 genes and genomic regions shown in Table 14.

In a further embodiment, the probes are composed of a collection of nucleic acids that specifically hybridize to the top 12 genes and genomic regions shown in Table 14.

By "specifically hybridize" it is meant that a nucleic acid probe binds preferentially to a target gene or genomic region under stringent conditions, and to a lesser extent or not at all to other genes or genomic regions.

"Stringent conditions" in the context of nucleic acid hybridization are known in the art, e.g., as described in Sambrook, *Molecular Cloning: A Laboratory Manual* ($2^{nd}$ ed.) vol. 1-3, Cold Spring Harbor Laboratory, Cold Spring Harbor Press, New York (1989). Generally, highly stringent hybridization and wash conditions are selected to be about 5° C. lower than the thermal melting point for a specific sequence at a defined ionic strength and pH. An example of highly stringent hybridization conditions is 42° C. in standard hybridization solutions. An example of highly stringent wash conditions include 0.2×SSC at 65° C. for 15 minutes. An example of medium stringent wash conditions is 1×SSC at 45° C. for 15 minutes. An example of a low stringency wash is 4×-6×SSC at room temperature to 40° C. for 15 minutes.

Nucleic acid probes for purposes of this invention should be at least 15 nucleotides in length to permit specific hybridization to a target gene or genomic region, and can be 50, 100, 200, 400, 600, 800, 1000, or more nucleotides in length, or of a length ranging between any of the two above-listed values. A nucleic acid probe designed to specifically hybridize to a target gene can include the full length sequence or a fragment of the gene. A nucleic acid probe designed to specifically hybridize to a specific target genomic region can include at least a fragment of the genomic region, e.g., at least the full length sequence or a fragment of a gene (any gene) within the genomic region. Alternatively, a nucleic acid probe shares at least 80%, 85%, 90%, 95%, 98%, 99% or greater sequence identity with the target gene to permit specific hybridization.

The hybridized nucleic acids can be detected by detecting one or more labels attached to the sample or probe nucleic acids. The labels can be incorporated by a variety of methods known in the art, and include detectable labels such as magnetic beads, a fluorescent compound (e.g., Texas red, rhodamine, green fluorescent protein and the like), radio isotope, enzymes, colorimetric labels (e.g., colloidal gold particles). In other embodiments, the sample or probe nucleic acids can be conjugated with one member of a binding pair, and the other member of the binding pair is conjugated with a detectable label. Binding pairs suitable for use herein include biotin and avidin, and hapten and a hapten-specific antibody.

A number of techniques for analyzing chromosomal alterations are well known in the art. For example, fluorescence in-situ hybridization (FISH) can be used to study copy numbers of individual genetic loci or regions on a chromosome. See, e.g., Pinkel et al., Proc. Natl. Acad. Sci. USA 85: 9138-9142 (1988). Comparative genomic hybridization (CGH) can also be used to detect copy number alterations of chromosomal regions. See, e.g., U.S. Pat. No. 7,638,278.

In some embodiments, hybridization is performed on a solid support. For example, probes that specifically hybridize to signature genes and genomic regions can be spotted or immobilized on a surface, e.g., in an array format, and subsequently samples containing genomic DNA are added to the array to permit specific hybridization.

Immobilization of nucleic acid probes on various solid surfaces and at desired densities (e.g., high densities with each probe concentrated in a small area) can be achieved by using methods and techniques known in the art. See, e.g., U.S. Pat. No. 7,482,123 B2. Examples of solid surfaces include nitrocellulose, nylon, glass, quartz, silicones, polyformaldehyde, cellulose, cellulose acetate; and plastics such as polyethylene, polypropylene, polystyrene, and the like; gelatins, agarose and silicates, among others. High density immobilization of nucleic acid probes are used for high complexity comparative hybridizations which will reduce the total amount of sample nucleic acids required for binding to each immobilized probe.

In some embodiments, the arrays of nucleic acid probes can be hybridized with one population of samples, or can be used with two populations of samples (one test sample and one reference sample). For example, in a comparative genomic hybridization assay, a first collection of nucleic acids (e.g., sample from a possible tumor) is labeled with a first label, while a second collection of nucleic acids (e.g., control from a healthy cell or tissue) is labeled with a second label. The ratio of hybridization of the nucleic acids is determined by the ratio of the two labels binding to each member in the array. Where there are genomic deletions or amplifications, differences in the ratio of the signals from the two labels will be detected and provide a measure of the copy number.

The calculated metastatic potential score is compared to a reference distribution of samples (the metastatic potential score determined from a population of men with prostate cancer with metastasis-free survival clinical outcome information). Such reference distributions can be predetermined or calculated side-by-side in the same experiment as the sample being investigated. Therefore, an increase in the metastatic potential score as compared to the reference distributions is correlated with an increased risk of metastasis of prostate cancer. According to this disclosure, a one-point increase in the metastatic potential score corresponds to an odds ratio of 6.3 for progression to metastasis (p=0.01).

Determination of Risk

Once copy number alterations for each of a metastatic signature gene set have been determined, the risk for metastasis can be correlated with the copy number alterations detected. An increase in the copy number per cell of the sample for one or more of the genes or genomic regions of a metastatic signature gene set disclosed herein, whose amplifications have been associated with metastatic prostate cancer, will indicate a higher risk of metastasis as compared to a control (e.g., a sample obtained from a healthy individual) in which no increase in the copy number occurs. On the other hand, a decrease in the sample in the copy number for one or more of the genes or genomic regions of a metastatic signature gene set disclosed herein, whose deletions have been associated with metastatic prostate cancer, will indicate a higher risk of metastasis as compared to a control in which no decrease in the copy number is observed.

For example, for a metastatic signature gene set composed of the top 20 genes and genomic regions listed in Table 6, an increase in the copy number per cell of the sample for all of the SLCO5A1 genomic region, the KCNB2 genomic region, the KCNH4 genomic region, the JPH1 genomic region, the NCALD genomic region, and the YWHAG gene, and a decrease in the sample in the copy number per cell of the sample for all of the PPP3CC genomic region, the SLC7A5 genomic region, the SLC7A2 genomic region, the CRISPLD2 genomic region, the CDH13 gene, the CDH8 gene, the CDH2 gene, the ASAH1 genomic region, the CTD8 gene, the MEST genomic region, the COL19A1 gene, the MAP3K7 genomic region, the NOL4 genomic region, and the ENOX1 gene, correlate with an increased risk of breast cancer or lung cancer metastasis. However, it is not necessary for all the genes and genomic regions within a signature set to change in the same direction as set forth in Table 6 in order to have a reasonably reliable prediction of the risk. That is, an increased risk can be predicted based on an increase in the copy number per cell of the sample for one or more, preferably a plurality of, the SLCO5A1 genomic region, the KCNB2 genomic region, the KCNH4 genomic region, the JPH1 genomic region, the NCALD genomic region, and the YWHAG gene, and/or a decrease in the sample in the copy number per cell of the sample for one or more, preferably a plurality of, the PPP3CC genomic region, the SLC7A5 genomic region, the SLC7A2 genomic region, the CRISPLD2 genomic region, the CDH13 gene, the CDH8 gene, the CDH2 gene, the ASAH1 genomic region, the CTD8 gene, the MEST genomic region, the COL19A1 gene, the MAP3K7 genomic region, the NOL4 genomic region, or the ENOX1 gene. By "plurality" it is meant at least 10, 11, 12, 13, 14, 15, 16, 17, 18, 19 or 20 of the top 20 genes and gene regions listed in Table 14.

This disclosure also provides a quantitative measure of the risk based on the copy number alterations of a signature gene set disclosed herein. More specifically, the risk of metastasis has been found to correlate with a metastatic potential score calculated based on the formula:

$$M(SM) = \sum_{i}^{n} Zadjust_i * Dir_{sig}(i) * Dir_{samp}(i)$$

That is, for a particular gene or genomic region, if the CNA of the signature and the sample are in the same direction (amplified or deleted), the coefficient (coefficient is shown as Dir, wherein Dir $(i)=Dir_{sig}(i)*Dir_{samp}(i)$ in the formula above) will be 1, the logistic adjusted Z-score (Zadjust) for this gene or genomic region will be added; if in opposing directions, the coefficient will be −1, the logistic adjusted Z-score (Zadjust) for the gene or genomic region will be substracted; and if $Dir_{samp}(i)=0$, then the entire term will not count towards the score. Thus, essentially, the logistic adjusted Z-scores from genes (i . . . n) that match the metastasis signature are added, whereas from genes that mismatch the signature are subtracted. The logistic adjusted Z-scores (Zadjust) for each of the 366 genes of the full metastatic signature set are found in Table 14.

The calculated metastatic potential score is compared to a reference distribution of samples (the metastatic potential score determined from a population of patients with breast or lung cancer with metastasis-free survival clinical outcome information, also called herein "the reference metastatic potential score"). Such reference distributions can be predetermined or calculated side-by-side in the same experiment as the sample being investigated. In many of the embodiments, the reference metastatic potential score equals to or is approximately 1.0. Therefore, an increase in the metastatic potential score of a test subject as compared to the control score from the reference distributions is correlated with an increased risk of metastasis of breast or lung cancer. According to this disclosure, a one-point increase in the metastatic potential score corresponds to an odds ratio of 6.3 for progression to metastasis (p=0.01). In some embodiments, an increase in the metastatic potential score as compared to a reference score by at least about 0.5, 0.53, 0.56, 0.58, 0.6, 0.65, 0.7 or greater, is considered to represent a significantly high risk of metastasis.

The disclosed method for predicting the likelihood of distant metastases represents a significant advancement in the diagnosis and treatment of breast and lung cancer. This predictor may be important for correctly categorizing patients at the time of diagnosis and can lead to a choice of therapy that would maximize their chances of survival and minimize adverse side effects if aggressive treatment can be avoided. Thus, both treatment outcomes and quality of life could be improved. In addition, because the proposed tool, tumor genomic analysis, is comprehensive for identifying the genetic changes that are associated with pathogenesis and metastases, there is a greater likelihood of selecting a sufficient number of markers that are both sensitive and specific predictors. Furthermore, because these genomic alterations are themselves susceptible to manipulation with drugs, radiation or other therapies, they could provide a basis for assessing intermediate endpoints, such as androgen sensitivity and response to radiation. Ultimately, copy number alterations could guide the development of individually tailored therapies, including for cancers other than prostate, breast or lung.

Methods for Detecting Copy Number Alterations (CNAs)

The following methods can be utilized in detection of copy number alterations.

Multiplex Ligation-dependent Probe Amplification (MLPA)

Multiplex Ligation-dependent Probe Amplification (MLPA®) is a high-throughput method developed to determine the copy number of up to 50 genomic DNA sequences in a single multiplex PCR-based reaction. MLPA is easy to perform, requires only 20 ng of sample DNA and can distinguish sequences differing in only a single nucleotide. The MLPA reaction results in a mixture of amplification fragments ranging between 100 and 500 nt in length which can be separated and quantified by capillary electrophoresis. The equipment necessary for MLPA is identical to that for performing standard sequencing reactions: a thermocycler and a fluorescent capillary electrophoresis system. Comparison of the peak pattern obtained on a DNA sample to that of a reference sample indicates which sequences show aberrant copy numbers.

Fundamental for the MLPA technique is that it is not the sample DNA that is amplified during the PCR reaction, but MLPA probes that hybridise to the sample DNA. Each MLPA probe consists of two probe oligonucleotides, which should hybridise adjacent to the target DNA for a successful ligation. Only ligated probes can be exponentially amplified by PCR. In contrast to standard multiplex PCR, only one pair of PCR primers is used for the MLPA PCR reaction, resulting in a more robust system. This way, the relative number of fragments present after the PCR reaction depends on the relative amount of the target sequence present in a DNA sample. MLPA protocol is described in detail in Eijk-Van Os PG. et al. (*Methods Mol Biol.* 2011; 688:97-126).

Quantitative Polymerase Chain Reaction (qPCR)

Quantitative real-time PCR (qPCR) is PCR visualized in real time by the use of fluorescent or intercalating dyes used to measure gene expression or gene quantification including including contiguous gene deletions or duplications. A simple method is described to quantify DNA copy number from human samples in Lijiang et al. (*Curr Protoc Hum Genet.* 2014 Jan. 21; 80:7.21.1-7.21.8).

PCR-Based Detection of DNA Copy Number Variation (dPCR)

A method for PCR-based detection of copy number of target genes in human genome using TaqMan copy number assay is described in MehrotraM. (Methods Mol Biol. 2016; 1392:27-32. doi: 10.1007/978-1-4939-3360-0_3).

Genomic Sequencing

Whole genome copy number alteration analyses and the computational approaches that can be utilized are discussed in Pirooznia et al. (*Front Genet.*, 2015; 6:138). In some embodiments, the whole genome analysis is a Next Generation (NextGen) sequencing based assay. Next-generation sequencing refers to non-Sanger-based high-throughput DNA sequencing technologies. Millions or billions of DNA strands can be sequenced in parallel, yielding substantially more throughput and minimizing the need for the fragment-cloning methods that are often used in Sanger sequencing of genomes. Next Generation Sequencing is described in Behjati et al. (*Arch Dis Child Educ Pract Ed.* 2013 December; 98 (6): 236-238).

The present description is further illustrated by the following examples, which should not be construed as limiting in any way. The contents of all cited references (including literature references, issued patents, and published patent applications as cited throughout this application) are hereby expressly incorporated by reference.

EXAMPLES

Example 1: Materials and Methods

Predictive CNAs, MPS and panMPS.

This disclosure provides an in-depth comparison of a set of 366 genes whose CNAs are predictive of breast or lung cancer metastasis. The contributions of these genes to MPS as $Z_{genes}$ scores were reported previously (Pearlman, A. et al., *J Probab Stat,* 2012, 873570 (2012) and US Patent Publication No. 2014/0221229). These are calculated by assigning each probe on the array to a gene, provided it falls within 10,000 bp upstream or downstream of the transcription start or stop site. $z=(X-\mu)/\sigma$ as described previously (4). The score for a gene, X, is subtracted by the mean, $\mu$, of the background distribution of selection model scores and divided by the standard deviation, $\sigma$, of the background distribution of selection model scores. A conservative background distribution of selection model scores was calculated by sampling the top 5th percentile of amplified or deleted probes from all genes on the array with the same number of probes as the gene in question. The result is a $Z_{genes}$ score for each gene in the genome that is represented on the array. Alternatively, the complete set of genomic CNAs was used to calculate percent genomic instability. The CNA methodology is assay platform-independent, but requires that genomic DNA signal intensities are measured within the regions of the metastasis signature. In this study, the analysis was conducted on primary data sets reported here utilizing the Affymetrix Oncoscan FFPE V3 array (Foster, J. M. et al., *BMC Med Genomics* 8, 5 406 (2015)), and on previously generated data sets assayed on Agilent 240K and other arrays (Hieronymus, H. et al., *Proc Natl Acad Sci USA* 111, 11139-44 (2014)). For comparison of cohorts from different platforms, the corresponding numbers of the MPS genes were reduced to include only those that overlapped (366 to 295 genes), representing the panMPS.

Cohorts, Tissue and Sample Processing

A prostate cancer radical prostatectomy cohort of 37 men that progressed to metastasis (mPTs) and 24 men that were free from biochemical recurrence and metastases (iPTs) after at least five years of follow up was collected at Duke University (Duke cohort-Table 10A). The Duke cohort had a case-control design that matched mPTs and iPTs for age, race, pathological stage, margin status, Gleason score, and surgery year. Tumor regions were microdissected, extracted for DNA, and assayed on the Oncoscan FFPE V3 array (Affymetrix Oncoscan Service, Santa Clara, California).

A second prostate cancer cohort, comprised of 25 mPTs along with 157 iPTs was collected at Memorial Sloan-Kettering Cancer Center (MSK cohort—Table 10A). The collection, extraction and data generation for the second cohort has been described previously (Hieronymus, H. et al., *Proc Natl Acad Sci USA* 111, 11139-44 (2014)). The MSK cohort represented a consecutive case-cohort design with non-recurrent, non-metastatic outcome samples making up a disproportionate number. Unlike the Duke samples, these samples were not matched on any criteria. The MSK cohort was comprised of fresh frozen radical prostatectomies. The Duke and MSK cohorts differed in their length of follow-up, clinical and pathologic attributes and biochemical recurrence and metastasis outcomes (Table 10A). The Duke cohort was collected for individuals with greater than five years follow-up since the majority of prostate cancers recur or metastasize within this timeframe. To achieve parity for prediction modeling and maximizing the metastasis informativeness of each patient, the MSK cohort was filtered for subjects that had at least five years of follow-up. Also, for both cohorts, metastasis negative subjects treated with radical prostatectomy and adjuvant radiation and/or hormonal therapy were excluded from analysis to provide a more homogeneous iPT group.

A triple negative breast cancer radical surgical cohort of 28 women that progressed to metastasis (mBCs) and 13 women that were free from local recurrence and metastasis (iBCs) after at least five years of follow up was collected at Montefiore Medical Center (Montefiore cohort—Table 10B). The Montefiore cohort had a case-control design that matched mBCs and iBCs for age, race, pathological stage, margin status, and surgery year. The breast cancer tumor blocks from each patient were handled in a fashion similar to the prostate cancer tumor blocks and reviewed by a single pathologist and shown to be negative for expression of the estrogen receptor, progresterone receptor and HER2/NEU protein, as judged by immunohistochemistry. Tumor regions were microdissected, extracted for DNA, and assayed on the Oncoscan FFPE V2 array (Affymetrix Oncoscan Service, Santa Clara, California).

Tumor tissue from 199 primary lung adenocarcinomas was collected at the time of resection between 1996 and 2006 at MSKCC and analyzed for CNAs on Agilent 44K CGH arrays, as described previously (Chitale, D. et al., Oncogene 28, 2773-83 (2009)). From this cohort, all available early stage (1A, B and 2A,B) samples that progressed to mortality (mLA, n=23) and late stage (3B and 4) samples that remained alive for greater than one year of follow up (iLA, n=10) (Table 10C) were selected.

This study was reviewed and approved by the Institutional Review Boards at Albert Einstein College of Medicine, New York University School of Medicine, and Duke University.

The copy number alterations (CNAs) level 3 data from cBioPortal for cancer genomics for 3998 patients with three tumor types (Gao J. et al., Sci Signal 6: pl1, 2013, Cerami E. et al., Cancer Discov, 2:401-4, 2012) were downloaded. Metabric and TCGA provisional study were selected for breast invasive carcinoma, TCGA provisional study was selected for Lung adenocarcinoma and TCGA provisional study was selected for prostate adenocarcinoma (Milioli H H. Et al., PLOS One, 10: e0129711, 2015, Pereira B. et al., Nat Commun, 7:11479, 2016). panMPS score was calculated based on CNAs for these studies. Univariate Cox proportional hazards model was used to examine the association between MPS and survival. Overall survival was used as the endpoint.

Cell Lines.

CNA data from 183 human cell lines of metastatic origin were available from the Cancer Cell Line Encyclopedia (CCLE). These cell lines included breast, lung adeno, pancreas, large intestine, lymphoid, melanoma, lung small cell and stomach cancers. The data were generated using the Affymetrix SNP 6.0 arrays, as described previously (Beroukhim R. et al., Nature, 463:899-905, 2010).

MPS and panMPS

MPS was calculated based on genomic CNAs overlapping 366 genes with a higher score indicating a greater likelihood of metastasis, as described previously (Pearlman, A. et al., J Probab Stat, 2012, 873570 (2012)). The pan cancer MPS or panMPS was derived from the MPS by using a subset of 295 genes from the MPS. Univariate and multivariate logistic regression and Cox proportional hazards survival models for prostate cancer were evaluated for panMPS, pre-surgery predictors (PSA, clinical stage, biopsy Gleason), demographic variables (age at diagnosis and race), and percent genomic instability, as described previously (Hieronymus, H. et al., Proc Natl Acad Sci USA 111, 11139-44 (2014)). The logistic regression and Cox models were also tested for triple negative breast cancer and lung adenocarcinoma. AUC and concordance index were calculated for the logistic and Cox models, respectively.

Functions of MPS Genes in Driving Metastases

To gauge whether the MPS genes played a role in metastasis, we performed in-silico analysis by running three comprehensive queries with the RISmed package from R. First we performed a general Pubmed citation query by searching for the 366 gene IDs and the terms "metastasis", "metastases" or "metastatic" in the title or abstract of the publication ("metastasis IDs"). Next, we appended this query to capture metastasis functions by adding search terms, "apoptosis assay", "TUNEL", "Matrigel", "invasion assay", "wound healing assay", "migration assay", "MTT", "BrDU", "proliferation assay", "SiRNA" and "xenograft" ("metastasis functions"). Then, the title query was appended to capture predictive biomarkers of metastasis by adding search terms, "Cox", "Kaplan-Meier" and "hazard ratio" ("metastasis biomarkers"). The MPS gene queries were manually curated and confirmed for accuracy by two reviewers. The annotation frequency was computed for each query type. To assess the significance of these annotations for the MPS genes compared to the remaining, non-overlapping 18,638 protein coding genes an enrichment analysis based on the hypergeometric distribution was performed for the MPS genes versus all 19,004 protein coding genes annotated using the same query search terms to create expanded gene sets for metastasis ID, metastasis functions, metastasis biomarkers and chemokine ID.

Reduction of Complexity

To determine whether the genes with the highest $Z_{genes}$ score among the clumps could predict outcomes as well as the full set of panMPS genes, we calculated AUC and $r^2$ for simplified MPS versions by using genes with $Z_{genes}$ score≥3, $Z_{genes}$ score≥4, or highest $Z_{genes}$ score within a clump.

Example 2. panMPS Predicts Risk of Metastasis Outcome for Prostate and Triple Negative Breast Cancers and Lung Adenocarcinomas.

The clinical validity of panMPS as a predictor of metastasis outcome was tested in studies of prostate and triple negative breast cancers and lung adenocarcinomas. For the outcome of prostate cancer metastasis, univariate logistic regression of panMPS resulted in significant odds ratios and areas under receiver-operator curves (AUCs) for the MSK (OR 6.01, AUC 0.71, p=0.001) and the Duke cohorts (OR 11.39, AUC 0.72, p=0.004) (Table 1A and FIG. 1). Preoperative PSA and pathology stage improved the AUC in logistic regression analysis of the MSK cohort, but, because of matching between mPTs and iPTs, did not lead to improvement in the Duke cohort (Table 5). In univariate logistic regression analysis of the MSK cohort, percent genomic instability as a predictor had an OR 1.17, AUC=0.74, p=1.4×10$^{-5}$; however, this predictor did not reach statistical significance in the Duke cohort (OR 1.04, AUC=0.80, p=0.12) (Table 5). This indicates that percent genomic instability, while useful in the MSK cohort, was not an independent and robust predictor of metastasis. Thus, the subset of genes comprised by panMPS contributes to prostate cancer metastasis formation when copy numbers are altered.

For the outcome of triple negative breast cancer metastasis, univariate logistic regression of panMPS resulted in a significant odds ratio and AUC for the Montefiore cohort (OR 44.74, AUC 0.75, p=0.02) (Table 1B and FIG. 1). Percent genomic instability was not an independent predictor of metastasis. Because matching had been performed for the triple negative breast cancers, stage was also not a predictor of outcome.

For the outcome of lung adenocarcinoma metastasis, univariate logistic regression of panMPS resulted in a significant AUC for the MSKCC cohort (OR $3.45 \times 10^3$, AUC 0.94, p=0.006) (Table 1C and FIG. 1). Because cases with advanced stage were selected for favorable outcome and cases with early stage were selected for unfavorable outcome, stage is thus not a valid predictor of metastasis.

Example 3. panMPS Predicts Metastasis-Free Survival for Prostate Cancer, Triple Negative Breast Cancer and Lung Adenocarcinomas As a continuous univariate predictor through a Cox model, panMPS was associated with prostate cancer metastasis-free survival in both the MSK (HR=5.4, p=0.0003, concordance index 0.74) and Duke (HR=3.4, p=0.03, concordance index 0.62) cohorts (Table 2A). In univariate Cox analysis of the MSK cohort, percent genomic instability was associated with metastasis-free survival (HR=1.11, p=$3.3 \times 10^{-2}$, concordance index=0.67), as previously reported for this cohort (Hieronymus, H. et al., *Proc Natl Acad Sci USA* 111, 11139-44 (2014)); however, this variable did not reach statistical significance in the Duke cohort. Biopsy and pathological Gleason scores, preoperative PSA and pathological stage and combinations of these with panMPS were predictors of metastasis-free survival in Cox analysis of the MSK cohort only (Table 6).

As a continuous univariate predictor in a Cox model, panMPS was associated with triple negative breast cancer metastasis-free survival in the Montefiore cohort (HR=4.1, p=0.05, concordance index 0.60) (Table 2B). Stage was also an independent predictor (HR=3.2, p=0.03), whereas percent genomic instability was not.

As a continuous Cox model univariate predictor, panMPS was associated with lung adenocarcinoma metastasis-free survival in the MSKCC cohort (HR=6.6, p=0.02, concordance index 0.67) (Table 2C). Stage cannot be used as a predictor as explained above.

Example 4. panMPS is Associated with Overall Survival in Breast Cancer, Prostate Cancer and Lung Adenocarcinoma.

Data about CNAs in primary cancers and their survival outcomes are available for a variety of cancer types from publically available datasets, including The Cancer Genome Atlas (TCGA) (Gao J. et al., *Sci Signal* 6: pl1, 2013, Cerami E. et al., *Cancer Discov*, 2:401-4, 2012) and Metabric (Milioli H H. Et al., *PLOS One*, 10: e0129711, 2015). To examine general utility as a predictor of survival outcome, Kaplan Meier analysis of panMPS was applied to the TGCA prostate cancer, breast cancer, and lung adenocarcinoma cohorts and the Metabric breast cancer cohort. panMPS (median cut point) was observed to be significantly associated with overall survival in the Metabric breast cancer cohort (n=1,980, p=$4.8 \times 10^{-08}$) and in three TCGA cohorts (breast: n=1054, p=0.015, prostate: n=483, p=0.015, and lung adenocarcinoma: n=482, p=0.025; FIG. 2), providing evidence that panMPS is a predictor not only of metastasis, but also survival. Metastasis-free survival data were not available for these cohorts.

Example 5. panMPS is Elevated in Many Metastatic Cancer Cell Lines of Epithelial Origin.

To test applicability in other cancer types, genomic instability and panMPS were evaluated in a set of 133 cell lines of different tissue origins from the Cancer Cell Line Encyclopedia (CCLE). All cell lines were reported to be from metastatic tumors. The median number of protein coding genes demonstrating CNAs ranged from 2091 for lymphoma to 6805 for pancreatic carcinoma and 6916 for stomach carcinoma, thereby confirming the high frequency of CNAs in metastases. By way of reference, the median number of genes demonstrating CNAs in a sample of clinical prostate cancer metastases was 3731. For metastatic cancer cell lines of epithelial origin, including breast, lung adenocarcinoma, pancreas and stomach, the frequency of CNAs was higher than those observed in prostate cancer metastases (p=0.04, 0.002, $3 \times 10^{-4}$, 0.005, respectively), whereas for metastatic cell lines of non-epithelial origin, including lymphoid tissue, melanoma, and lung small cell, the frequency of unstable genes was similar to that observed for prostate cancer metastases. Despite the higher frequencies of CNAs among metastatic cells lines of epithelial origin, the MPS of these cell lines, including breast, lung adenocarcinoma, pancreas, large intestine and stomach, was similar to that observed in prostate cancer metastasis. Cell lines of non-epithelial origin had either comparable (melanoma) or lower MPS (lymphoid—p=$8 \times 10^{-4}$, lung small cell—p=0.01) to those observed in clinical prostate cancer metastases. These findings extend the previous observation that the CNAs of cancer cell lines of a variety of origins display a specific CNA pattern (Pearlman A. et al., *J Probab Stat*, 2012: 873570, 2012), suggesting that panMPS might serve as a predictor of metastatic outcome across multiple cancer types.

Example 6. MPS Genes are More Likely to have Known Roles in Promoting Metastasis or Predicting Metastatic Outcomes than Randomly Selected Genes.

One way of gauging whether the MPS genes played a role in cancer metastasis beyond prostate and triple-negative breast cancers and lung adenocarcinomas was to identify Pubmed citations for these genes (Table 7). Further refinement of this search included metastatic functions such as cell viability, proliferation, invasion, and escape from apoptosis and for biomarker genes predictive of metastasis outcome when their copy number or expression is altered. Following guidelines for the functional interpretation of genes and their variants provided by the American College of Medical Genetics and Genomics (Richards S. et al., *Genet Med*, 17:405-24, 2015), the Association for Molecular Pathology (Rehm H L. Et al., *N Engl J Med*, 372:2235-42, 2015), and codified by the NIH-supported, Clinical Genome Resource (Strande N T., *Am J Hum Genet*, 100:895-906, 2017), each of the 366 MPS genes were annotated for literature reports. Statistical tests were then performed, first to compare MPS genes to random gene sets for metastatic functions and the second of protein coding gene sets that have known associations with metastasis functions, such as invasion, motility and escape from apoptosis when detached from matrix of origin, and chemokine activity, and for biomarker genes predictive of metastasis outcome when their copy number or expression is altered. The frequency of these citations was compared to the frequencies with which citations were observed for 100 random sets of 366 genes from the 18,638 protein coding genes that excluded overlapping MPS genes. Among the 366 MPS genes, 60 were found to have Pubmed citations for the search terms related to metastasis functions and metastasis biomarkers, whereas the range for the random sets was 26 to 69 (FIG. 2). In fact, only one random set had a larger number of genes cited (N=69) than the observed 60, indicating that both represented outliers of non-random gene sets based on current knowledge of annotated metastasis genes. In an alternative approach the 19,004 protein coding genes were annotated for whether they had known metastasis associations ("Metastasis ID," Table 3, Table 8A), metastasis functions ("Metastasis functions," Table 3, Table 8B) or whether they have been identified as biomarkers that were predictive of metastasis ("Metastasis biomarkers," Table 3, Table 8C). Of 2463 metastasis ID genes, 112 overlapped with MPS genes ($p=2.42 \times 10^{-20}$). Of 929 metastasis function genes, 40 overlapped with MPS genes ($p=1.18 \times 10^{-6}$). Of the 687 metastasis biomarker genes, 28 overlapped with MPS genes ($p=0.0001$). Thus, the MPS genes were enriched among gene sets with terms for metastasis function or metastasis biomarkers in the article.

Example 7. Elevated $Z_{genes}$ Scores Provide Evidence for Potential Metastasis-Driver Genes.

Figure 3:
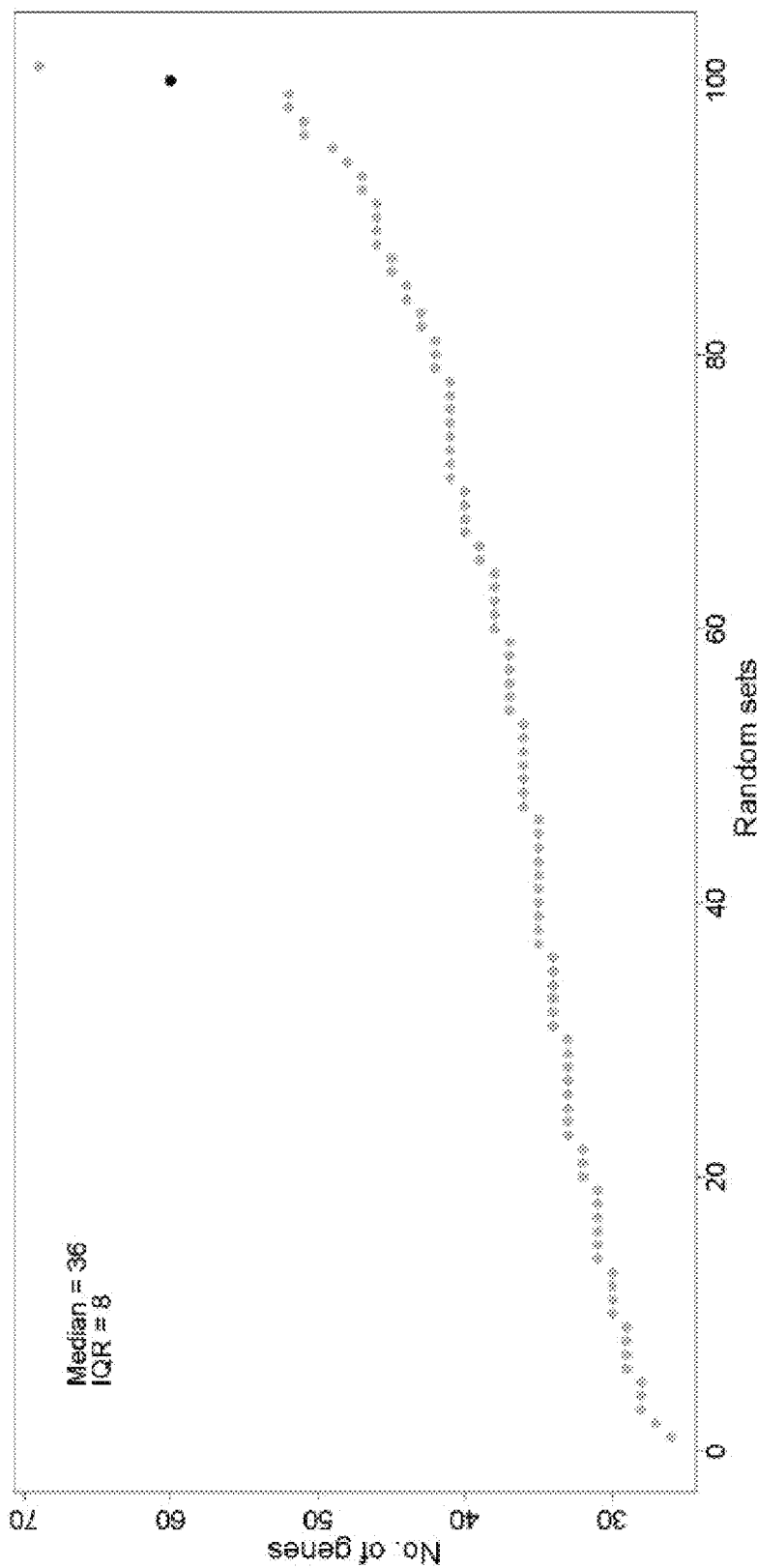
FIG. 3. MPS genes show higher functional and biomarker annotations than 100 random sets of 366 genes. Number of genes found to have Pubmed citations for metastasis functions for random sets of genes (grey) and MPS genes (black). There were 2 outliers the exceeded the upper fence, the MPS genes (N=60) and one random set (N=69).
Figures 4A, 4B, 4C:
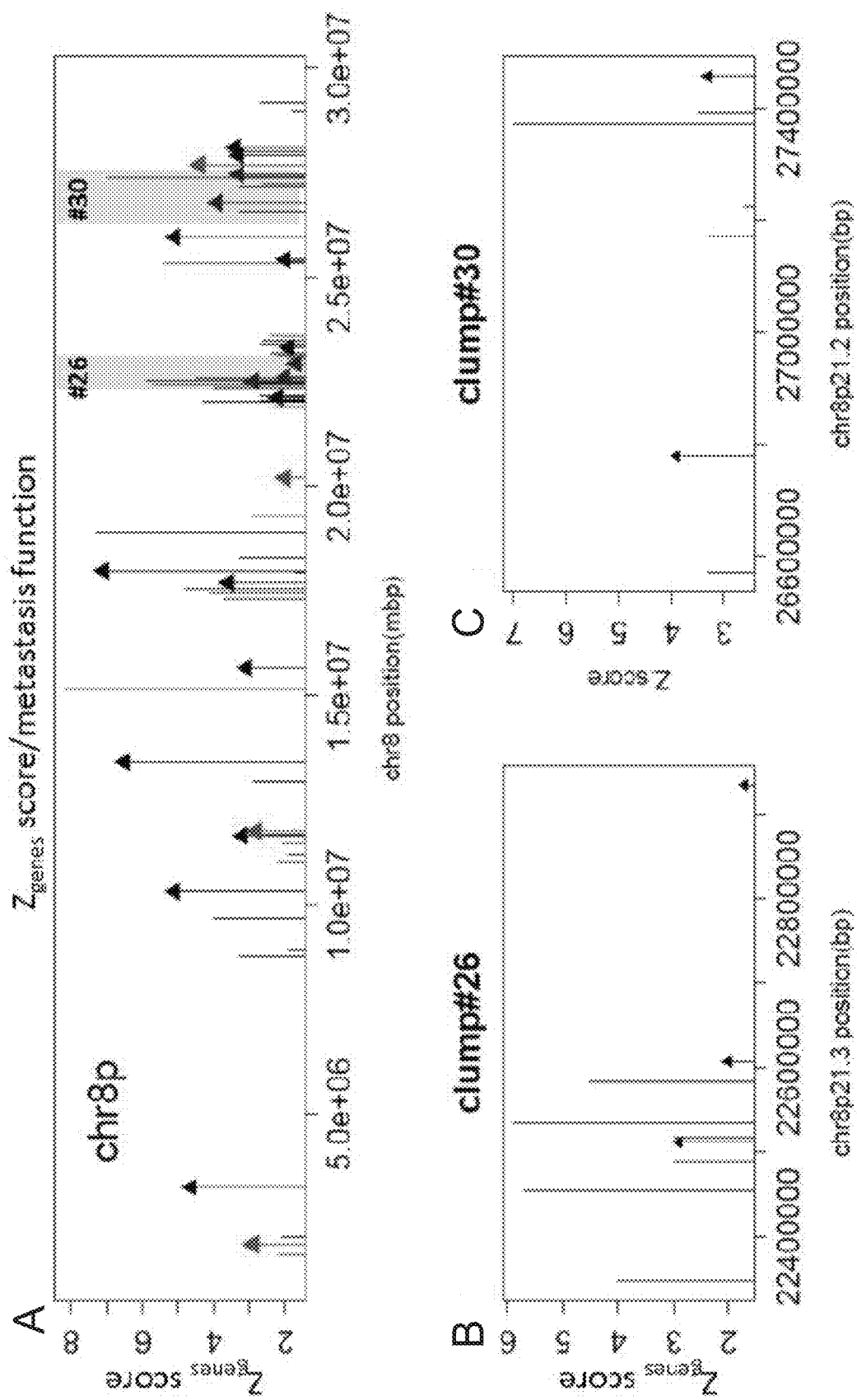
FIG. 4A-4C. Chromosome 8p exhibiting 70 genes predictive of metastatic potential, including genes that occur in clumps (A). Each bar represents a gene as it is located on the chromosome (X-axis) whereas the height of the bar denotes a Zgenes score (Y-axis) that measures the gene CNA profile's ability to predict the metastatic potential of a primary prostate cancer. Arrows on top of some of the bars indicate that the gene has been validated in prior metastasis studies as a biomarker or to have metastatic function. Clump region #26 (nine gene segment) and clump region #30 (seven gene segment) are highlighted in the top panel and zoomed in (B) (Clump region #26) and (C) (Clump region #30).
Figure 5A:
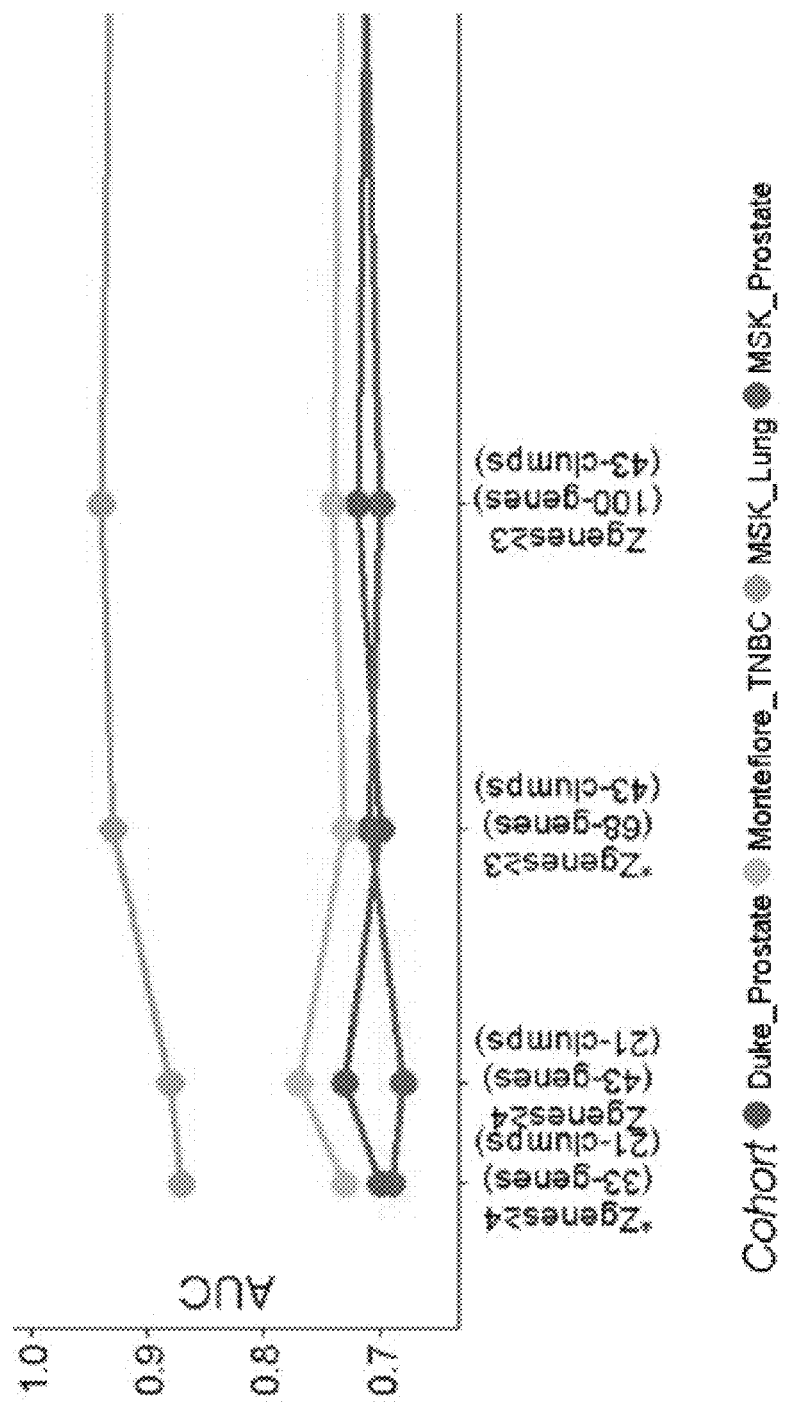
FIG. 5A-5B. Small sets of high Zgenes score genes predict metastatic outcome and panMPS almost as well as all MPS genes for all four cohorts. ROC-AUCs estimating metastatic outcome and linear regression ($r^2$) estimating panMPS for all four cohorts demonstrate reduction of complexity for high $Z_{genes}$ score genes. AUC (A) and $r^2$ (B) estimating metastatic outcome and panMPS, respectively, for simplified versions of MPS, including those with high $Z_{genes}$ scores. Numbers of genes and clumps are indicated for different $Z_{genes}$ scores. * one gene per clump.
Figure 5A:
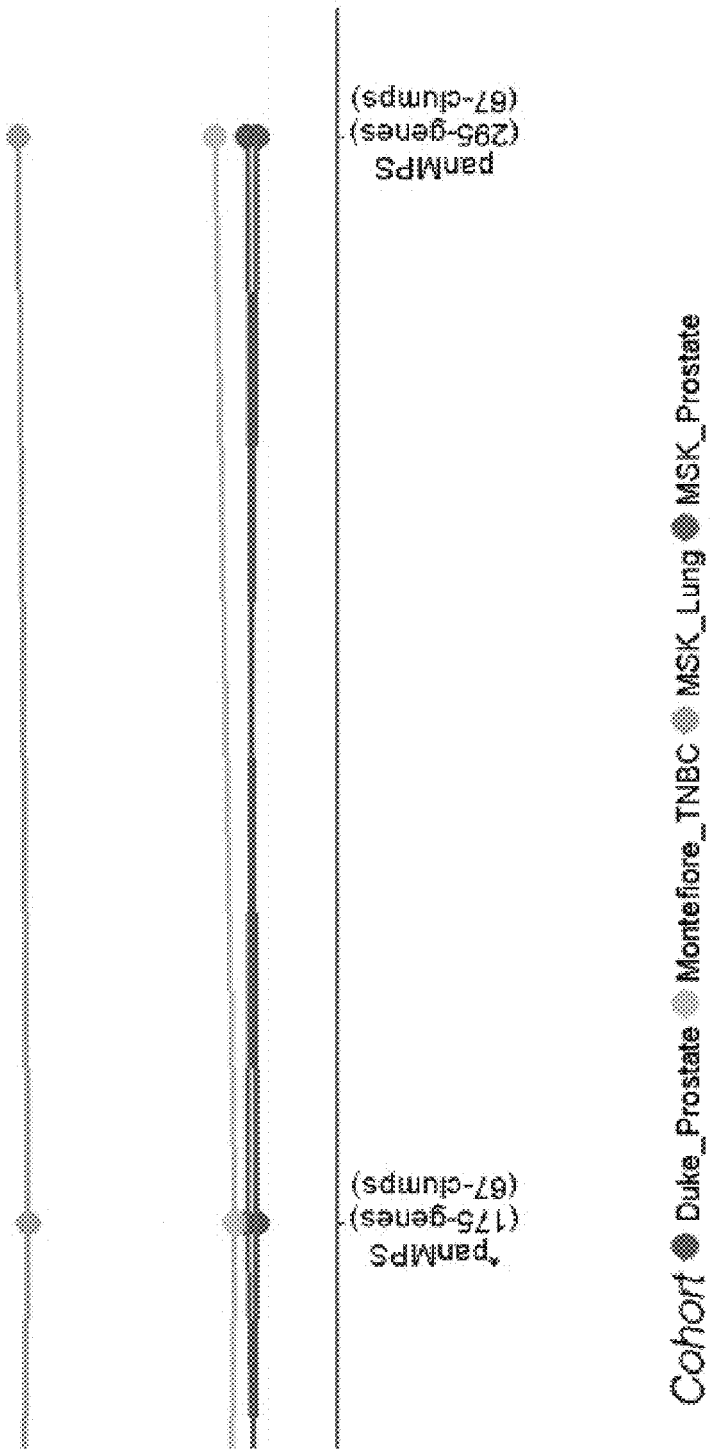
Figure 5B:
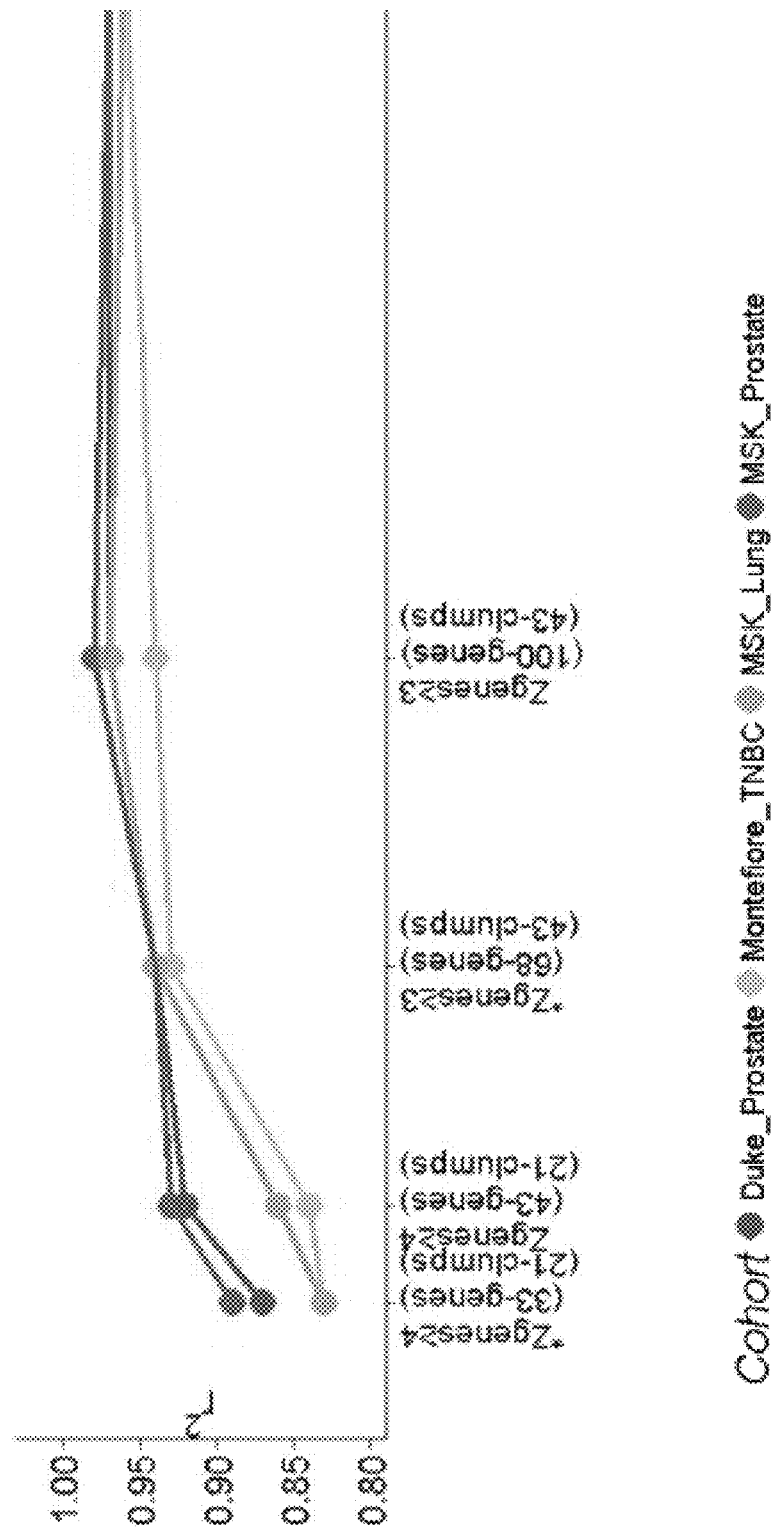
Figure 5B:
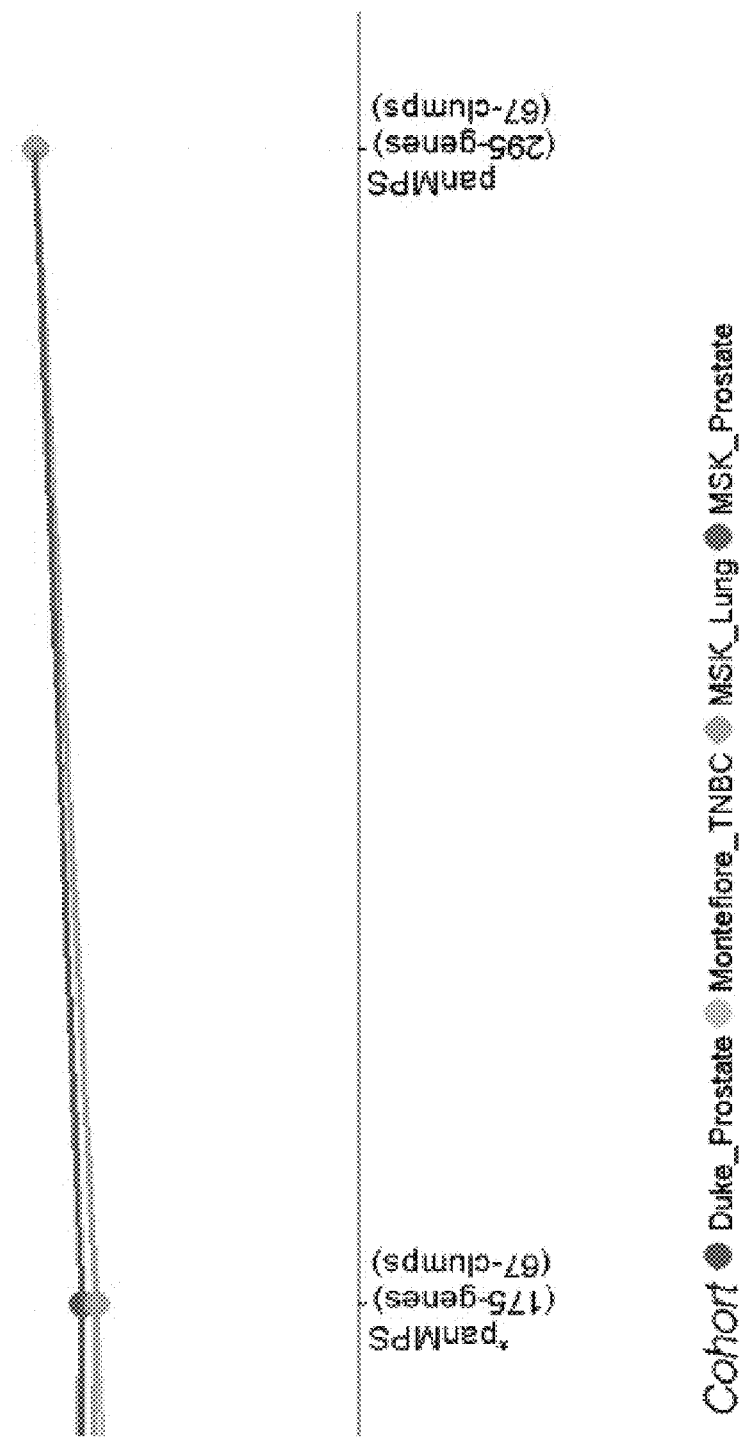
Figures 6A, 6B, 6C:
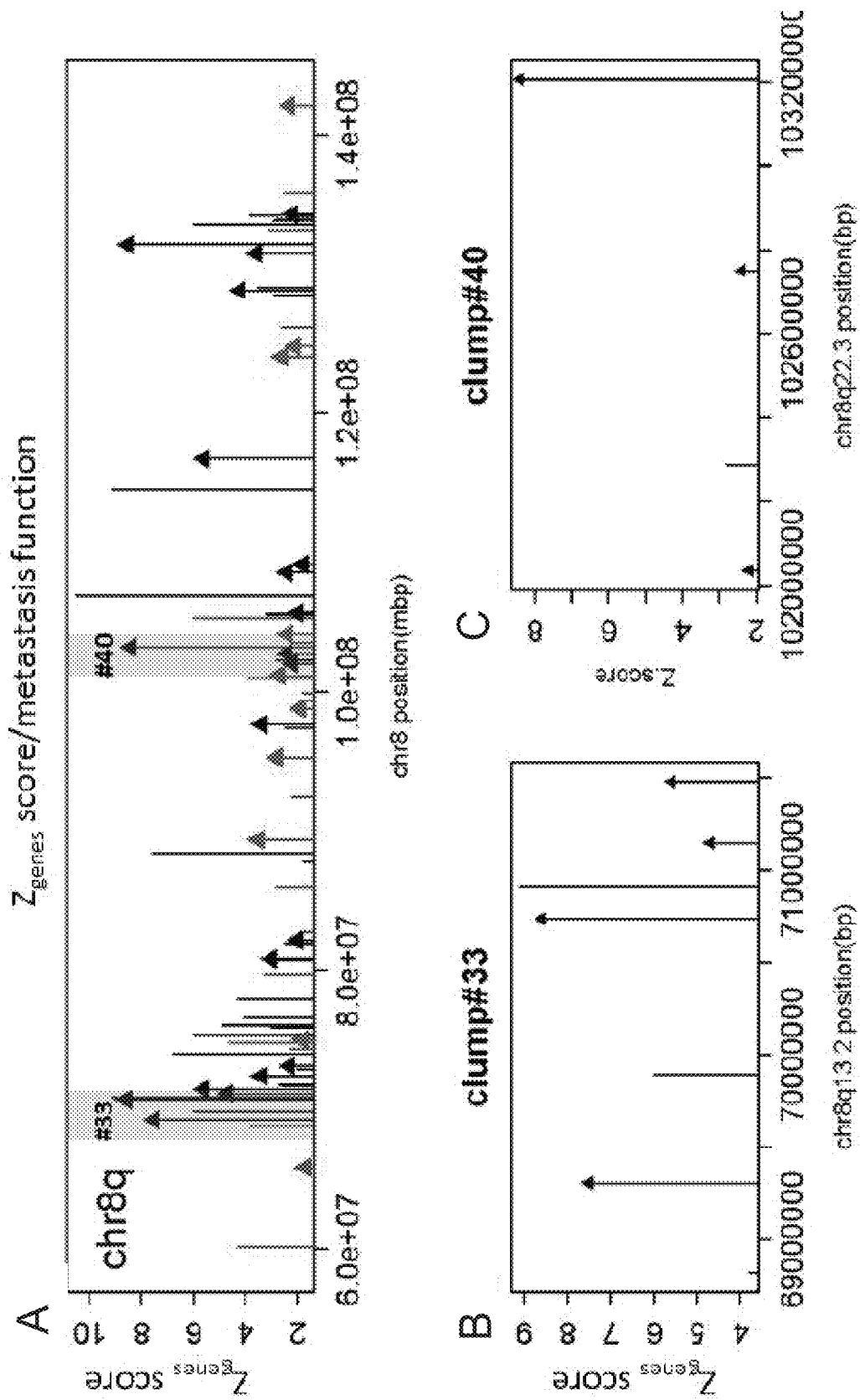
FIG. 6A-6C. Chromosome 8q exhibiting 75 genes predictive of metastatic potential, including genes that occur in clumps (A). Each bar represents a gene as it is located on the chromosome (X-axis) whereas the height of the bar denotes a $Z_{genes}$ score (Y-axis) that measures the gene CNA profile's ability to predict the metastatic potential of a primary prostate cancer. Arrows on top of some of the bars indicate that the gene has been validated in prior metastasis studies as a biomarker or to have metastatic function. Red colored bars/arrows indicate a singleton gene or one member clump. Clump region #33 (six-gene segment) and clump region #40 (four-gene segment) are highlighted in (A) and zoomed in (B) (Clump region #33) and (C) (Clump region #40).
Figures 7A, 7B, 7C:
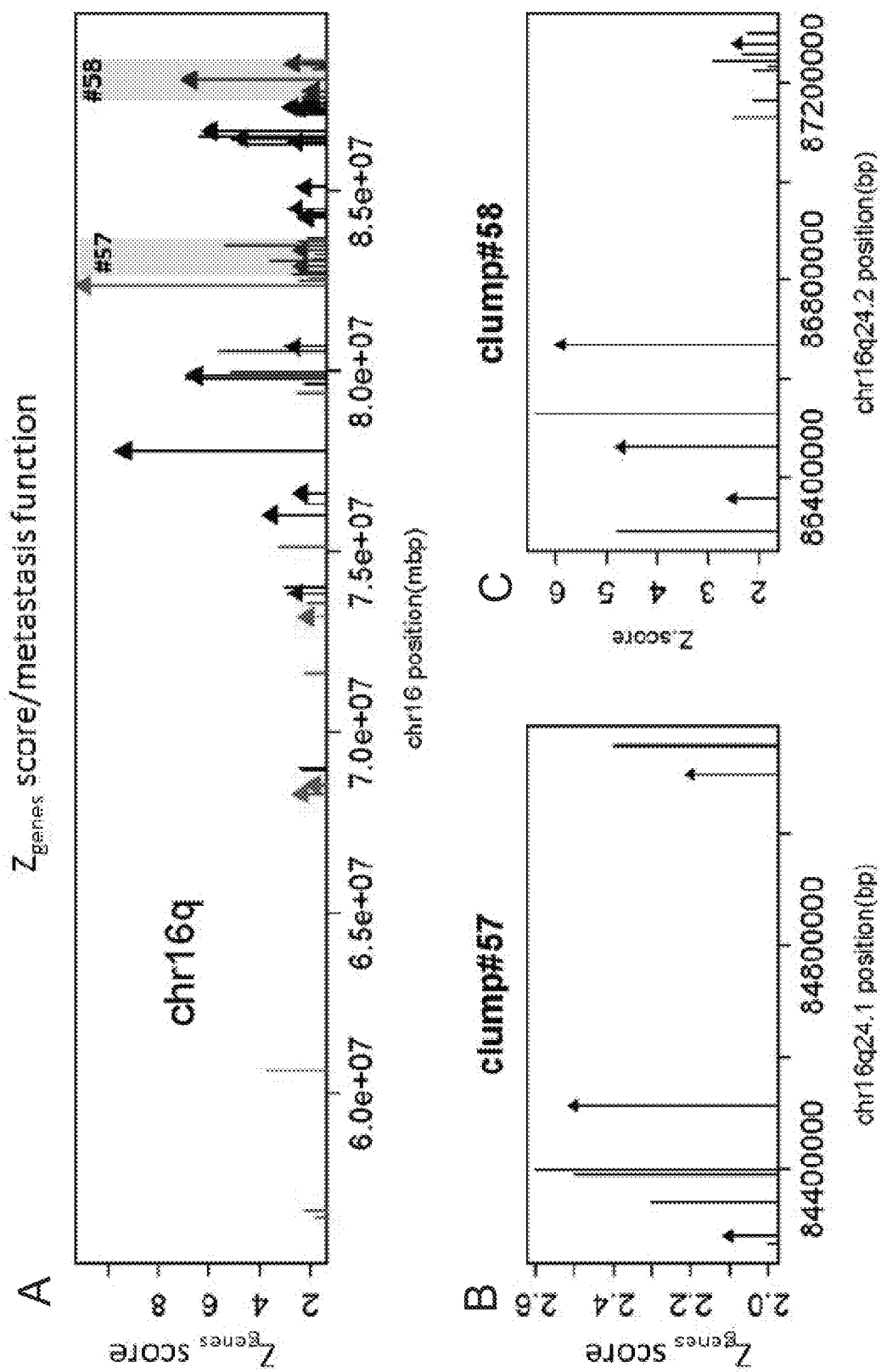
FIG. 7A-7C. Chromosome 16q exhibiting 74 genes predictive of metastatic potential, including genes that occur in clumps (A). Each bar represents a gene as it is located on the chromosome (X-axis) while the height of the bar denotes a $Z_{genes}$ score (Y-axis) that measures the gene CNA's ability to predict the metastatic potential of a primary prostate cancer tumor. Arrows on top of some of the bars indicate that the gene has been validated in prior metastasis studies as a biomarker or to have metastatic function. Red colored bars/arrows indicate a singleton gene or one member clump. Clump region #57 (8-gene segment) and clump region #58 (13-gene segment) are highlighted in (A) and zoomed in (B) (Clump region #57) and (C) (Clump region #58).

The MPS genes occur as singleton CNAs as well as in clumps that are distributed over 15 chromosomal arms (Table 7). The genes within a clump are likely to include both drivers that are directly associated with metastasis function and passengers that are indirectly associated with metastasis function, because of their proximity to a metastasis driver gene. For example, a clump index 26 on chromosome 8p21.3 includes the nine genes, PPP3CC, KIAA1967, BIN3, SORBS3, PDLIM2, RHOBTB2, SLC39A14, EGR3, and C8orf58 (Table 7). In this clump three of the 9 genes (EGR3, PDILMS, and RHOBTB2) overlapped with the gene sets, metastasis ID, metastasis functions and metastasis biomarkers. In addition to annotations, another way of gauging whether some of the MPS genes play a role as metastasis drivers is to compare the $Z_{genes}$ scores within clumps (Pearlman, A. et al., *J Probab Stat*, 2012, 873570 (2012) and US Patent Publication No. 2014/0221229). The clumps of genes vary by breakpoints in individual cancer genomes and the CNAs of some genes in a clump will yield higher $Z_{genes}$ scores by being overrepresented and in the right direction expected for metastasis, compared to cancer genomes that are not metastasis-prone. The range of $Z_{genes}$ scores within a clump varied from 1.7 to over 10 with no apparent pattern of decay for the highest $Z_{genes}$ score gene adjacent to those with the lowest $Z_{genes}$ score (FIG. 3). Multiple genes within a clump had Pubmed annotations, which were not necessarily those with the highest $Z_{genes}$ score. Some of the unannotated MPS genes with high $Z_{genes}$ scores may also act as drivers of metastasis, but may not have been studied yet for functional roles (FIG. 5).

Other genes, including CDH13, CDH8, CDH2, CTD8, COL19A1, YWHAG, and ENOX1, do not belong to any clump. Both the $Z_{genes}$ scores and the annotations of these genes suggest that they may act as drivers (Table 7). However, the functions of some of these genes may overlap with each other (e.g., the cadherin genes, CDH13, CDH8, CDH2). Thus, there may be some functional redundancy among the MPS genes and, as judged by $Z_{genes}$ scores, genes are not equally predictive of the predisposition to metastasis. Yet, some of these genes have higher $Z_{genes}$ scores suggesting that their contributions to metastasis are observed more frequently.

Example 8. High $Z_{genes}$ Score Genes within Clumps Predict Outcomes.

To test whether a reduced set of clumps could predict outcomes and produce similar values to those observed with panMPS, AUC and $r^2$ were calculated for simplified MPS versions that included genes with $Z_{genes}$ score≥4 (21 clumps) and $Z_{genes}$ score≥3 (43 clumps) or the highest $Z_{genes}$ score gene within a clump. The results were compared to all 295 panMPS genes. The 21 and 43 clumps predicted AUC and $r^2$ almost as well panMPS, whether calculated for all genes exceeding the threshold or for only the gene with the highest $Z_{genes}$ score (Table 9A and 9B). This result indicated that there was a hierarchy of clumps with 21 clumps ($Z_{genes}$ score≥4) performing as well as 43 clumps ($Z_{genes}$ score≥3) capturing almost all of the contribution of the clump to AUC and $r^2$. These result also indicated a lead gene within a clump could capture almost all of the contribution of the clump to AUC and panMPS $r^2$.

CNAs are the result of chromosomal instability and are far more common than mutations in human cancers, including prostate, triple negative breast cancer and lung adenocarcinoma (Vogelstein. B. & Kinzler, K. W., *Nat Med*, 10, 789-99 (2004), Kandoth et al., *Nature*, 502:333-9, 2013). CNAs may occur randomly across the genome or may be favored by repeated structural elements, including Alu or LINE sequences (Aguilera et al., *Annu Rev Genet.*, 47:1-32, 2013). Amplifications or deletions of genes may occur repeatedly within the same regions of genomes in populations of cancer cells within a tumor (Pearlman, A. et al., *J Probab Stat*, 2012, 873570 (2012), Shah et al., *Nature*, 486:395-9, 2012). This observation of specific CNA pattern enrichment is the basis for calculating Zgenes scores for specific genes within CNAs. In turn, MPS represents the sum of Zgenes scores, divided by the number of genes being summed. CNA burden alone (i.e. the frequency of chromosomal instability) was not an accurate predictor of outcome in most cohorts because it did not consider specific pattern nor functional contributions by specific metastatic genes.

This disclosure provides evidence that panMPS can be used as a predictor of metastasis and metastasis-free survival, not only in prostate cancer, as we have shown before (Pearlman, A. et al., *J Probab Stat*, 2012, 873570 (2012)), but also for triple negative breast cancer, other breast cancers, and lung adenocarcinoma and 133 CCLE metastasis cell lines of 8 different cancer origins. A panMPS was also able to predict overall survival in Metabric cohort of breast cancer and several large TCGA cohorts of prostate cancer, breast cancer and lung adenocarcinoma.

These observations fit a model of chromosomal rearrangements occurring in early tumorigenesis by punctuated bursts (Gao R. et al., *Nat Genet* 48:1119-30, 2016). Metastasis is driven by selection for rearrangements that promote invasion, escape from apoptosis and growth at distant sites (Nyugen D X. et al., *Nat Rev Genet* 8:341-52, 2007 PMID: 17440531). A study of mutated genes in multiple cancer types drew a similar conclusion that genes under positive selection, either in individual or multiple tumor sites, tend to display higher mutation frequencies above background (Kandoth et al., *Nature*, 502:333-9, 2013). However, large-scale targeted and whole genome sequence efforts have identified single nucleotide variants and short indels in a set of overlapping or related genes that account for carcinogenesis, but have not identified genes involved in metastasis (Kan Z. et al., *Nature* 466:869-73, 2010).

These CNAs occur on a segmental basis with multiple genes within a segment or clump being amplified or deleted. Within a clump, one or more genes could be drivers of metastasis (Kandoth et al., *Nature*, 502:333-9, 2013). The drivers showed elevated Zgenes scores and were annotated in the literature as having metastatic functions, including invasion, motility, escape from apoptosis when detached from matrix of origin, and chemokine activity. Other genes with elevated Zgenes scores, but no annotations, may also represent drivers whose functions have not yet been identified. However, the remainder of the genes may be passengers that are carried along with the CNA events. Not all of the drivers are required for predicting risk of metastasis. Testing only genes with the highest Zgenes score within a clump may capture most, if not all of the metastatic risk, reflected by the panMPS. These genes with high Zgenes score may act as proxies for all of the genes within the clump.

Based on the hypergeometric analysis, the MPS genes indeed represent a subset of all metastatic genes, specifically those that can be readily identified by CNA analysis. Other metastatic genes would not be readily detected as they are not subject to CNA events and may need to be detected by other molecular methods, such as sequencing.

Analyzing these genes in patient samples may be required to improve the accuracy of predicting metastasis—although the current study suggests that as few as 33 genes with high Zgenes score may be sufficient for many clinical applications.

The availability of a panMPS-based diagnostic tool may contribute to clinical care. Collectively, lung, breast and prostate cancer account for ~676,000 or 40% of newly diagnosed cancer cases and ~226,000 or 39% of cancer deaths in the United States each year (Siegel R L. et al., *CA Cancer J Clin*, 65:5-29, 2015). Currently, there are no clinical tests in common use for prediction of outcomes in triple negative breast cancer or lung adenocarcinoma. Future studies will assess the accuracy of panMPS derived from surgical specimens and biopsies for predicting outcomes of these diseases.

Having a test that would accurately predict across cancer-types which patients are likely to develop metastases would be extremely useful. For example, panMPS could improve the clinical management of men with prostate cancer. Men with early-stage disease and low-risk profiles would be candidates for active surveillance that might safely preserve quality of life by helping them to avoid erectile dysfunction and urinary incontinence that may occur in up to 50% of treated patients (Cooperberg et al., *J Natl Cancer Inst* 101:878-87, 2009, Paris P L. et al., *Clinical cancer research*, 16:195-202, 2010). Men with early-stage disease and high-risk profiles might benefit from aggressive treatment (Pound C R. et al., *The Urologic clinics of North America* 24:395-406, 1997). Men with higher-risk disease who underwent initial surgery might benefit from adjuvant radiation therapy (Thompson I M., *The Journal of urology* 181:956-62, 2009). Notably, the accuracy of combined panMPS and pre-operative PSA appears to be similar to the various RNA expression profile tests plus clinical predictors for use as a post-surgical tool (Table10A-10C). These tests, Genomic Prostate Score (GPS) (Cullen J. et al., *European Urology*, 68:123-31, 2015 PMID: 25465337., Klein E A. et al., *European Urology*, 66:550-60, 2014), Cell Cycle Progression Score (CCPS) (Cuzick J. et al., *The Lancet Oncology* 12:245-55, 2011), and Genomic Classifier (GC) (Ross A E et al., *Prostate Cancer Prostatic Dis.*, 17:64-9, 2014; Cooperberg M R et al. *European Urology* 67:326-33, 2015; Erho N et al., *PLOS One*, 8: e66855, 2013; Karnes R J. et al., *J Urol*, 190:2047-53, 2013; 4097302; Den R B et al., *Int J Radiat Oncol Biol Phys*, 89:1038-46, 2014), measure the altered expression of mostly non-overlapping sets of genes that have not been demonstrated to play a direct role with the biological events of prostate cancer progression and metastasis. As with panMPS, the accuracy of these tests was improved by the addition of clinical and pathological predictors, both as univariate predictors or as captured by the Cancer of the Prostate Risk Assessment (CAPRA-S) score (Cooperberg M R et al., *Cancer*, 117:5039-46, 2011; 3170662; Greene K L et al., *The Journal of Urology* 171: 2255-9, 2004), and the Stephenson nomogram (Brockman J A. et al., *Eur Urol*, 67:1160-7, 2015). Although Oncotype DX and Prosigna are two RNA expression profile tests in common use for prognostic prediction of breast cancer, their use is limited to estrogen receptor positive breast cancer (Nielsen T. et al., *BMC Cancer*, 14:177, 2014; Kaklamani V., *Expert Rev Mol Diagn.*, 6:803-9, 2006).

TABLE 1A

Univariate logistic regression model of panMPS predicts progression to metastasis for prostate cancer

| | Cohort | | | | | | | |
|---|---|---|---|---|---|---|---|---|
| | MSK prostate cancer (n = 182, mPT = 25, iPT = 157) | | | | Duke prostate cancer (n = 61, mPT = 37, iPT = 24) | | | |
| | Variable | | | | | | | |
| | Odds Ratio | P | 95% CI | AUC | Odds Ratio | P | 95% CI | AUC |
| panMPS | 6.01 | 0.001 | 2.21 to 17.89 | 0.71 | 11.39 | 0.004 | 2.39 to 70.36 | 0.72 |

TABLE 1B

Univariate logistic regression model of panMPS predicts progression to metastasis for triple negative breast cancer Montefiore triple negative breast cancer cohort (n = 41, mBC = 28, iBC = 13)

| Variable | Odds Ratio | P | 95% CI | AUC |
|---|---|---|---|---|
| panMPS | 44.74 | 0.02 | 2.91 to 1927.9 | 0.75 |

TABLE 1C

Univariate logistic regression model of panMPS predicts progression to metastasis for lung adenocarcinoma MSK lung adenocarcinoma cohort (n = 33, mLA = 23, iLA = 10)

| Variable | Odds Ratio | P | 95% CI | AUC |
|---|---|---|---|---|
| panMPS | $3.45 \times 10^3$ | 0.006 | 41.5 to $1.26 \times 10^7$ | 0.94 |

TABLE 2A

Univariate Cox proportional hazards model of panMPS predicts metastasis-free survival for prostate cancer

| Cohort | | | | | | | |
|---|---|---|---|---|---|---|---|
| MSK prostate cancer (n = 222, mPT = 25, iPT = 197) | | | | Duke prostate cancer (n = 76, mPT = 37, iPT = 39) | | | |
| Variable | | | | | | | |
| | Hazard Ratio | 95% CI | Conc-indx | P | Hazard Ratio | 95% CI | Conc-indx | P |
| panMPS | 5.42 | 2.18 to 13.49 | 0.74 | 0.0003 | 3.4 | 1.15 to 10.12 | 0.62 | 0.03 |

TABLE 2B

Univariate Cox proportional hazards model of panMPS predicts metastasis-free survival for triple negative breast cancer Montefiore triple negative breast cancer cohort (n = 41, mBC = 28, iBC = 13)

| Variable | Hazard Ratio | 95% CI | Conc-indx | P |
|---|---|---|---|---|
| panMPS | 4.1 | 1.03 to 16.04 | 0.60 | 0.05 |

TABLE 2C

Cox proportional hazards model of panMPS predicts metastasis-free survival for lung adenocarcinoma MSK lung adenocarcinoma (n = 33, mLA = 23, iLA = 10)

| Variable | Hazard Ratio | 95% CI | Conc-indx | P |
|---|---|---|---|---|
| panMPS | 6.57 | 1.31 to 33.04 | 0.67 | 0.02 |

TABLE 3

Hypergeometric analysis of MPS genes versus in silico gene sets for metastasis biomarker and metastasis function reviewed by cellular assays. Metastasis ID and chemokine ID terms in article title or abstract.

| Gene Set | Overlap | Gene set size | Overlap % | P |
|---|---|---|---|---|
| Metastasis biomarkers | 28 | 687 | 4.08 | 0.0001 |
| Metastasis function | 40 | 929 | 4.31 | $1.18 \times 10^{-6}$ |
| Metasiasis ID | 112 | 2463 | 4.55 | $2.42 \times 10^{-20}$ |
| Chemokine ID | 65 | 3126 | 2.08 | 0.04 |

TABLE 4

Left and Center: Logistic regression and Cox proportional hazards models predict progression to metastasis for full set (variable number by cohort) and panMPS (295) genes. Right: Linear regression model predicting correlation ($r^2$) between MPS and panMPS.

| Cohort | Variables | Logistic Regression | | | | Cox Regression | | | | Linear Regression |
|---|---|---|---|---|---|---|---|---|---|---|
| | | Odds Ratio | P | 95% CI | AUC | Hazard Ratio | 95% CI | Conc-Index | P | $r^2$ |
| MSK_Prostate | MPS (320 genes) | 5.39 | 0.001 | 2.03 to 15.49 | 0.69 | 4.85 | 2.00 to 11.77 | 0.72 | 0.0005 | 0.97 |
| | panMPS | 6.01 | 0.001 | 2.21 to 17.69 | 0.71 | 5.42 | 2.18 to 13.49 | 0.74 | 0.0003 | 0.97 |

TABLE 4-continued

Left and Center: Logistic regression and Cox proportional hazards models predict progression to metastasis for full set (variable number by cohort) and panMPS (295) genes. Right: Linear regression model predicting correlation ($r^2$) between MPS and panMPS.

| Cohort | Variables | Logistic Regression | | | | Cox Regression | | | | Linear Regression |
|---|---|---|---|---|---|---|---|---|---|---|
| | | Odds Ratio | P | 95% CI | AUC | Hazard Ratio | 95% CI | Conc-Index | P | $r^2$ |
| Duke_Prostate | MPS (351 genes) | 10.99 | 0.004 | 2.36 to 65.88 | 0.72 | 3.54 | 1.20 to 10.44 | 0.62 | 0.02 | 0.99 |
| | panMPS | 11.39 | 0.004 | 2.39 to 70.36 | 0.72 | 3.41 | 1.15 to 10.12 | 0.62 | 0.03 | 0.97 |
| Montefiore_TNBC | MPS (352 genes) | 44.36 | 0.02 | 2.87 to 2005.4 | 0.75 | 4.01 | 1.04 to 15.44 | 0.59 | 0.04 | 0.99 |
| | panMPS | 44.74 | 0.02 | 2.91 to 1927.9 | 0.75 | 4.06 | 1.03 to 16.04 | 0.59 | 0.05 | 0.96 |
| MSK_Lung | MPS (353 genes) | $3.78 \times 10^3$ | 0.006 | 42.79 to $1.04 \times 10^7$ | 0.94 | 4.55 | 1.04 to 20.63 | 0.65 | 0.04 | 0.96 |
| | panMPS | $3.45 \times 10^3$ | 0.006 | 41.5 to $1.25 \times 10^7$ | 0.94 | 6.57 | 1.31 to 33.04 | 0.67 | 0.02 | 0.96 |

TABLE 5

Logistic regression models predicting progression to metastasis for prostate cancer based on panMPS and clinical variables

| | Cohort | | | | | | | |
|---|---|---|---|---|---|---|---|---|
| | MSK Prostate CA (n = 182, mPT = 25, iPT = 157) | | | | Duke Prostate CA (n = 61, mPT = 37, iPT = 24) | | | |
| Variable | Odds Ratio | P | 95% CI | AUC | Odds Ratio | P | 95% CI | AUC |
| | Univariate | | | | | | | |
| panMPS | 5.98 | 0.001 | 2.12 to 18.57 | 0.7 | 11.84 | 0.002 | 2.78 to 67.71 | 0.75 |
| Preop PSA | 1.06 | 0.02 | 1.02 to 1.11 | 0.66 | 1.1 | 0.08 | 1.01 to 1.21 | 0.61 |
| Biopsy Gleason | 3.82 | 0.02 | 1.21 to 11.10 | 0.59 | 3.86 | 0.08 | 0.89 to 27.84 | 0.59 |
| Clinical Stage | 2.3 | 0.06 | 0.98 to 5.59 | 0.6 | 4 | 0.1 | 0.86 to 28.88 | 0.61 |
| Path Gleason | 68 | $1.3 \times 10^{-10}$ | 20.51 to 280.1 | 0.81 | 7.5 | 0.01 | 1.83 to 51.3 | 0.66 |
| Path Stage | 5.19 | 0.001 | 2.12 to 14.08 | 0.7 | 0.47 | 0.23 | 0.13 to 1.63 | 0.57 |
| % Genome Inst. | 1.17 | $1.4 \times 10^{-5}$ | 1.09 to 1.26 | 0.74 | 1.04 | 0.12 | 1.00 to 1.12 | 0.8 |
| | Multivariate | | | | | | | |
| panMPS | 4.09 | 0.01 | 1.38 to 13.19 | 0.75 | 14.32 | 0.003 | 2.7 to 103.6 | 0.78 |
| Preop PSA | 1.04 | 0.05 | 1.01 to 1.1 | | 1.1 | 0.06 | 1.01 to 1.24 | |
| panMPS | 5.09 | 0.003 | 1.6 to 15.54 | 0.73 | 6.06 | 0.06 | 2.4 to 70.4 | 0.68 |
| Biopsy Gleason | 2.32 | 0.15 | 0.69 to 7.17 | | 1.18 | 0.88 | 1.03 to 47.04 | |
| panMPS | 5.51 | 0.001 | 1.99 to 16.59 | 0.73 | 4.42 | 0.13 | 0.71 to 34.06 | 0.72 |
| Clinical Stage | 1.93 | 0.15 | 0.79 to 4.83 | | 2.76 | 0.26 | 0.52 to 21.2 | |
| panMPS | 1.5 | 0.55 | 0.39 to 5.88 | 0.86 | 7.45 | 0.03 | 1.4 to 49.38 | 0.77 |
| Path Gleason | 56.8 | $1.21 \times 10^{-8}$ | 15.57 to 263.14 | | 4.83 | 0.06 | 1.1 to 34.44 | |
| panMPS | 3.93 | 0.01 | 1.43 to 11.94 | 0.77 | 10.59 | 0.01 | 2.18 to 65.6 | 0.73 |
| Path Stage | 3.83 | 0.006 | 1.49 to 10.74 | | 0.59 | 0.45 | 0.15 to 2.32 | |
| panMPS | 1.79 | 0.32 | 0.59 to 5.97 | 0.75 | 8.45 | 0.03 | 1.41 to 62.2 | 0.73 |
| % Genome Inst. | 1.15 | 0.001 | 1.06 to 1.25 | | 1.01 | 0.53 | 0.98 to 1.07 | |
| panMPS | 1.49 | 0.52 | 0.45 to 5.39 | 0.8 | 9.93 | 0.02 | 1.47 to 85.45 | 0.78 |
| Preop PSA | 1.03 | 0.21 | 1.00 to 1.09 | | 1.1 | 0.06 | 1.01 to 1.24 | |
| % Genome Inst. | 1.14 | 0.004 | 1.05 to 1.25 | | 1.02 | 0.5 | 0.98 to 1.08 | |
| panMPS | 3.7 | 0.03 | 1.2 to 11.93 | 0.76 | 8.6 | 0.04 | 1.25 to 90.53 | 0.74 |
| Biopsy Gleason | 2.2 | 0.21 | 0.59 to 7.1 | | 1.35 | 0.78 | 0.17 to 13.8 | |
| Preop PSA | 1.04 | 0.05 | 1.01 to 1.09 | | 1.11 | 0.09 | 1.01 to 1.28 | |
| panMPS | 4.71 | 0.01 | 1.66 to 14.48 | 0.75 | 4.47 | 0.13 | 0.70 to 36.93 | 0.71 |
| Biopsy Gleason | 2.24 | 0.17 | 0.66 to 6.97 | | 0.93 | 0.95 | 0.12 to 8.55 | |
| Clinical Stage | 1.88 | 0.17 | 0.77 to 4.76 | | 2.8 | 0.26 | 0.51 to 22.16 | |
| panMPS | 1.29 | 0.71 | 0.34 to 4.99 | 0.85 | 6.88 | 0.03 | 1.27 to 45.95 | 0.77 |
| Path Gleason | 47.21 | $8.69 \times 10^{-8}$ | 12.71 to 224.2 | | 4.91 | 0.06 | 1.08 to 35.13 | |
| Path Stage | 2.87 | 0.08 | 0.87 to 9.88 | | 0.56 | 0.42 | 1.13 to 2.31 | |
| panMPS | 3.56 | 0.03 | 1.16 to 11.62 | 0.78 | 6.97 | 0.04 | 0.94 to 77.9 | 0.76 |
| Biopsy Gleason | 2.15 | 0.22 | 0.59 to 6.97 | | 1.07 | 0.08 | 0.11 to 11.94 | |
| Clinical Stage | 1.41 | 0.48 | 0.54 to 3.71 | | 2.73 | 0.46 | 0.46 to 22.54 | |
| Preop PSA | 1.04 | 0.07 | 1.01 to 1.08 | | 1.11 | 0.29 | 1.01 to 1.29 | |
| panMPS | 3.5 | 0.03 | 1.16 to 11.2 | 0.79 | 5.68 | 0.13 | 0.66 to 68.5 | 0.76 |
| Biopsy Gleason | 2.2 | 0.22 | 0.60 to 7.51 | | 1.34 | 0.82 | 0.12 to 31.9 | |

TABLE 5-continued

Logistic regression models predicting progression to metastasis
for prostate cancer based on panMPS and clinical variables

| | MSK Prostate CA (n = 182, mPT = 25, iPT = 157) | | | | Duke Prostate CA (n = 61, mPT = 37, iPT = 24) | | | |
|---|---|---|---|---|---|---|---|---|
| | Odds Ratio | P | 95% CI | AUC | Odds Ratio | P | 95% CI | AUC |
| Clinical Stage | 1.37 | 0.52 | 0.52 to 3.61 | | 2.39 | 0.37 | 0.38 to 20.3 | |
| Preop PSA | 1.04 | 0.06 | 1.01 to 1.09 | | 1.1 | 0.13 | 0.99 to 1.27 | |
| Age | 0.51 | 0.35 | 0.13 to 2.49 | | $7.85 \times 10^5$ | 0.99 | $3.85 \times 10^{-10.4}$ to NA | |

Table 5 Continued

TABLE 6

Cox proportional hazards model of panMPS and its association with metastasis-
free survival for prostate cancer based on panMPS and clinical variables

| | MSK Prostate CA (n = 222, mPT = 25, iPT = 197) | | | | Duke Prostate CA (n = 76, mPT = 37, iPT = 39) | | | |
|---|---|---|---|---|---|---|---|---|
| | Hazard Ratio | 95% CI | Conc-indx | P | Hazard Ratio | 95% CI | Conc-indx | P |
| | | | Univariate | | | | | |
| panMPS | 4.2 | 1.67 to 10.4 | 0.7 | 0.002 | 3.9 | 1.48 to 10.4 | 0.63 | 0.01 |
| Preop PSA | 1.01 | 1.00 to 1.01 | 0.63 | $7.60 \times 10^{-5}$ | 1 | 0.97 to 1.03 | 0.51 | 0.96 |
| Biopsy Gleason | 3.11 | 1.24 to 7.83 | 0.73 | 0.02 | 1.63 | 0.71 to 3.72 | 0.65 | 0.25 |
| Clinical Stage | 1.75 | 0.78 to 3.91 | 0.65 | 0.17 | 0.48 | 0.21 to 1.09 | 0.64 | 0.06 |
| Path Gleason | 17.34 | 7.63 to 39.4 | 0.97 | $9.90 \times 10^{-12}$ | 1.67 | 0.84 to 3.34 | 0.71 | 0.14 |
| Path Stage | 3.99 | 1.67 to 9.58 | 0.82 | 0.002 | 0.61 | 0.23 to 1.57 | 0.57 | 0.3 |
| % Genome Inst. | 1.11 | 1.07 to 1.16 | 0.67 | $3.30 \times 10^{-7}$ | 1.01 | 0.99 to 1.02 | 0.66 | 0.2 |
| | | | Multivariate | | | | | |
| panMPS | 4.31 | 1.72 to 10.8 | 0.74 | 0.002 | 3.52 | 1.18 to 10.5 | 0.71 | 0.02 |
| Preop PSA | 1.01 | 1.00 to 1.01 | | 0.0002 | 0.99 | 1.02 to 1.12 | | 0.7 |
| panMPS | 3.77 | 1.49 to 9.51 | 0.72 | 0.005 | 3.13 | 1.06 to 9.29 | 0.66 | 0.04 |
| Biopsy Gleason | 2.18 | 0.83 to 5.69 | | 0.1 | 1.86 | 0.88 to 3.93 | | 0.1 |
| panMPS | 4.59 | 1.83 to 11.6 | 0.71 | 0.001 | 2.25 | 0.62 to 8.17 | 0.6 | 0.22 |
| Clinical Stage | 1.81 | 0.81 to 4.03 | | 0.15 | 1.86 | 0.79 to 4.34 | | 0.15 |
| panMPS | 1.79 | 0.69 to 4.65 | 0.86 | 0.23 | 2.97 | 0.94 to 9.41 | 0.64 | 0.06 |
| Path Gleason | 14.34 | 5.96 to 34.5 | | $2.74 \times 10^{-9}$ | 1.29 | 0.62 to 2.69 | | 0.5 |
| panMPS | 2.96 | 1.19 to 7.33 | 0.76 | 0.02 | 3.19 | 1.05 to 9.64 | 0.62 | 0.04 |
| Path Stage | 3.03 | 1.22 to 7.55 | | 0.02 | 0.73 | 0.27 to 1.91 | | 0.5 |
| panMPS | 1.37 | 0.47 to 3.97 | 0.71 | 0.56 | 3.26 | 1.08 to 9.8 | 0.62 | 0.04 |
| % Genome Inst. | 1.1 | 1.04 to 1.16 | | 0.001 | 1.01 | 0.99 to 1.02 | | 0.32 |
| panMPS | 1.29 | 0.44 to 3.85 | 0.73 | 0.64 | 3.35 | 1.1 to 10.17 | 0.62 | 0.03 |
| Preop PSA | 1.01 | 1.00 to 1.01 | | 0.0001 | 0.99 | 0.97 to 1.02 | | 0.77 |
| % Genome Inst. | 1.09 | 1.04 to 1.16 | | 0.001 | 1.01 | 0.99 to 1.02 | | 0.35 |
| panMPS | 3.69 | 1.44 to 9.47 | 0.76 | 0.01 | 2.75 | 0.78 to 9.64 | 0.67 | 0.11 |
| Biopsy Gleason | 2.3 | 0.86 to 5.94 | | 0.09 | 1.19 | 0.49 to 2.92 | | 0.69 |
| Prep PSA | 1.01 | 1.00 to 1.01 | | 0.0001 | 1.06 | 1.01 to 1.11 | | 0.03 |
| panMPS | 4.07 | 1.58 to 10.5 | 0.74 | 0.01 | 1.96 | 0.53 to 7.23 | 0.6 | 0.31 |
| Biopsy Gleason | 2.09 | 0.81 to 5.42 | | 0.13 | 1.69 | 0.72 to 3.97 | | 0.23 |
| Clinical Stage | 1.76 | 0.78 to 3.94 | | 0.17 | 2.02 | 0.84 to 4.85 | | 0.11 |
| panMPS | 1.79 | 0.71 to 4.51 | 0.86 | 0.22 | 2.67 | 0.56 to 7.6 | 0.64 | 0.1 |
| Path Gleason | 11.98 | 4.98 to 28.8 | | $2.91 \times 10^{-8}$ | 1.35 | 0.49 to 3.14 | | 0.44 |
| Path Stage | 2.04 | 0.83 to 5.06 | | 0.12 | 1.91 | 0.78 to 4.64 | | 0.46 |
| panMPS | 3.95 | 1.51 to 10.3 | 0.76 | 0.01 | 2.06 | 0.56 to 7.61 | 0.65 | 0.28 |
| Biopsy Gleason | 2.19 | 0.84 to 5.72 | | 0.11 | 1.25 | 0.49 to 3.14 | | 0.63 |
| Clinical Stage | 1.57 | 0.68 to 3.58 | | 0.29 | 1.91 | 0.78 to 4.64 | | 0.15 |
| Preop PSA | 1.01 | 1.00 to 1.01 | | 0.001 | 1.05 | 1.01 to 1.11 | | 0.04 |
| panMPS | 3.95 | 1.49 to 10.5 | 0.76 | 0.01 | 1.73 | 0.46 to 6.55 | 0.66 | 0.42 |
| Biopsy Gleason | 2.21 | 0.84 to 5.76 | | 0.11 | 1.58 | 0.59 to 3.92 | | 0.37 |
| Clinical Stage | 1.56 | 0.68 to 3.6 | | 0.29 | 1.68 | 0.66 to 4.29 | | 0.27 |
| Preop PSA | 1.01 | 1.00 to 1.01 | | 0.001 | 1.04 | 0.99 to 1.11 | | 0.13 |
| Age | 0.89 | 0.26 to 3.09 | | 0.86 | $8.31 \times 10^7$ | 0 to Inf | | 0.99 |

Table 6 Continued

TABLE 7

Clump analysis of genes, including $Z_{genes}$ score, clump index, number of genes in clump and PubMed ID for metastasis function annotations, metastasis predictive biomarkers and metastasis in the article

| Gene | $Z_{genes}$ score | clump index | No. of genes in clump | Metastasis Function PubMed ID | Metastasis Predictive Biomarkers PubMed ID | Metastasis PubMed ID |
|---|---|---|---|---|---|---|
| ACTL8 | 1.9 | 1 | 2 | | | 23592437 |
| ARHGEF10L | 2.1 | 1 | 2 | | | |
| LEPREL1 | 2.6 | 2 | 2 | 24319452 | | |
| TP63 | 3.0 | 2 | 2 | 21760596, 24488880 | 15761962, 23913939 | 19142959, 26208975 |
| GLRB | 2.7 | 3 | 2 | | | |
| GRIA2 | 2.3 | 3 | 2 | | 16953328 | |
| CCDC125 | 2.0 | 4 | 7 | | | |
| CDK7 | 2.7 | 4 | 7 | 23393140, 25490451, 25820824 | | 25117707 |
| CENPH | 1.9 | 4 | 7 | | 22999412 | |
| MARVELD2 | 3.0 | 4 | 7 | | | |
| MRPS36 | 2.6 | 4 | 7 | | | |
| RAD17 | 2.6 | 4 | 7 | | | |
| TAF9 | 2.6 | 4 | 7 | | | |
| EPHA7 | 1.8 | 5 | 2 | | | 16007213 |
| MAP3K7 | 3.2 | 5 | 2 | 23370768, 25770290 | | 17785553 |
| ASCC3 | 1.8 | 6 | 2 | | | |
| SIM1 | 2.2 | 6 | 2 | | | |
| EPM2A | 2.4 | 7 | 2 | | | 18824542 |
| UTRN | 2.3 | 7 | 2 | | | |
| C6orf118 | 2.8 | 8 | 2 | | | |
| PDE10A | 4.7 | 8 | 2 | | | |
| CLIP2 | 3.1 | 9 | 4 | | | |
| EIF4H | 2.0 | 9 | 4 | | | |
| LAT2 | 2.0 | 9 | 4 | | | |
| RFC2 | 1.8 | 9 | 4 | | | |
| MDH2 | 2.0 | 10 | 3 | | | |
| STYXL1 | 2.3 | 10 | 3 | | | |
| TMEM120A | 1.7 | 10 | 3 | | | |
| PILRA | 1.9 | 11 | 2 | | | |
| PILRB | 2.9 | 11 | 2 | | | |
| ACTL6B | 1.7 | 12 | 9 | | | 21136596 |
| AGFG2 | 2.3 | 12 | 9 | | | |
| C7orf51 | 2.2 | 12 | 9 | | | |
| FBXO24 | 2.5 | 12 | 9 | | | |
| LRCH4 | 2.2 | 12 | 9 | | | |
| MOSPD3 | 2.3 | 12 | 9 | | | |
| PCOLCE | 1.8 | 12 | 9 | | | |
| TFR2 | 2.6 | 12 | 9 | | | |
| TSC22D4 | 2.1 | 12 | 9 | | | |
| COPG2 | 3.1 | 13 | 7 | | | |
| CPA1 | 2.1 | 13 | 7 | | | |
| CPA2 | 2.1 | 13 | 7 | | | |
| CPA4 | 1.9 | 13 | 7 | | | 27073726 |
| CPA5 | 2.8 | 13 | 7 | | | |
| MEST | 3.2 | 13 | 7 | | 23229728 | |
| TSGA14 | 9.4 | 13 | 7 | | | |
| CSMD1 | 4.6 | 14 | 2 | 18614856 | | |
| MYOM2 | 2.1 | 14 | 2 | | | |
| ERI1 | 1.9 | 15 | 2 | | | |
| MFHAS1 | 3.3 | 15 | 2 | | | |
| MSRA | 5.1 | 16 | 2 | | | 17784942 |
| TNKS | 4.0 | 16 | 2 | | | |
| C8orf16 | 2.2 | 17 | 2 | | | |
| MTMR9 | 1.9 | 17 | 2 | | | |
| GATA4 | 3.2 | 18 | 2 | 19509152 | 20222162 | 23239811, 24862985 |
| NEIL2 | 2.7 | 18 | 2 | | | |
| C8orf79 | 2.9 | 19 | 2 | | | |
| DLC1 | 6.5 | 19 | 2 | 11118037 | | |
| SGCZ | 8.2 | 20 | 2 | | | |
| TUSC3 | 3.1 | 20 | 2 | 23404293, 24096664, 24435307, 25735931 | 23096450 | |

TABLE 7-continued

Clump analysis of genes, including $Z_{genes}$ score, clump index, number of genes in clump and PubMed ID for metastasis function annotations, metastasis predictive biomarkers and metastasis in the article

| Gene | $Z_{genes}$ score | clump index | No. of genes in clump | Metastasis Function PubMed ID | Metastasis Predictive Biomarkers PubMed ID | Metastasis PubMed ID |
|---|---|---|---|---|---|---|
| MTMR7 | 3.7 | 21 | 4 | | | |
| MTUS1 | 3.6 | 21 | 4 | 19794912, 24299308, 25885343 | | 16650523 |
| PDGFRL | 4.8 | 21 | 4 | | | |
| SLC7A2 | 4.1 | 21 | 4 | | | |
| ASAH1 | 7.1 | 22 | 2 | 23423838 | | |
| PCM1 | 1.7 | 22 | 2 | | | |
| NAT2 | 3.3 | 23 | 3 | | | |
| PSD3 | 7.3 | 23 | 3 | | | |
| SH2D4A | 2.9 | 23 | 3 | | | |
| FAM160B2 | 4.3 | 24 | 5 | | | |
| HR | 2.7 | 24 | 5 | | | |
| LGI3 | 2.0 | 24 | 5 | | | |
| NUDT18 | 2.3 | 24 | 5 | | | |
| REEP4 | 2.5 | 24 | 5 | | | |
| BMP1 | 2.2 | 25 | 3 | | 19723875 | 23584484 |
| PHYHIP | 2.2 | 25 | 3 | | | |
| POLR3D | 2.7 | 25 | 3 | | | |
| BIN3 | 4.5 | 26 | 9 | | | |
| C8orf58 | 3.0 | 26 | 9 | | | |
| EGR3 | 2.0 | 26 | 9 | | | 23342064 |
| KIAA1967 | 5.9 | 26 | 9 | | | |
| PDLIM2 | 2.9 | 26 | 9 | 23584482 | | 24196835 |
| PPP3CC | 5.7 | 26 | 9 | | | |
| RHOBTB2 | 1.7 | 26 | 9 | 20930524, 21801820 | 15922864, 19173804, 19937980 | |
| SLC39A14 | 4.0 | 26 | 9 | | | |
| SORBS3 | 3.0 | 26 | 9 | | | |
| CHMP7 | 2.4 | 27 | 3 | | | |
| TNFRSF10A | 2.2 | 27 | 3 | | | |
| TNFRSF10D | 1.9 | 27 | 3 | | | |
| ENTPD4 | 2.7 | 28 | 2 | | | |
| LOXL2 | 1.9 | 28 | 2 | 25128648, 24014025, 24008674, 23971878, 23933800 | 27008697 | 23030485 |
| CDCA2 | 2.0 | 29 | 3 | 23418564 | | 17611626 |
| EBF2 | 5.1 | 29 | 3 | | | 19671856 |
| KCTD9 | 2.0 | 29 | 3 | | | |
| ADRA1A | 3.9 | 30 | 7 | | 21360568 | 24607827, 26276037 |
| CHRNA2 | 3.5 | 30 | 7 | | | |
| DPYSL2 | 3.3 | 30 | 7 | | | |
| EPHX2 | 3.3 | 30 | 7 | | | 16456776 |
| PTK2B | 7.0 | 30 | 7 | | | |
| STMN4 | 3.3 | 30 | 7 | | | |
| TRIM35 | 2.6 | 30 | 7 | | | |
| C8orf80 | 3.6 | 31 | 3 | | | |
| ELP3 | 3.4 | 31 | 3 | | 22740850 | |
| SCARA5 | 3.3 | 31 | 3 | 20038795, 24061576 | 22642751 | |
| HMBOX1 | 1.8 | 32 | 2 | | | |
| KIF13B | 2.7 | 32 | 2 | | | |
| C8orf34 | 6.0 | 33 | 7 | | | |
| CPA6 | 3.8 | 33 | 7 | | | |
| NCOA2 | 5.6 | 33 | 7 | | | 25295534 |
| PRDM14 | 4.7 | 33 | 7 | 21339739, 25233927, 25635424 | 17942894, 23690269 | |
| PREX2 | 7.5 | 33 | 7 | | 22622578, 25151370, 25829446 | |
| SLCO5A1 | 9.1 | 33 | 7 | | | |
| SULF1 | 8.6 | 33 | 7 | | 19780053, 21228115, 22653794 | 19373441 |
| EYA1 | 3.4 | 34 | 6 | | | 24729159 |
| KCNB2 | 6.8 | 34 | 6 | | | |

TABLE 7-continued

Clump analysis of genes, including $Z_{genes}$ score, clump index, number of genes in clump and PubMed ID for metastasis function annotations, metastasis predictive biomarkers and metastasis in the article

| Gene | $Z_{genes}$ score | clump index | No. of genes in clump | Metastasis Function PubMed ID | Metastasis Predictive Biomarkers PubMed ID | Metastasis PubMed ID |
|---|---|---|---|---|---|---|
| LACTB2 | 2.6 | 34 | 6 | | | |
| MSC | 2.0 | 34 | 6 | | | |
| TRPA1 | 2.3 | 34 | 6 | 24037916 | | |
| XKR9 | 2.7 | 34 | 6 | | | |
| CRISPLD1 | 4.9 | 35 | 6 | | | |
| GDAP1 | 2.0 | 35 | 6 | | | |
| HNF4G | 4.1 | 35 | 6 | | | |
| JPH1 | 6.0 | 35 | 6 | | | |
| PI15 | 3.0 | 35 | 6 | | | |
| ZFHX4 | 4.3 | 35 | 6 | | | |
| HEY1 | 3.0 | 36 | 2 | | 23226563 | |
| STMN2 | 2.8 | 36 | 2 | | | |
| PAG1 | 2.0 | 37 | 2 | 21092590, 21156787 | | 20388373, 21388951, 24675741 |
| ZNF704 | 2.5 | 37 | 2 | | | |
| CNBD1 | 7.6 | 38 | 2 | | | |
| CNGB3 | 1.8 | 38 | 2 | | | |
| PTDSS1 | 2.5 | 39 | 2 | | | |
| SDC2 | 3.4 | 39 | 2 | 20863401, 22745764 | 19288017, 20683009 | |
| GRHL2 | 2.4 | 40 | 4 | 18752864, 20938050, 23284647, 23814079, 24756056 | 23441166, 26355710 | |
| NCALD | 8.4 | 40 | 4 | | | 27027352 |
| YWHAZ | 2.2 | 40 | 4 | 20098429, 22912335 | | |
| ZNF706 | 2.8 | 40 | 4 | | | |
| DPYS | 3.2 | 41 | 3 | | | |
| LRP12 | 2.0 | 41 | 3 | | 22138261, 14676824 | |
| ZFPM2 | 10.5 | 41 | 3 | | | |
| ANGPT1 | 2.4 | 42 | 2 | | | 20651738 |
| RSPO2 | 1.8 | 42 | 2 | 21732367, 25769727 | 26416247 | 24476626 |
| CSMD3 | 9.1 | 43 | 2 | | | |
| TRPS1 | 5.6 | 43 | 2 | 24709795, 26183398 | 16043716, 23762646, 26377811 | |
| MYC | 4.2 | 44 | 3 | 20133671 | | 15810077, 9012485 |
| POU5F1B | 2.9 | 44 | 3 | | | |
| TMEM75 | 3.5 | 44 | 3 | | | |
| ADCY8 | 8.5 | 45 | 5 | | | 19082487, 22419659 |
| ASAP1 | 3.6 | 45 | 5 | 18519696, 20154719 | 24427349, 24788532 | |
| EFR3A | 3.1 | 45 | 5 | | | |
| KCNQ3 | 6.0 | 45 | 5 | | | |
| OC90 | 1.9 | 45 | 5 | | | |
| PHF20L1 | 2.8 | 46 | 5 | | | |
| SLA | 2.2 | 46 | 5 | | | |
| TG | 3.8 | 46 | 5 | | | |
| TMEM71 | 2.9 | 46 | 5 | | | |
| WISP1 | 2.2 | 46 | 5 | 19078974, 21109017, 21453685, 12865923 | 175787808, 20372786 | |
| CDC42BPG | 2.3 | 47 | 2 | | | |
| MEN1 | 2.1 | 47 | 2 | | | |
| ESD | 2.6 | 48 | 3 | 21596165 | | |
| HTR2A | 3.3 | 48 | 3 | | | |
| LRCH1 | 2.4 | 48 | 3 | | | |
| DACH1 | 1.9 | 49 | 3 | 16980615 | | |
| KLHL1 | 1.9 | 49 | 3 | | | |
| PCDH9 | 4.5 | 49 | 3 | 25172662 | 22300792, 25869928, 25979483 | |
| DDX19A | 2.3 | 50 | 2 | | | |

TABLE 7-continued

Clump analysis of genes, including $Z_{genes}$ score, clump index, number of genes in clump and PubMed ID for metastasis function annotations, metastasis predictive biomarkers and metastasis in the article

| Gene | $Z_{genes}$ score | clump index | No. of genes in clump | Metastasis Function PubMed ID | Metastasis Predictive Biomarkers PubMed ID | Metastasis PubMed ID |
|---|---|---|---|---|---|---|
| ST3GAL2 | 2.4 | 50 | 2 | | | |
| BCAR1 | 2.5 | 51 | 2 | 22476538 | 10539513, 15448007, 17192874, 23904007 | 15972849, 21765937, 22241677 |
| CFDP1 | 3.0 | 51 | 2 | | | |
| ADAMTS18 | 3.5 | 52 | 4 | 18449690 | 25569086 | 21196270, 21047771, 24896365 |
| CLEC3A | 2.3 | 52 | 4 | | | 19173304 |
| NUDT7 | 2.2 | 52 | 4 | | | |
| WWOX | 9.3 | 52 | 4 | 14695174, 18487009, 23824713 | 15073846, 16360296, 17289881, 21731849 | |
| BCMO1 | 6.5 | 53 | 7 | 23803888 | | |
| C16orf46 | 2.2 | 53 | 7 | | | |
| GAN | 5.1 | 53 | 7 | | | |
| GCSH | 1.9 | 53 | 7 | | | |
| HSD17B2 | 2.6 | 53 | 7 | | 25929810 | |
| PKD1L2 | 6.9 | 53 | 7 | | | |
| PLCG2 | 5.6 | 53 | 7 | | | |
| HSDL1 | 2.0 | 54 | 3 | | | |
| LRRC50 | 2.4 | 54 | 3 | | | |
| MBTPS1 | 2.7 | 54 | 3 | | | |
| ATP2C2 | 3.6 | 55 | 3 | | | |
| KIAA1609 | 1.9 | 55 | 3 | | | |
| WFDC1 | 2.3 | 55 | 3 | 18842679, 19468830 | 10967136, 12032731, 15305341 | |
| CRISPLD2 | 5.4 | 56 | 5 | | | |
| KIAA0513 | 2.1 | 56 | 5 | | | |
| KLHL36 | 1.8 | 56 | 5 | | | |
| USP10 | 2.3 | 56 | 5 | 24332849, 25168367 | 16773218 | 24343337 |
| ZDHHC7 | 2.5 | 56 | 5 | | | |
| C16orf74 | 2.3 | 57 | 8 | | 21203532 | |
| COX4I1 | 2.6 | 57 | 8 | | | |
| COX4NB | 2.5 | 57 | 8 | | | |
| FOXF1 | 2.2 | 57 | 8 | 24186199 | 23103611 | 20145151, 20587515, 23864317 |
| GINS2 | 2.1 | 57 | 8 | 21082043, 24273454 | 24137407, 25348432 | |
| IRF8 | 2.5 | 57 | 8 | 23308054 | 24091328 | 17409439, 19074829, 24175153 |
| KIAA0182 | 2.0 | 57 | 8 | | | |
| MTHFSD | 2.4 | 57 | 8 | | | |
| BANP | 5.9 | 58 | 13 | 17668048, 25086032 | | 20709157, 18981184, 18822384 |
| C16ORF85 | 2.1 | 58 | 13 | | | |
| CA5A | 6.4 | 58 | 13 | | | |
| CYBA | 2.9 | 58 | 13 | | | |
| IL17C | 1.8 | 58 | 13 | | | |
| JPH3 | 4.8 | 58 | 13 | | | |
| KLHDC4 | 2.5 | 58 | 13 | 27030985 | | |
| MVD | 2.3 | 58 | 13 | | | |
| RNF166 | 2.2 | 58 | 13 | | | |
| SLC7A5 | 4.7 | 58 | 13 | 21439283 | 23981989, 26244545 | |
| SNAI3 | 2.4 | 58 | 13 | | | |
| ZC3H18 | 2.1 | 58 | 13 | | | |
| ZFPM1 | 2.5 | 58 | 13 | | | |
| CDT1 | 2.0 | 59 | 2 | | 26408331 | 21159650 |
| FAM38A | 2.7 | 59 | 2 | 22792288 | | |
| CBFA2T3 | 1.9 | 60 | 3 | 12183414 | | 25749032 |
| GALNS | 2.3 | 60 | 3 | | | |
| TRAPPC2L | 1.9 | 60 | 3 | | | |
| ANKRD11 | 6.7 | 61 | 2 | 18840648 | | 21986947 |

TABLE 7-continued

Clump analysis of genes, including $Z_{genes}$ score, clump index, number of genes in clump and PubMed ID for metastasis function annotations, metastasis predictive biomarkers and metastasis in the article

| Gene | $Z_{genes}$ score | clump index | No. of genes in clump | Metastasis Function PubMed ID | Metastasis Predictive Biomarkers PubMed ID | Metastasis PubMed ID |
|---|---|---|---|---|---|---|
| CDH15 | 1.9 | 61 | 2 | | | 9615235 |
| FANCA | 1.9 | 62 | 4 | | | |
| SPIRE2 | 1.7 | 62 | 4 | | | |
| TCF25 | 2.1 | 62 | 4 | | | |
| TUBB3 | 2.6 | 62 | 4 | 25414139 | 24928347 | 20534991, 24053422 |
| AFG3L1 | 2.3 | 63 | 2 | | | |
| DEF8 | 1.9 | 63 | 2 | | | |
| DHX58 | 6.9 | 64 | 5 | | | |
| HSPB9 | 2.9 | 64 | 5 | | | |
| KAT2A | 3.2 | 64 | 5 | | | |
| KCNH4 | 3.8 | 64 | 5 | | | |
| RAB5C | 3.5 | 64 | 5 | | | |
| ASPSCR1 | 1.8 | 65 | 2 | | | |
| NOTUM | 2.7 | 65 | 2 | | | |
| DUS1L | 2.3 | 66 | 2 | | | |
| FASN | 3.0 | 66 | 2 | 18770866, 22266115, 22892389 | | 17882277 |
| DTNA | 2.2 | 67 | 2 | | | |
| NOL4 | 3.9 | 67 | 2 | | | |
| C19orf57 | 2.8 | 68 | 2 | | | |
| CC2D1A | 4.0 | 68 | 2 | | | |
| AR | 4.9 | 69 | 4 | | 7541709, 8604394 | 7723794, 11325816, |
| EDA2R | 2.0 | 69 | 4 | | | |
| HEPH | 1.8 | 69 | 4 | | | |
| OPHN1 | 5.8 | 69 | 4 | | | |
| ALCAM | 2.5 | NA | 1 | 16204050, 15140234 | 15509676, 10702391 | 9502422, 15986133, 16024937, 11206637, 18202807 |
| ANXA13 | 2.1 | NA | 1 | | 22294041 | 22559327 |
| ARHGEF10 | 2.9 | NA | 1 | | | 21412932 |
| ARHGEF5 | 2.7 | NA | 1 | | | 21525037 |
| ATP6V1C1 | 2.4 | NA | 1 | 24155651, 24454753 | 20404513 | 15558013, 19885577, 18638373, 19424568, 17467328 |
| BFSP2 | 2.4 | NA | 1 | | | |
| BLK | 2.1 | NA | 1 | | | |
| BOD1L | 2.4 | NA | 1 | | | |
| C13orf23 | 2.2 | NA | 1 | | | |
| C16orf80 | 2.2 | NA | 1 | | | |
| CCDC25 | 4.4 | NA | 1 | | 22202459 | |
| CD226 | 3.3 | NA | 1 | 24468679 | | 20008292 |
| CDH13 | 10.9 | NA | 1 | | | 11389090, 12067979, 16807071, 15245595, 20642860 |
| CDH17 | 2.8 | NA | 1 | 19676131, 20568120, 23298905, 23604127, 23554857 | 23326130, 22904132 | |
| CDH2 | 3.4 | NA | 1 | 19190132 | | 20848731 |
| CDH8 | 3.7 | NA | 1 | | | |
| CDYL2 | 2.5 | NA | 1 | | | |
| CLCNKB | 2.0 | NA | 1 | | | |
| CLDN3 | 2.6 | NA | 1 | 19208807 | | |
| CNGB1 | 1.8 | NA | 1 | | | |
| CNTNAP4 | 3.2 | NA | 1 | | | |
| COL11A1 | 1.9 | NA | 1 | | | 11375892, 19112599, 21047417 |
| COL12A1 | 1.8 | NA | 1 | 21462330 | | |
| COL19A1 | 3.4 | NA | 1 | | | |
| COL21A1 | 1.8 | NA | 1 | | | |

TABLE 7-continued

Clump analysis of genes, including $Z_{genes}$ score, clump index, number of genes in clump and PubMed ID for metastasis function annotations, metastasis predictive biomarkers and metastasis in the article

| Gene | $Z_{genes}$ score | clump index | No. of genes in clump | Metastasis Function PubMed ID | Metastasis Predictive Biomarkers PubMed ID | Metastasis PubMed ID |
|---|---|---|---|---|---|---|
| CTNNA2 | 1.8 | NA | 1 | | | 24100690 |
| CTSB | 2.8 | NA | 1 | 16707449, 20133781 | | |
| CYP7B1 | 1.7 | NA | 1 | | 17639508 | |
| DCC | 6.6 | NA | 1 | 26345965 | | 9387266 |
| DCHS2 | 2.8 | NA | 1 | | | 24898286 |
| DGKG | 1.9 | NA | 1 | | | |
| DIAPH3 | 3.3 | NA | 1 | 22593025 | | |
| DLGAP2 | 2.2 | NA | 1 | | | |
| DNAH2 | 1.8 | NA | 1 | | | |
| DOCK5 | 5.4 | NA | 1 | | | |
| DPYD | 2.9 | NA | 1 | | | |
| ENOX1 | 5.6 | NA | 1 | | | 21055930 |
| EPO | 2.0 | NA | 1 | | | 24497137 |
| FBXL18 | 1.9 | NA | 1 | | | |
| FBXL4 | 1.7 | NA | 1 | | | |
| FSTL5 | 2.2 | NA | 1 | | | |
| GABRA2 | 2.3 | NA | 1 | | | |
| GAS8 | 2.9 | NA | 1 | | | |
| GHDC | 1.8 | NA | 1 | | | |
| GIGYF1 | 2.7 | NA | 1 | | | |
| GLG1 | 2.1 | NA | 1 | 25301730 | 19148506 | |
| GPC5 | 2.1 | NA | 1 | 23962560 | 26631038 | 24260047, 25093697, 25818666, 26098560 |
| GRID2 | 5.1 | NA | 1 | | | |
| GRK5 | 2.4 | NA | 1 | 22099983, 24755472 | | |
| GRM1 | 1.9 | NA | 1 | 18435704, 23065756, 24491800, 16040064 | | |
| GYS2 | 2.8 | NA | 1 | | | |
| HIP1 | 4.4 | NA | 1 | 12163454 | 21697888 | 26595459 |
| IMPA1 | 1.9 | NA | 1 | | | |
| IQCE | 1.8 | NA | 1 | | | |
| KALRN | 2.4 | NA | 1 | | | |
| KCNAB1 | 5.8 | NA | 1 | | | |
| KCTD8 | 2.8 | NA | 1 | | | |
| KIAA0196 | 2.6 | NA | 1 | | 16130124 | |
| LPHN3 | 2.5 | NA | 1 | | 23317273 | |
| LZTS1 | 2.0 | NA | 1 | 18559591 | 18686028, 24466374 | 11410489, 23695671, 24525428 |
| MACROD1 | 4.8 | NA | 1 | | | |
| MDGA2 | 2.8 | NA | 1 | | | |
| ME1 | 2.5 | NA | 1 | 25753478 | | |
| MECOM | 2.0 | NA | 1 | | | |
| MEF2C | 2.3 | NA | 1 | 19584403 | | |
| MEIS2 | 3.9 | NA | 1 | | | |
| MEPCE | 2.1 | NA | 1 | | | |
| MLYCD | 2.4 | NA | 1 | | | |
| MMP16 | 3.5 | NA | 1 | | | 21600596 |
| MTDH | 1.9 | NA | 1 | 19111877, 21976539, 21371176, 24099913 | | 19723648, 22031094, 23851509 |
| MTMR9 | 1.9 | NA | 1 | | | |
| MYLK | 2.8 | NA | 1 | | 15970650, 25179839 | |
| NALCN | 2.2 | NA | 1 | | | |
| NECAB2 | 2.0 | NA | 1 | | | |
| NFAT5 | 2.3 | NA | 1 | | | 19011242, 22266867, 25152734, 25311085, 26299924 |
| NIPAL2 | 1.9 | NA | 1 | | | |
| NKIRAS2 | 2.0 | NA | 1 | | | |
| NKX2-6 | 2.4 | NA | 1 | | | |

TABLE 7-continued

Clump analysis of genes, including $Z_{genes}$ score, clump index, number of genes in clump and PubMed ID for metastasis function annotations, metastasis predictive biomarkers and metastasis in the article

| Gene | $Z_{genes}$ score | clump index | No. of genes in clump | Metastasis Function PubMed ID | Metastasis Predictive Biomarkers PubMed ID | Metastasis PubMed ID |
|---|---|---|---|---|---|---|
| NLGN4Y | 2.4 | NA | 1 | | | |
| NRXN1 | 3.2 | NA | 1 | | | |
| NUS1 | 2.2 | NA | 1 | | | |
| PDS5B | 2.0 | NA | 1 | | 23850494 | |
| PKIA | 3.3 | NA | 1 | | | |
| PLCB1 | 1.9 | NA | 1 | | 26620550 | |
| PPM1L | 2.0 | NA | 1 | | | |
| PPP2R5B | 1.8 | NA | 1 | | | |
| PTK2 | 2.3 | NA | 1 | 14578863 | | |
| RAB9A | 3.7 | NA | 1 | | | |
| RALYL | 2.8 | NA | 1 | | | |
| RCOR2 | 1.7 | NA | 1 | | | |
| RFX1 | 2.2 | NA | 1 | | | |
| RGS22 | 2.7 | NA | 1 | 21533872 | | 26323264 |
| RIMS2 | 6.0 | NA | 1 | | | |
| RNF40 | 2.1 | NA | 1 | | 22155569 | |
| RPL7 | 2.3 | NA | 1 | | | |
| SF1 | 2.5 | NA | 1 | | 18824866 | |
| SLC26A7 | 2.2 | NA | 1 | | | |
| SLC9A9 | 2.7 | NA | 1 | | 25835977 | |
| SMARCB1 | 1.8 | NA | 1 | | 15899790, 16528370, 17040295, 21057957, 24503755 | |
| STAG3 | 2.4 | NA | 1 | | | |
| STAU2 | 4.6 | NA | 1 | | | |
| STIP1 | 1.8 | NA | 1 | | 24163084, 24488757 | |
| STK3 | 1.8 | NA | 1 | | | |
| STX1A | 2.2 | NA | 1 | | | |
| TBC1D10B | 1.8 | NA | 1 | | | |
| TBC1D22A | 4.6 | NA | 1 | | | |
| TCEB1 | 1.8 | NA | 1 | 18844214 | | 25676555 |
| TFDP1 | 2.3 | NA | 1 | 14618416 | 26684807 | 19995430 |
| TFE3 | 2.1 | NA | 1 | | 11438465, 12459622, 19606011, 20154303, 20871214 | |
| TICAM2 | 1.8 | NA | 1 | | | |
| TOX | 4.3 | NA | 1 | | | |
| TRDN | 3.0 | NA | 1 | | | |
| UBE2CBP | 2.8 | NA | 1 | | | |
| UBR5 | 2.2 | NA | 1 | | | |
| VPS13B | 3.9 | NA | 1 | | | |
| VPS13C | 1.8 | NA | 1 | | | |
| WDR59 | 2.1 | NA | 1 | | | |
| WDR7 | 2.0 | NA | 1 | | | |
| WWP2 | 1.8 | NA | 1 | 26662306 | | 23938591, 26783238 |
| XPO7 | 2.3 | NA | 1 | | | |
| YWHAG | 2.7 | NA | 1 | | | |
| ZBTB20 | 1.8 | NA | 1 | 25311537 | 21702992 | |
| ZFAT | 2.5 | NA | 1 | | | |
| ZFHX3 | 2.2 | NA | 1 | | | |
| ZHX2 | 2.6 | NA | 1 | | 17447851 | |
| ZSWIM4 | 2.8 | NA | 1 | | | |

Table 7 Continued
Table 7 Continued
Table 7 Continued
Table 7 Continued
Table 7 Continued Table 7 Continued
Table 7 Continued
Table 7 Continued
Table 7 Continued . . .

TABLE 8A

Genes in gene set for Metastasis ID

SEPT9, DEC1, ABAT, ABCA13, ABCA2, ABCA3, ABCB1, ABCB11, ABCB5, ABCC10, ABCC2, ABCC3, ABCC5, ABCD1, ABCD3, ABCE1, ABCG1, ABCG2, ABCG4, ABHD11, ABHD4, ABI1, ABI2, ABL1, ABL2, ABR, ACACA, ACCS, ACE, ACE2, ACHE, ACP1, ACP5, ACP6, ACPT, ACR, ACRBP, ACSS2, ACTB, ACTG2, ACTN4, ADAM10, ADAM19, ADAM29, ADAM33, ADAM7, ADAM8, ADAM9, ADAMTS1, ADAMTS12, ADAMTS13, ADAMTS18, ADAMTS19, ADAMTS5, ADAMTS8, ADIPOQ, ADIPOR1, ADIPOR2, ADM, ADO, ADORA2B, ADRA2A, ADRB2, ADRBK2, ADRM1, AES, AFAP1, AFAP1L1, AFM, AFP, AGA, AGBL2, AGK, AGR2, AGR3, AGXT, AHNAK, AHR, AHSG, AIM1, AIM2, AKAP12, AKAP13, AKIRIN2, AKR1B10, AKR1C1, AKR1C3, AKT1, AKT2, AKT3, ALDH1A1, ALDH1A3, ALDH3A1, ALK, ALCAM, ALKBH5, ALOX5, AMN, AMOTL1, AMOTL2, ANG, ANGPT2, ANGPTL2, ANGPTL3, ANLN, ANKRD11, ANO1, ANO9, ANP32A, ANTXR1, ANXA1, ANXA11, ANXA2, ANXA5, ANXA7, APAF1, APC, APCS, API5, APLP2, APOA1, APOBEC3G, APOH, APP, APPL1, AQP1, AQP3, AQP5, AQP6, AQP9, AR, ARAF, AREG, ARF1, ARF6, ARFGAP1, ARG1, ARHGAP21, ARHGAP5, ARHGAP6, ARHGEF3, ARHGEF5, ARHGEF7, ARID1A, ARID2, ARID3B, ARID4A, ARID4B, ARL4C, ARMC3, ARNT, ARPC1B, ARRB1, ARRDC3, ASAP1, ASCL2, ASIP, ASL, ASPM, ASS1, ATAD2, ATF1, ATF3, ATF4, ATF5, ATF6, ATG10, ATG16L1, ATG4A, ATG5, ATIC, ATM, ATOH1, ATOH8, ATP11A, ATP4A, ATP5J, ATP6AP2, ATP6V1C1, ATP7B, ATR, ATRX, AURKA, AUTS2, AVEN, AXIN2, AZGP1, B3GALNT1, B3GNT3, B3GNT7, B4GALNT2, BACE1, BACH1, BAD, BAG1, BAG2, BAG3, BAIAP2L1, BAMBI, BARD1, BARX2, BATF2, BAX, BAZ2A, BCAM, BCAR1, BCAR3, BCAS2, BCAS3, BCAT1, BCL10, BCL2, BCL2L12, BCL2L2, BCL3, BCL6, BCL9, BCL9L, BCOR, BCORL1, BCR, BDKRB2, BDNF, BET1, BHMT, BID, BIK, BIN1, BIRC3, BIRC5, BIRC6, BLCAP, BLID, BMF, BMP1, BMP10, BMP3, BMP4, BMP6, BMP7, BMPER, BMPR1A, BNC1, BNIP3L, BOLL, BOP1, BPI, BPTF, BRCA1, BRCA2, BRCC3, BRD4, BRD8, BRE, BRF2, BRIP1, BRMS1, BRMS1L, BRSK2, BST2, BTBD7, BTC, BTG1, BTG2, BTG3, BTK, BTLA, BTRC, BUB1, BUB1B, BVES, C10orf10, C19orf48, C1orf61, C2orf40, C3, C5, C6, C6orf106, C7, C8orf44, C9, CA2, CA9, CACNA2D3, CACYBP, CAD, CADM1, CALU, CAMK2N1, CAMP, CAMSAP1, CANT1, CAPZA1, CARD10, CARM1, CARS, CASK, CASP4, CASP6, CASP8, CASR, CASS4, CAV1, CBL, CBX2, CBX4, CBX5, CBX7, CBX8, CCDC34, CDC6, CCDC67, CCDC8, CCL1, CCL11, CCL13, CCL14, CCL17, CCL18, CCL19, CCL2, CCL20, CCL21, CCL22, CCL4, CCL5, CCL7, CCL8, CCNA2, CCNB1, CCNE1, CCNG2, CCNH, CCNY, CCR1, CCR3, CCR4, CCR6, CCR7, CCR9, CCRL2, CCT2, CD109, CD14, CD163, CD163L1, CD164, CD1A, CD1C, CD1D, CD2, CD200, CD226, CD244, CD248, CD27, CD274, CD33, CD36, CD38, CD4, CD40, CD46, CD47, CD48, CD53, CD55, CD58, CD63, CD69, CD70, CD74, CD81, CD82, CD86, CD9, CD93, CD96, CD99, CDA, CDC14A, CDC20, CDC25A, CDC25B, CDC25C, CDC37, CDC42, CDC6, CDC7, CDC73, CDCA5, CDCA7L, CDCA8, CDCP1, CDH1, CDH13, CDH17, CDH2, CDH22, CDK2AP1, CDK3, CDK4, CDK5, CDK5RAP3, CDK6, CDK7, CDK8, CDKN1A, CDKN1C, CDKN2A, CDKN2B, CDKN3, CDT1, CDX1, CDX2, CEACAM1, CEACAM5, CEP55, CEP70, CES2, CFL1, CFTR, CGA, CHAD, CHAT, CHD1, CHD1L, CHD5, CHD8, CHEK1, CHEK2, CHGB, CHI3L1, CHL1, CHML, CHRM3, CHRNA1, CHRNA3, CHST11, CIAPIN1, CIITA, CISD2, CISH, CITED1, CITED2, CIZ1, CKAP2, CKAP4, CKB, CLC, CLCA1, CLCA2, CLCA4, CLDN10, CLDN11, CLDN16, CLDN3, CLEC3A, CLEC3B, CLEC5A, CLIC4, CLOCK, CLPTM1L, CLU, CMTM3, CMTM8, CNN3, CNOT7, CNTF, CNTN1, COIL, COL11A1, COL18A1, COL1A1, COL1A2, COL3A1, COL4A2, COL5A1, COL5A2, COL6A1, COMMD1, COMT, CORT, COTL1, COX7A2, CP, CPA4, CPE, CPEB4, CPM, CPNE3, CPOX, CPS1, CPSF2, CPT1A, CPZ, CR1, CRABP1, CRCT1, CREB1, CREB3, CREB3L1, CREB3L2, CREB5, CREBBP, CREBZF, CRH, CRHR1, CRHR2, CRIM1, CRISP3, CRK, CRKL, CRNN, CRP, CRTC1, CRTC3, CRX, CS, CSE1L, CSF1, CSF2, CSK, CSMD1, CSNK1A1, CSPG4, CST6, CST7, CTAG2, CTBP1, CTBP2, CTCF, CTCL, CTGF, CTHRC1, CTLA4, CTNNA1, CTNNB1, CTNND1, CTTN, CUEDC2, UL4A, CUX1, CX3CL1, CX3CR1, CXCL1, CXCL10, CXCL11, CXCL12, CXCL13, CXCL14, CXCL17, CXCL2, CXCL3, CXCL5, CXCL6, CXCL9, CXCR4, CXCR5, CXCR6, CXXC4, CXXC5, CYB5A, CYB5D2, CYFIP1, CYHR1, CYLD, CYP17A1, CYP19A1, CYP1A1, CYP1B1, CYP24A1, CYP26A1, CYP27A1, CYP2A6, CYP2B6, CYP2C8, CYP2E1, CYP2J2, CYP2R1, CYP39A1, CYP3A4, CYP3A43, CYP3A5, CYP4F8, CYR61, DAB1, DAB2, DAB2IP, DACH1, DACH2, DACT1, DACT2, DAND5, DAP, DAP3, DBF4, DBN1, DCC, DCK, DCLK1, DCN, DCT, DCTN1, DCUN1D1, DCX, DCXR, DDB2, DDC, DDIT3, DDR2, DDT, DDX1, DDX11, DDX20, DDX27, DDX43, DEDD, DEK, DEPDC1B, DES, DFNA5, DGCR6, DGCR6L, DGCR8, DHCR24, DHFR, DHRS7, DHX32, DIAPH1, DIAPH3, DICER1, DIO3, DIRAS1, DIRAS3, DIS3, DIXDC1, DKK1, DKK2, DLC1, DLD, DLEC1, DLG5, DLK1, DLK2, DLL4, DLX2, DLX5, DMGDH, DMP1, DNAJA1, DNAJB1, DNAJC13, DNM3, DNMT1, DNMT3A, DOCK1, DOCK2, DOCK3, DOCK4, DOCK5, DOCK8, DOT1L, DPF3, DPH3, DPP4, DPPA2, DPYD, DR1, DRD2, DSC1, DSG1, DSG3, DTX3L, DUOX2, DUSP1, DUSP4, DUSP6, DYRK1B, DYRK2, E2F1, E2F2, E2F3, E2F4, E2F5, E2F6, EBAG9, EBF2, EBP, ECD, ECH1, ECM1, ECT2, EDIL3, EDNRA, EDNRB, EEF1A2, EFEMP1, EFHD2, EFNA1, EFNA3, EFNB2, EGF, EGFL7, EGFR, EGR1, EGR3, EHD1, EHMT1, EI24, EIF3A, EIF3E, EIF3H, EIF3I, EIF4E, EIF5A2, EIF6, ELAC2, ELAVL1, ELF3, ELF5, ELMO2, ELP3, ELOVL6, EMILIN1, EMP2, EMX2, ENAH, ENG, ENO1, ENPP2, ENTPD5, EP300, EPAS1, EPB41L3, EPC1, EPCAM, EPHA1, EPHA2, EPHA3, EPHA4, EPHA6, EPHA7, EPHA8, EPHB2, EPHB3, EPHB4, EPHB6, EPHX2, EPO, EPS15, EPS8, EPSTI1, ERBB3, ERBB4, ERC1, ERCC1, ERCC2, ERCC3, ERCC5, ERG, ERGIC1, ERGIC3, ERP29, ESD, ESPL1, ESPN, ESR1, ESR2, ESRP1, ETS1, ETV1, ETV4, ETV5, ETV6, EVI5, EVL, EVX1, EWSR1, EXO1, EXT1, EXTL3, EYA1, EYA2, EYA4, EZH2, EZR, F10, F11, F2, F5, F8, F9, FABP1, FABP4, FABP5, FABP7, FADD, FAF1, FAIM2, FAM107A, FAM120A, FAM129B, FAM134B, FAM20C, FAM3B, FAM3C, FAM83D, FANCA, FANCC, FANCD2, FANCF, FAP, FAS, FASN, FASTKD2, FAT4, FBN1, FBN2, FBXL5, FBXO11, FBXO32, FBXO4, FBXO45, FBXW7, FCN2, FDPS, FECH, FEM1A, FER, FEV, FEZ1, FEZF1, FGD4, FGF1, FGF10, FGF14, FGF18, FGF2, FGF23, FGF3, FGF4, FGF5, FGF7, FGF8, FGF9, FGFBP1, FGFR1, FGFR2, FGFR3, FGFR4, FGG, FGR, FH, TABLE 8A-continued Genes in gene set for Metastasis ID FHIT, FHL1, FHL2, FHOD1, FHOD3, FJX1, FKBP14, FKBPL, FLI1, FLNA, FLOT2, FLT1, FLT3, FLT4,
FMNL2, FMNL3, FN1, FNDC3B, FOSB, FOXA1, FOXA2, FOXC1, FOXC2, FOXD3, FOXE1, FOXF1,
FOXF2, FOXG1, FOXH1, FOXJ1, FOXJ3, FOXL1, FOXL2, FOXM1, FOXO1, FOXO3, FOXO4,
FOXP1, FOXP2, FOXP3, FOXQ1, FOXR2, FRAS1, FRAT1, FRMD4A, FRY, FRYL, FSCN1, FSHR,
FST, FSTL1, FURIN, FUS, FUT3, FUT4, FUT5, FUT8, FXYD3, FXYD5, FXYD6, FYN, FZD1, FZD2,
FZD5, FZD8, G3BP1, GAB1, GAB2, GABARAPL1, GABRP, GADD45A, GADD45G, GAK, GAL,
GAL3ST2, GALC, GALNT14, GALNT2, GALNT3, GALNT9, GAN, GAS1, GAS6, GAS8, GAST,
GATA2, GATA4, GATA5, GATA6, GBP1, GBP2, GBX2, GC, GCG, GCKR, GDF15, GDF2, GDF3,
GDNF, GEM, GEMIN5, GFAP, GFI1, GGH, GHRH, GIP, GIPC1, GIT1, GJA3, GJB5, GKN1, GLA, GLB1,
GLE1, GLI1, GLI2, GLIPR1, GLO1, GMDS, GNA13, GNA15, GNAI2, GNAI3, GNAQ, GNAS, GNE,
GNG2, GNRH1, GOLPH3, GP2, GPC5, GPI, GPNMB, GPR171, GPR18, GPR32, GPR34, GPR39,
GPR55, GPR87, GPRC5A, GPX2, GPX3, GRB14, GRB2, GRHL2, GRHL3, GRIN2A, GRK5,
GRK6, GRM1, GRM4, GRM5, GRPR, GSC, GSN, GSPT1, GSTM3, GSTP1, GTSE1, GUCY2C,
GUK1, H3F3A, HABP2, HACE1, HADHA, HAO2, HAPLN3, HAS1, HAS2, HAX1, HBD, HBEGF, HBP1,
HCCS, HDAC1, HDAC2, HDAC4, HDAC6, HDAC7, HDAC8, HDGF, HECTD1, HECTD2, HELLS,
HEPACAM, HERC5, HES1, HES5, HEXA, HEXIM1, HEY1, HFE, HGS, HHIP, HIF1A, HINT1, HIP1,
HIPK1, HIPK2, HIRA, HJURP, HK1, HK3, HLTF, HMGA1, HMGA2, HMGB3, HMGCR, HMGCS2,
HMGN1, HMGN5, HMMR, HN1, HNF1A, HNF4A, HNRNPA2B1, HOMER1, HOOK1, HOPX, HOXA1,
HOXA11, HOXA13, HOXA5, HOXA9, HOXB2, HOXB9, HOXC11, HPD, HPGD, HPR, HPSE, HR,
HRG, HS3ST2, HSD17B2, HSD3B1, HSF1, HSP90B1, HSPA14, HSPA2, HSPA9, HSPB8, HTATIP2,
HTRA1, HTRA2, HTRA3, HTT, HUNK, HUWE1, HYOU1, IAPP, ICMT, ID1, ID2, ID3, ID4, IDH1, IDH2,
IDO1, IER2, IFI27, IFIT2, IFIT3, IFNG, IGF1R, IGF2, IGF2BP1, IGF2BP2, IGF2BP3, IGFBP1, IGFBP2,
IGFBP3, IGFBP5, IGFBP7, IGFBPL1, IKBKB, IKZF1, IL10, IL13, IL17A, IL17F, IL18, IL1A, IL1R1,
IL23R, IL24, IL33, IL4, IL6R, IL7, ILK, IMP3, IMPACT, INA, ING1, ING2, ING3, ING5, INHBA, INSIG2,
INSM1, IQGAP1, IQGAP2, IRAK1, IRF8, IRX2, IRX5, ITGA2, ITGA3, ITGA5, ITGA7, ITGA8, ITGA9,
ITGAV, ITGB1, ITGB3, ITGB4, ITGB8, ITGBL1, ITIH5, JAG1, JAG2, JAK1, JAK2, JAK3, JAZF1,
JMJD6, JUN, KAT2A, KCNJ1, KCNK9, KCNMA1, KCNQ1, KCNRG, KDM1A, KDM2A, KDM3A,
KDM4A, KDM4B, KDM4C, KDM5B, KDM5C, KDM6A, KDR, KEAP1, KIAA0101, KIF11, KIF14, KIF15,
KIF18A, KIF1B, KIF26B, KIF2A, KIF3A, KIF3C, KIF5B, KIFC1, KIN, KIR2DL4, KISS1, KIT, KITLG, KL,
KLB, KLF12, KLF15, KLF17, KLF2, KLF4, KLF5, KLF6, KLHDC4, KLK10, KLK14, KLK15, KLK3, KLK7,
KLK8, KLRG1, KMO, KPNA2, KPNB1, KRAS, KRT19, KRT20, KRT7, KY, LAMA4, LAMA5, LAMB1,
LAMB3, LAMB4, LAMC1, LAMC2, LAMP1, LAMP2, LAMP3, LAP3, LAPTM4B, LARP1, LARP7, LARS,
LASP1, LAT, LATS1, LATS2, LBH, LBX1, LCK, LCT, LDB1, LEMD3, LEP, LEPREL1, LETM1, LFNG,
LGALS3, LGALS3BP, LGALS9, LGI4, LGR5, LHCGR, LIF, LIFR, LIG4, LILRB1, LILRB2, LIMD2,
LIMK2, LIN28B, LMNA, LMO2, LMO4, LMO7, LMX1B, LOX, LOXL2, LPAR1, LPCAT1, LPHN3, LPIN2,
LPP, LRG1, LRP1, LRP1B, LRP5, LRP6, LRP8, LRPPRC, LRRC3B, LRRC4, LRRFIP1, LSAMP,
LSM1, LSP1, LTBP4, LXN, LY75, LYAR, LYN, LZTFL1, LZTS1, MACROD2, MADD, MAGEA1,
MAGEC2, MAGED4B, MAGI1, MAK, MAL, MAL2, MALL, MALT1, MAML1, MAML2, MAOA, MAP1B,
MAP1S, MAP2, MAP2K1, MAP2K4, MAP3K1, MAP3K2, MAP3K7, MAP3K8, MAP3K9, MAP4K3,
MAP4K4, MAPK1, MAPK8, MAPKAPK2, MAPT, MARCKS, MARCO, MARK4, MARVELD3, MAS1,
MAT2A, MAT2B, MAX, MB, MBD1, MBD2, MBD4, MBP, MCC, MCM2, MCM4, MCRS1, MDM4, ME1,
MED1, MED12, MED19, MED27, MEF2C, MEF2D, MEIS1, MEMO1, MEN1, MEST, MET, METTL13,
MFAP3L, MFSD2A, MGA, MGAT1, MGAT3, MGMT, MGST1, MIA, MIB1, MICAL2, MIF, MINA, MIP,
MITF, MKL1, MLF2, MLN, MME, MMP10, MMP11, MMP12, MMP13, MMP14, MMP16, MMP28,
MMP7, MMP9, MNT, MOBP, MOS, MOV10, MPI, MPL, MPO, MPZL1, MRC2, MSC, MSH3, MSH6,
MSMB, MSN, MSRA, MST1R, MSX2, MT3, MT4, MTA1, MTA2, MTA3, MTAP, MTBP, MTDH,
MTHFD2, MTHFR, MTMR3, MTOR, MTRR, MTSS1, MTUS1, MUC13, MUC16, MUC17, MUC2,
MUC20, MUC4, MUC7, MUM1, MUSK, MUT, MUTYH, MVD, MVP, MX1, MX2, MXD1, MXI1, MXRA5,
MYBL2, MYC, MYCN, MYD88, MYEOV, MYH9, MYL9, MYLK, MYO5B, MYO9B, MZF1, NAB2,
NAMPT, NAP1L1, NAT1, NAT2, NAV1, NBN, NCALD, NCK1, NCK2, NCL, NCOA1, NCOA2, NCOA3,
NCOA5, NCOR1, NCOR2, NCSTN, NDC80, NDP, NDRG2, NDRG3, NDRG4, NDUFB6, NDUFB9,
NDUFS6, NEB, NEDD1, NEDD4, NEDD4L, NEDD8, NEFL, NEIL1, NEIL2, NEK2, NEK6, NEK7, NES,
NET1, NETO2, NEU3, NEUROD1, NF1, NFAT5, NFATC2, NFIB, NFKB1, NFKBIA, NGF, NGFR, NHS,
NIPSNAP1, NISCH, NKD1, NKD2, NKTR, NLK, NLRP1, NLRP3, NME1, NME4, NME6, NMI, NMU,
NNAT, NNT, NOB1, NOD1, NOD2, NODAL, NOG, NOP14, NOS1, NOS2, NOS3, NOTCH1, NOTCH3,
NOTCH4, NOV, NOX1, NOX4, NPAS2, NPC1, NPL, NPM1, NPS, NPY, NPY1R, NQO2, NR0B1,
NR1D1, NR1I2, NR1I3, NR2F1, NR2F2, NR3C2, NR4A2, NR4A3, NR5A2, NR6A1, NRAS, NRK, NRL,
NT5E, NTRK1, NTRK3, NTS, NTSR1, NUAK1, NUCB2, NUCKS1, NUMB, NUP88, NUSAP1, OAT,
ODAM, ODF4, OLA1, OLFM4, OLIG1, OLIG2, ONECUT2, ORAI1, ORAOV1, OSM, OSMR, OTC, OTP,
OTUB1, OTUD3, P4HA1, P4HA2, PABPC1, PACRG, PADI4, PAFAH1B1, PAH, PAK2, PAK3, PAK4,
PAK6, PALB2, PAM, PARD3, PARG, PARP1, PARVA, PARVB, PAX3, PAX4, PAX5, PAX6, PAX7,
PAX8, PBK, PBRM1, PBX3, PC, PCBP1, PCBP2, PCDH10, PCDH9, PCK2, PCNA, PDC, PDCD4,
PDCD5, PDCD6, PDCL3, PDF, PDGFB, PDGFRA, PDGFRB, PDIA3, PDK3, PDLIM2, PDLIM5,
PDPN, PDSS2, PDX1, PEBP1, PEG10, PELP1, PER1, PER2, PERP, PFKFB2, PFKFB3, PFN2, PGC,
PGF, PGK1, PGRMC2, PHF10, PHF20, PHF8, PHIP, PHLDA1, PHLPP1, PHLPP2, PHOX2B, PIAS1,
PICK1, PIGF, PIGR, PIGS, PIEZO1, PIK3C2G, PIK3CA, PIK3CB, PIK3CD, PIK3CG, PIK3R1, PIK3R3,
PIKFYVE, PIN1, PINK1, PIP4K2B, PIR, PITPNC1, PITX1, PITX2, PIWIL1, PIWIL2, PIWIL4, PKN1,
PKP1, PKP2, PLA2G16, PLA2G7, PLAC1, PLAG1, PLAGL1, PLAU, PLAUR, PLCE1, PLCG1, PLD2,
PLEKHA5, PLK1, PLOD2, PLS3, PLXDC1, PLXNA2, PMAIP1, PMEPA1, PML, PMP22, PMS2,
PNLIPRP3, POLB, POLE, POLI, POLR2A, POMC, PON1, POSTN, POT1, POU2F1, POU3F2,
POU3F3, PPA1, PPARG, PPM1A, PPM1B, PPM1D, PPM1F, PPM1H, PPP1CA, PPP1R13L,
PPP1R3B, PPP2CA, PPP2R2C, PRAME, PRC1, PRDM10, PRDM14, PRDM5, PRDX1, PRDX4,
PRDX6, PREP, PAG1, PTK2B, PREX2, PRICKLE1, PRKAA1, PRKAR1A, PRKCD, PRKCDBP,
PRKCI, PRKCZ, PRKD1, PRKD2, PRKX, PRL, PRMT1, PRMT2, PRMT5, PRMT6, PRMT7, PRNP,
PROK1, PROM1, PROX1, PRR15, PRSS3, PRUNE, PRUNE2, PRX, PSAT1, PSCA, PTBP2, PTCH1,
PTEN, PTER, PTGIS, PTGS2, PTH, PTH1R, PTHLH, PTK6, PTK7, PTOV1, PTP4A1, PTP4A3,
PTPN12, PTPN13, PTPN14, PTPN4, PTPRF, PTPRG, PTPRT, PTS, PTTG1IP, PTX3, PVR, PYY,
QKI, QRFP, RAB11A, RAB14, RAB17, RAB1A, RAB22A, RAB25, RAB27B, RAB32, RAB3D, RAB40B, TABLE 8A-continued Genes in gene set for Metastasis ID RAB40C, RAB5C, RABL3, RAC1, RAC2, RACGAP1, RAD18, RAD21, RAD50, RAD51, RAD52,
RAD54B, RAF1, RAI2, RALA, RALB, RALBP1, RALY, RAMP3, RAN, RANGAP1, RAP1A, RAP1B,
RAP1GAP, RAP2A, RAP2B, RAPGEF2, RAPH1, RARB, RARRES1, RASA1, RASAL1, RASAL2,
RASGRF1, RASGRF2, RASGRP1, RASGRP3, RASSF1, RASSF3, RASSF7, RASSF8, RB1,
RB1CC1, RBBP4, RBBP6, RBBP8, RBM3, RBM47, RBM5, RBP1, RBP2, RBX1, RCAN3, RD3, REG4,
RELA, REPS2, RERG, RET, REV3L, RFC1, RFX6, RFXAP, RGMB, RGS1, RGS16, RGS17, RGS2,
RGS22, RGS6, RGSL1, RHBDD2, RHO, RHOB, RHOBTB2, RHOC, RHOD, RHOG, RHOJ, RHOT1,
RHOU, RIN1, RIOK3, RIPK1, RIPK2, RIPK3, RLF, RNASEL, RND3, RNF111, RNF13, RNF180, RNF2,
RNF4, RNF40, RNF43, RNH1, ROBO1, ROBO3, ROBO4, ROCK1, ROCK2, ROR1, ROR2, RORA,
RP1, RPA1, RPE, RPL15, RPL26, RPL39, RPL41, RPL7, RPN2, RPS12, RPS3, RPS6KB1, RPSA,
RRBP1, RRM1, RRM2, RRP1B, RSPO2, RTKN, RUFY3, RUNX1, RUNX1T1, RUNX2, RUNX3,
RXFP1, RXRA, RYBP, S100A11, S100A2, S100A6, S100A7, S100A8, S100A9, S100B, S100P,
S100PBP, S100Z, S1PR3, SAA2, SACS, SALL4, SAMD9, SARS, SART1, SART3, SASH1, SATB2,
SCAI, SCAMP1, SCARA5, SCGB2A2, SCN7A, SCRIB, SCUBE2, SCUBE3, SDC1, SDC2, SDC4,
SDCBP, SDHA, SDHC, SDPR, SEC14L2, SEC23A, SEC62, SEL1L, SELP, SEMA3E, SEMA3F, SEMA4C,
SEMA6D, SENP1, SENP2, SENP3, SERPINA1, SERPINA3, SERPINA5, SERPINB13,
SERPINB2, SERPINB3, SERPINB5, SETD2, SETDB1, SF3B1, SFPQ, SFRP1, SFRP2, SFRP4,
SGPP1, SGPP2, SGTA, SH2B1, SH3BGRL, SH3GL2, SH3GLB2, SH3PXD2B, SHB, SHE, SHH,
SHISA3, SHMT1, SHOC2, SHOX2, SI, SIAH2, SIN3A, SIPA1, SIRT1, SIRT2, SIRT3, SIX2, SIX3, SIX4,
SKA3, SKAP2, SKI, SKP1, SKP2, SLC19A1, SLC19A3, SLC22A17, SLC22A18, SLC25A1, SLC28A3,
SLC29A1, SLC29A3, SLC2A1, SLC38A1, SLC39A14, SLC5A8, SLC6A14, SLC7A11, SLC7A5,
SLCO1B1, SLCO1B3, SLIT3, SLITRK3, SLITRK6, SLK, SLN, SMAD1, SMAD2, SMAD3, SMAD4,
SMAD5, SMAD7, SMAP1, SMARCA4, SMARCA5, SMARCB1, SMARCC1, SMARCD1, SMC4, SMO,
SMR3A, SMS, SMURF1, SMURF2, SMYD2, SMYD3, SNAI2, SNAI3, SNAPIN, SND1, SNTB2, SNX6,
SNX9, SOCS1, SOCS2, SOCS3, SOD2, SOD3, SOHLH2, SOS1, SOST, SOX10, SOX11, SOX12,
SOX17, SOX2, SOX3, SOX4, SOX6, SOX7, SOX8, SOX9, SP1, SP100, SP3, SP6, SPAG5, SPAG9,
SPARC, SPARCL1, SPDEF, SPIN1, SPINT2, SPOCK1, SPOP, SPR, SPRED1, SPRR2A, SPRR3,
SPRY1, SPRY2, SPRY4, SPTAN1, SQLE, SQSTM1, SRC, SRD5A1, SRD5A2, SRF, SRPK1, SRRM4,
SSBP1, SSRP1, SST, SSTR2, SSTR3, SSTR5, SSX1, SSX2IP, ST13, SLC9A9, ST3GAL6,
ST6GALNAC2, STAG2, STARD10, STARD13, STAT1, STAT3, STAT4, STAT5B, STAT6, STC2, STEAP1,
STEAP2, STIM2, STIP1, STK33, STK39, STK4, STMN1, STRAP, STRN, STS, STX6, STYK1,
SUDS3, SUFU, SULF1, SULF2, SULT1E1, SUMO1, SUMO3, SUSD2, SUZ12, SVEP1, SYK, TAC1,
TACC2, TACC3, TACSTD2, TAGLN, TAGLN2, TANK, TARBP2, TAT, TBC1D16, TBK1, TBP, TBX2,
TBX21, TBX3, TBX4, TBX5, TBXAS1, TCEB1, TCF12, TCF21, TCF3, TCF4, TCF7, TCF7L2, TDGF1,
TDO2, TDP1, TDRD1, TEAD4, TEC, TEF, TEK, TERT, TES, TET1, TET2, TEX101, TF, TFAP2A,
TFAP2C, TFAP2E, TFCP2, TFEB, TFF1, TFF2, TFF3, TFG, TFPI, TFPI2, TG, TGFA, TGFB1, TGFBI,
TGFBR2, TGFBR3, TGIF1, TGM2, TGM3, THBS1, THBS4, THOC1, THRSP, THY1, TIAF1, TIAM2,
TIMELESS, TIMM17A, TIMP2, TIMP3, TIMP4, TJP1, TKTL1, TLE1, TLE4, TLN1, TLR3, TLR4, TLR5,
TLR7, TLR8, TLR9, TM4SF1, TM4SF5, TM9SF4, TMED3, TMEM100, TMEM127, TMEM14A,
TMEM174, TMEM207, TMEM25, TMEM33, TMEM45B, TMEM97, TMOD1, TMPRSS2, TMPRSS3,
TMPRSS4, TNFAIP1, TNFRSF10A, TNFRSF10B, TNFRSF1B, TNK2, TNS1, TNS3, TNS4, TOB1,
TOB2, TOM1, TOM1L1, TOMM34, TOP1, TOPBP1, TOX, TP53, TP53BP2, TP53INP1, TP63, TP73,
TPD52, TPM3, TPO, TPR, TRAF2, TRAF4, TRAF6, TREM2, TRH, TRIB1, TRIB2, TRIB3, TRIM16,
TRIM33, TRIM37, TRIM44, TRIM59, TRIM66, TRIM9, TRIT1, TRPA1, TRPC1, TRPC6,
TRPM2, TRPM7, TRPM8, TRPV1, TRPV5, TRPV6, TSC1, TSC2, TSG101, TSLP, TSPAN1,
TSPAN12, TSPAN7, TSPAN8, TSPAN9, TSPYL5, TSSC1, TTC4, TTF1, TTK, TTYH2, TUSC1,
TWIST1, TXN, TFE3, TRPS1, TUBB3, TUSC3, TYK2, TYMS, TYR, TYRO3, TYRP1, U2AF2, UBE2C,
UBE2D3, UBE2Q1, UBIAD1, UCHL1, UCN, UGT2B17, ULBP2, UNC5B, UPF1, USF1, USP10,
USP14, USP15, USP18, USP22, USP28, USP37, USP4, USP9X, UVRAG, VANGL2, VAPB, VASP,
VAV2, VAV3, VCAM1, VCP, VDAC1, VDR, VEGFC, VEZT, VGLL2, VHL, VIM, VIP, VPS25, VRK1,
VTCN1, VTI1A, VWF, WASF2, WBSCR22, WDR26, WEE1, WIF1, WIPI1, WIPI2, WISP1, WISP2, WISP3,
WNT10A, WNT10B, WNT11, WNT2, WNT3, WNT3A, WNT4, WNT5B, WNT6, WNT7A, WRN,
WT1, WTAP, WWP1, WWP2, WWTR1, XAF1, XBP1, XCR1, XG, XPA, XPO1, XPO5, XPO6, YBX1,
YTHDC2, YWHAG, YWHAH, YWHAZ, YY1, ZAP70, ZBED3, ZBTB16, ZBTB20, ZBTB7A, ZBTB8A,
ZEB2, ZFX, ZIC1, ZKSCAN3, ZMAT1, ZNF165, ZNF217, ZNF281, ZNF300, ZNF304, ZNF331, ZNF395,
ZNF419, ZNF444, ZNF488, WWOX Table 8A Continued . . .
Table 8A Continued . . .
Table 8A Continued . . .
Table 8A Continued . . .

TABLE 8B

Genes in gene set for metastasis function

ABCB1, ABCB5, ABCC3, ABCE1, ABCG2, ABL2, ABR, ACE2, ADAM10, ADAM19, ADAM8, ADAM9, ADAMTS1,
ADAMTS5, ADIPOR1, ADIPOR2, ADM, ADO, ADORA2B, ADRB2, AFAP1, AFAP1L1, AFP, AGR2, AHNAK,
AIM1, AKAP12, AKAP13, AKR1C3, AKT2, AKT3, ALDH1A1, ALDH1A3, ALK, AMOTL2, ANG, ANGPTL2,
AKT1ANO1, ANO9, ANXA1, ANXA11, ANXA7, APC, APLP2, AQP3, AQP5, AQP9, ARF6, ARID1A, ARID2, ARID3B,
ARID4A, ARRDC3, ATAD2, ATF3, AIF4, ATG4A, ATG5, ATM, ATOH1, ATOH8, ATP6AP2, ATP6V1C1, ATR,
AURKA, AXIN2, B3GNT7, B4GALNT2, BACE1, BAD, BAG3, BAMBI, BATF2, BAX, BCAR1, BCAS3, BCAT1,
BCL2, BCL2L2, BCL3, BCL6, BCL9, BDNFBIK, BIN1, BIRC5, BIRC6, BMP4, BMP7, BOLL, BPTF, BRCA1,
BRCA2, BRD4, BRD8, BRMS1, BTBD7, BTG1, BTG2, BTG3, BTK, BVES, C3, C5, C6, C8orf4, C9, CA2, CA9,
CACNA2D3, CACBP, CADM1, CALU, CAMP, CASP6, CBL, CBX7, CBX8, CCDC34, CCL17, CCL18, CCL19, TABLE 8B-continued Genes in gene set for metastasis function CCL2, CCL20, CCL21, CCL22, CCL5, CCL7, CCNE1, CCNG2, CCR1, CCR4, CCR6, CCR7, CCR9, CD164, CD36,
CD38, CD4, CD40, CD47, CD55, CD63, CD70, CD74, CD81, CD82, CD86, CD9, CD99, CDA, CDC20, CDC25A,
CDC25B, CDC25C, CDC37, C42, CDCP1, CDH1, CDH17, CDH22, CDK4, CDK5, CDK5RAP3, CDK6, CDK8,
CDKN1A, CDKN2A, CDX2, CEACAM1, CEACAM5, CFL1, CHD1L, CHEK1, CHI3L1, CHST11, CIAPIN1, CLCA1,
CLCA2, CLDN10, CLOCK, CLU, CMTM3, CNTN1, COIL, COMMD1, CP, CPE, CPT1A, CRCT1, CRHR2, CRK,
CRKL, CRP, CS, CSE1L, CSF1, CSK, CSPG4, CST6, CTBP1, CTBP2, CTGF, CTHRC1, CTLA4, CTTN, CUL4A,
CUX1, CX3CR1, CXCL1, CXCL10, CXCL12, CXCL13, CXCL14, CXCL17, CXCL3, CXCL5, CXCL6, CXCL9,
CXCR4, CXCR5, CXCR6, CYB5D2, CYLD, CYP1B1, CYP2E1, CYP2J2, CYP3A4, CYR61, DAB2IP, DACT2,
DAND5, DAP, DCC, DCLK1, DDR2, DDX11, DDX20, DEK, DES, DHRS7, DKK1, DKK2, DLL4, DNM3, DNMT1,
DNMT3A, DOCK1, DOT1L, DPH3, DPP4, DUSP1, DUSP6, DYRK1B, DYRK2, E2F1, E2F3, ECD, ECM1, ECT2,
EDIL3, EEF1A2, EFEMP1, EGF, EGFL7, EGFR, EGR1, EIF3I, EIF4E, EIF5A2, EIF6, EMILIN1, EMP2, ENAH,
ENG, ENO1, EPB41L3, EPCAM, EPHA2, EPHB2, EPHB4, EPHB6, ERBB3, ERBB4, ERCC1, ERCC2, ERCC3, ERG,
ERGIC1, ESR1, ETS1, ETV1, EXT1, EYA2, EZH2, F11, F6, F8, FABP7, FADD, FANCA, FANCC, FANCD2,
FAP, FAS, FASTKD2, FAT4, FBXL5, FBXO11, FBXW7, FGF10, FGF18, FGF2, FGFR1, FGFR2, FGFR3, FGFR4,
FH, FHIT, FHL1, FHL2, FJX1, FLI1, FLNA, FLOT2, FLT1, FN1, FOSB, FOXA1, FOXA2, FOXC1, FOXC2, FOXD3,
FOXL1, FOXM1, FOXO1, FOXO3, FOXO4, FOXP1, FOXP2, FOXP3, FOXO1, FRAT1, FSCN1, FSHR, FURIN,
FUS, FUT3, FUT4, FYN, FZD5, FZD8, GAB1, GAB2, GADD45A, GAL, GALNT14, GALNT2, GAS6, GATA6, GC,
GDNF, GEMIN5, GJA3, GKN1, GLB1, GLI1, GLI2, GLIPR1, GLO1, GNA13, GNAQ, GOLPH3, GPC5, GPI,
GPNMB, GPR171, GPR3P, GPR55, GPR87, GPX3, GRB14, GRB2, GRK6, GRM1, HABP2, HAS2, HBD, HBP1,
HDAC1, HDAC2, HDAC4, HDAC6, HES1, HES5, HEXA, HIF1A, HIPK2, HJURP, HMGA1, HMGA2, HMGB3,
HMMR, HNRNPA2B1, HOOK1, HOXA1, HOXA5, HOXA9, HOXB2, HOXB9, HPR, HRG, HS3ST2, HSPA14,
HTATIP2, HTRA1, HYOU1, ICMT, ID1, ID2, ID3, IDH2, IFIT2, IGF1R, IGF2, IGF2BP1, IGFBP1, IGFBP3, IGFBP5,
IGFBP7, IL13, ILK, IMP3, IMPACT, ING1, ING2, ING3, ING5, IQGAP1, IRAK1, IRX2, ITGA2, ITGA3, ITGA5, ITGAV,
ITGB1, ITGB3, JAG1, JAG2, JAK1, JAK2, JAK3, JMJD6, JUN, KCNJ1, KCNMA1, KDM2A, KDM4B, KDM5B, KDR,
KEAP1, KIF11, KIF14, KIF15, KIF2A, KIF3C, KISS1, KIT, KITLG, KL, KLF17, XLF2, KLF4, XLF5, KLF6, KPNA2,
KRAS, KRT19, KRT7, LAMB3, LAMC2, LAMP1, LAMP3, LAP3, LAPTM4B, LASP1, LATS1, LATS2, LIF, LIMK2,
LIN28B, LMX1B, LOX, LOXL2, LRP1, LRP1B, LRP5, LRPPRC, LRRC4, LSM1, LYN, LZTS1, MACROD2, MADD,
MAP2K4, MAP3K2, MAP3K9, MAP4K4, MAPK1, MAPKAPK2, MARCKS, MAX, MB, MBD2, MBP, MCM2, MDM4,
MED1, MED12, MED27, MEF2C, MEIS1, MET, MFAP3L, MGAT1, MGMT, MIA, MIB1, MIF, MIP, MITF, MKL1,
MLF2, MME, MMP10, MMP12, MMP13, MMP14, MMP28, MMP7, MMP9, MSC, MT3, MTA1, MTA2, MTA3, MTBP,
MTDH, MTMR3, MTOR, MTSS1, MTUS1, MUC16, MUC4, MUSK, MVD, MVP, MX1, MYC, MYCN, MYD88, MYH9,
MYD5B, NAP1L1, NAV1, NCK2, NCOA1, NDC80, NDRG2, NEDD1, NEDD4, NEDD4L, NET1, NF1, NFAT5, NGF,
NHS, NKD1, NKD2, NLK, NLRP3, NME1, NOB1, NODAL, NOG, NOTCH1, NOTCH3, NOV, NOX1, NOX4, NPM1,
NPS, NTSR1, NUAK1, NUMB, NUP88, OLA1, ORAI1, OSM, OTUB1, P4HA1, PAK2, PAK4, PALB2, PARP1,
PAX3, PAX7, RAX8, PBK, PC, PCBP1, PCNA, PDC, PDCD4, PDCD5. PDGFRA, PDK3, PDPN, PEG10. PELP1,,
PER2, PFKFB3, PGC, PHF8, PHLDA1, PIAS1, PICK1, PIGS, PIK3CA, PIKFYVE, PIN1, PIP4K2B, PIR, PIWIL1,
PIWIL2, PKN1, PLA2G16, PLAUR, PLD2, PLK1, PMAIP1, PMEPA1, PMP22, POLB, PPARG, PPP1CA, PRAME,
PRC1, PRDM14, PREX2, PRKCZ, PRXD1, PRL, PRMT1, PRMT5, PROK1, PROX1, PRSS3, PRUNE, PSCA,
PTEN, PTER, PTG82, PTH, PTK6, PTK7, PTP4A3, PTPN13, PVR, QKI, RAB17, RAB22A, RAB25, RAB27B,
RAB3D, RAB40B, RAB40C, RABL3, RAC1, RAC2, RACGAP1, RALA, RALB, RAMP3, RAN, RAP1A, RAP1B,
RAP1GAP, RAP2B, RASAL2, RASSF3, RB1, RBP2, RBX1, RCAN3, RET, RGMB, RGS16, RHBDD2, RHO,
RHOB, RHOBTB2, RHOC, RHOJ, RIN1, RIPK1, RIPK3, RNF111, RNF43, ROBO1, ROBO3, ROCK1, ROCK2,
ROR1, ROR2, RPA1, RPL39, RPS12, RPS3, RPS6KB1, RREB1, RRM1, RRM2, RRP1B, RSPO2, RUNX2, RUNX3,
RXFP1, S100A11, S100A2, S100A6, S100A7, S100A8, S100A9, S100B, S100P, S1PR3, SALL4, SART1, SASH1,
SATB2, SCAI, SCAMP1, SCRIB, SDC1, SERPINB2, SETDB1, SFRP1, SFRP2, SH3GL2, SHH, SHMT1, SI, SIAH2,
SIRT1, SIRT2, SKI, SKP2, SLC9A3, SLC38A1, SMAD1, SMAD2, SMAD3, SMAD4, SMAD7, SMO, SMYD3,
SNAI2, SND1, SNTB2, SOCS3, SOD2, SOD3, SOX10, SOX12, SOX17, SOX2, SOX4, SOX6, SOX7, SOX9, SP1,
SP3, SPAG5, SPAG9, SPARC, SPARCL1, SPDEF, SPOCK1, SPOP, SPRY1, SPRY4, SPTAN1, SQLE, SQSTM1,
SRC, SRD5A2, SRF, SRPK1, SRRM4, SSTR2, SSX2IP, STARD13, STAT1, STAT3, STAT5B, STIP1, STMN1,
STS, SULF1, SULF2, SUZ12, SYK, TACC3, TAGLN, TAT, TBK1,TBX2, TCEB1, TCF4, TCF7, TCF7L2, TDGF1,
TEAD4, TERT, TET1, TF, TFF1, TFF3, TFPI, TG, TGFB1, TGFBI, TGIF1, TGM2, THY1, TIMM17A, TIMP2, TKTL1,
TLR3; TLR4, TLR9, TM4SF1, TMED3, TMPRSS2, TMPRSS4, TNFAIP1, TNK2, TOB1, TOP1, TOPBP1, TP53,
TRAF2, TRAF4, TRAF6, TRIB3, TRIM59, TRPA1, TRPM7, TRPM8, TRPV6, TSC2, TSG101, TSPAN12, TSPAN8,
TSPAN9. TTYH2, TWIST1, TXN, TYR, UBE2Q1, UCHL1, UCN, UNC5B, USP10, USP15, USP18, USP22, USP37,
USP9X, UVRAG, VASP, VAV2, VAV3, VCP, VEGFC, VEZT, VHL, VIP, VRK1, VTCN1, WBSCR22, WDR26,
WEE1, WISP1, WNT10A, WNT10B, WNT3A, WNT5B, WT1, WTAP, WWP1, XAF1, XCR1, χPO1, YWHAZ,
YY1, ZBED3, ZBTB7A, ZEB2, ZFX, ZKSCAN3, ZNF217, ZNF300, ZNF304, ZNF488, ALCAM, AR, ASAP1, DACH1,
DLC1, PIEZO1, MMP16, PAG1, TUPS1, TUSC3, WWOX Table 8B Continued . . .

TABLE 8C

Genes in gene set for biomarker analysis

ABAT, ABCA13, ABCB1, ABCC2, ABCG2, ACE2, ACP1, ACTN4 ADAM10, ADAM8, ADAM9,
ADAMTS1, ADAMTS5, ADO, AFAP1, AFP, AGBL2, AGR2, AIM1, AKR1B10, AKT1, AKT2, ALDH1A1,
ALDH1A3, ALK, ALCAM, ANG, ANLN, ANXA1, ANXA2, APC, APOA1, APOBEC3G, AQP1, AQP3,
AQP5, AR, ARG1, ARHGEF7, ARID1A, ARPC1B, ASAP1, ASCL2, ASPM, ATAD2, ATF3, ATF5, ATM,
ATOH8, BAD, BAMBI, BARX2, BATF2, BAX, BCL10, BCL2, BCL2L12, BCL6, BCOR, BCORL1, BDNF,
BID, BIRC5, BMP4, BMP7, BMPR1A, BRCA1, BRCA2, BRE, BRMS1, BTBD7, BTC, BTG1, BTG3,
BVES, C10orf10, C3, C6orf106, CA9, CACBP, CAD, CADM1, CAMP, CASK, CASP8, CASR, CBX7,
CCL17, CCL19, CCL2, CCL20, CCL21, CCL4, CCL5, CCL7, CCNB1, CCNE1, CCNG2, CCNY, CCR6,,
CCR7, CCT2, CD109, CD14, CD163, CD1A, CD4, CD40, CD47, CD55, CD74, CD82, CD9, CDC20,
CDC25B, CDC25C, CDC42, CDC6, CDCP1, CDH1, CDH13, CDK4, CDK5, CDK8, CDKN2A, CDX2,
CEACAM1, CES2, CFL1, CHD1L, CHEK1, CHEK2, CHRM3, CHRNA3, CIAPIN1, CISH, CLDN16, TABLE 8C-continued Genes in gene set for biomarker analysis CLIC4, CLOCK, CLPTM1L, COIL, COL1A1, COL1A2, COMT, CP, CPE, CRK, CRKL, CRNN, CRP,
CRTC1, CRTC3, CSE1L, CSNK1A1, CSPG4, CTBP2, CTGF, CTHRC1, CTNNB1, CTTN, CX3CL1,
CX3CR1, CXCL1, CXCL10, CXCL12, CXCL14, CXCL5, CXCL9, CXCR4, CXCR6, CYB5A, CYP17A1,
CYP19A1, CYP1A1, CYP24A1, CYP2B6, CYP3A4, CYP3A5, CYR61, DAB2, DACH1, DACH2,
DACT2, DAND5, DAP, DCC, DCX, DDC, DDX1, DEC1, DEX, DES, DICER1, DIXDC1, DLC1, DLG5,
DLK1, DLL4, DLX2, DLX5, DPP4, E2F1, EBP, ECD, ECM1, ECT2, EDIL3, EEF1A2, EFEMP1, EGF,
EGR3, EGFL7, EGFR, EIF3E, EIF3I, EIF4E, EIF5A2, ENO1, EPAS1, EPCAM, EPHA2, EPHA3,
EPHA7, EPHB4, EPHB6, EPO, EPS15, EPS8, ERBB3, ERBB4, ERCC1, ERG, ERP29, ESR1, ESR2,
EVA2, EZH2, F2, FABP1, FABP4, FADD, FAM3C, FANCF, FAP, FAS, FBXO11, FBXW7, FER, FGF14,
FGF2, FGFBP1, FGFR1, FGFR2, FGFR3, FGFR4, FHIT, FHL1, FHL2, FKBPL, FLNA, FLT1, FLT3,
FLT4, FN1, FOXA1, FOXC1, FOXC2, FOXD3, FOXF2, FOXL1, FOXM1, FOXO3, FOXO4, FOXP1,
FOXP3, FOXQ1, FRAT1, FSCN1, FURIN, FZD1, GAB2, GAL, GALNT9, GAS6, GATA2, GATA5,
GATA6, GBP2, GC, GCG, GDF15, GGH, GIP, GIPC1, GLA, GLI1, GNAQ, GOLPH3, GPRC5A, GPX3,
GRB2, GRM4, GSTP1, GTSE1, HAPLN3, HDAC1, HDAC2, HDAC6, HDGF, HES1, HIF1A, HK1,
HMGA1, HMGA2, HMGB3, HNF1A, HOMER1, HOXA13, HOXA9, HOXB9, HPSE, HR, HSD3B1,
HSPA2, HTATIP2, HTR42, HTRA3, HUWE1, HYOU1, ID2, ID3, IGF1R, IGFBP7, IL10, IL13, ILK, IMP3,
IMPACT, ING3, IQGAP1, IQGAP2, IRX5, ITGA3, ITGA8, ITGB1, ITGB3, ITGB4, ITGBL1, JAK2,
JMJD6, JUN, KCNJ1, KDM3A, KDM5C, KDR, KEAP1, KIAA0101, KIF14, KIF18A, KIF26B, KIF2A,
KISS1, KIT, KLF17, KLF4, KLF6, KLK10, KLK3, KPNA2, KRAS, KRT7, LAMP3, LAPTM4B, LAT, LEP,
LETM1, LIFR, LIG4, LIN28B, LMO7, LOX, LOXL2, LRG1, LYN, LZTS1, MAGEC2, MAGI1, MAML2,
MAP4K3, MAP4K4, MARCKS, MAX, MB, MBP, MCM2, MET, MGMT, MGST1, MIA, MIB1, MIF, MIP,
MITF, MMP11, MMP13, MMP16, MMP14, MMP7, MMP9, MMPO, MSX2, MTA1, MTA2, MTA3, MTBP,
MTDH, MTHFD2, MTOR, MTSS1, MTUS1, MUC16, MUC2, MUC4, MVD, MVP, MYC, MYCN, MYD88,
MYH9, MZF1, NAT1, NCK1, NCK2, NCOA2, NCDA5, NCOR1, NCOR2, NCSTN, NDRG2, NDRG3,
NDRG4, NEDD4L, NEK2, NETO2, NEU3, NKD1, NKTR, NLK, NME1, NOB1, NOD2, NODAL,
NOTCH1, NOTCH3, NOTCH4, NOV, NPM1, NQD2, NR2F2, NR4A2, NRAS, NUCB2, NUCKS1, OAT,
OLA1, OLIG1, ORAI1, OTP, OTUB1, P4HA2, PAFAH1B1, PAK4, PARP1, PARVB, PAX3, PAX6,
PAX8, PBK, PBRM1, PBX3, PC, PCDH10, PCDH9, PCNA, PDCD4, PDCD6, PDGFRA, PEG10, PER1,
PER2, PFKPB2, PFN2PHIP, PHLDA1, PHLPP1, PHLPP2, PIGR, PIK3CA, PIK3CB, PIK3R1, PIP4K2B,
PITX2, PIWIL2, PLA2G16, PLAGL1, PLAUR, PML, POLE, POMC, PPARG, PPM1D, PRAME, PRDX1,
PRDX4, PRL, PROK1, PROM1, PROX1, PRSS3, PRUNE, PSCA, PTEN, PTGIS, PTGS2, PTK7,
PTOV1, PTP4A3, RAB25, RAB27B, RAC1, RACGAP1, RAD50, RAD51, RALBP1, RALY, RAN, RASGRP3,
RBM3, RBX1, REG4, RELA, REPS2, RET, RGS1, RGS6, RHO, RHOC, RIPK2, ROBO1, ROCK1,
ROCK2, ROR1, ROR2, RRM1, RUNX2, RUNX3, S100A11, S100A2, S100A6, S100A9, S100B,
S100P, SATB2, SCRIB, SCUBE2, SDC1, SDC2, SDHA, SELP, SEMA3F, SERPINB2, SETDB1,
SF3B1, SFRP1, SGTA, SH2B1, SIAH2, SIPA1, SIRT1, SIX3, SIX4, SKI, SKP2, SLC19A1, SLC9A9,
SLC22A18, SLC25A1, SLC29A3, SLCO1B1, SLCO1B3, SLN, SMAD1, SMAD2, SMAD3, SMAD4,
SMAD7, SMYD2, SMYD3, SNAI2, SOCS3, SOD2, SOX10, SOX11, SOX17, SOX2, SOX4, SOX7,
SOX8, SOX9, SP1, SPAG5, SPARC, SPARCL1, SRC, SRPK1, SST, STAG2, STARD10, STARD13,
STAT1, STAT3, STAT6, STC2, STIP1, ST8, STYK1, SULT1E1, SUZ12, SYK, TACC2, TACSTD2,
TAT, TBX2, TCF3, TEK, TFE3, TERT, TET1, TF, TFF3, TFPI, TGF81, TGFBI, TGM2, TGM3, THY1,
TIMM17A, TKTL1, TLR4, TMPRSS2, TMPRSS3, TMPRSS4, TP53, TPD52, TRAF2, TRAF6, TRPM7,
TRPS1, TSG101, TSPYL5, TUBB3, TWIST1, TYMS, UBE2C, UCN, USP10, USP14, USP22, USP9X,
VAV3, VDAC1, VHL, VIP, WNT10A, WNT10B, WNT11, WNT2, WNT7A, WWOX, WWP1,
XPA, XPO5, YY1, ZEB2, ZFX, ZMAT1, ZNF217

Table 8C Continued . . .

TABLE 9A

ROC-AUC comparisons of panMPS and other MPS versions developed by using subsets of genes based on $Z_{genes}$ score thresholds and clump representations.

| Distribution | No. of genes | No. of clumps | MSK_Prostate | Duke_Prostate | Montefiore_TNBC | MSK_Lung |
|---|---|---|---|---|---|---|
| *$Z_{genes}$ score ≥ 4 | 33 | 21 | 0.69 | 0.70 | 0.73 | 0.87 |
| $Z_{genes}$ score ≥ 4 | 43 | 21 | 0.68 | 0.73 | 0.77 | 0.88 |
| *$Z_{genes}$ score ≥ 3 | 68 | 43 | 0.71 | 0.70 | 0.73 | 0.93 |
| $Z_{genes}$ score ≥ 3 | 100 | 43 | 0.70 | 0.72 | 0.74 | 0.94 |
| panMPS | 295 | 67 | 0.71 | 0.72 | 0.75 | 0.94 |

*Only highest Zgenes-score gene in clump

TABLE 9B

Linear regression model ($r^2$) between panMPS and other MPS versions developed by using subsets of genes based on $Z_{genes}$ score thresholds and clump representations.

| Distribution | No. of genes | No. of clumps | MSK_Prostate | Duke_Prostate | Montefiore_TNBC | MSK_Lung |
|---|---|---|---|---|---|---|
| *$Z_{genes}$ score ≥ 4 | 33 | 21 | 0.89 | 0.87 | 0.83 | 0.83 |
| $Z_{genes}$ score ≥ 4 | 43 | 21 | 0.93 | 0.92 | 0.84 | 0.86 |
| *$Z_{genes}$ score ≥ 3 | 68 | 43 | 0.94 | 0.94 | 0.93 | 0.94 |
| $Z_{genes}$ score ≥ 3 | 100 | 43 | 0.97 | 0.97 | 0.94 | 0.96 |
| panMPS | 295 | 67 | 1 | 1 | 1 | 1 |

*Only highest $Z_{genes}$ score gene in clump

TABLE 10A

Clinical and histological characteristics of samples used to validate the panMPS model for metastatic outcome for prostate cancer

| | MSK Prostate CA | | Duke Prostate CA | | |
|---|---|---|---|---|---|
| | mPT | iPT | mPT | iPT | P |
| Outcome | | | | | |
| n | 25 | 260 | 37 | 39 | |
| Age | | | | | |
| Mean | 58.93 | 58.15 | 64.19 | 61.82 | 0.5 |
| Median | 59.47 | 58.13 | 64 | 62 | |
| Standard deviation | 7.23 | 6.82 | 6.48 | 8.41 | |
| Range | 46-71 | 37-75 | 47-77 | 46-77 | |
| Clinical stage | | | | | |
| T1C | 10 (3.51%) | 146 (51.22%) | 18 (23.68%) | 24 (31.57%) | $7.56 \times 18^{-8}$ |
| T2 | 11 (3.86%) | 106 (37.19%) | 9 (11.84%) | 4 (5.26%) | $3.86 \times 10^{-5}$ |
| T3 | 4 (1.40%) | 8 (2.81%) | 0 (0%) | 0 (0%) | |
| Path stage | | | | | |
| T2 | 7 (2.46%) | 156 (54.74%) | 6 (7.89%) | 9 (11.84%) | $1.53 \times 10^{-4}$ |
| T3 | 13 (4.56%) | 92 (32.28%) | 24 (31.57%) | 26 (34.21%) | $3.85 \times 10^{-6}$ |
| T4 | 5 (1.75%) | 12 (4.21%) | 7 (9.21%) | 4 (5.26%) | 0.12 |
| Biopsy Gleason score | | | | | |
| 3 | 0 (0%) | 0 (0%) | 0 (0%) | 1 (1.31%) | |
| 4 | 0 (0%) | 0 (0%) | 1 (1.31%) | 0 (0%) | |
| 5 | 0 (0%) | 2 (0.70%) | 0 (0%) | 4 (5.26%) | |
| 6 | 7 (2.46%) | 142 (49.82%) | 10 (13.51%) | 18 (23.68%) | $1.91 \times 10^{-5}$ |
| 7 | 12 (4.21%) | 92 (32.28%) | 14 (18.42%) | 12 (15.78%) | $1.19 \times 10^{-5}$ |
| 8 | 5 (1.75%) | 15 (5.26%) | 5 (6.57%) | 0 (0%) | 0.01 |
| 9 | 0 (0%) | 9 (3.16%) | 3 (3.94%) | 4 (5.26%) | 0.06 |
| 10 | 0 (0%) | 0 (0%) | 1 (1.31%) | 0 (0%) | |
| Path Gleason score | | | | | |
| 6 | 1 (0.35%) | 68 (23.86%) | 2 (2.63%) | 2 (2.63%) | 0.01 |
| 7 | 8 (2.81%) | 173 (60.70%) | 20 (26.31%) | 29 (38.16%) | $9.27 \times 10^{-10}$ |
| 8 | 6 (2.11%) | 10 (3.51%) | 2 (2.63%) | 3 (3.95%) | |
| 9 | 19 (6.66%) | 8 (2.81%) | 12 (15.785) | 5 (6.58%) | |
| 10 | 0 (0%) | 0 (0%) | 1 (1.31%) | 0 (0%) | |
| Preop PSA (ng/mL) | | | | | |
| Median | 8.49 | 5.6 | 7.5 | 7.3 | |
| <4 | 4 (1.40%) | 46 (16.14%) | 4 (5.26%) | 4 (5.26%) | |
| 4-10 | 10 (3.51%) | 163 (57.19%) | 16 (21.05%) | 27 (35.52%) | |
| >10 | 11 (3.86%) | 50 (17.54%) | 17 (22.36%) | 8 (10.52%) | |

P-values were determined by Wilcoxon Rank Sum Test and Fisher's Exact Test respectively for continuous and categorical variables for inter cohort significance.

TABLE 10B

Clinical and histological characteristics of samples used to validate the panMPS model for metastasis outcome for TNBC

| | Cohort Montefiore TNBC | |
|---|---|---|
| | mBC | iBC |
| Outcome | | |
| n | 28 | 13 |
| Age | | |
| Mean | 58.3 | 53 |
| Median | 61.5 | 49 |
| Standard deviation | 11.57 | 11.7 |
| Range | 35-82 | 34-74 |
| TNM Stage | | |
| T1 | 4 (9.75%) | 5 (12.19%) |
| T2 | 7 (17.07%) | 5 (12.19%) |
| T3 | 4 (9.75%) | 0 (0%) |
| T4 | 2 (4.88%) | 0 (0%) |

TABLE 10C

Clinical and histological characteristics of samples used to validate the panMPS model for metastasis outcome for TNBC

| | Cohort MSK Lung Adeno CA | |
|---|---|---|
| | mLA | iLA |
| Outcome | | |
| n | 23 | 10 |
| Sex | | |
| Male | 11 (26.83%) | 4 (9.76%) |
| Female | 12 (29.27%) | 6 (14.63%) |
| TNM Stage | | |
| 1B | 6 (14.63%) | 0 (0%) |
| 2 | 7 (17.07%) | 1 (2.44%) |
| 3 | 10 (24.39%) | 5 (12.20%) |
| 4 | 2 (4.88%) | 4 (9.76%) |

TABLE 11

AUC of Distribution of MPS genes based on lowest $Z_{genes}$ scores in clumps

| Distribution | No. of genes | No. of clumps | MSK_Prostate | Duke_Prostate | Montefiore_TNBC | MSK_Lung |
|---|---|---|---|---|---|---|
| | 33 | 21 | 0.67 | 0.67 | 0.78 | 0.87 |
| $Z_{genes}$ score ≥ 4 | 43 | 21 | 0.68 | 0.73 | 0.77 | 0.88 |
| | 68 | 43 | 0.69 | 0.69 | 0.75 | 0.93 |
| $Z_{genes}$ score ≥ 3 | 100 | 43 | 0.7 | 0.72 | 0.74 | 0.94 |
| *panMPS | 175 | 67 | 0.7 | 0.72 | 0.76 | 0.97 |
| panMPS | 295 | 67 | 0.71 | 0.72 | 0.75 | 0.94 |

*Only lowest Zgenes-score gene in clump

TABLE 12

$r^2$ of Distribution of MPS genes based on lowest Zgenes scores in clumps

| Distribution | No. of genes | No. of clumps | MSK_Prostate | Duke_Prostate | Montefiore_TNBC | MSK_Lung |
|---|---|---|---|---|---|---|
| | 33 | 21 | 0.75 | 0.57 | 0.67 | 0.59 |
| $Z_{genes}$ score ≥ 4 | 43 | 21 | 0.93 | 0.92 | 0.84 | 0.86 |
| | 68 | 43 | 0.81 | 0.64 | 0.73 | 0.71 |
| $Z_{genes}$ score ≥ 3 | 100 | 43 | 0.97 | 0.97 | 0.94 | 0.96 |
| *panMPS | 175 | 67 | 0.89 | 0.75 | 0.84 | 0.84 |
| panMPS | 295 | 67 | 1 | 1 | 1 | 1 |

*Only lowest $Z_{genes}$ score gene in clump

TABLE 13

| | MPS Genes | | | | | |
|---|---|---|---|---|---|---|
| index | gene | NYU_Z | NYU_dir | MSKs1_Z | MSKs1_dir | MSKs2_Z | MSKs2_dir |
| 1 | CLCNKB | NA | NA | NA | NA | 2.0 | 1 |
| 2 | ARHGEF10L | NA | NA | 2.1 | -1 | NA | NA |
| 3 | ACTL8 | NA | NA | 1.9 | -1 | NA | NA |
| 4 | DPYD | NA | NA | NA | NA | 2.9 | -1 |
| 5 | COL11A1 | NA | NA | NA | NA | 1.9 | -1 |
| 6 | NRXN1 | NA | NA | NA | NA | 3.2 | -1 |
| 7 | CTNNA2 | NA | NA | NA | NA | 1.8 | -1 |
| 8 | ALCAM | NA | NA | NA | NA | 2.5 | 1 |
| 9 | ZBTB20 | NA | NA | 1.8 | 1 | NA | NA |
| 10 | MYLK | NA | NA | 2.8 | 1 | NA | NA |
| 11 | KALRN | NA | NA | 2.4 | 1 | NA | NA |

TABLE 13-continued

| | | | MPS Genes | | | | |
|---|---|---|---|---|---|---|---|
| 12 | BFSP2 | NA | NA | 2.4 | 1 | NA | NA |
| 13 | SLC9A9 | NA | NA | 2.7 | 1 | NA | NA |
| 14 | KCNAB1 | NA | NA | 5.8 | 1 | NA | NA |
| 15 | PPM1L | NA | NA | 2 | 1 | NA | NA |
| 16 | MECOM | NA | NA | 2 | 1 | NA | NA |
| 17 | DGKG | NA | NA | 1.9 | 1 | NA | NA |
| 18 | TP63 | NA | NA | 3 | 1 | NA | NA |
| 19 | LEPREL1 | NA | NA | 2.6 | 1 | NA | NA |
| 20 | BOD1L | NA | NA | NA | NA | 2.4 | −1 |
| 21 | KCTD8 | NA | NA | NA | NA | 2.8 | −1 |
| 22 | GABRA2 | NA | NA | NA | NA | 2.3 | −1 |
| 23 | LPHN3 | NA | NA | NA | NA | 2.5 | −1 |
| 24 | GRID2 | NA | NA | NA | NA | 5.1 | −1 |
| 25 | DCHS2 | NA | NA | NA | NA | 2.6 | −1 |
| 26 | GLRB | NA | NA | NA | NA | 2.7 | −1 |
| 27 | GRIA2 | NA | NA | NA | NA | 2.3 | −1 |
| 28 | FSTL5 | NA | NA | NA | NA | 2.2 | −1 |
| 29 | CENPH | NA | NA | 1.9 | −1 | NA | NA |
| 30 | MRPS36 | NA | NA | 2.6 | −1 | NA | NA |
| 31 | CDK7 | NA | NA | 2.7 | −1 | NA | NA |
| 32 | CCDC125 | NA | NA | 2 | −1 | NA | NA |
| 33 | TAF9 | NA | NA | 2.6 | −1 | NA | NA |
| 34 | RAD17 | NA | NA | 2.6 | −1 | NA | NA |
| 35 | MARVELD2 | NA | NA | 3 | −1 | NA | NA |
| 36 | MEF2C | NA | NA | NA | NA | 2.3 | −1 |
| 37 | TICAM2 | NA | NA | NA | NA | 1.8 | −1 |
| 38 | COL21A1 | NA | NA | NA | NA | 1.8 | −1 |
| 39 | COL19A1 | NA | NA | NA | NA | 3.4 | −1 |
| 40 | COL12A1 | NA | NA | NA | NA | 1.6 | −1 |
| 41 | UBE2CBP | 2.8 | −1 | NA | NA | NA | NA |
| 42 | ME1 | 2.5 | −1 | NA | NA | NA | NA |
| 43 | MAP3K7 | NA | NA | NA | NA | 3.2 | −1 |
| 44 | EPHA7 | NA | NA | NA | NA | 1.8 | −1 |
| 45 | FBXL4 | NA | NA | NA | NA | 1.7 | −1 |
| 46 | SIM1 | NA | NA | NA | NA | 2.2 | −1 |
| 47 | ASCC3 | NA | NA | NA | NA | 1.8 | −1 |
| 48 | NUS1 | NA | NA | NA | NA | 2.2 | −1 |
| 49 | TRDN | NA | NA | NA | NA | 3.0 | −1 |
| 50 | UTRN | NA | NA | NA | NA | 2.3 | −1 |
| 51 | EPM2A | NA | NA | NA | NA | 2.4 | −1 |
| 52 | GRM1 | NA | NA | NA | NA | 1.9 | −1 |
| 53 | C6orf118 | NA | NA | NA | NA | 2.8 | −1 |
| 54 | PDE10A | NA | NA | NA | NA | 4.7 | −1 |
| 55 | IQCE | NA | NA | NA | NA | 1.8 | 1 |
| 56 | FBXL18 | NA | NA | NA | NA | 1.9 | 1 |
| 57 | STX1A | NA | NA | NA | NA | 2.2 | 1 |
| 58 | CLDN3 | NA | NA | NA | NA | 2.6 | 1 |
| 59 | EIF4H | NA | NA | NA | NA | 2.0 | 1 |
| 60 | LAT2 | NA | NA | NA | NA | 2.0 | 1 |
| 61 | RFC2 | NA | NA | NA | NA | 1.8 | 1 |
| 62 | CLIP2 | NA | NA | NA | NA | 3.1 | 1 |
| 63 | HIP1 | NA | NA | NA | NA | 4.4 | 1 |
| 64 | TMEM120A | NA | NA | NA | NA | 1.7 | 1 |
| 65 | STYXL1 | NA | NA | NA | NA | 2.3 | 1 |
| 66 | MDH2 | NA | NA | NA | NA | 2.0 | 1 |
| 67 | YWHAG | NA | NA | NA | NA | 2.7 | 1 |
| 68 | STAG3 | NA | NA | NA | NA | 2.4 | 1 |
| 69 | PILRB | NA | NA | NA | NA | 2.9 | 1 |
| 70 | PILRA | NA | NA | NA | NA | 1.9 | 1 |
| 71 | MEPCE | NA | NA | NA | NA | 2.1 | 1 |
| 72 | TSC22D4 | NA | NA | NA | NA | 2.1 | 1 |
| 73 | C7orf51 | NA | NA | NA | NA | 2.2 | 1 |
| 74 | AGFG2 | NA | NA | NA | NA | 2.3 | 1 |
| 75 | LRCH4 | NA | NA | NA | NA | 2.2 | 1 |
| 76 | FBXO24 | NA | NA | NA | NA | 2.5 | 1 |
| 77 | PCOLCE | NA | NA | NA | NA | 1.8 | 1 |
| 78 | MOSPD3 | NA | NA | NA | NA | 2.3 | 1 |
| 79 | TFR2 | NA | NA | NA | NA | 2.6 | 1 |
| 80 | ACTL6B | NA | NA | NA | NA | 1.7 | 1 |
| 81 | GIGYF1 | NA | NA | NA | NA | 2.7 | 1 |
| 82 | EPO | NA | NA | NA | NA | 2.0 | 1 |
| 83 | CPA2 | NA | NA | NA | NA | 2.1 | 1 |
| 84 | CPA4 | NA | NA | NA | NA | 1.9 | 1 |
| 85 | CPA5 | NA | NA | NA | NA | 2.8 | 1 |
| 86 | CPA1 | NA | NA | NA | NA | 2.1 | 1 |
| 87 | TSGA14 | NA | NA | NA | NA | 9.4 | 1 |
| 88 | MEST | NA | NA | NA | NA | 3.2 | 1 |
| 89 | COPG2 | NA | NA | NA | NA | 3.1 | 1 |

TABLE 13-continued

| | MPS Genes | | | | | | |
|---|---|---|---|---|---|---|---|
| 90 | ARHGEF5 | NA | NA | NA | NA | 2.7 | 1 |
| 91 | DLGAP2 | NA | NA | 2.2 | −1 | NA | NA |
| 92 | ARHGEF10 | NA | NA | 2.9 | −1 | NA | NA |
| 93 | MYOM2 | 2.1 | −1 | NA | NA | NA | NA |
| 94 | CSMD1 | NA | NA | NA | NA | 4.6 | −1 |
| 95 | MFHAS1 | 3.3 | −1 | NA | NA | NA | NA |
| 96 | ERI1 | 1.9 | −1 | NA | NA | NA | NA |
| 97 | TNKS | 4 | −1 | NA | NA | NA | NA |
| 98 | MSRA | 5.1 | −1 | NA | NA | NA | NA |
| 99 | C8orf16 | 2.2 | −1 | NA | NA | NA | NA |
| 100 | MTMR9 | 1.9 | −1 | NA | NA | NA | NA |
| 101 | BLK | 2.1 | −1 | NA | NA | NA | NA |
| 102 | GATA4 | 3.2 | −1 | NA | NA | NA | NA |
| 103 | NEIL2 | 2.7 | −1 | NA | NA | NA | NA |
| 104 | CTSB | 2.8 | −1 | NA | NA | NA | NA |
| 105 | C8orf79 | 2.9 | −1 | NA | NA | NA | NA |
| 106 | DLC1 | 6.5 | −1 | NA | NA | NA | NA |
| 107 | SGCZ | 4.7 | −1 | NA | NA | 3.5 | −1 |
| 108 | TUSC3 | 3.1 | −1 | NA | NA | NA | NA |
| 109 | MTMR7 | 3.7 | −1 | NA | NA | NA | NA |
| 110 | SLC7A2 | 4.1 | −1 | NA | NA | NA | NA |
| 111 | PDGFRL | 4.8 | −1 | NA | NA | NA | NA |
| 112 | MTUS1 | 3.6 | −1 | NA | NA | NA | NA |
| 113 | PCM1 | 1.7 | −1 | NA | NA | NA | NA |
| 114 | ASAH1 | 7.1 | −1 | NA | NA | NA | NA |
| 115 | NAT2 | 3.3 | −1 | NA | NA | NA | NA |
| 116 | PSD3 | 7.3 | −1 | NA | NA | NA | NA |
| 117 | SH2D4A | 2.9 | −1 | NA | NA | NA | NA |
| 118 | LZTS1 | 2 | −1 | NA | NA | NA | NA |
| 119 | XPO7 | 2.3 | −1 | NA | NA | NA | NA |
| 120 | FAM160B2 | 2.5 | −1 | 1.8 | −1 | NA | NA |
| 121 | NUDT18 | NA | NA | 2.3 | −1 | NA | NA |
| 122 | HR | NA | NA | 2.7 | −1 | NA | NA |
| 123 | REEP4 | NA | NA | 2.5 | −1 | NA | NA |
| 124 | LGI3 | NA | NA | 2 | −1 | NA | NA |
| 125 | BMP1 | NA | NA | 2.2 | −1 | NA | NA |
| 126 | PHYHIP | NA | NA | 2.2 | −1 | NA | NA |
| 127 | POLR3D | NA | NA | 2.7 | −1 | NA | NA |
| 128 | SLC39A14 | 1.8 | −1 | 2.2 | −1 | NA | NA |
| 129 | PPP3CC | 3.1 | −1 | 2.6 | −1 | NA | NA |
| 130 | SORBS3 | NA | NA | 3 | −1 | NA | NA |
| 131 | PDLIM2 | NA | NA | 2.9 | −1 | NA | NA |
| 132 | C8orf58 | NA | NA | 3 | −1 | NA | NA |
| 133 | KIAA1967 | 2.8 | −1 | 3.1 | −1 | NA | NA |
| 134 | BIN3 | 1.7 | −1 | 2.8 | −1 | NA | NA |
| 135 | EGR3 | NA | NA | 2 | −1 | NA | NA |
| 136 | RHOBTB2 | NA | NA | 1.7 | −1 | NA | NA |
| 137 | TNFRSF10D | 1.9 | −1 | NA | NA | NA | NA |
| 138 | TNFRSF10A | NA | NA | 2.2 | −1 | NA | NA |
| 139 | CHMP7 | NA | NA | 2.4 | −1 | NA | NA |
| 140 | LOXL2 | NA | NA | 1.9 | −1 | NA | NA |
| 141 | ENTPD4 | 2.7 | −1 | NA | NA | NA | NA |
| 142 | erw | 2.6 | −1 | NA | NA | NA | NA |
| 143 | NKX2-6 | 2.4 | −1 | NA | NA | NA | NA |
| 144 | DOCK5 | 5.4 | −1 | NA | NA | NA | NA |
| 145 | KCTD9 | 2 | −1 | NA | NA | NA | NA |
| 146 | CDCA2 | 2 | −1 | NA | NA | NA | NA |
| 147 | EBF2 | 5.1 | −1 | NA | NA | NA | NA |
| 148 | DPYSL2 | 3.3 | −1 | NA | NA | NA | NA |
| 149 | ADRA1A | 3.9 | −1 | NA | NA | NA | NA |
| 150 | STMN4 | 3.3 | −1 | NA | NA | NA | NA |
| 151 | TRIM35 | 2.6 | −1 | NA | NA | NA | NA |
| 152 | PTK2B | 7 | −1 | NA | NA | NA | NA |
| 153 | CHRNA2 | 3.5 | −1 | NA | NA | NA | NA |
| 154 | EPHX2 | 3.3 | −1 | NA | NA | NA | NA |
| 155 | CCDC25 | 4.4 | −1 | NA | NA | NA | NA |
| 156 | SCARA5 | 3.3 | −1 | NA | NA | NA | NA |
| 157 | C8orf80 | 3.6 | −1 | NA | NA | NA | NA |
| 158 | ELP3 | 3.4 | −1 | NA | NA | NA | NA |
| 159 | HMBOX1 | 1.8 | −1 | NA | NA | NA | NA |
| 160 | KIF13B | 2.7 | −1 | NA | NA | NA | NA |
| 161 | TOX | 4.3 | 1 | NA | NA | NA | NA |
| 162 | CYP7B1 | NA | NA | 1.7 | 1 | NA | NA |
| 163 | CPA6 | 3.8 | 1 | NA | NA | NA | NA |
| 164 | PREX2 | 7.5 | 1 | NA | NA | NA | NA |
| 165 | C8orf34 | 6 | 1 | NA | NA | NA | NA |
| 166 | SULF1 | 5.2 | 1 | 3.4 | 1 | NA | NA |
| 167 | SLCO5A1 | 4.9 | 1 | 4.2 | 1 | NA | NA |

TABLE 13-continued

| | | MPS Genes | | | | | |
|---|---|---|---|---|---|---|---|
| 168 | PRDM14 | 4.7 | 1 | NA | NA | NA | NA |
| 169 | NCOA2 | 3.2 | 1 | 2.4 | 1 | NA | NA |
| 170 | LACTB2 | 2.6 | 1 | NA | NA | NA | NA |
| 171 | XKR9 | 2.7 | 1 | NA | NA | NA | NA |
| 172 | EYA1 | 3.4 | 1 | NA | NA | NA | NA |
| 173 | MSC | 2 | 1 | NA | NA | NA | NA |
| 174 | TRPA1 | 2.3 | 1 | NA | NA | NA | NA |
| 175 | KCNB2 | 6.8 | 1 | NA | NA | NA | NA |
| 176 | RPL7 | 2.3 | 1 | NA | NA | NA | NA |
| 177 | STAU2 | 4.6 | 1 | NA | NA | NA | NA |
| 178 | TCEB1 | 1.8 | 1 | NA | NA | NA | NA |
| 179 | JPH1 | 6 | 1 | NA | NA | NA | NA |
| 180 | GDAP1 | 2 | 1 | NA | NA | NA | NA |
| 181 | PI15 | 3 | 1 | NA | NA | NA | NA |
| 182 | CRISPLD1 | 4.9 | 1 | NA | NA | NA | NA |
| 183 | HNF4G | 4.1 | 1 | NA | NA | NA | NA |
| 184 | ZFHX4 | 4.3 | 1 | NA | NA | NA | NA |
| 185 | PKIA | 3.3 | 1 | NA | NA | NA | NA |
| 186 | STMN2 | 2.8 | 1 | NA | NA | NA | NA |
| 187 | HEY1 | 3 | 1 | NA | NA | NA | NA |
| 188 | ZNF704 | NA | NA | 2.5 | 1 | NA | NA |
| 189 | PAG1 | NA | NA | 2 | 1 | NA | NA |
| 190 | IMPA1 | NA | NA | 1.9 | 1 | NA | NA |
| 191 | RALYL | 2.8 | 1 | NA | NA | NA | NA |
| 192 | CNGB3 | 1.8 | 1 | NA | NA | NA | NA |
| 193 | CNBD1 | 3.8 | 1 | 3.8 | 1 | NA | NA |
| 194 | MMP16 | NA | NA | 3.5 | 1 | NA | NA |
| 195 | SLC26A7 | NA | NA | 2.2 | 1 | NA | NA |
| 196 | CDH17 | 2.8 | 1 | NA | NA | NA | NA |
| 197 | PTDSS1 | 2.5 | 1 | NA | NA | NA | NA |
| 198 | SDC2 | 3.4 | 1 | NA | NA | NA | NA |
| 199 | MTDH | NA | NA | 1.9 | 1 | NA | NA |
| 200 | NIPAL2 | 1.9 | 1 | NA | NA | NA | NA |
| 201 | STK3 | 1.8 | 1 | NA | NA | NA | NA |
| 202 | VPS13B | 3.9 | 1 | NA | NA | NA | NA |
| 203 | RGS22 | 2.7 | 1 | NA | NA | NA | NA |
| 204 | YWHAZ | NA | NA | 2.2 | 1 | NA | NA |
| 205 | ZNF706 | NA | NA | 2.8 | 1 | NA | NA |
| 206 | GRHL2 | NA | NA | 2.4 | 1 | NA | NA |
| 207 | NCALD | 5.5 | 1 | 2.9 | 1 | NA | NA |
| 208 | UBR5 | NA | NA | 2.2 | 1 | NA | NA |
| 209 | ATP6V1C1 | NA | NA | 2.4 | 1 | NA | NA |
| 210 | RIMS2 | 2 | 1 | 4 | 1 | NA | NA |
| 211 | DPYS | 3.2 | 1 | NA | NA | NA | NA |
| 212 | LRP12 | NA | NA | 2 | 1 | NA | NA |
| 213 | ZFPM2 | 4.2 | 1 | 6.3 | 1 | NA | NA |
| 214 | ANGPT1 | 2.4 | 1 | NA | NA | NA | NA |
| 215 | RSPO2 | 1.8 | 1 | NA | NA | NA | NA |
| 216 | CSMD3 | 4.9 | 1 | 4.2 | 1 | NA | NA |
| 217 | TRPS1 | 2.9 | 1 | 2.7 | 1 | NA | NA |
| 218 | ZHX2 | NA | NA | 2.6 | 1 | NA | NA |
| 219 | ANXA13 | 2.1 | 1 | NA | NA | NA | NA |
| 220 | KIAA0196 | 2.6 | 1 | NA | NA | NA | NA |
| 221 | POU5F1B | 2.9 | 1 | NA | NA | NA | NA |
| 222 | MYC | 4.2 | 1 | NA | NA | NA | NA |
| 223 | TMEM75 | 3.5 | 1 | NA | NA | NA | NA |
| 224 | ASAP1 | NA | NA | 3.6 | 1 | NA | NA |
| 225 | ADCY8 | 3.1 | 1 | 5.4 | 1 | NA | NA |
| 226 | EFR3A | 3.1 | 1 | NA | NA | NA | NA |
| 227 | OC90 | 1.9 | 1 | NA | NA | NA | NA |
| 228 | KCNQ3 | 6 | 1 | NA | NA | NA | NA |
| 229 | TMEM71 | 2.9 | 1 | NA | NA | NA | NA |
| 230 | PHF20L1 | 2.8 | 1 | NA | NA | NA | NA |
| 231 | TG | 3.8 | 1 | NA | NA | NA | NA |
| 232 | SLA | 2.2 | 1 | NA | NA | NA | NA |
| 233 | WISP1 | 2.2 | 1 | NA | NA | NA | NA |
| 234 | ZFAT | 2.5 | 1 | NA | NA | NA | NA |
| 235 | PTK2 | NA | NA | 2.3 | 1 | NA | NA |
| 236 | GRK5 | NA | NA | 2.4 | −1 | NA | NA |
| 237 | RCOR2 | NA | NA | NA | NA | 1.7 | 1 |
| 238 | MACROD1 | NA | NA | 1.9 | 1 | 2.9 | 1 |
| 239 | STIP1 | NA | NA | NA | NA | 1.8 | 1 |
| 240 | SF1 | NA | NA | NA | NA | 2.5 | 1 |
| 241 | MEN1 | NA | NA | NA | NA | 2.1 | 1 |
| 242 | CDC42BPG | NA | NA | NA | NA | 2.3 | 1 |
| 243 | PPP2R5B | NA | NA | NA | NA | 1.8 | 1 |
| 244 | GYS2 | NA | NA | NA | NA | 2.8 | −1 |
| 245 | PDS5B | NA | NA | NA | NA | 2.0 | −1 |

TABLE 13-continued

| | MPS Genes | | | | | | |
|---|---|---|---|---|---|---|---|
| 246 | C13orf23 | NA | NA | NA | NA | 2.2 | −1 |
| 247 | ENOX1 | NA | NA | NA | NA | 5.6 | −1 |
| 248 | LRCH1 | NA | NA | NA | NA | 2.4 | −1 |
| 249 | ESD | NA | NA | NA | NA | 2.6 | −1 |
| 250 | HTR2A | NA | NA | NA | NA | 3.3 | −1 |
| 251 | DIAPH3 | NA | NA | NA | NA | 3.3 | −1 |
| 252 | PCDH9 | NA | NA | NA | NA | 4.5 | −1 |
| 253 | KLHL1 | NA | NA | NA | NA | 1.9 | −1 |
| 254 | DACH1 | NA | NA | NA | NA | 1.9 | −1 |
| 255 | GPC5 | NA | NA | NA | NA | 2.1 | −1 |
| 256 | NALCN | NA | NA | NA | NA | 2.2 | −1 |
| 257 | TFDP1 | NA | NA | 2.3 | −1 | NA | NA |
| 258 | MDGA2 | NA | NA | NA | NA | 2.8 | −1 |
| 259 | MEIS2 | NA | NA | NA | NA | 3.9 | −1 |
| 260 | VPS13C | NA | NA | NA | NA | 1.8 | −1 |
| 261 | TBC1D10B | NA | NA | NA | NA | 1.8 | 1 |
| 262 | RNF40 | NA | NA | NA | NA | 2.1 | 1 |
| 263 | CNGB1 | 1.8 | −1 | NA | NA | NA | NA |
| 264 | C16orf80 | 2.2 | −1 | NA | NA | NA | NA |
| 265 | CDH8 | NA | NA | NA | NA | 3.7 | −1 |
| 266 | NFAT5 | 2.3 | −1 | NA | NA | NA | NA |
| 267 | WWP2 | 1.8 | −1 | NA | NA | NA | NA |
| 268 | DDX19A | 2.3 | −1 | NA | NA | NA | NA |
| 269 | ST3GAL2 | 2.4 | −1 | NA | NA | NA | NA |
| 270 | ZFHX3 | 2.2 | −1 | NA | NA | NA | NA |
| 271 | GLG1 | 2.1 | −1 | NA | NA | NA | NA |
| 272 | WDR59 | 2.1 | −1 | NA | NA | NA | NA |
| 273 | BCAR1 | 2.5 | −1 | NA | NA | NA | NA |
| 274 | CFDP1 | 3 | −1 | NA | NA | NA | NA |
| 275 | CNTNAP4 | 3.2 | −1 | NA | NA | NA | NA |
| 276 | ADAMTS18 | 3.5 | −1 | NA | NA | NA | NA |
| 277 | NUDT7 | 2.2 | −1 | NA | NA | NA | NA |
| 278 | CLEC3A | 2.3 | −1 | NA | NA | NA | NA |
| 279 | WWOX | 9.3 | −1 | NA | NA | NA | NA |
| 280 | CDYL2 | 2.5 | −1 | NA | NA | NA | NA |
| 281 | C16orf46 | NA | NA | 2.2 | −1 | NA | NA |
| 282 | GCSH | NA | NA | 1.9 | −1 | NA | NA |
| 283 | PKD1L2 | 4.9 | −1 | 2 | −1 | NA | NA |
| 284 | BCMO1 | 2.9 | −1 | 3.6 | −1 | NA | NA |
| 285 | GAN | 2.7 | −1 | 2.4 | −1 | NA | NA |
| 286 | PLCG2 | 2.9 | −1 | 2.7 | −1 | NA | NA |
| 287 | HSD17B2 | 2.6 | −1 | NA | NA | NA | NA |
| 288 | CDH13 | 8 | −1 | 2.9 | −1 | NA | NA |
| 289 | MLYCD | 2.4 | −1 | NA | NA | NA | NA |
| 290 | NECAB2 | NA | NA | 2 | −1 | NA | NA |
| 291 | MBTPS1 | 2.7 | −1 | NA | NA | NA | NA |
| 292 | HSDL1 | NA | NA | 2 | −1 | NA | NA |
| 293 | LRRC50 | 2.4 | −1 | NA | NA | NA | NA |
| 294 | WFDC1 | 2.3 | −1 | NA | NA | NA | NA |
| 295 | ATP2C2 | 3.6 | −1 | NA | NA | NA | NA |
| 296 | KIAA1609 | NA | NA | 1.9 | −1 | NA | NA |
| 297 | KLHL36 | NA | NA | 1.8 | −1 | NA | NA |
| 298 | USP10 | 2.3 | −1 | NA | NA | NA | NA |
| 299 | CRISPLD2 | 2.5 | −1 | 2.9 | −1 | NA | NA |
| 300 | ZDHHC7 | NA | NA | 2.5 | −1 | NA | NA |
| 301 | KIAA0513 | NA | NA | 2.1 | −1 | NA | NA |
| 302 | KIAA0182 | NA | NA | 2 | −1 | NA | NA |
| 303 | GINS2 | NA | NA | 2.1 | −1 | NA | NA |
| 304 | C16orf74 | NA | NA | 2.3 | −1 | NA | NA |
| 305 | COX4NB | NA | NA | 2.5 | −1 | NA | NA |
| 306 | COX4I1 | NA | NA | 2.6 | −1 | NA | NA |
| 307 | IRF8 | NA | NA | 2.5 | −1 | NA | NA |
| 308 | FOXF1 | NA | NA | 2.2 | −1 | NA | NA |
| 309 | MTHFSD | NA | NA | 2.4 | −1 | NA | NA |
| 310 | JPH3 | 2.4 | −1 | 2.4 | −1 | NA | NA |
| 311 | KLHDC4 | NA | NA | 2.5 | −1 | NA | NA |
| 312 | SLC7A5 | 1.7 | −1 | 3 | −1 | NA | NA |
| 313 | CA5A | 2.6 | −1 | 3.8 | −1 | NA | NA |
| 314 | BANP | 2.6 | −1 | 3.3 | −1 | NA | NA |
| 315 | ZFPM1 | NA | NA | 2.5 | −1 | NA | NA |
| 316 | C16orf85 | NA | NA | 2.1 | −1 | NA | NA |
| 317 | ZC3H18 | NA | NA | 2.1 | −1 | NA | NA |
| 318 | IL17C | NA | NA | 1.8 | −1 | NA | NA |
| 319 | CYBA | NA | NA | 2.9 | −1 | NA | NA |
| 320 | MVD | NA | NA | 2.3 | −1 | NA | NA |
| 321 | SNAI3 | NA | NA | 2.4 | −1 | NA | NA |
| 322 | RNF166 | NA | NA | 2.2 | −1 | NA | NA |
| 323 | FAM38A | NA | NA | 2.7 | −1 | NA | NA |

TABLE 13-continued

MPS Genes

| | | | | | | | |
|---|---|---|---|---|---|---|---|
| 324 | CDT1 | NA | NA | 2 | −1 | NA | NA |
| 325 | GALNS | NA | NA | 2.3 | −1 | NA | NA |
| 326 | TRAPPC2L | NA | NA | 1.9 | −1 | NA | NA |
| 327 | CBFA2T3 | NA | NA | 1.9 | −1 | NA | NA |
| 328 | CDH15 | NA | NA | 1.9 | −1 | NA | NA |
| 329 | ANKRD11 | 3 | −1 | 3.7 | −1 | NA | NA |
| 330 | FANCA | NA | NA | 1.9 | −1 | NA | NA |
| 331 | SPIRE2 | NA | NA | 1.7 | −1 | NA | NA |
| 332 | TCF25 | NA | NA | 2.1 | −1 | NA | NA |
| 333 | TUBB3 | NA | NA | 2.6 | −1 | NA | NA |
| 334 | DEF8 | NA | NA | 1.9 | −1 | NA | NA |
| 335 | AFG3L1 | NA | NA | 2.3 | −1 | NA | NA |
| 336 | GAS8 | NA | NA | 2.9 | −1 | NA | NA |
| 337 | DNAH2 | 1.8 | −1 | NA | NA | NA | NA |
| 338 | NKIRAS2 | NA | NA | NA | NA | 2.0 | 1 |
| 339 | DHX58 | NA | NA | NA | NA | 8.9 | 1 |
| 340 | KAT2A | NA | NA | NA | NA | 3.2 | 1 |
| 341 | HSPB9 | NA | NA | NA | NA | 2.9 | 1 |
| 342 | RAB5C | NA | NA | NA | NA | 3.5 | 1 |
| 343 | KCNH4 | NA | NA | NA | NA | 3.8 | 1 |
| 344 | GHDC | NA | NA | NA | NA | 1.8 | 1 |
| 345 | NOTUM | NA | NA | NA | NA | 2.7 | 1 |
| 346 | ASPSCR1 | NA | NA | NA | NA | 1.8 | 1 |
| 347 | DUS1L | NA | NA | NA | NA | 2.3 | 1 |
| 348 | FASN | NA | NA | NA | NA | 3.0 | 1 |
| 349 | CDH2 | NA | NA | NA | NA | 3.4 | −1 |
| 350 | NOL4 | NA | NA | NA | NA | 3.9 | −1 |
| 351 | DTNA | NA | NA | NA | NA | 2.2 | −1 |
| 352 | DCC | NA | NA | NA | NA | 6.6 | −1 |
| 353 | WDR7 | NA | NA | NA | NA | 2.0 | −1 |
| 354 | CD226 | NA | NA | NA | NA | 3.3 | −1 |
| 355 | ZSWIM4 | NA | NA | NA | NA | 2.8 | 1 |
| 356 | C19orf57 | NA | NA | NA | NA | 2.8 | 1 |
| 357 | CC2D1A | NA | NA | NA | NA | 4.0 | 1 |
| 358 | RFX1 | NA | NA | NA | NA | 2.2 | 1 |
| 359 | PLCB1 | NA | NA | NA | NA | 1.9 | −1 |
| 360 | SMARCB1 | NA | NA | 1.8 | −1 | NA | NA |
| 361 | TBC1D22A | NA | NA | 4.6 | −1 | NA | NA |
| 362 | RAB9A | NA | NA | 3.7 | 1 | NA | NA |
| 363 | TFE3 | NA | NA | 2.1 | 1 | NA | NA |
| 364 | HEPH | 1.8 | 1 | NA | NA | NA | NA |
| 365 | EDA2R | 2 | 1 | NA | NA | NA | NA |
| 366 | AR | 2.3 | 1 | 2.6 | 1 | NA | NA |
| 367 | OPHN1 | 5.8 | 1 | NA | NA | NA | NA |
| 368 | NLGN4Y | NA | NA | NA | NA | 2.4 | −1 |

| index | gene | gene_Chr | gene_Cytoband | gene_start | gene_end |
|---|---|---|---|---|---|
| 1 | CLCNKB | 1 | p36.13 | 16242834 | 16256390 |
| 2 | ARHGEF10L | 1 | p36.13 | 17738917 | 17896956 |
| 3 | ACTL8 | 1 | p36.13 | 17954395 | 18026145 |
| 4 | DPYD | 1 | p21.3 | 97315890 | 98159203 |
| 5 | COL11A1 | 1 | p21.1 | 1.03E+08 | 1.03E+08 |
| 6 | NRXN1 | 2 | p16.3 | 49999148 | 51113178 |
| 7 | CTNNA2 | 2 | p12 | 79732191 | 80729415 |
| 8 | ALCAM | 3 | q13.11 | 1.07E+08 | |
| 9 | ZBTB20 | 3 | q13.31 | 1.18E+08 | |
| 10 | MYLK | 3 | q21.1 | 124811586 | 125085868 |
| 11 | KALRN | 3 | q21.1 | 125296275 | 125922726 |
| 12 | BFSP2 | 3 | q22.1 | 134601480 | 134676746 |
| 13 | SLC9A9 | 3 | q24 | 144466755 | 145049979 |
| 14 | KCNAB1 | 3 | q25.31 | 157321095 | 157739621 |
| 15 | PPM1L | 3 | q26.1 | 161956791 | 162271511 |
| 16 | MECOM | 3 | q26.2 | 170283981 | 170347054 |
| 17 | DGKG | 3 | q27.3 | 187347686 | 187562717 |
| 18 | TP63 | 3 | q28 | 190831910 | 191107935 |
| 19 | LEPREL1 | 3 | q28 | 191157213 | 191321407 |
| 20 | BOD1L | 4 | p15.33 | 13179464 | 13238426 |
| 21 | KCTD8 | 4 | p13 | 43870683 | 44145581 |
| 22 | GABRA2 | 4 | p12 | 45946341 | 46086561 |
| 23 | LPHN3 | 4 | q13.1 | 62045434 | 62620762 |
| 24 | GRID2 | 4 | q22.1 | 93444831 | 94914730 |
| 25 | DCHS2 | 4 | q32.1 | 155375138 | 155632318 |
| 26 | GLRB | 4 | q32.1 | 158216788 | 158312299 |
| 27 | GRIA2 | 4 | q32.1 | 158361186 | 158506677 |
| 28 | FSTL5 | 4 | q32.2 | 162524501 | 163304636 |
| 29 | CENPH | 5 | q13.2 | 68521131 | 68541939 |
| 30 | MRPS36 | 5 | q13.2 | 68549329 | 68577710 |

TABLE 13-continued

| | MPS Genes | | | | |
|---|---|---|---|---|---|
| 31 | CDK7 | 5 | q13.2 | 68566471 | 68609004 |
| 32 | CCDC125 | 5 | q13.2 | 68612278 | 68664392 |
| 33 | TAF9 | 5 | q13.2 | 68696327 | 68701596 |
| 34 | RAD17 | 5 | q13.2 | 68700880 | 68746384 |
| 35 | MARVELD2 | 5 | q13.2 | 68746699 | 68773646 |
| 36 | MEF2C | 5 | q14.3 | 88051922 | 88214780 |
| 37 | TICAM2 | 5 | q22.3 | 114942247 | 114989610 |
| 38 | COL21A1 | 6 | p12.1 | 56029347 | 56366851 |
| 39 | COL19A1 | 6 | q13 | 70633169 | 70978878 |
| 40 | COL12A1 | 6 | q14.1 | 75850762 | 75972343 |
| 41 | UBE2CBP | 6 | q14.1 | 83658836 | 83832269 |
| 42 | ME1 | 6 | q14.2 | 83976827 | 84197498 |
| 43 | MAP3K7 | 6 | q15 | 91282074 | 91353628 |
| 44 | EPHA7 | 6 | q16.1 | 94007864 | 94185993 |
| 45 | FBXL4 | 6 | q16.2 | 99428055 | 99502570 |
| 46 | SIM1 | 6 | q16.3 | 100939606 | 101019494 |
| 47 | ASCC3 | 6 | q16.3 | 101062791 | 101435961 |
| 48 | NUS1 | 6 | q22.2 | 118103310 | 118138577 |
| 49 | TRDN | 6 | q22.31 | 123579182 | 123999937 |
| 50 | UTRN | 6 | q24.2 | 144654566 | 145215859 |
| 51 | EPM2A | 6 | q24.3 | 145988141 | 146098684 |
| 52 | GRM1 | 6 | q24.3 | 146390611 | 146800427 |
| 53 | C6orf118 | 6 | q27 | 165613148 | 165643101 |
| 54 | PDE10A | 6 | q27 | 165660766 | 165995578 |
| 55 | IQCE | 7 | p22.2 | 2565158 | 2620893 |
| 56 | FBXL18 | 7 | p22.1 | 5481955 | 5523646 |
| 57 | STX1A | 7 | q11.23 | 72751472 | 72771925 |
| 58 | CLDN3 | 7 | q11.23 | 72821263 | 72822536 |
| 59 | EIF4H | 7 | q11.23 | 73226625 | 73249358 |
| 60 | LAT2 | 7 | q11.23 | 73261662 | 73282099 |
| 61 | RFC2 | 7 | q11.23 | 73283770 | 73306674 |
| 62 | CLIP2 | 7 | q11.23 | 73341739 | 73458196 |
| 63 | HIP1 | 7 | q11.23 | 75001345 | 75206215 |
| 64 | TMEM120A | 7 | q11.23 | 75454238 | 75461913 |
| 65 | STYXL1 | 7 | q11.23 | 75463592 | 75515257 |
| 66 | MDH2 | 7 | q11.23 | 75515329 | 75533864 |
| 67 | YWHAG | 7 | q11.23 | 75794053 | 75826252 |
| 68 | STAG3 | 7 | q22.1 | 99613474 | 99659778 |
| 69 | PILRB | 7 | q22.1 | 99771673 | 99803388 |
| 70 | PILRA | 7 | q22.1 | 99809004 | 99835650 |
| 71 | MEPCE | 7 | q22.1 | 99865190 | 99869676 |
| 72 | TSC22D4 | 7 | q22.1 | 99902080 | 99914838 |
| 73 | C7orf51 | 7 | q22.1 | 99919486 | 99930358 |
| 74 | AGFG2 | 7 | q22.1 | 99974770 | 100003778 |
| 75 | LRCH4 | 7 | q22.1 | 100009570 | 100021712 |
| 76 | FBXO24 | 7 | q22.1 | 100021892 | 100036674 |
| 77 | PCOLCE | 7 | q22.1 | 100037818 | 100043732 |
| 78 | MOSPD3 | 7 | q22.1 | 100047661 | 100050932 |
| 79 | TFR2 | 7 | q22.1 | 100055975 | 100077109 |
| 80 | ACTL6B | 7 | q22.1 | 100078678 | 100092007 |
| 81 | GIGYF1 | 7 | q22.1 | 100115066 | 100124806 |
| 82 | EPO | 7 | q22.1 | 100156359 | 100159257 |
| 83 | CPA2 | 7 | q32.2 | 129693939 | 129716870 |
| 84 | CPA4 | 7 | q32.2 | 129720230 | 129751249 |
| 85 | CPA5 | 7 | q32.2 | 129771892 | 129795807 |
| 86 | CPA1 | 7 | q32.2 | 129807468 | 129815165 |
| 87 | TSGA14 | 7 | q32.2 | 129823611 | 129868133 |
| 88 | MEST | 7 | q32.2 | 129913282 | 129933363 |
| 89 | COPG2 | 7 | q32.2 | 129933404 | 129935887 |
| 90 | ARHGEF5 | 7 | q35 | 143683366 | 143708657 |
| 91 | DLGAP2 | 8 | p23.3 | 1436939 | 1644048 |
| 92 | ARHGEF10 | 8 | p23.3 | 1759549 | 1894206 |
| 93 | MYOM2 | 8 | p23.3 | 1980565 | 2080779 |
| 94 | CSMD1 | 8 | p23.2 | 2780282 | 3258996 |
| 95 | MFHAS1 | 8 | p23.1 | 8679409 | 8788541 |
| 96 | ERI1 | 8 | p23.1 | 8897856 | 8928139 |
| 97 | TNKS | 8 | p23.1 | 9450855 | 9677266 |
| 98 | MSRA | 8 | p23.1 | 9949189 | 10323803 |
| 99 | C8orf16 | 8 | p23.1 | 11021390 | 11025155 |
| 100 | MTMR9 | 8 | p23.1 | 11179410 | 11223062 |
| 101 | BLK | 8 | p23.1 | 11388930 | 11459516 |
| 102 | GATA4 | 8 | p23.1 | 11599162 | 11654918 |
| 103 | NEIL2 | 8 | p23.1 | 11664627 | 11682263 |
| 104 | CTSB | 8 | p23.1 | 11737442 | 11763055 |
| 105 | C8orf79 | 8 | p22 | 12847554 | 12931653 |
| 106 | DLC1 | 8 | p22 | 12985243 | 13416766 |
| 107 | SGCZ | 8 | p22 | 13991744 | 15140219 |
| 108 | TUSC3 | 8 | p22 | 15442101 | 15666366 |

TABLE 13-continued

MPS Genes

| 109 | MTMR7 | 8 | p22 | 17199923 | 17315207 |
| 110 | SLC7A2 | 8 | p22 | 17398975 | 17472357 |
| 111 | PDGFRL | 8 | p22 | 17478443 | 17545655 |
| 112 | MTUS1 | 8 | p22 | 17545584 | 17702666 |
| 113 | PCM1 | 8 | p22 | 17824646 | 17935562 |
| 114 | ASAH1 | 8 | p22 | 17958214 | 17986787 |
| 115 | NAT2 | 8 | p22 | 18293035 | 18303003 |
| 116 | PSD3 | 8 | p22 | 18429093 | 18915476 |
| 117 | SH2D4A | 8 | p21.3 | 19215483 | 19297594 |
| 118 | LZTS1 | 8 | p21.3 | 20147956 | 20205754 |
| 119 | XPO7 | 8 | p21.3 | 21833126 | 21920041 |
| 120 | FAM160B2 | 8 | p21.3 | 22002660 | 22017835 |
| 121 | NUDT18 | 8 | p21.3 | 22020328 | 22023403 |
| 122 | HR | 8 | p21.3 | 22027877 | 22045326 |
| 123 | REEP4 | 8 | p21.3 | 22051478 | 22055393 |
| 124 | LGI3 | 8 | p21.3 | 22060290 | 22070290 |
| 125 | BMP1 | 8 | p21.3 | 22078645 | 22125782 |
| 126 | PHYHIP | 8 | p21.3 | 22133162 | 22145796 |
| 127 | POLR3D | 8 | p21.3 | 22158564 | 22164624 |
| 128 | SLC39A14 | 8 | p21.3 | 22280737 | 22347462 |
| 129 | PPP3CC | 8 | p21.3 | 22354541 | 22454580 |
| 130 | SORBS3 | 8 | p21.3 | 22465196 | 22488952 |
| 131 | PDLIM2 | 8 | p21.3 | 22492199 | 22511483 |
| 132 | C8orf58 | 8 | p21.3 | 22513067 | 22517605 |
| 133 | KIAA1967 | 8 | p21.3 | 22518202 | 22533920 |
| 134 | BIN3 | 8 | p21.3 | 22533906 | 22582553 |
| 135 | EGR3 | 8 | p21.3 | 22601119 | 22606760 |
| 136 | RHOBTB2 | 8 | p21.3 | 22913059 | 22933655 |
| 137 | TNFRSF10D | 8 | p21.3 | 23049051 | 23077485 |
| 138 | TNFRSF10A | 8 | p21.3 | 23104916 | 23138584 |
| 139 | CHMP7 | 8 | p21.3 | 23157095 | 23175450 |
| 140 | LOXL2 | 8 | p21.3 | 23210097 | 23317667 |
| 141 | ENTPD4 | 8 | p21.3 | 23299386 | 23371081 |
| 142 | erw | 8 | p21.2 | 23442308 | 23486008 |
| 143 | NKX2-6 | 8 | p21.2 | 23615909 | 23620056 |
| 144 | DOCK5 | 8 | p21.2 | 25098204 | 25326536 |
| 145 | KCTD9 | 8 | p21.2 | 25341283 | 25371837 |
| 146 | CDCA2 | 8 | p21.2 | 25372428 | 25421353 |
| 147 | EBF2 | 8 | p21.2 | 25758042 | 25958292 |
| 148 | DPYSL2 | 8 | p21.2 | 26491327 | 26571607 |
| 149 | ADRA1A | 8 | p21.2 | 26661584 | 26778839 |
| 150 | STMN4 | 8 | p21.2 | 27149738 | 27171843 |
| 151 | TRIM35 | 8 | p21.2 | 27198321 | 27224751 |
| 152 | PTK2B | 8 | p21.2 | 27224916 | 27372820 |
| 153 | CHRNA2 | 8 | p21.2 | 27373196 | 27392730 |
| 154 | EPHX2 | 8 | p21.1 | 27404562 | 27458403 |
| 155 | CCDC25 | 8 | p21.1 | 27646756 | 27686089 |
| 156 | SCARA5 | 8 | p21.1 | 27783672 | 27906117 |
| 157 | C8orf80 | 8 | p21.1 | 27935607 | 27997307 |
| 158 | ELP3 | 8 | p21.1 | 27999759 | 28104584 |
| 159 | HMBOX1 | 8 | p21.1 | 28803830 | 28966706 |
| 160 | KIF13B | 8 | p21.1 | 28980715 | 29176529 |
| 161 | TOX | 8 | q12.1 | 59880531 | 60194321 |
| 162 | CYP7B1 | 8 | q12.3 | 65671246 | 65873902 |
| 163 | CPA6 | 8 | q13.2 | 68496963 | 68821134 |
| 164 | PREX2 | 8 | q13.2 | 69026907 | 69306451 |
| 165 | C8orf34 | 8 | q13.2 | 69405511 | 69893810 |
| 166 | SULF1 | 8 | q13.2 | 70541427 | 70735701 |
| 167 | SLCO5A1 | 8 | q13.3 | 70747129 | 70909762 |
| 168 | PRDM14 | 8 | q13.3 | 71126574 | 71146116 |
| 169 | NCOA2 | 8 | q13.3 | 71178380 | 71478574 |
| 170 | LACTB2 | 8 | q13.3 | 71712045 | 71743946 |
| 171 | XKR9 | 8 | q13.3 | 71755848 | 71809213 |
| 172 | EYA1 | 8 | q13.3 | 72272222 | 72437021 |
| 173 | MSC | 8 | q13.3 | 72916332 | 72919285 |
| 174 | TRPA1 | 8 | q13.3 | 73096040 | 73150373 |
| 175 | KCNB2 | 8 | q13.3 | 73642524 | 74012880 |
| 176 | RPL7 | 8 | q21.11 | 74365073 | 74375857 |
| 177 | STAU2 | 8 | q21.11 | 74495160 | 74821629 |
| 178 | TCEB1 | 8 | q21.11 | 75021184 | 75046959 |
| 179 | JPH1 | 8 | q21.11 | 75309493 | 75396117 |
| 180 | GDAP1 | 8 | q21.11 | 75425173 | 75441888 |
| 181 | PI15 | 8 | q21.11 | 75899327 | 75929819 |
| 182 | CRISPLD1 | 8 | q21.11 | 76059531 | 76109346 |
| 183 | HNF4G | 8 | q21.11 | 76482732 | 76641600 |
| 184 | ZFHX4 | 8 | q21.11 | 77756078 | 77942076 |
| 185 | PKIA | 8 | q21.12 | 79590891 | 79678040 |
| 186 | STMN2 | 8 | q21.13 | 80685916 | 80740868 |

TABLE 13-continued

MPS Genes

| | | | | | |
|---|---|---|---|---|---|
| 187 | HEY1 | 8 | q21.13 | 80838801 | 80842653 |
| 188 | ZNF704 | 8 | q21.13 | 81713324 | 81949571 |
| 189 | PAG1 | 8 | q21.13 | 82042605 | 82186858 |
| 190 | IMPA1 | 8 | q21.13 | 82732751 | 82761115 |
| 191 | RALYL | 8 | q21.2 | 85604112 | 85963979 |
| 192 | CNGB3 | 8 | q21.3 | 87655277 | 87825017 |
| 193 | CNBD1 | 8 | q21.3 | 87947840 | 88435220 |
| 194 | MMP16 | 8 | q21.3 | 89118580 | 89408833 |
| 195 | SLC26A7 | 8 | q21.3 | 92330692 | 92479554 |
| 196 | CDH17 | 8 | q22.1 | 95208566 | 95289986 |
| 197 | PTDSS1 | 8 | q22.1 | 97343340 | 97415950 |
| 198 | SDC2 | 8 | q22.1 | 97575058 | 97693213 |
| 199 | MTDH | 8 | q22.1 | 98725583 | 98807711 |
| 200 | NIPAL2 | 8 | q22.2 | 99273563 | 99375797 |
| 201 | STK3 | 8 | q22.2 | 99536037 | 99907074 |
| 202 | VPS13B | 8 | q22.2 | 100094670 | 100958983 |
| 203 | RGS22 | 8 | q22.2 | 101042452 | 101187520 |
| 204 | YWHAZ | 8 | q22.3 | 101999980 | 102034745 |
| 205 | ZNF706 | 8 | q22.3 | 102278444 | 102287136 |
| 206 | GRHL2 | 8 | q22.3 | 102574162 | 102750995 |
| 207 | NCALD | 8 | q22.3 | 102767947 | 103206311 |
| 208 | UBR5 | 8 | q22.3 | 103334748 | 103493671 |
| 209 | ATP6V1C1 | 8 | q22.3 | 104102424 | 104154461 |
| 210 | RIMS2 | 8 | q22.3 | 104582291 | 105333263 |
| 211 | DPYS | 8 | q22.3 | 105460829 | 105548453 |
| 212 | LRP12 | 8 | q22.3 | 105570643 | 105670344 |
| 213 | ZFPM2 | 8 | q23.1 | 106400323 | 106885939 |
| 214 | ANGPT1 | 8 | q23.1 | 108330899 | 108579459 |
| 215 | RSPO2 | 8 | q23.1 | 108980721 | 109165052 |
| 216 | CSMD3 | 8 | q23.3 | 113304337 | 114518418 |
| 217 | TRPS1 | 8 | q23.3 | 116489900 | 116750429 |
| 218 | ZHX2 | 8 | q24.13 | 123863082 | 124055936 |
| 219 | ANXA13 | 8 | q24.13 | 124762216 | 124818828 |
| 220 | KIAA0196 | 8 | q24.13 | 126105691 | 126173191 |
| 221 | POU5F1B | 8 | q24.21 | 128497039 | 128498621 |
| 222 | MYC | 8 | q24.21 | 128816862 | 128822853 |
| 223 | TMEM75 | 8 | q24.21 | 129029046 | 129029462 |
| 224 | ASAP1 | 8 | q24.21 | 131133535 | 131483399 |
| 225 | ADCY8 | 8 | q24.22 | 131861736 | 132123854 |
| 226 | EFR3A | 8 | q24.22 | 132985517 | 133095071 |
| 227 | OC90 | 8 | q24.22 | 133105667 | 133167084 |
| 228 | KCNQ3 | 8 | q24.22 | 133210438 | 133561961 |
| 229 | TMEM71 | 8 | q24.22 | 133779633 | 133842010 |
| 230 | PHF20L1 | 8 | q24.22 | 133856786 | 133930234 |
| 231 | TG | 8 | q24.22 | 133948387 | 134216325 |
| 232 | SLA | 8 | q24.22 | 134118155 | 134184479 |
| 233 | WISP1 | 8 | q24.22 | 134272494 | 134310751 |
| 234 | ZFAT | 8 | q24.22 | 135559215 | 135794463 |
| 235 | PTK2 | 8 | q24.3 | 141737683 | 142080514 |
| 236 | GRK5 | 10 | q26.11 | 120957091 | 121205118 |
| 237 | RCOR2 | 11 | q13.1 | 63435303 | 63440892 |
| 238 | MACROD1 | 11 | q13.1 | 63522607 | 63690109 |
| 239 | STIP1 | 11 | q13.1 | 63709873 | 63728596 |
| 240 | SF1 | 11 | q13.1 | 64288654 | 64302817 |
| 241 | MEN1 | 11 | q13.1 | 64327564 | 64335342 |
| 242 | CDC42BPG | 11 | q13.1 | 64348240 | 64368617 |
| 243 | PPP2R5B | 11 | q13.1 | 64448756 | 64458523 |
| 244 | GYS2 | 12 | p12.1 | 21580390 | 21649048 |
| 245 | PDS5B | 13 | q13.1 | 32058564 | 32250157 |
| 246 | C13orf23 | 13 | q13.3 | 38482003 | 38510252 |
| 247 | ENOX1 | 13 | q14.11 | 42685704 | 43259044 |
| 248 | LRCH1 | 13 | q14.13 | 46025304 | 46222786 |
| 249 | ESD | 13 | q14.2 | 46243393 | 46269368 |
| 250 | HTR2A | 13 | q14.2 | 46305514 | 46368176 |
| 251 | DIAPH3 | 13 | q21.2 | 59137718 | 59636120 |
| 252 | PCDH9 | 13 | q21.32 | 65774970 | 66702578 |
| 253 | KLHL1 | 13 | q21.33 | 69172727 | 69580592 |
| 254 | DACH1 | 13 | q21.33 | 70910099 | 71339331 |
| 255 | GPC5 | 13 | q31.3 | 90848919 | 92316693 |
| 256 | NALCN | 13 | q33.1 | 100504131 | 100866814 |
| 257 | TFDP1 | 13 | q34 | 113287057 | 113343500 |
| 258 | MDGA2 | 14 | q21.3 | 46379045 | 47213703 |
| 259 | MEIS2 | 15 | q14 | 34970519 | 35189740 |
| 260 | VPS13C | 15 | q22.2 | 59931884 | 60139939 |
| 261 | TBC1D10B | 16 | p11.2 | 30275925 | 30288587 |
| 262 | RNF40 | 16 | p11.2 | 30681100 | 30695129 |
| 263 | CNGB1 | 16 | q13 | 56475004 | 56562513 |
| 264 | C16orf80 | 16 | q21 | 56705000 | 56720797 |

TABLE 13-continued

| | MPS Genes | | | | |
|---|---|---|---|---|---|
| 265 | CDH8 | 16 | q21 | 60244866 | 60628240 |
| 266 | NFAT5 | 16 | q22.1 | 68156498 | 68296054 |
| 267 | WWP2 | 16 | q22.1 | 68353710 | 68533145 |
| 268 | DDX19A | 16 | q22.1 | 68938322 | 68964780 |
| 269 | ST3GAL2 | 16 | q22.1 | 68970839 | 69030492 |
| 270 | ZFHX3 | 16 | q22.3 | 71374285 | 71639775 |
| 271 | GLG1 | 16 | q22.3 | 73043357 | 73198518 |
| 272 | WDR59 | 16 | q23.1 | 73464975 | 73576518 |
| 273 | BCAR1 | 16 | q23.1 | 73820429 | 73859452 |
| 274 | CFDP1 | 16 | q23.1 | 73885109 | 74024888 |
| 275 | CNTNAP4 | 16 | q23.1 | 74868677 | 75150636 |
| 276 | ADAMTS18 | 16 | q23.1 | 75873527 | 76026512 |
| 277 | NUDT7 | 16 | q23.1 | 76313912 | 76333652 |
| 278 | CLEC3A | 16 | q23.1 | 76613944 | 76623495 |
| 279 | WWOX | 16 | q23.1 | 76691052 | 77803532 |
| 280 | CDYL2 | 16 | q23.2 | 79195176 | 79395680 |
| 281 | C16orf46 | 16 | q23.2 | 79644603 | 79668373 |
| 282 | GCSH | 16 | q23.2 | 79673430 | 79687481 |
| 283 | PKD1L2 | 16 | q23.2 | 79691985 | 79811477 |
| 284 | BCMO1 | 16 | q23.2 | 79829797 | 79882248 |
| 285 | GAN | 16 | q23.2 | 79906076 | 79971441 |
| 286 | PLCG2 | 16 | q23.2 | 80370408 | 80549399 |
| 287 | HSD17B2 | 16 | q23.3 | 80626364 | 80689638 |
| 288 | CDH13 | 16 | q23.3 | 81439761 | 82387705 |
| 289 | MLYCD | 16 | q23.3 | 82490231 | 82507286 |
| 290 | NECAB2 | 16 | q23.3 | 82559738 | 82593878 |
| 291 | MBTPS1 | 16 | q24.1 | 82644872 | 82708018 |
| 292 | HSDL1 | 16 | q24.1 | 82713389 | 82736265 |
| 293 | LRRC50 | 16 | q24.1 | 82736366 | 82769024 |
| 294 | WFDC1 | 16 | q24.1 | 82885822 | 82920888 |
| 295 | ATP2C2 | 16 | q24.1 | 82959634 | 83055293 |
| 296 | KIAA1609 | 16 | q24.1 | 83068608 | 83095794 |
| 297 | KLHL36 | 16 | q24.1 | 83239632 | 83253416 |
| 298 | USP10 | 16 | q24.1 | 83291050 | 83371026 |
| 299 | CRISPLD2 | 16 | q24.1 | 83411113 | 83500614 |
| 300 | ZDHHC7 | 16 | q24.1 | 83565573 | 83602642 |
| 301 | KIAA0513 | 16 | q24.1 | 83618911 | 83685327 |
| 302 | KIAA0182 | 16 | q24.1 | 84202524 | 84267311 |
| 303 | GINS2 | 16 | q24.1 | 84268782 | 84280089 |
| 304 | C16orf74 | 16 | q24.1 | 84298426 | 84342190 |
| 305 | COX4NB | 16 | q24.1 | 84369737 | 84390601 |
| 306 | COX4I1 | 16 | q24.1 | 84390697 | 84398109 |
| 307 | IRF8 | 16 | q24.1 | 84490275 | 84513710 |
| 308 | FOXF1 | 16 | q24.1 | 85101634 | 85105570 |
| 309 | MTHFSD | 16 | q24.1 | 85121284 | 85157509 |
| 310 | JPH3 | 16 | q24.2 | 86194000 | 86289263 |
| 311 | KLHDC4 | 16 | q24.2 | 86298920 | 86357056 |
| 312 | SLC7A5 | 16 | q24.2 | 86421131 | 86460615 |
| 313 | CA5A | 16 | q24.2 | 86479126 | 86527613 |
| 314 | BANP | 16 | q24.2 | 86542539 | 86668425 |
| 315 | ZFPM1 | 16 | q24.2 | 87047226 | 87128890 |
| 316 | C16orf85 | 16 | q24.2 | 87147613 | 87164049 |
| 317 | ZC3H18 | 16 | q24.2 | 87164343 | 87225756 |
| 318 | IL17C | 16 | q24.3 | 87232502 | 87234385 |
| 319 | CYBA | 16 | q24.3 | 87237199 | 87244958 |
| 320 | MVD | 16 | q24.3 | 87245849 | 87257019 |
| 321 | SNAI3 | 16 | q24.3 | 87271591 | 87280383 |
| 322 | RNF166 | 16 | q24.3 | 87290411 | 87300312 |
| 323 | FAM38A | 16 | q24.3 | 87302916 | 87330317 |
| 324 | CDT1 | 16 | q24.3 | 87397687 | 87403166 |
| 325 | GALNS | 16 | q24.3 | 87407644 | 87450885 |
| 326 | TRAPPC2L | 16 | q24.3 | 87451007 | 87455020 |
| 327 | CBFA2T3 | 16 | q24.3 | 87468768 | 87570902 |
| 328 | CDH15 | 16 | q24.3 | 87765664 | 87789400 |
| 329 | ANKRD11 | 16 | q24.3 | 87861536 | 88084470 |
| 330 | FANCA | 16 | q24.3 | 88331460 | 88410566 |
| 331 | SPIRE2 | 16 | q24.3 | 88422408 | 88465228 |
| 332 | TCF25 | 16 | q24.3 | 88467520 | 88505287 |
| 333 | TUBB3 | 16 | q24.3 | 88513168 | 88530006 |
| 334 | DEF8 | 16 | q24.3 | 88542684 | 88561968 |
| 335 | AFG3L1 | 16 | q24.3 | 88566489 | 88594696 |
| 336 | GAS8 | 16 | q24.3 | 88616509 | 88638880 |
| 337 | DNAH2 | 17 | p13.1 | 7562746 | 7677783 |
| 338 | NKIRAS2 | 17 | q21.2 | 37422564 | 37431180 |
| 339 | DHX58 | 17 | q21.2 | 37506979 | 37518277 |
| 340 | KAT2A | 17 | q21.2 | 37518657 | 37526872 |
| 341 | HSPB9 | 17 | q21.2 | 37528361 | 37528897 |
| 342 | RAB5C | 17 | q21.2 | 37530524 | 37560548 |

TABLE 13-continued

| | | MPS Genes | | | |
|---|---|---|---|---|---|
| 343 | KCNH4 | 17 | q21.2 | 37562439 | 37586822 |
| 344 | GHDC | 17 | q21.2 | 37594632 | 37599722 |
| 345 | NOTUM | 17 | q25.3 | 77503689 | 77512353 |
| 346 | ASPSCR1 | 17 | q25.3 | 77528715 | 77568569 |
| 347 | DUS1L | 17 | q25.3 | 77609043 | 77629242 |
| 348 | FASN | 17 | q25.3 | 77629504 | 77649395 |
| 349 | CDH2 | 18 | q12.1 | 23784934 | 24011189 |
| 350 | NOL4 | 18 | q12.1 | 29685062 | 30057513 |
| 351 | DTNA | 18 | q12.1 | 30327279 | 30725806 |
| 352 | DCC | 18 | q21.2 | 48121156 | 49311780 |
| 353 | WDR7 | 18 | q21.31 | 52469614 | 52848040 |
| 354 | CD226 | 18 | q22.2 | 65681175 | 65775140 |
| 355 | ZSWIM4 | 19 | p13.13 | 13767274 | 13804044 |
| 356 | C19orf57 | 19 | p13.12 | 13854168 | 13877909 |
| 357 | CC2D1A | 19 | p13.12 | 13878014 | 13902691 |
| 358 | RFX1 | 19 | p13.12 | 13933353 | 13978097 |
| 359 | PLCB1 | 20 | p12.3 | 8061296 | 8813547 |
| 360 | SMARCB1 | 22 | q11.23 | 22459150 | 22506703 |
| 361 | TBC1D22A | 22 | q13.31 | 45537193 | 45948399 |
| 362 | RAB9A | 23 | p22.2 | 13617262 | 13637681 |
| 363 | TFE3 | 23 | p11.23 | 48772613 | 48787722 |
| 364 | HEPH | 23 | q12 | 65299388 | 65403956 |
| 365 | EDA2R | 23 | q12 | 65732204 | 65775608 |
| 366 | AR | 23 | q12 | 66680599 | 66860844 |
| 367 | OPHN1 | 23 | q12 | 67179440 | 67570372 |
| 368 | NLGN4Y | 24 | q11.221 | 15144026 | 15466924 |

Table 13 Cont'd . . .
Table 13 Cont'd . . .
Table 13 Cont'd . . .

Table 13 Cont'd . . .
Table 13 Cont'd . . .
Table 13 Cont'd . . .

TABLE 14

Table14-1a

| Final-RANK | gene | index | gene-start | gene-end | NYU-2 | NYU-dir | NYU-count | contg | clump-index | MSKs1-Z | MSKs1-dir | dstprev | dstnext | MSKs2-count | MSKs2-Z | MSKs2-dir | MSKs2 count | logrank-n52random | logrank-n271random | logrank-composite | gene-Chr | gene-Cytoband |
|---|---|---|---|---|---|---|---|---|---|---|---|---|---|---|---|---|---|---|---|---|---|---|
| 1 | PPP3CC | 129 | | 3.1 | | −1 | 958 | | | 2.6 | | | | 965 | NA | NA | NA | 48 | 41 | 45 | 8 | p21.3 |
| 2 | SLCO5A1 | 167 | | 4.9 | | 1 | 1000 | | | 4.2 | 1 | | | 982 | NA | NA | NA | 31 | 13 | 19 | 8 | q13.3 |
| 3 | SLC7A5 | 312 | | 1.7 | | −1 | 508 | | | 3 | −1 | | | 980 | NA | NA | NA | 43 | 37 | 40 | 18 | q24.2 |
| 4 | SLC7A2 | 110 | | 4.1 | | −1 | 1000 | | | NA | NA | | | NA | NA | NA | NA | 44 | 43 | 44 | 8 | p22 |
| 5 | CRISPLD2 | 299 | | 2.5 | | −1 | 735 | | | 2.9 | −1 | | | 939 | NA | NA | NA | 54 | 67 | 61 | 16 | q24.1 |
| 6 | CDH13 | 288 | | 8 | | −1 | 984 | | | 2.9 | −1 | | | 767 | NA | NA | NA | 46 | 86 | 63 | 16 | q23.3 |
| 7 | CDH8 | 265 | | | NA | NA | NA | | | NA | NA | | | NA | 3.7344 | −1 | 989 | 15 | 10 | 11 | 16 | q21 |
| 8 | CDH2 | 348 | | | NA | NA | NA | | | NA | NA | | | NA | 3.4486 | −1 | 967 | 16 | 15 | 17 | 18 | q12.1 |
| 9 | ASAH1 | 114 | | 7.1 | | −1 | 1000 | | | NA | NA | | | NA | NA | NA | NA | 105 | 64 | 80 | 8 | p22 |
| 10 | KCNB2 | 175 | | 8.8 | | 1 | NA | | | NA | NA | | | NA | 3.7501 | 1 | 983 | 59 | 74 | 66 | 8 | q13.3 |
| 11 | KCNH4 | 343 | | NA | | NA | NA | | | NA | NA | | | NA | 2.8192 | −1 | 921 | 1 | 1 | 1 | 17 | q21.2 |
| 12 | KCTD8 | 21 | | NA | | NA | NA | | | NA | NA | | | NA | NA | NA | NA | 30 | 24 | 29 | 4 | p13 |
| 13 | JPH1 | 179 | | 6.8 | | 1 | 1000 | | | NA | NA | | | NA | 3.2232 | 1 | 940 | 29 | 35 | 31 | 8 | q21.11 |
| 14 | MEST | 88 | | NA | | NA | NA | | | NA | NA | | | NA | NA | NA | NA | 32 | 32 | 32 | 7 | q32.2 |
| 15 | NCALD | 200 | | 5.5 | | 1 | 1000 | | | 2.9 | 1 | | | NA | 3.4333 | −1 | 953 | 13 | 12 | 13 | 8 | q22.3 |
| 16 | COL19A1 | 39 | | NA | | NA | NA | | | NA | NA | | | NA | 3.1873 | −1 | 936 | 27 | 20 | 21.5 | 6 | q13 |
| 17 | MAP3K7 | 43 | | NA | | NA | NA | | | NA | NA | | | NA | 2.7386 | 1 | 929 | 47 | 54 | 49 | 6 | q15 |
| 18 | YWHAG | 67 | | NA | | NA | NA | | | NA | NA | | | NA | 3.9113 | 1 | 951 | 40 | 62 | 47 | 7 | q11.23 |
| 19 | NOL4 | 350 | | NA | | NA | NA | | | NA | NA | | | NA | 5.6235 | −1 | 993 | 4 | 2 | 2 | 18 | q12.1 |
| 20 | ENOX1 | 247 | | NA | | NA | NA | | | NA | NA | | | NA | 4.6280 | −1 | 1000 | 2 | 8 | 4 | 13 | q14.11 |
| 21 | CSMD1 | 94 | | NA | | NA | NA | | | NA | NA | | | NA | 3.5107 | −1 | 971 | 7 | 6 | 6 | 8 | p23.2 |
| 22 | SGCZ | 107 | | 4.7 | | −1 | 926 | | | NA | NA | | | NA | NA | NA | 861 | 9 | 5 | 7 | 8 | p22 |
| 23 | PDE10A | 54 | | NA | | NA | NA | | | NA | NA | | | NA | 4.5945 | −1 | 999 | 8 | 7 | 8 | 5 | q27 |
| 24 | PCDH9 | 252 | | NA | | NA | NA | | | NA | NA | | | NA | 4.5416 | −1 | 962 | 5 | 19 | 9 | 13 | q21.32 |
| 25 | HTR2A | 250 | | NA | | NA | NA | | | NA | NA | | | NA | 3.2974 | −1 | 966 | 10 | 11 | 10 | 13 | q14.2 |
| 26 | HIP1 | 63 | | NA | | NA | NA | | | NA | NA | | | NA | 4.4416 | 1 | 1000 | 11 | 14 | 12 | 7 | q11.23 |
| 27 | CD226 | 354 | | NA | | NA | NA | | | NA | NA | | | NA | 3.3032 | −1 | 1000 | 18 | 9 | 14 | 18 | q22.2 |
| 28 | DCC | 352 | | NA | | NA | NA | | | NA | NA | | | NA | 6.6211 | −1 | 996 | 12 | 17 | 15 | 18 | q21.2 |
| 29 | CC2D1A | 357 | | NA | | NA | NA | | | NA | NA | | | NA | 3.9705 | 1 | NA | 17 | 18 | 18 | 19 | p13 12 |
| 30 | PTK2B | 152 | | 7 | | −1 | NA | | | NA | NA | | | NA | NA | NA | NA | 20 | 27 | 21.5 | 8 | p21.2 |
| 31 | BCMO1 | 284 | | 2.9 | | −1 | 943 | | | 3.6 | 1 | | | 957 | 2.8909 | 1 | 973 | 26 | 21 | 23 | 16 | q23.2 |
| 32 | MACROD1 | 233 | | NA | | NA | NA | | | 1.9 | −1 | | | 533 | 5.1108 | −1 | 983 | 25 | 22 | 24 | 11 | q13.1 |
| 33 | GRID2 | 24 | | NA | | NA | NA | | | NA | NA | | | NA | 3.2653 | −1 | 982 | 22 | 25 | 25 | 4 | q22.1 |
| 34 | DIAPH3 | 251 | | NA | | NA | NA | | | NA | NA | | | NA | 2.9352 | 1 | 996 | 24 | 29 | 27 | 13 | q21.2 |
| 35 | PILRB | 69 | | NA | | NA | NA | | | NA | NA | | | NA | NA | NA | 1000 | 25 | 25 | 28 | 7 | q22.1 |
| 36 | MEIS2 | 259 | | NA | | NA | NA | | | NA | NA | | | NA | 3.9428 | −1 | 999 | 19 | 39 | 30 | 15 | q14 |
| 37 | MSRA | 98 | | 5.1 | | −1 | 999 | | | NA | NA | | | NA | NA | NA | NA | 34 | 31 | 33 | 8 | p23.1 |
| 38 | DPYD | 4 | | NA | | NA | NA | | | NA | NA | | | NA | 2.8861 | −1 | 847 | 33 | 34 | 34 | 1 | p21.3 |

Table 14-1b

| Final-RANK | gene | gene-start | gene-end | genesBtwn | IndexO-Proxyl | NYU-Zadjust | MSKs1-Zadjust | min-distro-ROI | MSKS2-Zadjust |
|---|---|---|---|---|---|---|---|---|---|
| 1 | PPP3CC | 22354541 | 22454580 | 0 | 1 | 0.52 | 0.29 | −7079 | NA |
| 2 | SLCO5A1 | 70747129 | 70909762 | 0 | 1 | 1.63 | 1.16 | −11428 | NA |

TABLE 14-continued

| Final-RANK | gene | index | NYU-2 | NYU-dir | NYU-count | MSKs1-Z | MSKs1-dir | MSKs2-count | MSKs2-Z | MSKs2-dir | MSKs2 count | logrank-n52random | logrank-n271random | logrank-composite | | |
|---|---|---|---|---|---|---|---|---|---|---|---|---|---|---|---|---|
| 3 | SLC7A5 | 86421131 | 86460815 | 0 | 1 | 58 | 18511 | 1 | 18511 | 1 | 0.00 | 0.47 | | | | |
| 4 | SLC7A2 | 17398975 | 17472357 | 0 | 1 | 21 | 6086 | 1 | 6086 | 1 | 1.10 | NA | | | | |
| 5 | CRISPLD2 | 83411113 | 83500814 | 1 | 1 | 56 | 64959 | 1 | -40087 | 1 | 0.25 | 0.42 | | | | |
| 6 | CDH13 | 81439751 | 82387705 | 0 | 0 | NA | 102526 | NA | 102526 | NA | 3.67 | 0.42 | | | | |
| 7 | CDH8 | 60244866 | 60626240 | 82 | 0 | NA | 7528258 | NA | -3524069 | NA | NA | NA | | | | |
| 8 | CDH2 | 23784934 | 24011189 | 19 | 0 | NA | 5673873 | NA | -3524069 | NA | 0.87 | NA | | | | |
| 9 | ASAH1 | 17958214 | 17986787 | 1 | 1 | 22 | 306248 | NA | 5673873 | NA | 0.70 | NA | | | | |
| 10 | KCNB2 | 73642524 | 74012880 | 1 | 1 | 34 | 352193 | NA | -22652 | NA | NA | NA | | | | |
| 11 | KCNH4 | 37582439 | 37586822 | 1 | 0 | 6.4 | 7810 | NA | 352193 | NA | 3.10 | NA | | | | |
| 12 | KCTD8 | 43870883 | 44145681 | 3 | 1 | NA | -1891 | NA | -1891 | NA | 2.91 | NA | | | | |
| 13 | JPH1 | 75308493 | 75361117 | 0 | 0 | NA | 1800760 | NA | 1800760 | NA | NA | NA | | | | |
| 14 | MEST | 129913282 | 129933363 | 1 | 1 | 35 | 29058 | NA | 29058 | NA | 0.88 | NA | | | | |
| 15 | NCALD | 102767947 | 103206311 | 0 | 1 | 13 | 41 | NA | 41 | NA | 0.38 | NA | | | | |
| 16 | COL19A1 | 70833169 | 70978878 | 20 | 1 | 40 | 128437 | NA | -16952 | NA | 227 | NA | | | | |
| 17 | MAP3K7 | 91282074 | 91353828 | 0 | 1 | 5 | NA | NA | 4871884 | NA | NA | NA | | | | |
| 18 | YWHAG | 75794053 | 75828252 | 126 | 0 | NA | 2654236 | NA | 2654236 | NA | 0.56 | NA | | | | |
| 19 | NOL4 | 29686062 | 30057513 | 0 | 1 | 67 | 23787222 | NA | -260189 | NA | 2.03 | 0.42 | | | | |
| 20 | ENOX1 | 42886704 | 43259044 | 18 | 0 | NA | -5673873 | NA | -260189 | NA | NA | NA | | | | |
| 21 | CSMD1 | 2780262 | 3258996 | 46 | 1 | 14 | 269766 | NA | 269766 | NA | NA | NA | | | | |
| 22 | SGCZ | 13991744 | 15140219 | 0 | 0 | 20 | -4175452 | NA | 2766260 | NA | 0.70 | NA | | | | |
| 23 | PDE10A | 165560755 | 166995578 | NA | 1 | 8 | 5420413 | NA | -699503 | NA | 0.58 | NA | | | | |
| 24 | PCDH9 | 65774970 | 66702579 | 0 | 1 | 49 | 301882 | NA | 301882 | NA | 0.34 | NA | | | | |
| 25 | HTR2A | 46305514 | 46368175 | 44 | 1 | 48 | 2470149 | NA | -17655 | NA | 0.98 | NA | | | | |
| 26 | HIP1 | 75001345 | 75206215 | 5 | 0 | NA | 12769542 | NA | 2470149 | NA | 2.12 | NA | | | | |
| 25 | CD226 | 65881175 | 65775140 | NA | 0 | NA | 248023 | NA | -36146 | NA | 1.44 | NA | | | | |
| 26 | DCC | 48121155 | 49311780 | 10 | 0 | NA | NA | NA | -1543149 | NA | 0.74 | NA | | | | |
| 29 | CC2D1A | 1387814 | 13902691 | 0 | 1 | 68 | 3157834 | NA | 248023 | NA | 1.49 | NA | | | | |
| 30 | PTK2B | 27224915 | 27372820 | 0 | 1 | 30 | 30662 | NA | -12833135 | NA | 1.38 | NA | | | | |
| 31 | BCMO1 | 79829797 | 79882248 | 0 | 1 | 53 | 376 | NA | -17395350 | NA | 0.62 | NA | | | | |
| 32 | MACROD1 | 63522607 | 63690109 | 1 | 0 | NA | 23828 | NA | 3157834 | NA | 1.32 | NA | | | | |
| 33 | GRID2 | 93444831 | 94914730 | 186 | 0 | NA | 19764 | NA | -105 | NA | 0.63 | NA | | | | |
| 34 | DIAPH3 | 59137718 | 59636120 | 2 | 0 | NA | 60460408 | NA | -165 | NA | 2.79 | NA | | | | |
| 35 | PILRB | 99771673 | 99803388 | 0 | 0 | NA | 6138850 | NA | -18320 | NA | 1.02 | NA | | | | |
| 36 | MEIS2 | 34970519 | 35189740 | 193 | 1 | 11 | 5616 | NA | 19784 | NA | NA | NA | | | | |
| 37 | MSRA | 9949189 | 10323803 | 4 | 1 | NA | 24742144 | NA | -3084089 | NA | 0.42 | 0.80 | | | | |
| 38 | DPYD | 97315890 | 98159203 | 19 | 0 | NA | 897587 | NA | 6138850 | NA | NA | 0.05 | | | | |

Table 14-2a

| Final-RANK | gene | index | NYU-2 | NYU-dir | NYU-count | MSKs1-Z | MSKs1-dir | MSKs2-count | MSKs2-Z | MSKs2-dir | MSKs2 count | logrank-n52random | logrank-n271random | logrank-composite | gene-Chr | gene-Cytoband |
|---|---|---|---|---|---|---|---|---|---|---|---|---|---|---|---|---|
| 39 | ANKRD11 | 329 | 3 | -1 | 948 | 3.7 | -1 | 988 | NA | NA | NA | 37 | 33 | 35 | 18 | q24.3 |
| 40 | NRXN1 | 6 | NA | NA | NA | NA | NA | NA | 3.2327 | -1 | 840 | 39 | 38 | 38 | 2 | p16.3 |
| 41 | ADCY8 | 225 | 3.1 | 1 | 980 | 5.4 | 1 | 1000 | NA | NA | NA | 52 | 30 | 39 | 8 | q24.22 |
| 42 | TRDN | 49 | NA | NA | NA | NA | NA | NA | 3.0342 | -1 | 898 | 38 | 44 | 41 | 6 | q22.31 |
| 43 | STAU2 | 177 | 4.6 | 1 | 1000 | NA | NA | NA | NA | NA | NA | 45 | 42 | 43 | 8 | q21.11 |
| 44 | SF1 | 240 | NA | NA | NA | NA | NA | NA | 2.4710 | 1 | 888 | 56 | 48 | 48 | 11 | q13.1 |
| 45 | CLIP2 | 62 | NA | NA | NA | NA | NA | NA | 3.0945 | 1 | 998 | 57 | 47 | 50 | 7 | q11.23 |
| 46 | CLDN3 | 58 | NA | NA | NA | NA | NA | NA | 2.6179 | 1 | 984 | 51 | 53 | 51 | 7 | q11.23 |
| 47 | ZSWIM4 | 355 | NA | NA | NA | NA | NA | NA | 2.8120 | -1 | 975 | 60 | 51 | 57 | 19 | p13.13 |
| 48 | GLRB | 26 | NA | NA | NA | NA | NA | NA | 2.6600 | -1 | 963 | 64 | 48 | 58 | 4 | q32.1 |
| 49 | DCHS2 | 25 | NA | NA | NA | NA | NA | NA | 2.7883 | 1 | 954 | 68 | 80 | 84 | 4 | q32.1 |

TABLE 14-continued

| Final-RANK | gene | gene-start | gene-end | genesBtwn | contg | clump-index | dstprev | dstnext | min-disto-ROL | IndexO-Proxy1 | NYU-Zadjust | MSKs1-Zadjust | MSKS2-Zadjust | chr | band |
|---|---|---|---|---|---|---|---|---|---|---|---|---|---|---|---|
| 50 | TRPS1 | 217 | | 1 | 1 | 2.7 | 246990 | 751 | −72136 | 1 | 0.47 | 0.85 | NA | 63 | 65 | 65 | 8 | q23.3 |
| 51 | MDGA2 | 258 | 2.9 | NA | 0 | NA | 28619013 | NA | 28619013 | −1 | NA | NA | 0.59 | 69 | 66 | 68 | 14 | q21.3 |
| 52 | CNBD1 | 193 | NA | 1 | 1 | 3.8 | 861663 | 940 | −378337 | 1 | 0.52 | 1.97 | NA | 57 | 70 | 69 | 8 | q21.3 |
| 53 | STAG3 | 68 | 38 | NA | 0 | NA | 20654529 | −5440605 | −5440605 | 1 | NA | NA | 0.48 | 78 | 68 | 71 | 7 | q22.1 |
| 54 | GATA4 | 102 | NA | 1 | 0 | NA | 199555 | −119303 | −119303 | 1 | 1.43 | NA | NA | 72 | 77 | 72 | 8 | p23.1 |
| 55 | VPS13B | 202 | 3.2 | 1 | 1 | 2.6 | 24747 | NA | 24747 | 1 | NA | NA | 0.23 | 85 | 69 | 74 | 8 | q22.2 |
| 56 | DOCK5 | 144 | 3.9 | −1 | 1 | NA | 1543149 | −560058 | −35055 | NA | NA | NA | NA | 81 | 78 | 76 | 8 | p21.2 |
| 57 | ZHX2 | 218 | 5.4 | NA | 0 | 2.6 | 404089 | 771 | −49338 | 1 | NA | NA | 0.52 | 82 | 80 | 78 | 8 | q24.13 |
| 58 | ARHGEF5 | 90 | NA | NA | 1 | NA | NA | NA | 50124 | NA | NA | NA | 0.29 | 66 | 102 | 81 | 7 | q35 |
| 59 | SDC2 | 198 | 3.4 | 1 | 0 | 2.8 | NA | NA | NA | 1 | NA | NA | NA | 75 | 90 | 82 | 8 | q22.1 |
| 60 | MYLK | 10 | NA | NA | 1 | NA | 50124 | 842 | NA | NA | NA | NA | 0.38 | 93 | 75 | 83 | 3 | q21.1 |
| 61 | LPHN3 | 23 | NA | NA | 0 | NA | 48887 | NA | 48887 | NA | NA | NA | 0.31 | 80 | 92 | 85 | 4 | q13.1 |
| 62 | MOSPD3 | 78 | NA | NA | 1 | 2.9 | 2584470 | 2584470 | 2584470 | 1 | NA | NA | 0.37 | 90 | 82 | 86 | 7 | q22.1 |
| 63 | GYS2 | 244 | NA | NA | 0 | 2.9 | 7112653 | NA | −1971482 | NA | NA | NA | NA | 99 | 83 | 92 | 12 | p12.1 |
| 64 | GAS8 | 336 | NA | NA | 1 | 2.9 | NA | NA | NA | 1 | NA | NA | 0.39 | 84 | 103 | 95 | 16 | q24.3 |
| 65 | RAB9A | 382 | 3.2 | NA | 0 | 3.7 | NA | 870 | 2.7616 | NA | NA | NA | NA | 98 | 97 | 97 | 23 | p22.2 |
| 66 | POLA3D | 127 | NA | NA | 1 | 2.7 | NA | 955 | NA | −1 | NA | NA | NA | 91 | 109 | 98 | 8 | p21.3 |
| 67 | PSD3 | 116 | 7.3 | −1 | 1 | 6.3 | NA | 996 | NA | NA | NA | NA | NA | 97 | 104 | 100 | 8 | p22 |
| 68 | ZFPM2 | 213 | 4.2 | 1 | 1 | 2.4 | 1 | 858 | NA | 1 | NA | NA | NA | 149 | 71 | 101 | 8 | q23.1 |
| 69 | ATP6V1C1 | 309 | NA | NA | 1 | NA | NA | NA | NA | NA | NA | NA | NA | 114 | 93 | 102 | 8 | q22.3 |
| 70 | MEF2C | 36 | NA | NA | 1 | NA | NA | NA | 2.2584 | −1 | NA | NA | NA | 109 | 98 | 103 | 5 | q14.3 |
| 71 | PKIA | 185 | 3.3 | 1 | 0 | NA | NA | NA | NA | NA | 0.42 | 0.33 | NA | 115 | 99 | 104 | 8 | q21.12 |
| 72 | ADAMTS18 | 276 | 3.5 | −1 | 1 | NA | NA | 999 | NA | NA | NA | NA | NA | 100 | 114 | 105 | 16 | q23.1 |
| 73 | STYXL1 | 65 | NA | NA | 1 | NA | NA | NA | 2.3049 | 1 | NA | NA | NA | 104 | 110 | 106 | 7 | q11.23 |
| 74 | EPM2A | 51 | NA | NA | 0 | 2.6 | 683350 | 755 | 2.3972 | −1 | 0.91 | 0.91 | 0.21 | 113 | 105 | 108 | 6 | q24.3 |
| 75 | CLIP2 | 19 | NA | NA | 1 | NA | 111895 | NA | NA | −1 | NA | NA | NA | 106 | 119 | 110 | 3 | q28 |
| 76 | GABRA2 | 22 | NA | NA | 0 | 2.6 | 9709 | NA | 2.2755 | −1 | 0.57 | NA | NA | 119 | 107 | 111 | 4 | p12 |
| 77 | RCOR2 | 230 | NA | NA | 1 | NA | 83469 | NA | 1.7131 | NA | 0.98 | NA | NA | 108 | 120 | 114 | 11 | q13.1 |
| 78 | MFHAS1 | 95 | 3.3 | −1 | 0 | NA | 14747 | NA | 14747 | NA | 1.97 | NA | NA | 121 | 108 | 115 | 8 | p23.1 |

Table 14-2b

| Final-RANK | gene | gene-start | gene-end | genesBtwn | contg | clump-index | dstprev | dstnext | min-disto-ROL | IndexO-Proxy1 | NYU-Zadjust | MSKs1-Zadjust | MSKS2-Zadjust |
|---|---|---|---|---|---|---|---|---|---|---|---|---|---|
| 39 | ANKRD11 | 87881536 | 88084470 | 11 | 1 | 61 | 246990 | −72136 | −72136 | 1 | 0.47 | 0.85 | NA |
| 40 | NRXN1 | 49999148 | 51113178 | 155 | 0 | NA | 28619013 | NA | 28619013 | −1 | NA | NA | 0.59 |
| 41 | ADCY8 | 131861736 | 132123654 | 0 | 1 | 45 | 861663 | −378337 | −378337 | 1 | 0.52 | 1.97 | NA |
| 42 | TRDN | 123579182 | 123999937 | 96 | 0 | NA | 20654529 | −5440605 | −5440605 | 1 | NA | NA | 0.48 |
| 43 | STAU2 | 74495160 | 74821629 | NA | 0 | NA | 199555 | −119303 | −119303 | 1 | 1.43 | NA | NA |
| 44 | SF1 | 64288654 | 64302817 | 1 | 1 | 9 | 24747 | −560058 | 24747 | 1 | NA | NA | 0.23 |
| 45 | CLIP2 | 84288654 | 73458196 | 15 | 0 | NA | 1543149 | −35065 | −35055 | NA | NA | NA | NA |
| 46 | CLDN3 | 73341739 | 72822536 | 5 | 1 | NA | 404089 | −49338 | −49338 | 1 | NA | NA | 0.52 |
| 47 | ZSWIM4 | 72821283 | 13804044 | 1 | 0 | NA | NA | NA | 50124 | NA | NA | NA | 0.29 |
| 48 | GLRB | 13767274 | 158312299 | 0 | 1 | 3 | 50124 | NA | 48887 | NA | NA | NA | 0.38 |
| 49 | DCHS2 | 158216788 | 155832318 | 14 | 1 | NA | 48887 | −2584470 | 2584470 | −1 | NA | NA | 0.31 |
| 50 | TRPS1 | 155375138 | 116750429 | 20 | 0 | 43 | 2584470 | −60480408 | −1971482 | 1 | 0.42 | 0.33 | 0.37 |
| 51 | MDGA2 | 116489900 | 47213703 | NA | NA | NA | 7112653 | −1971482 | NA | 1 | NA | NA | NA |
| 52 | CNBD1 | 46379045 | 88435220 | 1 | 1 | 38 | 683350 | −23787222 | −122823 | −1 | 0.91 | NA | 0.39 |
| 53 | STAG3 | 87947840 | 99659778 | 2 | 0 | NA | 111895 | −139646 | 111895 | −1 | NA | 0.91 | NA |
| 54 | GATA4 | 99613474 | 11854918 | 0 | 1 | 18 | 9709 | −187596 | 9709 | −1 | 0.57 | NA | 0.21 |
| 55 | VPS13B | 11599162 | 100958983 | 1 | 0 | NA | 83469 | 83469 | 83469 | −1 | 0.98 | NA | NA |
| 56 | DOCK5 | 100094670 | 25326636 | 2 | 0 | NA | 14747 | −1478148 | 14747 | NA | 1.97 | NA | NA |

TABLE 14-continued

| | gene | index | NYU-2 | NYU-dir | NYU-count | MSKs1-Z | MSKs1-dir | MSKs1-count | MSKs2-Z | MSKs2-dir | MSKs2-count | logrank-n52random | logrank-n271random | logrank-composite | gene-Chr | gene-Cytoband |
|---|---|---|---|---|---|---|---|---|---|---|---|---|---|---|---|---|
| 57 | ZHX2 | 123863082 | 3.3 | 9 | 0 | NA | NA | 706230 | NA | NA | NA | 0.29 | NA | NA | 116 | 8 | p21.1 |
| 58 | ARHGEF5 | 143683366 | 4.4 | NA | 0 | NA | NA | NA | -13747479 | NA | NA | NA | NA | 0.35 | 117 | 8 | p21.1 |
| 59 | SDC2 | 97575058 | | 1 | 1 | NA | NA | 1032370 | -159108 | NA | NA | NA | NA | NA | 119 | 16 | q24.3 |
| 60 | MYLK | 124811586 | 2.8 | 2 | 0 | 2.7 | NA | 210407 | -8482769 | NA | NA | 0.68 | NA | 0.68 | 122 | 8 | p23.1 |
| 61 | LPHN3 | 62045434 | | 157 | 1 | NA | NA | 30824069 | 210407 | NA | NA | NA | NA | NA | 123 | 8 | q24.3 |
| 62 | MOSPD3 | 100047651 | | 0 | 0 | 2.3 | NA | NA | 30824089 | NA | NA | 0.38 | NA | 0.24 | 124 | 16 | q24.3 |
| 63 | GYS2 | 100050932 | NA | NA | 1 | 1.7 | NA | -3929 | 3929 | NA | NA | NA | NA | 0.17 | 125 | 13 | q13.3 |
| 64 | GAS8 | 21580390 | NA | NA | NA | NA | NA | NA | NA | NA | NA | 0.42 | NA | 0.38 | 126 | 4 | p15.33 |
| 65 | RAB9A | 88616509 | | NA | 0 | NA | NA | NA | -21813 | NA | NA | 0.85 | NA | NA | 129 | 8 | p21.3 |
| 66 | POLA3D | 13617262 | 2.5 | 191 | 0 | 1.8 | NA | NA | 35134932 | NA | NA | 0.33 | NA | NA | 130 | 6 | q22.2 |
| 67 | PSD3 | 22158584 | NA | 1 | 1 | NA | NA | 116113 | -12768 | NA | NA | NA | NA | NA | 131 | 16 | q24.1 |
| 68 | ZFPM2 | 18429093 | NA | 0 | 0 | NA | NA | 300007 | -128090 | NA | NA | 3.23 | NA | NA | 135.5 | 16 | q22.3 |
| 69 | ATP6V1C1 | 108400323 | NA | 2 | 1 | 2.4 | NA | 1444960 | -729979 | NA | NA | 1.16 | NA | NA | 137 | 16 | q24.3 |
| 70 | MEF2C | 104102424 | NA | 5 | 0 | NA | NA | 608753 | 427830 | NA | NA | 0.21 | NA | 0.15 | 140 | 4 | q32.2 |
| 71 | PKIA | 88051922 | NA | 63 | 1 | 2.2 | NA | 26727467 | -19278276 | NA | NA | NA | NA | NA | 141 | 6 | q16.3 |
| 72 | ADAMTS18 | 79590891 | NA | 2 | 0 | 2.3 | NA | 1007876 | 1007878 | NA | NA | 0.63 | NA | NA | 144 | 16 | q24.22 |
| 73 | STYXL1 | 76026512 | NA | 2 | 1 | NA | NA | 287400 | 287400 | NA | NA | 0.74 | NA | 0.17 | 148 | 8 | q22.1 |
| 74 | EPM2A | 75873527 | 3.8 | 0 | 0 | 52 | NA | NA | 72 | NA | NA | NA | NA | 0.20 | 149 | 3 | q21.3 |
| 75 | LEPREL1 | 75615257 | | 0 | 1 | 10 | NA | -1679 | 291927 | NA | NA | NA | NA | NA | 150 | 8 | q22.3 |
| 76 | GABRA2 | 145088884 | 2 | 2 | 1 | 7 | NA | -772282 | -49278 | NA | NA | NA | NA | 0.16 | 151 | 13 | q13.1 |
| 77 | RCOR2 | 191157213 | | 2 | 0 | 2 | NA | 291927 | -1800760 | NA | NA | 0.29 | NA | NA | 153 | 5 | 913.2 |
| 78 | MFHAS1 | 191321407 | 3.2 | NA | NA | NA | NA | -49278 | 81715 | NA | NA | NA | NA | 0.00 | 156 | 16 | q23.1 |
|  | | 45945341 | 3 | 3 | 0 | 15 | NA | 81715 | 109315 | NA | NA | 0.63 | NA | NA | 157 | 16 | q23.1 |
|  | | 6344892 | NA | NA | 1 | NA | NA | NA | NA | NA | NA | NA | NA | 158 | 6 | q16.2 |
|  | | 888541 | NA | 0 | | NA | NA | -5420413 | | NA | NA | | NA | 163 | 19 | p13.12 |

Table 14-3a

| Final-RANK | gene | index | NYU-2 | NYU-dir | NYU-count | MSKs1-Z | MSKs1-dir | MSKs1-count | MSKs2-Z | MSKs2-dir | MSKs2-count | logrank-n52random | logrank-n271random | logrank-composite | gene-Chr | gene-Cytoband |
|---|---|---|---|---|---|---|---|---|---|---|---|---|---|---|---|---|
| 79 | SCARA5 | 158 | | -1 | 925 | NA | NA | NA | NA | NA | NA | 130 | 101 | 116 | 8 | p21.1 |
| 80 | CCDC25 | 155 | | -1 | 995 | NA | NA | NA | NA | NA | NA | 132 | 100 | 117 | 8 | p21.1 |
| 81 | FAM3RA | 323 | NA | NA | NA | NA | NA | 885 | NA | NA | NA | 110 | 130 | 119 | 16 | q24.3 |
| 82 | CTSB | 104 | NA | -1 | 941 | 2.7 | NA | NA | NA | NA | NA | 111 | 135 | 122 | 8 | p23.1 |
| 83 | PTK2 | 235 | NA | NA | NA | 2.3 | NA | 654 | NA | NA | NA | 107 | 144 | 123 | 8 | q24.3 |
| 84 | SPIRE2 | 331 | NA | NA | NA | 1.7 | NA | 508 | NA | NA | NA | 124 | 128 | 124 | 16 | q24.3 |
| 85 | C13orf123 | 246 | NA | NA | NA | NA | NA | NA | 2.2139 | -1 | 748 | 141 | 113 | 125 | 13 | q13.3 |
| 86 | BOD1L | 20 | NA | NA | 899 | 1.8 | NA | NA | 2.3508 | -1 | 884 | 129 | 127 | 126 | 4 | p15.33 |
| 87 | FAM16OB2 | 120 | 2.5 | -1 | NA | NA | NA | 567 | NA | NA | NA | 127 | 133 | 129 | 8 | p21.3 |
| 88 | NUS1 | 46 | NA | NA | NA | NA | NA | NA | 2.2269 | -1 | 859 | 123 | 139 | 130 | 6 | q22.2 |
| 89 | MTHFSD | 309 | NA | NA | NA | 2.4 | NA | 824 | NA | NA | NA | 112 | 153 | 131 | 16 | q24.1 |
| 90 | UBA5 | 208 | NA | NA | NA | 2.2 | 1 | 733 | NA | NA | NA | 122 | 155 | 135.5 | 16 | q22.3 |
| 91 | GALNS | 325 | NA | NA | NA | 2.3 | 1 | 856 | 2.2407 | -1 | 541 | 131 | 147 | 137 | 16 | q24.3 |
| 92 | FSTL5 | 28 | NA | NA | NA | NA | NA | NA | 2.1943 | -1 | 833 | 133 | 143 | 140 | 4 | q32.2 |
| 93 | SIM1 | 46 | NA | NA | NA | NA | NA | NA | NA | NA | NA | 120 | 165 | 141 | 6 | q16.3 |
| 94 | TG | 231 | 3.8 | 1 | 997 | 2.4 | 1 | 678 | NA | NA | NA | 136 | 149 | 144 | 8 | q24.22 |
| 95 | BFSP2 | 12 | NA | NA | NA | 3.5 | NA | 931 | NA | NA | NA | 139 | 154 | 148 | 3 | q22.1 |
| 96 | MMP16 | 194 | NA | NA | NA | 4 | 1 | 939 | NA | NA | NA | 158 | 139 | 149 | 8 | q21.3 |
| 97 | RIMS2 | 210 | 2 | 1 | 692 | NA | NA | NA | NA | NA | NA | 161 | 141 | 150 | 8 | q22.3 |
| 98 | PDS5B | 245 | NA | NA | NA | NA | NA | 988 | 2.0408 | -1 | 661 | 145 | 159 | 151 | 13 | q13.1 |
| 99 | CDK7 | 31 | NA | NA | 825 | 2.7 | NA | NA | NA | NA | NA | 156 | 148 | 153 | 5 | 913.2 |
| 100 | CNTNAP4 | 275 | 3.2 | -1 | 925 | NA | NA | NA | NA | NA | NA | 196 | 126 | 156 | 16 | q23.1 |
| 101 | CFDP1 | 274 | 3 | -1 | NA | NA | NA | NA | NA | NA | NA | 137 | 187 | 157 | 16 | q23.1 |
| 102 | FBXL4 | 45 | NA | NA | NA | NA | NA | NA | 1.7473 | -1 | 537 | 154 | 167 | 158 | 6 | q16.2 |
| 103 | RFX1 | 358 | NA | NA | NA | NA | NA | NA | 2.1724 | 1 | 861 | 134 | 201 | 163 | 19 | p13.12 |

TABLE 14-continued

| | gene | | | | | | | | | | | | | |
|---|---|---|---|---|---|---|---|---|---|---|---|---|---|---|
| 104 | NALCN | 256 | | NA | NA | NA | NA | NA | NA | NA | -1 | 2.1845 | 165 | 13 | q33.1 |
| 105 | SIX1A | 57 | | NA | NA | NA | NA | NA | NA | NA | 1 | 2.1787 | 167 | 7 | q11.23 |
| 106 | CYP7B1 | 162 | | NA | NA | NA | NA | 1.7 | 508 | NA | NA | NA | 168 | 8 | q12.3 |
| 107 | ARHGEF10 | 92 | | NA | NA | NA | NA | 2.9 | 923 | NA | NA | NA | 171 | 8 | p23.3 |
| 108 | ENIPD4 | 141 | 2.7 | -1 | NA | 875 | NA | 2.5 | 815 | NA | NA | NA | 173 | 8 | p21.3 |
| 109 | ZNF704 | 188 | | NA | NA | NA | 0 | NA | NA | NA | NA | NA | 174 | 8 | q21.13 |
| 110 | C8or179 | 105 | 2.9 | -1 | NA | 93 | 1 | 2.7 | 746 | NA | 1 | NA | 176 | 8 | p22 |
| 111 | SLC9A9 | 13 | | NA | NA | NA | 0 | 2.4 | 925 | NA | NA | NA | 177 | 3 | q24 |
| 112 | CHMP7 | 139 | | NA | NA | NA | 0 | NA | NA | NA | -1 | NA | 178 | 8 | p21.3 |
| 113 | GPC5 | 255 | | NA | NA | NA | 0 | NA | NA | NA | NA | 2.1374 | 180 | 13 | q31.3 |
| 114 | MYC | 222 | 4.2 | 1 | NA | 972 | 1 | NA | NA | NA | NA | NA | 184 | 8 | q24.21 |
| 115 | STIP1 | 239 | | NA | NA | NA | 0 | 1.8 | 513 | NA | NA | 1.7766 | 185 | 11 | q13.1 |
| 116 | ZBTB20 | 9 | | NA | NA | NA | 1 | NA | NA | NA | 1 | NA | 188 | 3 | q13.31 |
| 117 | MEN1 | 241 | | NA | NA | NA | 0 | NA | NA | NA | NA | 2.0513 | 188 | 11 | q13.1 |
| 118 | SLC26A7 | 195 | | NA | NA | NA | 1 | 2.2 | 747 | NA | NA | NA | 189 | 8 | q21.3 |

Table 14-3b

| Final-RANK | gene | gene-start | gene-end | genesBtwn | contg | clump-index | dstprev | dstnext | min-distto-ROI | IndexO-Proxy1 | NYU-Zadjust | MSKs1-Zadjust | MSKS2-Zadjust |
|---|---|---|---|---|---|---|---|---|---|---|---|---|---|
| 79 | SCARA5 | 27783672 | 27906117 | 0 | 1 | 31 | 29490 | -97583 | 29490 | 1 | 0.63 | NA | NA |
| 80 | CCDC25 | 27646756 | 27686089 | 2 | 0 | NA | 97583 | -188353 | 97583 | 1 | 1.29 | NA | NA |
| 81 | FAM3RA | 87302916 | 67730317 | 0 | 1 | 58 | 67370 | -2604 | -2604 | 1 | NA | 0.33 | NA |
| 82 | CTSB | 11737442 | 11763055 | 7 | 0 | NA | 1084499 | -55179 | -55179 | 1 | 0.38 | NA | NA |
| 83 | PTK2 | 141737883 | 142080514 | NA | 0 | NA | -5943220 | -5943220 | -5943220 | 1 | NA | 0.17 | 0.15 |
| 84 | SPIRE2 | 88422408 | 88485228 | 0 | 1 | 62 | 2292 | -11842 | 2292 | 1 | NA | 0.00 | NA |
| 85 | C13or123 | 38482003 | 38510252 | 21 | 0 | NA | 4175452 | -6231846 | 4175452 | 1 | NA | NA | 0.14 |
| 86 | BOD1L | 13179484 | 13238426 | 76 | 0 | NA | 30632257 | NA | 30632257 | 1 | NA | NA | 0.19 |
| 87 | FAM16OB2 | 22002660 | 22017835 | 0 | 1 | 24 | 2493 | -82519 | 2493 | 1 | 0.25 | 0.02 | NA |
| 88 | NUS1 | 118103310 | 118138577 | 15 | 1 | NA | 5440605 | -16667349 | 5440605 | 1 | NA | NA | 0.14 |
| 89 | MTHFSD | 85121284 | 85157509 | 5 | 1 | 57 | 1036491 | -15714 | -15714 | 1 | NA | 0.21 | NA |
| 90 | UBA5 | 103334748 | 103493671 | 3 | 0 | NA | 606753 | -128437 | -128437 | 1 | NA | 0.14 | NA |
| 91 | GALNS | 87407644 | 87450885 | 0 | 1 | 60 | 122 | -4478 | 122 | 1 | NA | 0.17 | 0.17 |
| 92 | FSTL5 | 162524501 | 183304836 | NA | 0 | NA | NA | 4017824 | -4017824 | 1 | NA | NA | 0.15 |
| 93 | SIM1 | 100939606 | 101019494 | 0 | 1 | 6 | 43297 | -1437036 | 43297 | 1 | NA | NA | 0.13 |
| 94 | TG | 133948387 | 134216325 | 7 | 0 | 48 | -98170 | -18153 | -18153 | 1 | 0.91 | NA | NA |
| 95 | BFSP2 | 134601480 | 134676746 | 58 | 0 | NA | 9790009 | -8678754 | -8678754 | 1 | NA | 0.21 | 0.08 |
| 96 | MMP16 | 89118580 | 89408833 | 9 | 0 | NA | 2921859 | -683360 | -683360 | 1 | NA | 0.74 | NA |
| 97 | RIMS2 | 104582291 | 106333263 | 1 | 0 | 6 | 127586 | 427830 | 127566 | 1 | NA | 1.04 | 0.14 |
| 98 | PDS5B | 32058564 | 32250157 | 21 | 0 | NA | 6231846 | NA | 6231846 | 1 | NA | NA | NA |
| 99 | CDK7 | 68566471 | 68609004 | 0 | 1 | 4 | 3274 | 11239 | 3274 | 1 | NA | 0.33 | 0.01 |
| 100 | CNTNAP4 | 74868677 | 75150636 | 1 | 0 | NA | 722891 | -843789 | 722891 | 1 | 0.57 | NA | 0.13 |
| 101 | CFDP1 | 73885109 | 74024888 | 7 | 0 | 51 | 843789 | -25857 | -25857 | 1 | 0.47 | NA | NA |
| 102 | FBXL4 | 99428055 | 99502570 | 7 | 0 | NA | 1437036 | -5242052 | 1437036 | 1 | NA | NA | 0.13 |
| 103 | RFX1 | 13953353 | 13978097 | NA | 0 | NA | NA | -30682 | -30682 | 1 | NA | NA | 0.13 |
| 104 | NALCN | 100504131 | 100866814 | 42 | 0 | NA | 12420243 | -8187438 | -8187438 | 1 | NA | NA | NA |
| 105 | SIX1A | 72751472 | 72771925 | 1 | 0 | NA | NA | NA | 49338 | 1 | NA | 0.00 | 0.08 |
| 107 | CYP7B1 | 65671248 | 65873902 | 21 | 0 | NA | 2823061 | -5476925 | 2623061 | 1 | NA | 0.42 | NA |
| 108 | ARHGEF10 | 1759549 | 1894208 | 1 | 1 | 28 | 86359 | -115501 | 86359 | 1 | NA | NA | 0.01 |
| 108 | ENIPD4 | 23299386 | 23371081 | 0 | 0 | 37 | 71227 | 18281 | 18281 | 1 | 0.33 | NA | NA |
| 109 | ZNF704 | 81713324 | 81949571 | 0 | 1 | 28 | 93034 | 870671 | 98034 | 1 | NA | 0.25 | NA |
| 110 | C8or179 | 12847554 | 12931653 | 0 | 1 | 19 | 53590 | -1084499 | 53590 | 1 | 0.42 | NA | NA |

TABLE 14-continued

| | gene | index | NYU-2 | NYU-dir | NYU-count | MSKs1-Z | MSKs1-dir | MSKs2-count | MSKs2-Z | MSKs2-dir | MSKs2 count | logrank-n52random | logrank-n271random | logrank-composite | | gene-Chr | gene-Cytoband |
|---|---|---|---|---|---|---|---|---|---|---|---|---|---|---|---|---|---|
| 111 | SLC9A9 | | | | | | 12271116 | | -9790009 | 1 | 586 | 194 | 188 | 191 | NA | 3 | q13.11 |
| 112 | CHMP7 | | | | | | 34647 | | -18511 | 1 | NA | 188 | 194 | 192 | 0.33 | 8 | p21.1 |
| 113 | GPC5 | | | | | | 8187438 | | 8187438 | 1 | NA | 183 | 192 | 193 | 0.21 | 16 | q24.1 |
| 114 | MYC | | | | | | 205193 | | 206193 | 1 | 580 | 189 | 202 | 195 | NA | 11 | q13.1 |
| 115 | STIP1 | | | | | | 560068 | | -19764 | 1.16 | 550 | 201 | 180 | 197 | NA | 15 | q22.2 |
| 116 | ZBTB20 | | | | | | 8462769 | | -8761797 | 1 | 549 | 219 | 178 | 198 | 0.01 | 17 | q25.3 |
| 117 | MEN1 | | | | | | 12898 | | 12898 | 1 | 735 | 169 | 235 | 201 | NA | 7 | q22.1 |
| 118 | SLC26A7 | | | | | | 2729012 | | 2729012 | 1 | NA | 206 | 195 | 203 | 0.09 | 8 | q21.13 |

Table 14-4a

| Final-RANK | gene | index | NYU-2 | NYU-dir | NYU-count | MSKs1-Z | MSKs1-dir | MSKs2-count | MSKs2-Z | MSKs2-dir | MSKs2 count | logrank-n52random | logrank-n271random | logrank-composite | | gene-Chr | gene-Cytoband |
|---|---|---|---|---|---|---|---|---|---|---|---|---|---|---|---|---|---|
| 119 | ALCAM | 8 | NA | NA | NA | NA | NA | NA | 2.4802 | 1 | NA | 197 | 205 | 204 | | 3 | q21.1 |
| 120 | KIF13B | 160 | 2.7 | -1 | 854 | NA | NA | NA | NA | NA | NA | 191 | 215 | 205 | | 8 | q22.2 |
| 121 | MBTPS1 | 291 | 2.7 | -1 | 906 | NA | NA | NA | NA | NA | NA | 200 | 217 | 210 | | 18 | q21.31 |
| 122 | PPP2R5B | 243 | NA | NA | NA | NA | NA | NA | 1.8055 | 1 | 653 | 233 | 206 | 213 | | 1 | p21.1 |
| 123 | VPS13C | 260 | NA | NA | NA | NA | NA | NA | 1.7860 | -1 | 591 | 221 | 218 | 215 | | 17 | q21.2 |
| 124 | ASPSCR1 | 346 | NA | NA | NA | NA | NA | NA | 1.7635 | 1 | 523 | 216 | 236 | 216 | | 16 | q24.1 |
| 125 | EPO | 82 | NA | NA | NA | NA | NA | NA | 1.9843 | 1 | NA | 227 | 216 | 217 | | 8 | q22.1 |
| 126 | HEY1 | 187 | 3 | 1 | 988 | NA | NA | NA | NA | NA | 674 | 192 | 258 | 219 | | 3 | q27.3 |
| 127 | KALRN | 11 | NA | NA | NA | 2.4 | 1 | NA | NA | NA | NA | 210 | 237 | 220 | | 10 | q26.11 |
| 128 | RGS22 | 203 | 2.7 | 1 | 956 | NA | NA | 568 | NA | NA | 568 | 179 | 283 | 223 | | 6 | q24.3 |
| 129 | WDH7 | 353 | NA | NA | NA | NA | NA | 831 | 1.9953 | -1 | NA | 243 | 210 | 224 | | 8 | q21.13 |
| 130 | COL11A1 | 5 | NA | NA | NA | 1.9 | 1 | NA | 1.8924 | -1 | 58 | 261 | 211 | 229 | | 8 | q21.11 |
| 131 | CHDC | 344 | NA | NA | NA | NA | NA | 647 | 1.7523 | -1 | NA | 235 | 245 | 232 | | 1 | p12.1 |
| 132 | ATP2C2 | 296 | 3.6 | -1 | 943 | NA | NA | NA | NA | NA | NA | 241 | 240 | 233 | | 17 | q14.1 |
| 133 | CDH17 | 196 | 2.8 | 1 | 976 | NA | NA | NA | NA | NA | NA | 234 | 248 | 234 | | 16 | q23.3 |
| 134 | CGKG | 17 | NA | NA | NA | NA | NA | 805 | NA | NA | NA | 256 | 221 | 235 | | 8 | q12 |
| 135 | GAK5 | 236 | NA | NA | NA | 2.5 | 1 | 582 | 1.8983 | NA | NA | 181 | 330 | 240 | | 3 | p12.3 |
| 136 | GAM1 | 52 | NA | NA | NA | 2.4 | -1 | 729 | NA | NA | NA | 264 | 229 | 242 | | 10 | p36.13 |
| 137 | IMPA1 | 190 | NA | NA | NA | NA | NA | NA | NA | NA | NA | 1 | 283 | 248 | | 6 | q34 |
| 138 | RPL7 | 176 | 2.3 | 1 | 813 | 1.9 | 1 | 523 | NA | NA | 580 | 205 | 304 | 255 | | 8 | p22.2 |
| 139 | COL21A1 | 38 | NA | NA | NA | 1.8 | -1 | 584 | 1.8487 | 1 | 595 | 250 | 260 | 256 | | 6 | p12.1 |
| 140 | COL12A1 | 40 | NA | NA | NA | 1.9 | -1 | 688 | 1.8241 | -1 | 59 | 239 | 275 | 259 | | 6 | q14.1 |
| 141 | MLYCD | 289 | 2.4 | -1 | 819 | NA | NA | 678 | NA | NA | NA | 225 | 301 | 262 | | 16 | q23.3 |
| 142 | AR | 366 | 2.3 | 1 | 690 | 2 | 1 | NA | 1.9352 | 1 | 579 | 255 | 271 | 266 | | 23 | q12 |
| 143 | PLCB1 | 359 | NA | NA | NA | 1.9 | -1 | NA | NA | NA | NA | 214 | 335 | 270 | | 20 | p12.3 |
| 144 | ACTL8 | 3 | NA | NA | NA | NA | NA | NA | NA | NA | NA | 320 | 227 | 271 | | 1 | p36.13 |
| 145 | IFDPI | 257 | NA | NA | NA | 2.5 | NA | NA | 2.0578 | 1 | 774 | 303 | 241 | 273 | | 13 | q34 |
| 146 | IOCE | 55 | NA | NA | NA | 2.3 | -1 | NA | 1.8257 | -1 | 589 | 327 | 225 | 277 | | 7 | p22.2 |
| 147 | SMARCB1 | 380 | NA | NA | NA | 1.9 | NA | NA | NA | NA | NA | 279 | 283 | 278 | | 22 | q11.23 |
| 148 | MIDH | 199 | NA | NA | NA | 1.9 | -1 | NA | NA | NA | 580 | 275 | 301 | | | 22 | q22.1 |
| 149 | NECAB2 | 290 | NA | NA | NA | NA | NA | NA | NA | NA | NA | | | | | 16 | q23.3 |
| 150 | DEF8 | 334 | NA | NA | NA | NA | NA | NA | NA | NA | NA | | | | | 16 | q24.3 |
| 151 | RNF40 | 262 | NA | NA | NA | NA | NA | NA | NA | NA | NA | | | | | 16 | q11.2 |
| 152 | TICAM2 | 37 | NA | NA | NA | NA | NA | NA | NA | NA | NA | | | | | 5 | q22.3 |
| 153 | GLG1 | 271 | 2.1 | -1 | 64 | NA | NA | NA | NA | NA | NA | | | | | 18 | q22.2 |
| 154 | MECOM | 16 | NA | NA | NA | NA | NA | 587 | NA | NA | NA | | | | | 3 | q26.2 |
| 155 | TCEB1 | 178 | 1.8 | 1 | 590 | 2 | 1 | NA | NA | NA | NA | | | | | 8 | q21.11 |

TABLE 14-continued

| | | | | | | | | | | | | | | | | |
|---|---|---|---|---|---|---|---|---|---|---|---|---|---|---|---|---|
| 156 | CTNNA2 | | | 7 | NA | NA | NA | NA | NA | NA | NA | NA | 1.8228 | -1 | 533 | 331 | 231 | 280 | 2 |
| 157 | NIPAL2 | | | 200 | 1.9 | 1 | 654 | | | | | | NA | NA | NA | 289 | 265 | 282 | 8 | q22.2 |
| 158 | CDCA2 | | | 148 | 2 | 1 | 88 | | | | | | NA | NA | NA | 301 | 255 | 283 | 8 | p21.2 |

Table 14-4b

| Final-RANK | gene | gene-start | gene-end | genesBtwn | contg | clump-index | dstprev | dstnext | min-disto-ROI | IndexO-Proxy1 | NYU-Zadjust | MSKs1-Zadjust | MSKS2-Zadjust |
|---|---|---|---|---|---|---|---|---|---|---|---|---|---|
| 119 | ALCAM | 106568403 | 106778433 | 49 | 0 | NA | 8761797 | NA | 8761797 | 1 | NA | NA | 0.23 |
| 120 | KIF13B | 28980715 | 29176629 | NA | 1 | 32 | NA | -14009 | -14009 | 1 | 0.33 | NA | NA |
| 121 | MBTPS1 | 82644872 | 82708018 | 0 | 1 | 54 | 5371 | -50994 | 5371 | 1 | 0.33 | NA | NA |
| 122 | PPP2R5B | 64448756 | 64458523 | NA | 0 | NA | NA | -80139 | -80139 | 1 | NA | NA | 0.02 |
| 123 | VPS13C | 59931884 | 60138939 | NA | 0 | NA | NA | -24742144 | -24742144 | 1 | NA | NA | 0.02 |
| 124 | ASPSCR1 | 77528715 | 77568569 | 6 | 1 | 85 | 40474 | -16362 | -18382 | 1 | NA | NA | 0.01 |
| 125 | EPO | 100156359 | 100159257 | 146 | 0 | NA | 29534582 | -31553 | -31553 | 1 | NA | NA | 0.07 |
| 126 | HEY1 | 80838801 | 80842653 | 3 | 1 | 38 | 87061 | -97933 | -97833 | 1 | 0.47 | NA | NA |
| 127 | KALRN | 125296275 | 125922726 | 76 | 0 | NA | 8678754 | -210407 | -210407 | 1 | NA | 0.21 | NA |
| 128 | RGS22 | 101042452 | 101187520 | 7 | 0 | NA | 812460 | -83469 | -83469 | 1 | 0.33 | NA | NA |
| 129 | WDH7 | 52489614 | 52848040 | 45 | 0 | NA | 12833135 | -3157834 | -3157834 | 1 | NA | NA | 0.07 |
| 130 | COL11A1 | 103114611 | 103346640 | NA | 0 | NA | NA | -4955408 | -4955408 | 1 | NA | NA | 0.04 |
| 131 | CHDC | 37594632 | 37599722 | 482 | 0 | NA | 39903967 | -7810 | -7810 | 1 | NA | NA | 0.01 |
| 132 | ATP2C2 | 82959534 | 83055293 | 0 | 1 | 55 | 13315 | -38746 | 13315 | 1 | NA | NA | NA |
| 133 | CDH17 | 95206566 | 95289986 | 14 | 0 | NA | 2053354 | -2729012 | 2053354 | 1 | 0.80 | NA | NA |
| 134 | CGKG | 18347686 | 18562717 | 23 | 0 | NA | 3269193 | -17000632 | 3269193 | 1 | 0.38 | NA | NA |
| 135 | GAK5 | 120957091 | 121205118 | NA | NA | NA | NA | NA | NA | 1 | NA | NA | NA |
| 136 | GAM1 | 148390611 | 148800427 | 83 | 0 | NA | 1881221 | -291927 | -291927 | 1 | NA | NA | 0.04 |
| 137 | IMPA1 | 82732751 | 82751115 | 4 | 0 | NA | 2842997 | -545893 | -545893 | 1 | NA | NA | NA |
| 138 | RPL7 | 74365073 | 74375857 | 1 | 0 | NA | 119303 | -352193 | 119303 | 1 | 0.17 | NA | NA |
| 139 | COL21A1 | 56029347 | 56368851 | NA | NA | NA | NA | NA | NA | 1 | NA | NA | 0.03 |
| 140 | COL12A1 | 75850762 | 75972343 | 18 | 0 | NA | 7686493 | -4871884 | -4871884 | 1 | NA | NA | 0.03 |
| 141 | MLYCD | 82490231 | 82507286 | 1 | 0 | NA | 52452 | -102526 | 52452 | 1 | 0.21 | NA | NA |
| 142 | AR | 66680599 | 65860344 | 0 | 1 | 69 | 318585 | 904991 | 318585 | 1 | 0.17 | 0.29 | NA |
| 143 | PLCB1 | 8061296 | 8813547 | NA | NA | NA | NA | NA | NA | 1 | NA | NA | 0.05 |
| 144 | ACTL8 | 17954395 | 18026145 | 662 | 1 | 1 | 79289745 | -57439 | -57439 | 1 | NA | NA | NA |
| 145 | IFDPI | 113287057 | 113343500 | NA | 0 | NA | NA | -1242043 | -1242043 | 1 | NA | 0.05 | NA |
| 146 | IOCE | 2565158 | 2820893 | 13 | 0 | NA | 2861082 | -1242043 | 2881062 | 1 | NA | 0.17 | 0.03 |
| 147 | SMARCB1 | 22459150 | 22506703 | 290 | 0 | NA | 23030490 | NA | 23030490 | 1 | NA | 0.02 | NA |
| 148 | MIDH | 98725583 | 98807711 | 7 | 0 | NA | 465852 | -1032370 | 465852 | 1 | NA | 0.05 | NA |
| 149 | NECAB2 | 82559738 | 82593878 | 1 | 0 | NA | 50994 | -52452 | 50994 | 1 | NA | 0.07 | NA |
| 150 | DEF8 | 88542684 | 88561968 | 0 | 1 | 63 | 4521 | -12678 | 4521 | 1 | NA | 0.05 | NA |
| 151 | RNF40 | 30681100 | 30695129 | NA | 0 | NA | NA | -392513 | -392513 | 1 | NA | NA | 0.09 |
| 152 | TICAM2 | 114942247 | 114989610 | NA | 0 | NA | NA | -26727467 | -26727467 | 1 | NA | NA | 0.03 |
| 153 | GLG1 | 73043357 | 73198518 | 3 | 0 | NA | 284457 | -1403582 | 286457 | 1 | 0.10 | NA | NA |
| 154 | MECOM | 170283981 | 170347054 | 89 | 0 | NA | 17000632 | -8012470 | -8012470 | 1 | NA | 0.07 | NA |
| 155 | TCEB1 | 75021184 | 75046959 | 2 | 0 | NA | 262534 | -199555 | -199555 | 1 | 0.02 | NA | NA |
| 156 | CTNNA2 | 79732191 | 80729415 | NA | 0 | NA | NA | -28619013 | -28619013 | 1 | NA | NA | 0.03 |
| 157 | NIPAL2 | 99273563 | 99375797 | 1 | 0 | NA | 160240 | 465852 | 160240 | 1 | 0.05 | NA | NA |
| 158 | CDCA2 | 25372428 | 25421353 | 0 | 1 | 29 | 336689 | -591 | -591 | 1 | 0.07 | NA | NA |

TABLE 14-continued

Table 14-5a

| Final-RANK | gene | index | NYU-2 | NYU-dir | NYU-count | MSKs1-Z | MSKs1-dir | MSKs2-count | MSKs2-Z | MSKs2-dir | MSKs2 count | logrank-n52random | logrank-n271random | logrank-composite | gene-Chr | gene-Cytoband |
|---|---|---|---|---|---|---|---|---|---|---|---|---|---|---|---|---|
| 159 | WWP2 | 267 | 1.8 | -1 | 527 | NA | NA | NA | NA | NA | NA | 251 | 315 | 284 | 16 | q22.1 |
| 160 | DDX19A | 268 | 2.3 | -1 | 755 | NA | NA | NA | NA | NA | NA | 220 | 383 | 285 | 16 | q22.1 |
| 161 | STK3 | 201 | 1.8 | -1 | 614 | NA | NA | NA | NA | NA | NA | 265 | 309 | 287 | 8 | q22.2 |
| 162 | DNAH2 | 337 | 1.8 | -1 | 541 | NA | NA | NA | NA | NA | NA | 247 | 332 | 288 | 17 | p13.1 |
| 163 | NFAT5 | 266 | 2.3 | -1 | 760 | NA | NA | NA | NA | NA | NA | 326 | 254 | 291 | 16 | q22.1 |
| 164 | CNGB1 | 283 | 1.8 | -1 | 524 | NA | NA | NA | NA | NA | NA | 297 | 280 | 292 | 16 | q13 |
| 165 | UBE2CBP | 41 | 2.8 | -1 | 891 | NA | NA | NA | NA | NA | NA | 256 | 325 | 293 | 6 | q14.1 |
| 186 | C8orf16 | 99 | 2.2 | -1 | 725 | NA | NA | NA | NA | NA | NA | 285 | 293 | 294 | 8 | p23.1 |
| 165 | KIAA0196 | 270 | 2.6 | 1 | 819 | NA | NA | NA | NA | NA | NA | 253 | 334 | 295 | 8 | q24.13 |
| 167 | CLCNKB | 1 | NA | NA | NA | NA | NA | NA | NA | NA | NA | 276 | 30 | 297 | 1 | p36.13 |
| 168 | C16orf180 | 264 | 2.2 | -1 | 677 | NA | NA | NA | NA | NA | 746 | 281 | 302 | 298 | 16 | q21 |
| 169 | ZFHX3 | 270 | 2.2 | -1 | 656 | NA | NA | NA | NA | NA | NA | 313 | 273 | 299 | 16 | q22.3 |
| 170 | PPM1L | 15 | NA | NA | NA | 2 | NA | NA | NA | NA | NA | 270 | 329 | 303 | 3 | q26.1 |
| 171 | NKIRAS2 | 338 | NA | NA | NA | NA | NA | NA | 1.9834 | 1 | 679 | 298 | 290 | 304 | 17 | q21.2 |
| 172 | RSPO2 | 215 | 1.8 | 1 | 550 | NA | NA | NA | NA | NA | NA | 306 | 292 | 305 | 8 | q23.1 |
| 173 | XPO7 | 119 | 2.3 | -1 | 735 | NA | NA | NA | NA | NA | NA | 329 | 272 | 306 | 8 | p21.3 |
| 174 | ME1 | 42 | 2.5 | -1 | 728 | NA | NA | NA | NA | NA | NA | 282 | 321 | 307 | 6 | q14.2 |
| 175 | NLGN4Y | 363 | NA | NA | NA | NA | NA | NA | 2.4183 | -1 | 734 | 339 | 275 | 312 | 24 | q11.221 |
| 176 | LZTS1 | 118 | 2 | -1 | 645 | NA | NA | NA | NA | NA | NA | 300 | 316 | 316 | 8 | p21.3 |
| 177 | FBXL18 | 56 | NA | NA | NA | NA | NA | NA | 1.8646 | 1 | 652 | 323 | 294 | 317 | 7 | p22.1 |
| 178 | TBC1D108 | 251 | NA | NA | NA | NA | NA | NA | 1.8243 | 1 | 573 | 278 | 347 | 321 | 16 | p11.2 |
| 179 | WDR59 | 272 | 2.1 | -1 | 653 | NA | NA | NA | NA | NA | NA | 304 | 320 | 322 | 16 | q23.1 |
| 180 | BLK | 101 | 2.1 | -1 | 671 | NA | NA | NA | NA | NA | NA | 315 | 314 | 325 | 8 | p23.1 |
| 181 | MEPCE | 71 | NA | NA | NA | 2.2 | NA | NA | 2.1134 | 1 | 782 | 350 | 285 | 327 | 7 | q22.1 |
| 182 | DLGAP2 | 91 | NA | NA | NA | NA | NA | NA | NA | NA | 882 | 358 | 288 | 330 | 8 | p23.3 |
| 183 | ZFAT | 234 | 2.5 | 1 | 796 | NA | NA | NA | NA | NA | NA | 325 | 317 | 331 | 8 | q24.22 |
| 184 | FASN | 348 | NA | NA | NA | NA | NA | NA | 3.0027 | 1 | 963 | 296 | 350 | 332 | 17 | q25.3 |
| 185 | GIGYF1 | 81 | NA | NA | NA | NA | NA | NA | 2.7127 | 1 | 957 | 335 | 311 | 335 | 7 | q22.1 |
| 186 | ANXA13 | 219 | 2.1 | 1 | 692 | NA | NA | NA | NA | NA | NA | 310 | 345 | 336 | 8 | q24.13 |
| 187 | CDYL2 | 280 | 2.5 | -1 | 899 | NA | NA | NA | NA | NA | NA | 316 | 351 | 339 | 16 | q23.2 |
| 188 | TOX | 161 | 4.3 | 1 | 993 | NA | NA | NA | NA | NA | NA | 338 | 342 | 349 | 8 | q12.1 |
| 189 | NKX2-6 | 143 | 2.4 | 1 | 870 | NA | NA | NA | NA | NA | NA | 340 | 366 | 357 | 8 | p21.2 |
| 190 | RAILYL | 191 | 2.8 | 1 | 985 | NA | NA | NA | NA | NA | NA | 345 | 362 | 359 | 2 | q21.2 |
| 191 | TBC1D22A | 361 | NA | NA | NA | 4.6 | 1 | NA | NA | NA | 999 | 367 | 346 | 363 | 22 | q13.31 |
| 192 | TFE3 | 383 | NA | NA | NA | 2.1 | NA | NA | NA | NA | 591 | 362 | 350 | 364 | 23 | p11.23 |
| 193 | KCNAB1 | 14 | NA | NA | NA | 5.8 | 1 | NA | NA | NA | 996 | 363 | 367 | 367 | 3 | q25.31 |
| 194 | SULF1 | 166 | 5.2 | 1 | 1000 | 3.4 | 1 | NA | NA | NA | 994 | 3 | 4 | 3 | 8 | q13.2 |
| 195 | RAB6C | 342 | NA | NA | NA | NA | NA | NA | 3.5399 | 1 | 998 | 6 | 3 | 5 | 17 | q21.2 |
| 196 | DHX58 | 339 | NA | NA | NA | NA | NA | NA | 8.9116 | 1 | 952 | 14 | 16 | 16 | 17 | q21.2 |
| 197 | ASAP1 | 224 | NA | NA | NA | 3.6 | 1 | NA | NA | NA | 974 | 21 | 23 | 20 | 8 | q24.21 |

Table 14-5b

| Final-RANK | gene | gene-start | gene-end | genesBtwn | contg | clump-index | MSKs1-Zadjust | dstprev | dstnext | MSKs2-count | min-distoROL | IndexOProxy1 | NYU-Zadjust | MSKs1-Zadjust | MSKs2-Zadjust |
|---|---|---|---|---|---|---|---|---|---|---|---|---|---|---|---|
| 159 | WWP2 | 88353710 | 68533145 | 5 | 0 | NA | NA | 405177 | -57856 | NA | -57658 | 1 | 0.02 | NA | NA |
| 160 | DDX19A | 68938322 | 68984780 | 0 | 1 | 50 | NA | 6059 | 405177 | NA | 6059 | 1 | 0.17 | NA | NA |

TABLE 14-continued

| | gene | index | NYU-1 | NYU-2 | NYU-dir | NYU-count | MSKs1-Z | MSKs1-dir | MSKs1-count | MSKs1 | MSKs2-Z | MSKs2-dir | MSKs2-count | logrank-n52random | logrank-n271random | logrank-composite | gene-Chr | gene-Cytoband |
|---|---|---|---|---|---|---|---|---|---|---|---|---|---|---|---|---|---|---|
| 161 | STK3 | 313 | 99536037 | 99907074 | 1 | 0 | NA | 187596 | NA | -160240 | NA | NA | 0.02 | NA | NA | NA | 16 | q24.2 |
| 162 | DNAH2 | 53 | 7562745 | 7577783 | NA | NA | NA | NA | NA | NA | NA | NA | 0.02 | NA | NA | NA | 6 | q27 |
| 163 | NFAT5 | 169 | 68156498 | 68296054 | 2 | 0 | NA | 57656 | 57656 | -7528258 | NA | NA | 0.17 | NA | NA | NA | 8 | q13.3 |
| 164 | CNGB1 | 283 | 56475004 | 58582513 | 3 | 0 | NA | 142487 | 142487 | -7685493 | NA | NA | 0.02 | NA | NA | NA | 15 | q23.3 |
| 165 | UBE2CBP | 314 | 83658836 | 83832269 | 3 | 0 | NA | 144558 | 144558 | -697587 | NA | NA | 0.38 | NA | NA | NA | 16 | q24.2 |
| 166 | C8orf16 | 133 | 11021390 | 11025155 | 0 | 1 | 17 | 154255 | 154255 | -1286863 | NA | NA | 0.14 | NA | NA | NA | 8 | p21.3 |
| 167 | KIAA0196 | | 125105691 | 125173191 | 3 | 0 | NA | 2323848 | -1286853 | -1286863 | NA | NA | 0.29 | NA | NA | NA | | |
| 168 | CLCNKB | | 16242834 | 16256390 | 29 | 0 | NA | 1482527 | 1482527 | 1482527 | NA | NA | NA | NA | NA | 0.07 | | |
| 169 | C16orf180 | | 56706000 | 5672097 | 10 | 0 | NA | 3524069 | NA | -142487 | NA | NA | 0.14 | NA | NA | NA | | |
| 170 | ZFHX3 | | 71374285 | 7163975 | 2 | 0 | NA | 1403582 | 1403582 | 1403582 | NA | NA | 0.14 | NA | NA | NA | | |
| 171 | PPM1L | | 161956791 | 162271511 | 13 | 0 | NA | 2343793 | -2343793 | -142487 | NA | NA | NA | NA | NA | NA | | |
| 172 | NKIRAS2 | | 37422564 | 37431180 | 1 | 0 | NA | 8012470 | -4217170 | -4217170 | NA | NA | NA | NA | NA | 0.07 | | |
| 173 | RSPO2 | | 108980721 | 109165062 | 9 | 1 | 42 | 4139285 | 75799 | 75799 | NA | NA | NA | NA | NA | 0.06 | | |
| 174 | XPO7 | | 21833126 | 21920041 | 3 | 0 | NA | 82619 | 82619 | -401262 | NA | NA | 0.02 | NA | NA | NA | | |
| 175 | ME1 | | 83976827 | 84197498 | 41 | 0 | NA | 7084576 | -144558 | -144558 | NA | NA | 0.17 | NA | NA | NA | | |
| 176 | NLGN4Y | | 15144026 | 15466924 | NA | NA | NA | NA | NA | NA | NA | NA | 0.25 | NA | NA | 0.21 | | |
| 177 | LZTS1 | | 20147956 | 20205754 | 2 | 0 | NA | 1627372 | 1627372 | 850362 | NA | NA | NA | NA | NA | NA | | |
| 178 | FBXL18 | | 5481955 | 5523646 | NA | 0 | NA | NA | NA | -2861062 | NA | NA | 0.07 | NA | NA | 0.04 | | |
| 179 | TBC1D10B | | 30275925 | 30288587 | 14 | 0 | NA | 392513 | 392513 | 392513 | NA | NA | NA | NA | NA | 0.00 | | |
| 180 | WDR59 | | 73464975 | 73576518 | 5 | 0 | NA | 243911 | 243911 | -266457 | NA | NA | 0.10 | NA | NA | NA | | |
| 181 | BLK | | 11388930 | 11459518 | 1 | 0 | NA | 139848 | 139848 | -185868 | NA | NA | 0.10 | NA | NA | NA | | |
| 182 | MEPCE | | 99865190 | 99869676 | 2 | 0 | NA | 32404 | 32404 | -29640 | NA | NA | NA | NA | NA | 0.11 | | |
| 183 | DLGAP2 | | 1436939 | 1644048 | 1 | 0 | NA | 115501 | 115501 | -29540 | NA | NA | NA | NA | NA | NA | | |
| 184 | ZFAT | | 135559215 | 135794453 | 8 | 0 | NA | 5943220 | -1248464 | -1248464 | NA | NA | 0.14 | NA | NA | NA | | |
| 185 | FASN | | 77629504 | 77649395 | NA | 1 | 66 | NA | NA | -262 | NA | NA | 0.25 | NA | NA | 0.47 | | |
| 186 | GIGYF1 | | 100115066 | 100124806 | 1 | 0 | NA | 31553 | 31553 | -23069 | NA | NA | NA | NA | NA | 0.33 | | |
| 187 | ANXA13 | | 124762216 | 124818828 | 11 | 0 | NA | 1286863 | 1286863 | -706280 | NA | NA | 0.10 | NA | NA | NA | | |
| 188 | CDYL2 | | 79195176 | 79395680 | 3 | 0 | NA | 248923 | 248923 | 248823 | NA | NA | 0.25 | NA | NA | NA | | |
| 189 | TOX | | 59880531 | 60194321 | 10 | 1 | NA | 5476925 | 5476925 | 5476925 | NA | NA | 1.23 | NA | NA | NA | | |
| 190 | NCX2-6 | | 23615909 | 23620056 | 6 | 0 | NA | 14478148 | -129901 | -129901 | NA | NA | 0.21 | NA | NA | NA | | |
| 191 | RAILYL | | 85601112 | 85963979 | 12 | 0 | NA | 1691298 | 1691298 | 1691298 | NA | NA | 0.38 | NA | NA | NA | | |
| 192 | TBC1D22A | | 45537193 | 45948399 | NA | NA | NA | NA | NA | -2842997 | NA | NA | NA | 1.43 | NA | NA | | |
| 193 | TFE3 | | 48772813 | 48787722 | NA | NA | NA | NA | NA | -28030490 | NA | NA | NA | 0.10 | NA | NA | | |
| 194 | KCNAB1 | | 157321095 | 157739821 | 22 | 1 | 33 | 4217170 | 4217170 | -35134932 | NA | NA | 1.83 | 2.24 | NA | NA | | |
| 195 | SULF1 | | 70541427 | 70735701 | 0 | 0 | NA | 11428 | 11428 | -12271116 | NA | NA | NA | 0.68 | NA | NA | | |
| 195 | RAB6C | | 37530524 | 37560548 | 0 | 1 | 64 | 1891 | 1891 | 647617 | NA | NA | NA | NA | NA | 0.76 | | |
| 197 | DHX58 | | 37506979 | 37518277 | 0 | 1 | 64 | 380 | 380 | -1627 | NA | NA | NA | NA | NA | 4.22 | | |
| 198 | ASAP1 | | 131133535 | 131483399 | 0 | 1 | 45 | 378337 | 378337 | 378337 | NA | NA | 0.80 | NA | NA | NA | | |

Table 14-6a

| Final-RANK | gene | index | NYU-1 | NYU-2 | NYU-dir | NYU-count | MSKs1-Z | MSKs1-dir | MSKs1-count | MSKs1 | MSKs2-Z | MSKs2-dir | MSKs2-count | logrank-n52random | logrank-n271random | logrank-composite | gene-Chr | gene-Cytoband |
|---|---|---|---|---|---|---|---|---|---|---|---|---|---|---|---|---|---|---|
| 199 | CA5A | 313 | 99536037 | | | | 3.8 | -1 | 832 | NA | NA | NA | 955 | 23 | 28 | 26 | 16 | q24.2 |
| 200 | C6orf118 | 53 | 7562745 | NA | NA | NA | NA | NA | NA | 2.7921 | -1 | 976 | NA | 35 | 36 | 36 | 6 | q27 |
| 201 | NCOA2 | 169 | 68156498 | | 3.2 | 1 | 2.4 | 1 | 997 | NA | NA | NA | 806 | 35 | 40 | 37 | 8 | q13.3 |
| 202 | PKD1L2 | 283 | 56475004 | | 4.9 | -1 | 2 | -1 | 999 | NA | NA | NA | 715 | 41 | 45 | 42 | 15 | q23.2 |
| 203 | BANP | 314 | 83658836 | | 2.6 | -1 | 3.3 | -1 | 901 | NA | NA | NA | 957 | 43 | 49 | 46 | 16 | q24.2 |
| 204 | KIAA1967 | 133 | 11021390 | | 2.8 | -1 | 3.1 | -1 | 925 | NA | NA | NA | 989 | 50 | 57 | 52 | 8 | p21.3 |
| 205 | COPG2 | 89 | 85601112 | NA | NA | NA | NA | NA | NA | NA | 1 | 935 | NA | 56 | 52 | 53 | 7 | q32.2 |
| 206 | ZNF706 | 205 | 56706000 | NA | NA | NA | 2.8 | 1 | NA | NA | NA | NA | 889 | 53 | 56 | 54 | 8 | q22.3 |
| 207 | GAN | 285 | 131133535 | | 2.7 | -1 | 2.4 | -1 | 889 | 3.1195 | NA | NA | 902 | 54 | 61 | 55 | 16 | q23.2 |

TABLE 14-continued

| | gene | gene-start | gene-end | | genesBtwn | contg | clump-index | | | | | | | | | | |
|---|---|---|---|---|---|---|---|---|---|---|---|---|---|---|---|---|---|
| 208 | PLCG2 | 88479126 | | 2.9 | | 833 | | 2.7 | NA | NA | NA | NA | 61 | 50 | 56 | 16 | q23.2 |
| 209 | C19orf157 | 165613148 | | NA | -1 | NA | | NA | 2.7945 | 1 | 992 | NA | 59 | 58 | 59 | 19 | p13.12 |
| 210 | PDGFRL | 71178380 | 71478574 | 4.8 | -1 | 998 | | NA | NA | NA | NA | NA | 60 | 55 | 60 | 8 | p22 |
| 211 | ESD | 79591985 | 79811477 | | NA | NA | | NA | 2.5793 | -1 | 973 | NA | 65 | 59 | 62 | 13 | q14.2 |
| 212 | CPA5 | 86542539 | 86666425 | 1.7 | NA | 507 | | 2.8 | 2.7623 | -1 | 924 | NA | 70 | 63 | 67 | 7 | q32.2 |
| 213 | BIN3 | 22518202 | 22533920 | 4.3 | -1 | 1000 | | NA | NA | NA | NA | NA | 71 | 73 | 70 | 8 | p21.3 |
| 214 | ZFHX4 | 129933404 | 129935887 | 3.8 | 1 | 1000 | | NA | NA | NA | NA | NA | 74 | 76 | 73 | 8 | q21.11 |
| 215 | CPA6 | 102278444 | 102287136 | 3.4 | 1 | 997 | | NA | NA | NA | NA | NA | 77 | 81 | 75 | 8 | q13.2 |
| 216 | EYA1 | 79906076 | 79971441 | 3.5 | -1 | 999 | | NA | NA | NA | NA | NA | 73 | 89 | 77 | 8 | q13.3 |
| 217 | CHRNA2 | 80370408 | 80549399 | 4 | 1 | 1000 | | NA | NA | NA | NA | NA | 76 | 87 | 79 | 8 | p21.2 |
| 218 | TNKS | 13854168 | 13877909 | | 1 | 1000 | | NA | NA | NA | NA | NA | 77 | 84 | 84 | 8 | p23.1 |
| 219 | HNF4O | 17478443 | 17545655 | 4.1 | 1 | 1000 | | NA | NA | NA | NA | NA | 103 | 72 | 87 | 8 | q21.11 |
| 220 | LHCH1 | 48243393 | 46269368 | | NA | NA | | NA | 2.3847 | -1 | NA | NA | 79 | 94 | 88 | 13 | p14.13 |
| 221 | ADHA1A | 129771892 | 129795807 | 3.9 | NA | 991 | | NA | NA | NA | NA | NA | 98 | 79 | 89 | 8 | p21.2 |
| 222 | EPHX2 | 112 | | 3.3 | -1 | 997 | | NA | NA | NA | NA | NA | 89 | 88 | 90 | 8 | p21.1 |
| 223 | SORBS3 | 130 | | | NA | NA | | 3 | NA | NA | NA | NA | 83 | 95 | 91 | 8 | p21.3 |
| 224 | GRIA2 | 27 | | NA | NA | NA | | NA | 2.2933 | -1 | 843 | NA | 94 | 95 | 93 | 4 | q32.1 |
| 225 | POLIM2 | 131 | | NA | NA | NA | | 2.9 | NA | NA | NA | NA | 91 | 91 | 94 | 8 | p21.3 |
| 226 | MTMR7 | 109 | | 3.7 | NA | 971 | | NA | 993 | NA | NA | NA | 86 | 108 | 96 | 8 | p22 |
| 227 | FBXO24 | 76 | | NA | NA | NA | | 2.4 | NA | NA | NA | NA | 118 | 85 | 99 | 7 | q22.1 |
| 228 | CRISPLD1 | 182 | | 4.9 | -1 | 1000 | | NA | 2.4831 | 1 | 817 | NA | 95 | 124 | 107 | 8 | q21.11 |
| 229 | DPY5 | 211 | | 3.2 | 1 | 975 | | NA | NA | NA | NA | NA | 92 | 129 | 109 | 8 | q22.3 |
| 230 | DTNA | 351 | | | NA | NA | | 2.5 | 2.2378 | -1 | 734 | NA | 102 | 125 | 112 | 18 | q12.1 |
| 231 | KLHDC4 | 311 | | NA | -1 | NA | | 2.9 | NA | -1 | NA | NA | 116 | 111 | 113 | 16 | q24.3 |
| 232 | CYBA | 319 | | NA | -1 | NA | | 2.4 | 987 | -1 | NA | NA | 117 | 121 | 118 | 16 | q24.2 |
| 233 | JPH3 | 310 | | 2.4 | -1 | 788 | | NA | 941 | -1 | NA | NA | 101 | 142 | 120 | 16 | q24.2 |
| 234 | TMEM120A | 64 | | NA | 1 | NA | | NA | 908 | 1 | 511 | NA | 128 | 115 | 121 | 7 | q11.23 |
| 235 | MTUS1 | 112 | | 3.6 | -1 | 976 | | NA | NA | NA | NA | NA | 143 | 116 | 127 | 8 | p22 |
| 236 | C8orf34 | 165 | | 6 | 1 | 1000 | | 2.4 | NA | 1 | NA | NA | 126 | 132 | 128 | 8 | q13.2 |
| 237 | GRHL2 | 206 | | NA | NA | NA | | NA | 790 | NA | NA | NA | 125 | 140 | 132 | 8 | q22.3 |
| 238 | CPA2 | 83 | | NA | NA | NA | | 2.4 | NA | NA | 717 | NA | 153 | 117 | 133 | 7 | q32.2 |

Table 14-6b

| Final-RANK | gene | gene-start | gene-end | genesBtwn | dstprev | dstnext | min-distro-ROL | IndexO-Proxy1 | NYU-Zadjust | MSKs1-Zadjust | MSKS2-Zadjust |
|---|---|---|---|---|---|---|---|---|---|---|---|
| 199 | CA5A | 88479126 | 88527813 | 0 | 14926 | -18511 | 14928 | 0 | 0.29 | 0.91 | NA |
| 200 | C6orf1118 | 165613148 | 165643101 | 0 | 17665 | -18812721 | 17665 | 0 | NA | NA | 0.37 |
| 201 | NCOA2 | 71178380 | 71478574 | 1 | 233471 | -32264 | -32264 | C | 0.57 | 0.21 | NA |
| 202 | PKD1L2 | 79591985 | 79811477 | 0 | 18320 | -4504 | 4504 | 0 | 1.63 | 0.07 | NA |
| 203 | BANP | 86542539 | 86666425 | 0 | 378801 | -14926 | -14926 | 0 | 0.29 | 0.63 | NA |
| 204 | KIAA1967 | 22518202 | 22533920 | 0 | -14 | -597 | -14 | 0 | 0.38 | 0.52 | 0.53 |
| 205 | COPG2 | 129933404 | 129935887 | 106 | 13747479 | -41 | -41 | 0 | NA | NA | NA |
| 206 | ZNF706 | 102278444 | 102287136 | 0 | 287028 | -243699 | -243699 | 0 | 0.33 | 0.38 | NA |
| 207 | GAN | 79906076 | 79971441 | 0 | 398967 | -23828 | -23828 | 0 | 0.42 | 0.21 | NA |
| 208 | PLCG2 | 80370408 | 80549399 | 0 | 76965 | -398967 | 76965 | 0 | NA | 0.33 | 0.37 |
| 209 | C19orf157 | 13854168 | 13877909 | 0 | -71 | 105 | 105 | 0 | NA | NA | NA |
| 210 | PDGFRL | 17478443 | 17545655 | 0 | -50124 | -6086 | -71 | 0 | 1.56 | NA | 0.28 |
| 211 | ESD | 48243393 | 46269368 | 0 | 36148 | 20807 | -20607 | 0 | NA | NA | 0.36 |
| 212 | CPA5 | 129771892 | 129795807 | 0 | 11551 | -20643 | 11651 | 0 | NA | NA | NA |
| 213 | BIN3 | 22533906 | 22582553 | 0 | 18566 | 14 | 14 | 0 | 0.00 | 0.38 | NA |
| 214 | ZFHX4 | 77756078 | 77942076 | 1 | 1648815 | -1114478 | -1114478 | 0 | 1.23 | NA | NA |

TABLE 14-continued

| Final-RANK | gene | index | | | | | | | | | | | | | | | gene-Chr | gene-Cytoband |
|---|---|---|---|---|---|---|---|---|---|---|---|---|---|---|---|---|---|---|
| 215 | CPA6 | 68496963 | | | | | | 68821134 | | 0 | 33 | 205773 | -2623061 | 205773 | 0 | 0.91 | NA | 8 | p22 |
| 216 | EYA1 | 72272222 | | | | | | 72437021 | | 0 | 34 | 479311 | -463009 | -463009 | 0 | 0.68 | NA | 8 | p21.2 |
| 217 | CHRNA2 | 27373195 | | | | | | 27392730 | | 0 | 30 | 11832 | -376 | -375 | 0 | 0.74 | NA | 16 | q24.1 |
| 218 | TNKS | 9450855 | | | | | | 9677266 | | 0 | 16 | 271923 | -522716 | 271923 | 0 | 1.04 | NA | 8 | p21.1 |
| 219 | HNF4O | 76482732 | | | | | | 76641600 | | 0 | 35 | 1114478 | -373386 | -373386 | 0 | 1.10 | NA | 8 | p21.3 |
| 220 | LHCH1 | 46025304 | | | | | | 46222786 | | 0 | 48 | 20607 | -2766260 | 20607 | 0 | 0.20 | NA | 8 | p21.3 |
| 221 | ADHA1A | 26661584 | | | | | | 26778839 | | 0 | 30 | 370899 | -89977 | -89977 | 0 | 0.98 | NA | 8 | p21.3 |
| 222 | EPHX2 | 27404552 | | | | | | 27458403 | | 2 | 30 | 188353 | -11832 | -11832 | 0 | 0.53 | NA | 8 | p21.3 |
| 223 | SORBS3 | 22465196 | | | | | | 22488852 | | 1 | 28 | 3247 | 324 | 324 | 0 | NA | NA | 8 | p23.1 |
| 224 | GRIA2 | 158361186 | | | | | | 158506577 | | 1 | 3 | 4017824 | -48887 | -48887 | 0 | 0.47 | 0.17 | 8 | q24.22 |
| 225 | POLIM2 | 22492199 | | | | | | 22511483 | | 9 | 26 | 1584 | -3247 | 1584 | 0 | 0.42 | NA | 8 | p21.2 |
| 226 | MTMR7 | 17199923 | | | | | | 17315207 | | 0 | 21 | 83768 | 83768 | 83768 | 0 | NA | NA | 8 | q13.3 |
| 227 | FBXO24 | 100021892 | | | | | | 10006574 | | 1 | 12 | 1144 | -180 | -180 | 0 | 0.85 | NA | 5 | q13.2 |
| 228 | CRISPLD1 | 76059531 | | | | | | 76109346 | | 0 | 35 | 373386 | -129712 | -129712 | 0 | NA | 0.24 | 8 | p21.3 |
| 229 | DPYS | 106466029 | | | | | | 105548453 | | 0 | 41 | 22190 | -127565 | 22190 | 0 | 1.63 | NA | 7 | q22.1 |
| 230 | DTNA | 30327279 | | | | | | 30725806 | | 62 | 67 | 17395350 | -269766 | -269766 | 0 | 0.57 | NA | 8 | p22 |
| 231 | KLHDC4 | 86298920 | | | | | | 86357056 | | 0 | 58 | 64075 | -9657 | -9657 | 0 | NA | 0.15 | 16 | q24.1 |
| 232 | CYBA | 87237199 | | | | | | 67244958 | | 0 | 58 | 891 | -2814 | 891 | 0 | NA | NA | 16 | q13.3 |
| 233 | JPH3 | 86194000 | | | | | | 86289263 | | 0 | 58 | 9657 | -1036491 | 9657 | 0 | 0.25 | NA | 16 | q23.2 |
| 234 | TMEM120A | 75454238 | | | | | | 75461913 | | 0 | 10 | 1679 | 71 | 1679 | 0 | 0.42 | NA | 5 | q13.2 |
| 235 | MTUS1 | 17545584 | | | | | | 17702666 | | 1 | 21 | 121980 | -248023 | 71 | 0 | 0.21 | NA | 8 | q24.22 |
| 236 | C8or134 | 69406511 | | | | | | 69893810 | | 0 | 33 | 647617 | -99060 | -99060 | 0 | NA | 0.00 | 6 | q24.2 |
| 237 | GRHL2 | 102574162 | | | | | | 102750995 | | 0 | 40 | 16952 | 16952 | 16952 | 0 | 0.80 | NA | 5 | q13.2 |
| 238 | CPA2 | 129693939 | | | | | | 129716870 | | 0 | 13 | 3360 | 3360 | 3360 | 0 | 2.37 | 0.21 | 16 | q24.2 |
| | | | | | | | | | | | | | | | | | 0.11 | 8 | q22.1 |

Table 14-7a

| Final-RANK | gene | index | NYU-2 | NYU-dir | NYU-count | MSKs1-Z | MSKs1-dir | MSKs2-count | MSKs2-Z | MSKs2-dir | MSKs2-count | logrank-n52random | logrank-n271random | logrank-composite | gene-Chr | gene-Cytoband |
|---|---|---|---|---|---|---|---|---|---|---|---|---|---|---|---|---|
| 239 | NAT2 | 115 | 3.3 | -1 | 993 | NA | NA | NA | NA | NA | NA | 140 | 134 | 134 | 8 | p22 |
| 240 | DPYSL2 | 148 | 3.3 | -1 | 967 | NA | NA | NA | NA | NA | NA | 155 | 122 | 135.5 | 8 | p21.2 |
| 241 | ZDHHC7 | 300 | NA | NA | NA | 2.5 | -1 | 839 | NA | NA | NA | 159 | 123 | 138 | 16 | q24.1 |
| 242 | ELP3 | 153 | 3.4 | -1 | 939 | NA | NA | NA | NA | NA | NA | 165 | 118 | 139 | 8 | p21.1 |
| 243 | RHOBTB2 | 136 | NA | NA | NA | 1.7 | -1 | 501 | NA | NA | NA | 133 | 150 | 142 | 8 | p21.3 |
| 244 | NEIL2 | 103 | 2.7 | -1 | 921 | NA | NA | NA | NA | NA | NA | 150 | 135 | 143 | 8 | p21.3 |
| 245 | HR | 122 | NA | NA | NA | 2.7 | -1 | 895 | NA | NA | NA | 186 | 112 | 145 | 8 | p21.3 |
| 246 | EFA3A | 226 | 3.1 | 1 | 985 | NA | NA | NA | NA | NA | NA | 144 | 148 | 146 | 8 | q24.22 |
| 247 | STMN4 | 150 | 3.3 | -1 | 994 | NA | NA | NA | NA | NA | NA | 162 | 131 | 147 | 8 | p21.2 |
| 248 | PRDM14 | 168 | 4.7 | 1 | 996 | NA | NA | NA | NA | NA | NA | 135 | 171 | 152 | 8 | q13.3 |
| 249 | MARVELD2 | 35 | NA | NA | NA | 3 | -1 | 988 | NA | NA | NA | 142 | 184 | 154 | 5 | q13.2 |
| 250 | SLC39A14 | 128 | 1.8 | -1 | 560 | 2.2 | -1 | 791 | NA | NA | NA | 152 | 160 | 155 | 8 | p21.3 |
| 251 | ACTL6B | 80 | NA | NA | NA | NA | NA | NA | NA | NA | NA | 188 | 158 | 159 | 7 | q22.1 |
| 252 | TUSC3 | 108 | 3.1 | -1 | 945 | 2.5 | -1 | 938 | 1.7362 | 1 | 538 | 157 | 170 | 180 | 8 | p22 |
| 253 | COX4NB | 305 | NA | NA | NA | NA | NA | NA | NA | NA | NA | 148 | 172 | 161 | 16 | q24.1 |
| 254 | XKR9 | 171 | 2.7 | 1 | 929 | NA | NA | NA | NA | NA | NA | 165 | 183 | 162 | 8 | q13.3 |
| 255 | TAF9 | 281 | NA | NA | NA | 2.2 | -1 | 768 | NA | NA | NA | 151 | 183 | 164 | 16 | q23.2 |
| 256 | C16or146 | 33 | NA | NA | NA | 2.8 | -1 | 983 | NA | NA | NA | 175 | 162 | 166 | 16 | q13.2 |
| 257 | KCNO3 | 228 | 5 | 1 | 1000 | NA | NA | NA | 2.3296 | -1 | 766 | 167 | 180 | 169 | 8 | q24.22 |
| 258 | UTRN | 50 | NA | NA | NA | NA | NA | NA | NA | NA | NA | 174 | 174 | 170 | 6 | q24.2 |
| 259 | RAD17 | 34 | NA | NA | NA | 2.6 | -1 | 959 | NA | NA | NA | 172 | 182 | 172 | 5 | q13.2 |
| 260 | ZFPM1 | 315 | NA | NA | NA | 2.5 | -1 | 924 | NA | NA | NA | 146 | 219 | 175 | 16 | q24.2 |
| 261 | PTDSS1 | 197 | 2.5 | 1 | 874 | NA | NA | NA | NA | NA | NA | 184 | 177 | 179 | 8 | q22.1 |

TABLE 14-continued

| | gene | | | | | | | | | | | | | | | |
|---|---|---|---|---|---|---|---|---|---|---|---|---|---|---|---|---|
| 262 | IRF8 | 300 | NA | NA | NA | 2.5 | -1 | 976 | NA | NA | NA | 199 | 169 | 181 | 16 | q24.1 |
| 263 | YWHAZ | 204 | NA | NA | NA | 2.2 | 1 | 722 | NA | NA | NA | 204 | 168 | 182 | 8 | q22.3 |
| 264 | MRPS36 | 30 | NA | NA | NA | 2.6 | -1 | 952 | NA | NA | NA | 195 | 175 | 183 | 5 | q13.2 |
| 265 | LACTB2 | 170 | 2.6 | 1 | 932 | NA | NA | NA | NA | NA | NA | 160 | 223 | 187 | 8 | q13.3 |
| 266 | SNAI3 | 321 | NA | NA | NA | 2.4 | -1 | 914 | NA | NA | NA | 231 | 156 | 190 | 16 | q24.3 |
| 267 | TMEM71 | 229 | 2.9 | 1 | 983 | NA | NA | NA | NA | NA | NA | 180 | 207 | 194 | 8 | q24.22 |
| 268 | PREX2 | 184 | 7.5 | 1 | 1000 | NA | NA | NA | NA | NA | NA | 190 | 199 | 195 | 8 | 913.2 |
| 269 | CPA1 | 86 | NA | NA | NA | NA | NA | NA | NA | NA | NA | 228 | 173 | 199 | 7 | q32.2 |
| 270 | PHF20L1 | 230 | 2.8 | 1 | 901 | NA | NA | NA | NA | NA | 716 | 198 | 200 | 200 | 8 | q24.22 |
| 271 | KIAA0513 | 301 | NA | NA | NA | 2.1 | -1 | 816 | NA | NA | 1 | 212 | 188 | 202 | 16 | q24.1 |
| 272 | PI15 | 181 | NA | NA | NA | NA | NA | NA | NA | NA | NA | 238 | 179 | 206 | 8 | q21.11 |
| 273 | PCM1 | 113 | 3 | 1 | 991 | NA | NA | NA | NA | NA | NA | 183 | 234 | 207 | 8 | p22 |
| 274 | SH204A | 117 | 1.7 | -1 | 529 | NA | NA | NA | NA | NA | NA | 249 | 172 | 208 | 8 | p21.3 |
| 275 | C16orf174 | 304 | 2.9 | -1 | 908 | NA | NA | NA | NA | NA | NA | 202 | 214 | 209 | 16 | q24.1 |
| 276 | TP63 | 18 | NA | NA | NA | 2.3 | -1 | 939 | NA | NA | NA | 203 | 223 | 211 | 3 | q28 |
| 277 | DACH1 | 254 | NA | NA | NA | 3 | 1 | 822 | 2.0683 | NA | 570 | 252 | 185 | 212 | 13 | q21.33 |
| 278 | TNFRSF10A | 130 | NA | NA | NA | 2.2 | -1 | 774 | 1.8675 | NA | NA | 245 | 196 | 214 | 8 | p21.3 |

Table 14-7b

| Final-RANK | gene | gene-start | gene-end | genesBtwn | contg | clump-index | dstprev | dstnext | min-distto-ROL | IndexO-Proxy1 | NYU-Zadjust | MSKs1-Zadjust | MSKS2-Zadjust |
|---|---|---|---|---|---|---|---|---|---|---|---|---|---|
| 239 | NAT2 | 18283035 | 18303003 | 0 | 1 | 23 | 126090 | -306248 | 126090 | 0 | 0.63 | NA | NA |
| 240 | DPYSL2 | 26491327 | 26571607 | 0 | 1 | 30 | 89977 | -533035 | 89977 | 0 | 0.63 | NA | NA |
| 241 | ZDHHC7 | 83565573 | 83602642 | 6 | 1 | 56 | 16269 | -64959 | 16269 | 0 | NA | 0.25 | NA |
| 242 | ELP3 | 27999759 | 28104584 | 2 | 1 | 31 | 899246 | -2452 | -2452 | 0 | 0.68 | NA | NA |
| 243 | RHOBTB2 | 22913059 | 22933655 | 1 | 1 | 26 | 115396 | -306299 | 115396 | 0 | NA | 0.00 | NA |
| 244 | NEIL2 | 11664827 | 11882283 | 0 | 1 | 18 | 55179 | -9709 | -9709 | 0 | 0.33 | NA | NA |
| 245 | EFA3A | 22027877 | 22045325 | 0 | 1 | 24 | 6152 | -4474 | 4474 | 0 | NA | 0.33 | NA |
| 246 | HR | 132985517 | 133095071 | 1 | 1 | 45 | 10596 | -861863 | 10596 | 0 | 0.52 | NA | NA |
| 247 | STMN4 | 27148078 | 27171843 | 0 | 1 | 30 | 26478 | 370899 | 25478 | 0 | 0.63 | NA | NA |
| 248 | PRDM14 | 71126574 | 71146116 | 0 | 1 | 33 | 32264 | -216812 | 32264 | 0 | 1.49 | NA | NA |
| 249 | MARVELD2 | 68746699 | 88773646 | 82 | 1 | 4 | 19278276 | -315 | -315 | 0 | NA | 0.47 | NA |
| 250 | SLC39A14 | 22280737 | 22347462 | 0 | 1 | 26 | 7079 | -116113 | 7079 | 0 | 0.02 | 0.14 | NA |
| 251 | ACTL6B | 10007868 | 100092007 | 1 | 1 | 12 | 23059 | -1569 | -1569 | 0 | NA | NA | 0.01 |
| 252 | TUSC3 | 15442101 | 15688368 | 6 | 1 | 20 | 1533557 | 301882 | -301882 | 0 | 0.52 | NA | NA |
| 253 | COX4NB | 24369737 | 84390601 | 0 | 1 | 57 | 96 | 27547 | 96 | 0 | NA | 0.25 | NA |
| 254 | XKR9 | 7175584a | 71809213 | 0 | 1 | 34 | 483009 | -11902 | -11902 | 0 | 0.33 | NA | NA |
| 255 | C16orf146 | 79644603 | 79668373 | 0 | 1 | 53 | 5057 | -248923 | 5057 | 0 | NA | 0.14 | NA |
| 256 | TAF9 | 68696327 | 68701596 | 0 | 1 | 4 | -716 | -31935 | -716 | 0 | NA | 0.29 | NA |
| 257 | KCNO3 | 133210438 | 133551961 | 1 | 1 | 45 | 217672 | -43354 | -43354 | -1 | 2.37 | NA | NA |
| 258 | UTRN | 144654566 | 145215859 | 0 | 1 | 7 | 772282 | -20654629 | 772282 | NA | NA | NA | 0.18 |
| 259 | RAD17 | 68700880 | 68746384 | 0 | 1 | 4 | 315 | 716 | 315 | 0 | NA | NA | NA |
| 260 | ZFPM1 | 87047226 | 87126890 | 0 | 1 | 58 | 18723 | -378801 | 16723 | 0 | 0.29 | 0.25 | NA |
| 261 | PTDSS1 | 97343340 | 97415950 | 0 | 1 | 39 | 159108 | -2053354 | 159108 | 0 | NA | NA | NA |
| 262 | IRF8 | 84490275 | 84513710 | 0 | 1 | 57 | 587924 | -92165 | -92166 | 0 | 0.25 | 0.25 | NA |
| 263 | YWHAZ | 101999980 | 102034745 | 0 | 1 | 40 | 243699 | -812460 | 243699 | 0 | NA | 0.14 | NA |
| 264 | MRPS36 | 68548329 | 68577710 | 0 | 1 | 4 | -11239 | -7390 | -7390 | 0 | NA | 0.29 | NA |
| 265 | LACTB2 | 71712045 | 71743946 | 0 | 1 | 34 | 11902 | -233471 | 11902 | 0 | 0.29 | NA | NA |
| 266 | SNAI3 | 872771591 | 87280583 | 0 | 1 | 58 | 10028 | -14572 | 10028 | 0 | NA | 0.21 | NA |
| 267 | TMEM71 | 133779833 | 133842010 | 0 | 1 | 46 | 14776 | -217672 | 14776 | 0 | 0.42 | NA | NA |
| 268 | PREX2 | 69028907 | 69308451 | 0 | 1 | 33 | 99060 | -205773 | 99060 | 0 | 3.36 | NA | NA |

TABLE 14-continued

| | gene | index | NYU-2 | NYU-dir | NYU-count | MSKs1-Z | MSKs1-dir | MSKs2-count | MSKs2-Z | MSKs2-dir | MSKs2-count | logrank-n52random | logrank-n271random | logrank-composite | gene-Chr | gene-Cytoband |
|---|---|---|---|---|---|---|---|---|---|---|---|---|---|---|---|---|
| 269 | CPA1 | 129807458 | NA | NA | NA | 13 | | 8445 | 1.9653 | 1 | 728 | NA | 236 | 208 | 218 | 7 | q11.23 |
| 270 | PHF20L1 | 133856786 | NA | NA | NA | 46 | | 18153 | NA | NA | NA | 0.38 | 173 | 290 | 221 | 8 | q21.13 |
| 271 | KIAA0513 | 83618911 | NA | NA | NA | 56 | | 517197 | NA | NA | NA | 0.10 | 226 | 222 | 222 | 8 | p21.2 |
| 272 | PI15 | 75899327 | NA | NA | NA | 35 | | 129712 | NA | NA | NA | 0.47 | 240 | 213 | 225 | 16 | q23.1 |
| 273 | PCM1 | 17824646 | NA | NA | NA | 22 | | 22652 | NA | NA | NA | 0.00 | 178 | 269 | 226 | 16 | q24.1 |
| 274 | SH204A | 19215483 | NA | NA | NA | 23 | | 850362 | NA | NA | NA | 0.42 | 224 | 236 | 227 | 7 | q11.23 |
| 275 | C16orf74 | 84298624 | NA | NA | NA | 57 | | 300007 | NA | NA | NA | 0.17 | 217 | 198 | 228 | 16 | q24.2 |
| 276 | TP63 | 190831910 | NA | NA | NA | 2 | | 27547 | NA | NA | NA | 0.47 | 284 | 244 | 230 | 8 | q21.3 |
| 277 | DACH1 | 70910099 | NA | NA | NA | 49 | | 49278 | NA | NA | NA | NA | 254 | 198 | 231 | 16 | q24.3 |
| 278 | TNFRSF10A | 23104916 | NA | NA | NA | 27 | | 18511 | NA | NA | NA | 0.04 | 229 | 224 | 236 | 16 | q24.3 |
| | | | | | | | | | | | | 0.14 | 223 | 250 | 237 | 16 | p22 |

Table 14-8a

| Final-RANK | gene | index | NYU-2 | NYU-dir | NYU-count | MSKs1-Z | MSKs1-dir | MSKs2-count | MSKs2-Z | MSKs2-dir | MSKs2-count | logrank-n52random | logrank-n271random | logrank-composite | gene-Chr | gene-Cytoband |
|---|---|---|---|---|---|---|---|---|---|---|---|---|---|---|---|---|
| 279 | MDH2 | 66 | NA | NA | NA | NA | NA | NA | NA | NA | NA | 207 | 288 | 238 | 6 | q16.1 |
| 280 | PAG1 | 189 | NA | NA | NA | 2 | 1 | NA | NA | NA | NA | 237 | 252 | 239 | 6 | p21.2 |
| 281 | SLC25A37 | 142 | 2.6 | -1 | 845 | NA | NA | 776 | NA | NA | NA | 209 | 287 | 241 | 8 | q24.1 |
| 282 | BCAR1 | 273 | 2.5 | -1 | 846 | NA | NA | NA | NA | NA | NA | 232 | 262 | 243 | 16 | q21.3 |
| 283 | COX4I1 | 306 | NA | NA | NA | 2.6 | -1 | 911 | NA | NA | NA | 319 | 191 | 244 | 8 | q16.3 |
| 284 | EIF4H | 59 | NA | NA | NA | NA | NA | 878 | NA | NA | NA | 246 | 249 | 245 | 7 | q11.23 |
| 285 | ZC3H18 | 317 | NA | NA | NA | 2.1 | -1 | 947 | 2.0065 | 1 | 625 | 208 | 296 | 246 | 16 | q23.1 |
| 286 | STMN2 | 188 | 2.8 | 1 | 982 | NA | NA | NA | NA | NA | NA | 257 | 232 | 247 | 8 | q24.2 |
| 287 | AFG3L1 | 335 | NA | NA | NA | 2.3 | -1 | 901 | NA | NA | NA | 244 | 256 | 249 | 16 | q24.3 |
| 288 | HSD17B2 | 287 | 2.6 | -1 | 791 | NA | NA | NA | 1.7755 | 1 | 529 | 259 | 242 | 250 | 16 | q23.3 |
| 289 | MVD | 320 | 2.4 | 1 | NA | 2.3 | -1 | NA | NA | NA | NA | 242 | 261 | 251 | 16 | q24.3 |
| 290 | DLC1 | 106 | 1.8 | -1 | 1000 | NA | NA | 639 | NA | NA | NA | 262 | 243 | 252 | 8 | p22 |
| 291 | EPHA7 | 44 | 6.5 | -1 | NA | NA | NA | 819 | NA | NA | NA | 292 | 220 | 253 | 6 | q16.1 |
| 292 | TRIM35 | 151 | 2.6 | -1 | 936 | NA | NA | NA | 1.9432 | 1 | 632 | 277 | 233 | 254 | 8 | p21.2 |
| 293 | LHRC50 | 290 | 2.6 | -1 | 830 | 1.8 | -1 | 635 | NA | NA | NA | 317 | 212 | 257 | 16 | q24.1 |
| 294 | CNOB3 | 192 | 1.8 | 1 | 534 | 2.2 | -1 | NA | NA | NA | NA | 257 | 263 | 258 | 8 | q21.3 |
| 295 | ASCC3 | 47 | NA | NA | NA | 2 | 1 | NA | 2.2839 | 1 | 749 | 268 | 253 | 260 | 6 | q16.3 |
| 296 | AFC2 | 61 | NA | NA | NA | 2.1 | -1 | 861 | NA | NA | NA | 222 | 233 | 261 | 7 | q22.3 |
| 297 | CLEC3A | 278 | 2.3 | -1 | 781 | 1.8 | -1 | 693 | NA | NA | NA | 286 | 312 | 263 | 16 | q22.1 |
| 298 | IL17C | 318 | NA | NA | NA | 1.9 | -1 | 606 | NA | NA | NA | 258 | 289 | 264 | 16 | q24.3 |
| 299 | BMP1 | 125 | NA | NA | NA | 1.8 | -1 | 730 | NA | NA | NA | 302 | 230 | 265 | 8 | p21.3 |
| 300 | CPA4 | 84 | NA | NA | NA | 2 | 1 | 670 | NA | NA | NA | 272 | 264 | 267 | 7 | q32.2 |
| 301 | OC90 | 227 | 1.9 | 1 | 640 | NA | NA | 821 | NA | NA | NA | 288 | 250 | 268 | 8 | q24.22 |
| 302 | HEPH | 364 | 1.8 | 1 | 537 | NA | NA | NA | NA | NA | NA | 295 | 245 | 269 | 23 | q12 |
| 303 | LAP12 | 212 | NA | NA | NA | NA | NA | NA | NA | NA | NA | 248 | 295 | 272 | 8 | q22.3 |
| 304 | AGFQ2 | 74 | 2.3 | -1 | 803 | NA | NA | NA | NA | NA | NA | 260 | 284 | 274 | 7 | q22.1 |
| 305 | TAPA1 | 174 | NA | NA | NA | 2.1 | -1 | NA | NA | NA | NA | | | | 8 | q13.3 |
| 306 | GINS2 | 303 | 2.3 | 1 | NA | 1.9 | -1 | NA | NA | NA | NA | | | | 16 | q24.1 |
| 307 | CENPH | 29 | NA | NA | NA | 1.8 | -1 | 603 | NA | NA | NA | | | | 5 | q13.2 |
| 308 | KLHL36 | 297 | NA | NA | NA | 2.1 | -1 | 705 | NA | NA | NA | | | | 16 | q24.1 |
| 309 | ARHGEF1OL | 2 | NA | NA | NA | NA | NA | NA | NA | NA | NA | | | | 1 | p36.13 |
| 310 | TRAPPC2L | 326 | NA | NA | NA | NA | NA | NA | NA | NA | NA | | | | 16 | q24.3 |
| 311 | TCF25 | 332 | NA | NA | NA | NA | NA | NA | NA | NA | NA | | | | 16 | q24.3 |
| 312 | TNFRSF10D | 137 | 1.9 | -1 | NA | NA | NA | NA | NA | NA | NA | | | | 8 | p21.3 |
| 313 | MYCM2 | 93 | 2.1 | NA | NA | 1.9 | NA | NA | NA | NA | NA | | | | 5 | q23.3 |
| 314 | GCSH | 282 | NA | NA | NA | 1.9 | NA | NA | NA | NA | NA | | | | 16 | q23.2 |
| 315 | KIAA1609 | 296 | NA | NA | NA | NA | NA | NA | NA | NA | NA | | | | 16 | q24.1 |

TABLE 14-continued

| | | | | | | | | | | | | | | | | | |
|---|---|---|---|---|---|---|---|---|---|---|---|---|---|---|---|---|---|
| 316 | FANCA | 330 | NA | NA | NA | 1.9 | −1 | 612 | NA | NA | NA | 299 | 247 | 275 | 0.06 | 16 | q24.3 |
| 317 | ERI1 | 96 | 1.9 | −1 | 600 | NA | NA | NA | NA | NA | NA | 312 | 239 | 276 | NA | 8 | q23.1 |
| 318 | HSDL1 | 292 | NA | NA | NA | 2 | −1 | 885 | NA | NA | NA | 273 | 278 | 278 | NA | 16 | q24.1 |

Table 14-8b

| Final-RANK | gene | gene-start | gene-end | genesBtwn | contg | clump-index | dstprev | dstnext | min-disto-ROL | IndexO-Proxy1 | NYU-Zadjust | MSKs1-Zadjust | | | MSKS2-Zadjust |
|---|---|---|---|---|---|---|---|---|---|---|---|---|---|---|---|
| 279 | MDH2 | 75515329 | 75533864 | 2 | 1 | 10 | 260189 | −72 | −72 | 0 | NA | NA | NA | NA | 0.06 |
| 280 | PAG1 | 82042605 | 82186858 | 8 | 1 | 37 | 545883 | −93034 | −930334 | 0 | NA | 0.07 | NA | NA | NA |
| 281 | SLC25A37 | 23442308 | 23486008 | 1 | 1 | 28 | 129901 | −71227 | −71227 | 0 | 0.29 | NA | NA | NA | NA |
| 282 | BCAR1 | 73820429 | 73859452 | 0 | 1 | 51 | 25657 | −243911 | 25657 | 0 | 0.25 | NA | NA | NA | NA |
| 283 | COX4I1 | 84390697 | 84396109 | 0 | 1 | 57 | 92166 | −96 | −96 | 0 | NA | 0.29 | NA | NA | NA |
| 284 | EIF4H | 73226625 | 73249358 | 0 | 1 | 9 | 12304 | −404089 | 12304 | 0 | NA | NA | NA | NA | 0.07 |
| 285 | ZC3H18 | 87164343 | 87225755 | 0 | 1 | 58 | 6745 | −294 | −294 | 0 | NA | 0.10 | NA | NA | NA |
| 286 | STMN2 | 80685916 | 80740888 | 0 | 1 | 36 | 97933 | −1007876 | 9933 | 0 | 0.38 | NA | NA | NA | NA |
| 287 | AFG3L1 | 88566489 | 88594595 | 1 | 1 | 63 | 21813 | −4521 | 4521 | 0 | NA | 0.17 | NA | NA | NA |
| 288 | HSD17B2 | 80626364 | 80689638 | 1 | 1 | 53 | 750123 | −76965 | −76965 | 0 | 0.29 | NA | NA | NA | NA |
| 289 | MVD | 87245849 | 87257019 | 0 | 1 | 58 | 14572 | −891 | −891 | 0 | NA | 0.17 | NA | NA | NA |
| 290 | DLC1 | 12985243 | 13416766 | 1 | 1 | 19 | 574978 | −53590 | −53590 | 0 | 2.71 | NA | NA | NA | NA |
| 291 | EPHA7 | 94007864 | 94185993 | 9 | 1 | 5 | 5242062 | −2654236 | −2654238 | 0 | NA | 0.01 | NA | NA | 0.01 |
| 292 | TRIM35 | 27198321 | 27224751 | 0 | 1 | 30 | 155 | 26478 | 165 | 0 | 0.29 | NA | NA | NA | NA |
| 293 | LHRC50 | 82736366 | 82769024 | 3 | 1 | 54 | 116798 | −101 | −101 | 0 | 0.21 | NA | NA | NA | NA |
| 294 | CNOB3 | 87656277 | 87825017 | 0 | 1 | 38 | 122823 | −1691298 | 122823 | 0 | 0.02 | NA | NA | NA | NA |
| 295 | ASCC3 | 101062791 | 101435961 | 79 | 1 | 6 | 16667349 | −43297 | −43297 | 0 | NA | NA | NA | NA | 0.02 |
| 296 | AFC2 | 73283770 | 73306674 | 0 | 1 | 9 | 35065 | −1671 | −1871 | 0 | NA | NA | NA | NA | 0.03 |
| 297 | CLEC3A | 76613944 | 76623495 | 0 | 1 | 52 | 67557 | −280292 | 67557 | 0 | 0.17 | NA | NA | NA | NA |
| 298 | IL17C | 87232502 | 87234385 | 0 | 1 | 56 | 2814 | −6746 | 2814 | 0 | NA | 0.02 | NA | NA | NA |
| 299 | BMP1 | 22078645 | 22125782 | 0 | 1 | 25 | 7380 | −8355 | 7380 | 0 | NA | 0.14 | NA | NA | NA |
| 300 | CPA4 | 129720230 | 129751249 | 0 | 1 | 13 | 20643 | −3360 | −3360 | 0 | NA | NA | NA | NA | 0.06 |
| 301 | OC90 | 133105687 | 133167084 | 0 | 1 | 45 | 43354 | −10596 | −10596 | 0 | 0.05 | NA | NA | NA | NA |
| 302 | HEPH | 65298388 | 65403955 | 0 | 1 | 69 | 328248 | NA | 328848 | 0 | 0.02 | NA | NA | NA | NA |
| 303 | LAP12 | 105570643 | 105670344 | 0 | 1 | 41 | 72999 | −22190 | −22190 | 0 | NA | 0.07 | NA | NA | NA |
| 304 | AGFQ2 | 99974770 | 100003778 | 0 | 1 | 12 | 5792 | −44412 | 5792 | 0 | NA | NA | NA | NA | 0.16 |
| 305 | TAPA1 | 73086040 | 73150373 | 0 | 1 | 34 | 492151 | −176755 | −176755 | 0 | 0.17 | NA | NA | NA | NA |
| 306 | GINS2 | 84268782 | 84280089 | 0 | 1 | 57 | 18535 | −1471 | −1471 | 0 | NA | 0.10 | NA | NA | NA |
| 307 | CENPH | 68521131 | 68541939 | 0 | 1 | 4 | 7390 | NA | 7390 | 0 | NA | 0.05 | NA | NA | NA |
| 308 | KLHL36 | 83239632 | 83253416 | 0 | 1 | 56 | 37634 | −143838 | 37634 | 0 | NA | 0.02 | NA | NA | NA |
| 309 | ARHGEF1OL | 17738917 | 17898956 | 0 | 1 | 1 | 57439 | −1482527 | 57439 | 0 | NA | 0.10 | NA | NA | NA |
| 310 | TRAPPC2L | 87451007 | 87455020 | 0 | 1 | 60 | 13748 | −122 | −122 | 0 | NA | 0.05 | NA | NA | NA |
| 311 | TCF25 | 88467520 | 88505287 | 0 | 1 | 82 | 7881 | −2292 | −2292 | 0 | NA | 0.10 | NA | NA | NA |
| 312 | TNFRSF10D | 23049051 | 23077485 | 0 | 1 | 27 | 27431 | −115396 | 27431 | 0 | 0.05 | NA | NA | NA | NA |
| 313 | MYCM2 | 1980566 | 2080779 | 0 | 1 | 14 | 699503 | −86359 | −86369 | 0 | 0.10 | NA | NA | NA | NA |
| 314 | GCSH | 79673430 | 79587481 | 0 | 1 | 53 | 4504 | −5057 | 4504 | 0 | NA | 0.05 | NA | NA | NA |
| 315 | KIAA1609 | 83068608 | 83095794 | 1 | 1 | 55 | 143838 | −13315 | −13315 | 0 | NA | 0.05 | NA | NA | NA |
| 316 | FANCA | 88331460 | 88410565 | 0 | 1 | 62 | 11842 | 11842 | 11842 | 0 | NA | 0.05 | NA | NA | NA |
| 317 | ERI1 | 8897856 | 8928139 | 1 | 1 | 15 | 522716 | −246990 | −109315 | 0 | 0.05 | NA | NA | NA | NA |
| 318 | HSDL1 | 82713389 | 82736285 | 0 | 1 | 54 | 101 | −5371 | 101 | 0 | NA | 0.07 | NA | NA | NA |

TABLE 14-continued

Table 14-9a

| Final-RANK | gene | index | gene-start | gene-end | NYU-2 | NYU-dir | NYU-count | MSKs1-Z | MSKs1-dir | MSKs2-count | MSKs2-Z | MSKs2-dir | MSKs2-count | logrank-n52random | logrank-n271random | logrank-composite | gene-Chr | gene-Cytoband |
|---|---|---|---|---|---|---|---|---|---|---|---|---|---|---|---|---|---|---|
| 319 | KIAA0182 | 302 | | | NA | NA | NA | 2 | -1 | 781 | NA | NA | NA | 305 | 251 | 281 | 16 | q24.1 |
| 320 | CBFA2T3 | 327 | | | NA | NA | NA | 1.9 | -1 | 698 | NA | NA | NA | 274 | 297 | 286 | 16 | q24.3 |
| 321 | EGR3 | 135 | | | NA | NA | NA | 2 | -1 | 751 | NA | NA | NA | 308 | 267 | 289 | 8 | p21.3 |
| 322 | PCOLCE | 77 | | | NA | NA | NA | | | NA | 1.8050 | 1 | 608 | 294 | 281 | 290 | 7 | q22.1 |
| 323 | C16orlB5 | 316 | | | NA | NA | NA | 2.1 | -1 | 801 | NA | NA | NA | 290 | 291 | 295 | 16 | q24.2 |
| 324 | HMBOX1 | 159 | | | 1.8 | -1 | 553 | NA | NA | NA | NA | NA | NA | 287 | 306 | 300 | 8 | p21.1 |
| 325 | MTMR9 | 100 | | | 1.9 | 1 | 674 | NA | NA | NA | NA | NA | NA | 343 | 257 | 301 | 8 | p23.1 |
| 326 | MSC | 173 | | | 2 | 1 | 675 | NA | NA | NA | NA | NA | NA | 291 | 305 | 302 | 8 | q13.3 |
| 327 | ST3GAL2 | 289 | | | 2.4 | -1 | 774 | NA | NA | NA | NA | NA | NA | 259 | 344 | 308 | 16 | q22.1 |
| 328 | FOXF1 | 308 | | | NA | NA | NA | 2.2 | -1 | 894 | NA | NA | NA | 344 | 270 | 309 | 16 | q24.1 |
| 329 | C8or158 | 132 | | | NA | NA | NA | 3 | -1 | 999 | NA | NA | NA | 334 | 279 | 310 | 8 | p21.3 |
| 330 | KCTD9 | 145 | | | 2 | -1 | 663 | NA | NA | NA | NA | NA | NA | 271 | 344 | 311 | 8 | p21.2 |
| 331 | ANGPT1 | 214 | | | 2.4 | 1 | 818 | NA | NA | NA | NA | NA | NA | 333 | 282 | 313 | 8 | q23.1 |
| 332 | GDAP1 | 180 | | | 2 | 1 | 683 | NA | NA | NA | NA | NA | NA | 283 | 333 | 314 | 8 | q21.11 |
| 333 | HNF166 | 322 | | | NA | NA | NA | 2.2 | -1 | 877 | NA | NA | NA | 263 | 360 | 315 | 16 | q24.3 |
| 334 | KLHL1 | 253 | | | NA | NA | NA | NA | NA | NA | 1.8630 | -1 | 568 | 293 | 325 | 318 | 13 | q21.33 |
| 335 | LOXL2 | 140 | | | 1.9 | -1 | 777 | NA | NA | NA | NA | NA | NA | 322 | 298 | 319 | 8 | p21.3 |
| 336 | WISP1 | 233 | | | 2.2 | 1 | 957 | NA | NA | NA | NA | NA | NA | 280 | 343 | 320 | 8 | q24.22 |
| 337 | C8or180 | 157 | | | 3.6 | -1 | NA | NA | NA | NA | NA | NA | NA | 357 | 274 | 323 | 8 | p21.1 |
| 338 | LA12 | 60 | | | NA | -1 | 691 | NA | NA | NA | 1.9646 | 1 | 697 | 328 | 300 | 324 | 7 | q11.23 |
| 339 | USP10 | 298 | | | 2.3 | -1 | NA | NA | NA | NA | NA | NA | NA | 321 | 310 | 326 | 16 | q24.1 |
| 340 | CDH15 | 328 | | | NA | NA | NA | 1.9 | -1 | 673 | NA | NA | NA | 330 | 303 | 328 | 16 | q24.3 |
| 341 | WFCC1 | 294 | | | 2.3 | -1 | 713 | NA | NA | NA | NA | NA | NA | 311 | 327 | 329 | 16 | q24.1 |
| 342 | C7or151 | 73 | | | NA | -1 | 999 | NA | NA | NA | 2.1914 | 1 | 773 | 307 | 339 | 333 | 7 | q22.1 |
| 343 | EBF2 | 14 | | | 5.1 | -1 | NA | 2 | NA | NA | NA | NA | NA | 309 | 337 | 334 | 8 | p21.2 |
| 344 | CCCC125 | 32 | | | NA | NA | NA | 2 | NA | 721 | NA | NA | NA | 336 | 319 | 337 | 5 | q13.2 |
| 345 | LG13 | 124 | | | NA | NA | NA | 2.3 | NA | 678 | NA | NA | NA | 332 | 323 | 338 | 8 | p21.3 |
| 346 | NUDT18 | 121 | | | NA | NA | NA | 2.2 | NA | 786 | NA | NA | NA | 314 | 354 | 340 | 8 | p21.3 |
| 347 | PHYHIP | 125 | | | NA | NA | NA | NA | NA | 860 | NA | NA | NA | 351 | 308 | 341 | 8 | p21.3 |
| 348 | PILRA | 70 | | | NA | -1 | NA | NA | NA | NA | 1.8998 | 1 | 701 | 353 | 318 | 342 | 7 | q22.1 |
| 349 | KATZA | 340 | | | NA | NA | NA | NA | NA | NA | 3.1978 | 1 | 993 | 318 | 357 | 343 | 17 | q921.2 |
| 350 | CSMD3 | 216 | | | 4.9 | 1 | 998 | 4.2 | 1 | 809 | NA | NA | NA | 351 | 324 | 344 | 8 | q23.3 |
| 351 | REEP4 | 123 | | | NA | NA | NA | 2.5 | -1 | 847 | NA | NA | NA | 324 | 352 | 345 | 8 | p21.3 |
| 352 | TUBB3 | 333 | | | NA | NA | NA | 2.6 | -1 | 843 | NA | NA | NA | 348 | 328 | 346 | 16 | q24.3 |
| 353 | CDT1 | 324 | | | NA | NA | NA | 2 | -1 | 745 | NA | NA | NA | 365 | 313 | 347 | 16 | q24.3 |
| 354 | EDA2R | 365 | | | 2 | 1 | 629 | NA | NA | NA | NA | NA | NA | 349 | 331 | 348 | 23 | q12 |
| 355 | DUS1L | 34 | | | NA | NA | NA | NA | NA | NA | 2.2705 | 1 | 904 | 364 | 322 | 350 | 17 | q25.3 |
| 356 | LACH4 | 75 | | | NA | NA | NA | NA | NA | NA | 2.2304 | 1 | 831 | 342 | 349 | 351 | 8 | q22.1 |
| 357 | TMEM75 | 223 | | | 3.5 | 1 | 992 | NA | NA | NA | NA | NA | NA | 337 | 356 | 352 | 8 | q24.21 |
| 358 | NUDT7 | 277 | | | 2.2 | -1 | 730 | NA | NA | NA | NA | NA | NA | 355 | 338 | 353 | 16 | q23.1 |

Table 14-9b

| Final-RANK | gene | genesBtwn | contg | clump-index | dstprev | dstnext | min-disto-ROL | IndexO-Proxy1 | NYU-Zadjust | MSKs1-Zadjust | MSKs2-Zadjust |
|---|---|---|---|---|---|---|---|---|---|---|---|
| 319 | KIAA0182 | 0 | 1 | 57 | 1471 | -517197 | 1471 | 0 | NA | 0.07 | NA |
| 320 | CBFA2T3 | 2 | 1 | 60 | 194752 | -13748 | -13748 | 0 | NA | 0.05 | NA |

TABLE 14-continued

| | gene | index | NYU-2 | NYU-dir | NYU-count | MSKs1-Z | MSKs1-dir | MSKs1-count | MSKs2-Z | MSKs2-dir | MSKs2 count | logrank-n52random | logrank-n271random | logrank-composite |
|---|---|---|---|---|---|---|---|---|---|---|---|---|---|---|
| 321 | EGR3 | 22601119 | NA | NA | NA | 26 | 306299 | -18566 | 0 | NA | NA | NA | NA |
| 322 | PCOLCE | 100037818 | NA | NA | NA | 12 | 3929 | -1144 | 0 | NA | 0.07 | NA | 0.02 |
| 323 | C16orf1B5 | 87147613 | NA | NA | NA | 58 | 294 | -18723 | 0 | NA | 0.10 | NA | NA |
| 324 | HMBOX1 | 28803830 | NA | NA | NA | 32 | 14009 | 14009 | 0 | NA | NA | NA | NA |
| 325 | MTMR9 | 11179410 | NA | NA | NA | 17 | 165868 | -154255 | 0 | 0.02 | NA | NA | NA |
| 326 | MSC | 72916332 | NA | NA | NA | 34 | 176755 | -479311 | 0 | 0.05 | NA | NA | NA |
| 327 | ST3GAL2 | 68970839 | NA | NA | NA | 50 | 2343793 | 176755 | 0 | 0.07 | NA | NA | NA |
| 328 | FOXF1 | 85101634 | NA | NA | NA | 57 | 15714 | -6059 | 0 | 0.21 | 0.07 | NA | NA |
| 329 | C8orf158 | 22513067 | NA | NA | NA | 26 | 597 | 15714 | 0 | NA | 0.14 | NA | NA |
| 330 | KCTD9 | 25541283 | NA | NA | NA | 29 | 591 | -1584 | 0 | 0.07 | 0.47 | NA | NA |
| 331 | ANGPT1 | 108330899 | NA | NA | NA | 42 | 401282 | -14747 | 0 | 0.21 | NA | NA | NA |
| 332 | GDAP1 | 75425173 | NA | NA | NA | 35 | 457439 | 401262 | 0 | 0.07 | NA | NA | NA |
| 333 | HNF166 | 87290411 | NA | NA | NA | 58 | 2604 | -1444960 | 0 | NA | NA | NA | NA |
| 334 | KLHL1 | 69172727 | NA | NA | NA | 49 | 1329507 | -23056 | 0 | NA | 0.14 | NA | 0.04 |
| 335 | LOXL2 | 23210097 | NA | NA | NA | 28 | -18281 | -10028 | 0 | NA | 0.05 | NA | NA |
| 336 | WISP1 | 134272494 | NA | NA | NA | 46 | 1248464 | -2470149 | 0 | 0.14 | NA | NA | NA |
| 337 | C8orf180 | 27936607 | NA | NA | NA | 31 | 2452 | -18281 | 0 | 0.80 | NA | NA | 0.06 |
| 338 | LA12 | 73261662 | NA | NA | NA | 9 | 1671 | -88015 | 0 | NA | NA | NA | NA |
| 339 | USP10 | 83291050 | NA | NA | NA | 56 | 40087 | -29490 | 0 | 0.17 | NA | NA | NA |
| 340 | COH15 | 87765664 | NA | NA | NA | 61 | 72136 | -12304 | 0 | NA | 0.05 | NA | NA |
| 341 | WFCC1 | 82885822 | NA | NA | NA | 55 | 38748 | 1671 | 0 | 0.17 | NA | NA | 0.13 |
| 342 | C7orf151 | 99919485 | NA | NA | NA | 12 | 44412 | -37634 | 0 | NA | NA | NA | NA |
| 343 | EBF2 | 25758042 | NA | NA | NA | 29 | 533035 | 72136 | 0 | 1.78 | NA | NA | NA |
| 344 | CCCC125 | 68612278 | NA | NA | NA | 4 | 31935 | -116798 | 0 | NA | NA | NA | NA |
| 345 | LGI3 | 22060290 | NA | NA | NA | 24 | 8355 | 38746 | 0 | NA | 0.07 | NA | 0.07 |
| 346 | NUDT18 | 20202328 | NA | NA | NA | 25 | 4474 | -4648 | 0 | NA | 0.07 | NA | NA |
| 347 | PHYHIP | 22133162 | NA | NA | NA | 25 | 12768 | -3274 | 0 | NA | 0.17 | NA | NA |
| 348 | PILRA | 99808004 | NA | NA | NA | 11 | 29540 | -4897 | 0 | NA | 0.14 | NA | 0.05 |
| 349 | KATZA | 37518657 | NA | NA | NA | 64 | 1489 | -2493 | 0 | NA | NA | NA | 0.57 |
| 350 | CSMD3 | 113304337 | NA | 114518418 | NA | 43 | 1971482 | -7380 | 0 | 1971482 | 1.16 | NA | NA |
| 351 | REEP4 | 22051478 | NA | 22055393 | NA | 24 | 4897 | -5616 | 0 | 489 | 0.25 | NA | NA |
| 352 | TUBB3 | 88513168 | NA | 88530006 | NA | 62 | 12678 | -380 | 0 | -7881 | 0.29 | NA | NA |
| 353 | CDT1 | 87397687 | NA | 87403186 | NA | 59 | 4478 | -4139285 | 0 | 4478 | 0.07 | NA | NA |
| 354 | EDA2R | 65732204 | NA | 65775508 | NA | 69 | 904991 | -8152 | 0 | -328248 | NA | NA | 0.16 |
| 355 | DUS1L | 77609043 | NA | 77629242 | NA | 66 | 262 | -7881 | 0 | 262 | 0.07 | NA | 0.14 |
| 356 | LACH4 | 100009570 | NA | 100021712 | NA | 12 | 180 | -67370 | 0 | -40474 | NA | NA | NA |
| 357 | TMEM75 | 129029046 | NA | 129029462 | NA | 44 | 2104073 | 328248 | 0 | -5792 | 0.74 | NA | NA |
| 358 | NUDT7 | 76313912 | NA | 76333852 | NA | 52 | 280292 | -40474 | 0 | 180 | 0.14 | NA | NA |

Table 14-10a

| Final-RANK | gene | index | NYU-2 | NYU-dir | NYU-count | MSKs1-Z | MSKs1-dir | MSKs1-count | MSKs2-Z | MSKs2-dir | MSKs2 count | logrank-n52random | logrank-n271random | logrank-composite | gene-Chr | gene-Cytoband |
|---|---|---|---|---|---|---|---|---|---|---|---|---|---|---|---|---|
| 359 | TSGA14 | 87 | NA | NA | NA | NA | NA | NA | 9.3754 | 1 | 968 | 354 | 341 | 354 | 7 | q32.2 |
| 360 | CDC428PG | 242 | NA | NA | NA | NA | NA | NA | 2.3279 | 1 | 813 | 360 | 335 | 355 | 11 | q13.1 |
| 361 | TSC22D4 | 72 | NA | NA | NA | NA | NA | NA | 2.1304 | 1 | 867 | 341 | 359 | 356 | 7 | q22.1 |
| 362 | NOITUM | 345 | NA | NA | NA | NA | NA | NA | 2.6756 | 1 | 983 | 358 | 348 | 358 | 17 | q25.3 |
| 363 | HSPB9 | 341 | NA | NA | NA | NA | NA | NA | 2.9366 | 1 | 987 | 346 | 361 | 360 | 17 | q21.2 |
| 364 | TFA2 | 79 | NA | NA | NA | NA | NA | NA | 2.6230 | 1 | 950 | 352 | 355 | 361 | 7 | q22.1 |
| 365 | SLA | 232 | 2.2 | 1 | 786 | NA | NA | NA | NA | NA | NA | 347 | 365 | 362 | 8 | q24.22 |
| 366 | WWOX | 279 | 9.3 | -1 | 1000 | NA | NA | NA | NA | NA | NA | 359 | 364 | 365 | 16 | q23.1 |

TABLE 14-continued

| | | gene-start | gene-end | genesBtwn | contg | clump-index | dstprev | dstnext | min-distoROL | IndexO-Proxy1 | NYU-Zadjust | MSKs1-Zadjust | | MSKS2-Zadjust | | | |
|---|---|---|---|---|---|---|---|---|---|---|---|---|---|---|---|---|---|
| 367 | POUSF1B | 221 | 2.9 | | 1 | NA | NA | NA | NA | NA | NA | 366 | 358 | 366 | NA | 8 | q24.21 |
| 368 | CPHN1 | 367 | 5.8 | | 1 | NA | NA | NA | NA | NA | NA | 368 | 368 | 368 | NA | 23 | q12 |

Table 14-10b

| Final-RANK | gene | gene-start | gene-end | genesBtwn | contg | clump-index | dstprev | dstnext | min-distoROL | IndexO-Proxy1 | NYU-Zadjust | MSKs1-Zadjust | MSKS2-Zadjust |
|---|---|---|---|---|---|---|---|---|---|---|---|---|---|
| 359 | TSGA14 | 129823611 | 129868133 | 0 | 1 | 13 | 45149 | -8446 | -8446 | 0 | NA | NA | 4.49 |
| 360 | CDC42BPG | 64348240 | 64368517 | 2 | 1 | 47 | 80139 | -12898 | -12888 | 0 | NA | NA | 0.18 |
| 361 | TSC22D4 | 99902080 | 99914838 | 0 | 1 | 12 | 4648 | -32404 | 4648 | 0 | NA | NA | 0.11 |
| 362 | NOTUM | 77503689 | 77512353 | 0 | 1 | 65 | 16362 | -39903857 | 16352 | 0 | NA | NA | 0.32 |
| 363 | HSPB9 | 37528361 | 37526897 | 0 | 1 | 64 | 1627 | -1489 | -1489 | 0 | NA | NA | 0.44 |
| 364 | TFA2 | 100055975 | 100077109 | 0 | 1 | 12 | 1589 | -5043 | 1589 | 0 | NA | NA | 0.29 |
| 365 | SLA | 134118155 | 134184479 | 0 | 1 | 46 | 88015 | 98170 | 88015 | 0 | 0.14 | NA | NA |
| 366 | WWOX | 76891052 | 77803532 | 2 | 1 | 52 | 1391644 | -67557 | -67557 | 0 | 4.45 | NA | NA |
| 367 | POUSF1B | 128497039 | 128498621 | 0 | 1 | 44 | 318241 | -23233848 | 318241 | 0 | 0.42 | NA | NA |
| 368 | OPHN1 | 67179440 | 67570372 | NA | 1 | 69 | NA | -318596 | -318596 | 0 | 2.24 | NA | NA |

What is claimed is:
1. A method of diagnosing and treating a human subject who has or had breast or lung cancer, the method comprising
(a) obtaining a tissue or DNA sample from the subject,
(b) determining in the sample the number of copies per cell of at least 12 genes and/or genomic regions of a metastatic gene signature set, wherein the metastatic gene signature set consists of the PPP3CC genomic region, the SLCO5A1 genomic region, the SLC7A5 genomic region, the SLC7A2 genomic region, the CRISPLD2 genomic region, the CDH13 gene, the CDH8 gene, the CDH2 gene, the ASAH1 genomic region, the KCNB2 genomic region, the KCNH4 genomic region, the CTD8 gene, the JPH1 genomic region, the MEST genomic region, the NCALD genomic region, the COL19A1 gene, the MAP3K7 genomic region, the YWHAG gene, the NOLA genomic region, and the ENOX1 gene, wherein said detecting comprises performing nucleic acid hybridization, and wherein the PPP3CC genomic region consists of the genes PPP3CC, KIAA1967, BIN3, SORBS3, PDLIM2, RHOBTB2, SLC39A14, EGR3, and C8orf58, the SLCO5A1 genomic region consists of the genes SLCOSA1, SULF1, NCOA2, CPA6, C8orf34, PRDM14, and PREX2, the SLC7A5 genomic region consists of the genes SLC7A5, CASA, BANP, KLHDC4, CYBA, JPH3, ZFPM1, SNAI3, ZC3H18, MVD, IL17C, C16orf85, and RNF166, the SLC7A2 genomic region consists of the genes SLC7A2, MTMR7 and MTUS1, the CRISPLD2 genomic region consists of the genes CRISPLD2, ZDHHC7, KIAA0513, KLHL36, and USP10, the ASAH1 genomic region consists of the genes ASAH1 and PCM1, the KCNB2 genomic region consists of the genes KCNB2, EYA1, XKR9, and TRPA1, the KCNH4 genomic region consists of the genes KCNH4, RAB5C, DHX58, KAT2A, and HSPB9, the JPH1 genomic region consists of the genes JPH1, HNF4G, CRISPLD1, PI15, and GDAP1, the MEST genomic region consists of the genes MEST, COPG2, CPA5, CPA2, CPA1, CPA4, and TSGA14, the NCALD genomic region consists of the genes NCALD, ZNF706, GRHL2, and YWHAZ, the MAP3K7 genomic region consists of the genes MAP3K7 and EPHA7, and the NOL4 genomic region consists of the genes NOLA and DTNA, (c) determining an aggregate score for the at least 12 members as compared to the number of copies per cell in non-cancer cells, (d) based on the determination in step (c), diagnosing that the subject has risk of metastasis, (e) developing a pan-cancer metastatic potential score (panMPS) based on CNA (copy number alternation) genes, (f) predicting a metastasis-free survival for breast or lung cancer based on the panMPS in step (e), and (g) treating the subject with at least one therapy selected from the group consisting of surgery, radiation therapy, chemotherapy or biologically targeted therapy.

2. The method of claim 1, wherein the at least 12 genes and/or genomic regions include the PPP3CC genomic region, the SLCOSA1 genomic region, the SLC7A5 genomic region, the SLC7A2 genomic region, the CRISPLD2 genomic region, the CDH13 gene, the CDH8 gene, the CDH2 gene, the ASAH1 genomic region, the KCNB2 genomic region, the KCNH4 genomic region, and the CTD8 gene.

3. The method of claim 1, wherein the at least 12 genes and/or genomic regions include all of the genes and genomic regions in said metastatic gene signature set.

4. The method of claim 3, further comprising determining the number of copies per cell of at least one additional gene or genomic region selected from the group consisting of PPP3CC, SLCO5A1, SLC7A5, SLC7A2, CRISPLD2, CDH13, CDH8, CDH2, ASAH1, KCNB2, KCNH4, KCTD8, JPH1, MEST, NCALD, COL19A1, MAP3K7, YWAHG, NOLA, ENOX1, CSMD1, SGCZ, PDE10A, PCDH9, HTR2A, HIP1, CD226, DCC, CC2D1A, PTK2B, BCMO1, MACRDO1, GRID2, DIAPH3, PILRB, MEIS2, MSRA, DPYD, ANKRD11, NRXN1, ADCY8, TRDN, STAU2, SF1, CLIP2, CLDN3, ZSWIM4, GLRB, DCHS2, TRPS1, MDGA2, CNBD1, STAG3, GATA4, VPS13B, DOCK5, ZHX2, ARHGEF5, SDC2, MYLK, LPHN3, MOSPD3, GYS2, GAS8, RAB9A, POLR3D, PSD3, ZFPM2, ATP6V1C1, MEF2C, PKIA, ADAMTS18, STYXL1, EPM2A, LEPREL1, GABRA2, RCOR2, MFHAS1, SCARA5, CCDC25, FAM38A, CTSB, PTK2, SPIRE2, C13orf23, BOD1L, FAM160B2, NUS1, MTHFSD, UBR5, GALNS, FSTL5, SIM1, TG, BFSP2, MMP16, RIMS2, PDS5B, CDK7, CNTNAP4, CFDP1, FBXL4, RFX1, NALCN, STX1A, CYP7B1, ARHGEF10, ENTPD4, ZNF704, C8orf79, SLC9A9, CHMP7, GPC5, MYC, STIP1, ZBTB20, MEN1, SLC26A7, ALCAM, KIF13B, MBTPS1, PPP2R5B, VPS13C, ASPRSCR1, EPO, HEY1, KALRN, RGS22, WDR7, COL11A1, GHDC, ATP2C2, CDH17, DGKG, GRK5, GRM1, IMPA1, RPL7, COL21A1, COL12A1, MLYCD, AR, PLCB1, ACTL8, TFDP1, IQCE, SMARCB1, MTDH, NECAB2, DEF8, RNF40, TICAM2, GLG1, MECOM, TCEB1, CTNNA2, NIPAL2, CDCA2, WWP2, DDX19A, STK3, DNAH2, NFAT5, CNGB1, UBE2CBP, C8orf16, KIAA0196, CLCNKB, C16orf80, ZFHX3, PPM1L, NKIRAS2, RSPO2, XPO7, ME1, NLGN4Y, LZTS1, FBXL18, TBC1D10B, WDR59, BLK, MEPCE, DLGAP2, ZFAT, FASN, GIGYF1, ANXA13, CDYL2, TOX, NKX2-6, RALYL, TBC1D22A, TFE3, KCNAB1, SULF1, RAB5C, DHX58, ASAP1, CASA, C6orf118, NCOA2, PKD1L2, BANP, KIAA1967, COPG2, ZNF706, GAN, PLCG2, C19orf57, PDGFRL, ESD, CPA5, BIN3, ZFHX4, CPA6, EYA1, CHRNA2, TNKS, HNF4G, LRCH1, ADRA1A, EPHX2, SORBS3, GRIA2, PDLIM2, MTMR7, FBXO24, CRISPLD1, DPYS, DTNA, KLHDC4, CYBA, JPH3, TMEM120A, MTUS1, C8orf34, GRHL2, CPA2, NAT2, DPYSL2, ZDHHC7, ELP3, RHOBTB2, NEIL2, HR, EFR3A, STMN4, PRDM14, MARVELD2, SLC39A14, ACTL6B, TUSC3, COX4NB, XKR9, C16orf46, TAF9, KCNQ3, UTRN, RAD17, ZFPM1, PTDSS1, IRF8, YWHAZ, MRPS36, LACTB2, SNAI3, TMEM71, PREX2, CPA1, PHF20L1, KIAA0513, PI15, PCM1, SH2D4A, C16orf74, TP63, DACH1, TNFRSF10A, MDH2, PAG1, SLC25A37, BCAR1, COX411, EIF4H, ZC3H18, STMN2, AFG3L1, HSD17B2, MVD, DLC1, EPHA7, TRIM35, LRRC50, CNGB3, ASCC3, RFC2, CLEC3A, IL17C, BMP1, CPA4, OC90, HEPH, LRP12, AGFG2, TRPA1, GINS2, CENPH, KLHL36, ARHGEF10L, TRAPPC2L, TCF25, TNFRSF10D, MYOM2, GCSH, KIAA1609, FANCA, ERI1, HSDL1, KIAA0182, CBFA2T3, EGR3, PCOLCE, C16orf85, HMBOX1, MTMR9, MSC, ST3GAL2, FOXF1, C8orf58, KCTD9, ANGPT1, GDAP1, RNF166, KLHL1, LOXL2, WISP1, C8orf80, LAT2, USP10, CDH15, WFDC1, C7orf51, EBF2, CCDC125, LGI3, NUDT18, PHYHIP, PILRA, KAT2A, CSMD3, REEP4, TUBB3, CDT1, EDA2R, DUS1L, LRCH4, TMEM75, NUDT7, TSGA14, CDC42BPG, TSC22D4, NOTUM, HSPB9, TFR2, SLA, WWOX, POU5F1B, and OPHN1.

5. The method of claim 4, wherein said at least one additional gene or genomic region comprises 20 genes and/or genomic regions selected from the group consisting of PPP3CC, SLCOSA1, SLC7A5, SLC7A2, CRISPLD2, CDH13, CDH8, CDH2, ASAH1, KCNB2, KCNH4, KCTD8, JPH1, MEST, NCALD, COL19A1, MAP3K7, YWAHG, NOL4, ENOX1, CSMD1, SGCZ, PDE10A, PCDH9, HTR2A, HIP1, CD226, DCC, CC2D1A, PTK2B, BCMO1, MACRDO1, GRID2, DIAPH3, PILRB, MEIS2, MSRA, DPYD, ANKRD11, NRXN1, ADCY8, TRDN, STAU2, SF1, CLIP2, CLDN3, ZSWIM4, GLRB, DCHS2, TRPS1, MDGA2, CNBD1, STAG3, GATA4, VPS13B, DOCK5, ZHX2, ARHGEF5, SDC2, MYLK, LPHN3, MOSPD3, GYS2, GAS8, RAB9A, POLR3D, PSD3, ZFPM2, ATP6V1C1, MEF2C, PKIA, ADAMTS18, STYXL1, EPM2A, LEPREL1, GABRA2, RCOR2, MFHAS1, SCARA5, CCDC25, FAM38A, CTSB, PTK2, SPIRE2, C13orf23, BOD1L, FAM160B2, NUS1, MTHFSD, UBR5, GALNS, FSTL5, SIM1, TG, BFSP2, MMP16, RIMS2, PDS5B, CDK7, CNTNAP4, CFDP1, FBXL4, RFX1, NALCN, STX1A, CYP7B1, ARHGEF10, ENTPD4, ZNF704, C8orf79, SLC9A9, CHMP7, GPC5, MYC, STIP1, ZBTB20, MEN1, SLC26A7, ALCAM, KIF13B, MBTPS1, PPP2R5B, VPS13C, ASPRSCR1, EPO, HEY1, KALRN, RGS22, WDR7, COL11A1, GHDC, ATP2C2, CDH17, DGKG, GRK5, GRM1, IMPA1, RPL7, COL21A1, COL12A1, MLYCD, AR, PLCB1, ACTL8, TFDP1, IQCE, SMARCB1, MTDH, NECAB2, DEF8, RNF40, TICAM2, GLG1, MECOM, TCEB1, CTNNA2, NIPAL2, CDCA2, WWP2, DDX19A, STK3, DNAH2, NFAT5, CNGB1, UBE2CBP, C8orf16, KIAA0196, CLCNKB, C16orf80, ZFHX3, PPM1L, NKIRAS2, RSPO2, XPO7, ME1, NLGN4Y, LZTS1, FBXL18, TBC1D10B, WDR59, BLK, MEPCE, DLGAP2, ZFAT, FASN, GIGYF1, ANXA13, CDYL2, TOX, NKX2-6, RALYL, TBC1D22A, TFE3, KCNAB1, SULF1, RAB5C, DHX58, ASAP1, CA5A, C6orf118, NCOA2, PKD1L2, BANP, KIAA1967, COPG2, ZNF706, GAN, PLCG2, C19orf57, PDGFRL, ESD, CPA5, BIN3, ZFHX4, CPA6, EYA1, CHRNA2, TNKS, HNF4G, LRCH1, ADRA1A, EPHX2, SORBS3, GRIA2, PDLIM2, MTMR7, FBXO24, CRISPLD1, DPYS, DTNA, KLHDC4, CYBA, JPH3, TMEM120A, MTUS1, C8orf34, GRHL2, CPA2, NAT2, DPYSL2, ZDHHC7, ELP3, RHOBTB2, NEIL2, HR, EFR3A, STMN4, PRDM14, MARVELD2, SLC39A14, ACTL6B, TUSC3, COX4NB, XKR9, C16orf46, TAF9, KCNQ3, UTRN, RAD17, ZFPM1, PTDSS1, IRF8, YWHAZ, MRPS36, LACTB2, SNAI3, TMEM71, PREX2, CPA1, PHF20L1, KIAA0513, PI15, PCM1, SH2D4A, C16orf74, TP63, DACH1, TNFRSF10A, MDH2, PAG1, SLC25A37, BCAR1, COX4I1, EIF4H, ZC3H18, STMN2, AFG3L1, HSD17B2, MVD, DLC1, EPHA7, TRIM35, LRRC50, CNGB3, ASCC3, RFC2, CLEC3A, IL17C, BMP1, CPA4, OC90, HEPH, LRP12, AGFG2, TRPA1, GINS2, CENPH, KLHL36, ARHGEF10L, TRAPPC2L, TCF25, TNFRSF10D, MYOM2, GCSH, KIAA1609, FANCA, ERI1, HSDL1, KIAA0182, CBFA2T3, EGR3, PCOLCE, C16orf85, HMBOX1, MTMR9, MSC, ST3GAL2, FOXF1, C8orf58, KCTD9, ANGPT1, GDAP1, RNF166, KLHL1, LOXL2, WISP1, C8orf80, LAT2, USP10, CDH15, WFDC1, C7orf51, EBF2, CCDC125, LGI3, NUDT18, PHYHIP, PILRA, KAT2A, CSMD3, REEP4, TUBB3, CDT1, EDA2R, DUS1L, LRCH4, TMEM75, NUDT7, TSGA14, CDC42BPG, TSC22D4, NOTUM, HSPB9, TFR2, SLA, WWOX, POU5F1B, and OPHN1.

6. The method of claim 5, wherein said 20 genes and/or genomic regions consist of CSMD1, SGCZ, PDE10A, PCDH9, HTR2A, HIP1, CD226, DCC, CC2D1A, PTK2B, BCMO1, MACRDO1, GRID2, DIAPH3, PILRB, MEIS2, MSRA, DPYD, ANKRD11, and NRXN1.

* * * * *